(12) United States Patent
Findlay et al.

(10) Patent No.: US 12,178,791 B2
(45) Date of Patent: Dec. 31, 2024

(54) HALOALLYLAMINE SULFONE DERIVATIVE INHIBITORS OF LYSYL OXIDASES AND USES THEREOF

(71) Applicant: Syntara Limited, Frenchs Forest (AU)

(72) Inventors: Alison Dorothy Findlay, Frenchs Forest (AU); Craig Ivan Turner, Frenchs Forest (AU); Mandar Deodhar, Frenchs Forest (AU); Jonathan Stuart Foot, Frenchs Forests (AU); Wolfgang Jarolimek, Frenchs Forest (AU); Wenbin Zhou, Frenchs Forest (AU); Alberto Buson, Frenchs Forest (AU); Angelique Elsa Greco, Cammeray (AU)

(73) Assignee: SYNTARA LIMITED, Frenchs Forest (AU)

( * ) Notice: Subject to any disclaimer, the term of this patent is extended or adjusted under 35 U.S.C. 154(b) by 917 days.

(21) Appl. No.: 17/265,402

(22) PCT Filed: Aug. 2, 2019

(86) PCT No.: PCT/AU2019/050811
§ 371 (c)(1),
(2) Date: Feb. 2, 2021

(87) PCT Pub. No.: WO2020/024017
PCT Pub. Date: Feb. 6, 2020

(65) Prior Publication Data
US 2021/0353571 A1 Nov. 18, 2021

(30) Foreign Application Priority Data
Aug. 3, 2018 (AU) ................ 2018902829

(51) Int. Cl.
| | | |
|---|---|---|
| *C07D 209/08* | (2006.01) | |
| *A61K 31/145* | (2006.01) | |
| *A61K 31/18* | (2006.01) | |
| *A61K 31/4409* | (2006.01) | |
| *A61K 31/47* | (2006.01) | |
| *A61P 17/02* | (2006.01) | |
| *A61P 19/04* | (2006.01) | |
| *A61P 35/00* | (2006.01) | |
| *A61P 35/04* | (2006.01) | |
| *C07C 311/29* | (2006.01) | |
| *C07C 317/32* | (2006.01) | |
| *C07D 213/71* | (2006.01) | |
| *C07D 215/36* | (2006.01) | |
| *C07D 277/64* | (2006.01) | |

(52) U.S. Cl.
CPC ............ *A61K 31/18* (2013.01); *A61K 31/145* (2013.01); *A61K 31/4409* (2013.01); *A61K 31/47* (2013.01); *A61P 17/02* (2018.01); *A61P 19/04* (2018.01); *A61P 35/00* (2018.01); *A61P 35/04* (2018.01); *C07C 311/29* (2013.01); *C07C 317/32* (2013.01); *C07D 209/08* (2013.01); *C07D 213/71* (2013.01); *C07D 215/36* (2013.01); *C07D 277/64* (2013.01); *C07B 2200/05* (2013.01); *C07C 2601/16* (2017.05); *C07C 2602/10* (2017.05)

(58) Field of Classification Search
CPC .. C07D 209/08; C07D 213/71; C07D 215/36; C07D 277/64
See application file for complete search history.

(56) References Cited

U.S. PATENT DOCUMENTS

| | | |
|---|---|---|
| RE28,819 E | 5/1976 | Thompson |
| 4,358,603 A | 11/1982 | Cheng-Der |
| 4,454,158 A | 6/1984 | Bey |
| 4,522,811 A | 6/1985 | Eppstein et al. |
| 4,699,928 A | 10/1987 | McDonald |
| 4,943,593 A | 7/1990 | Palfreyman et al. |
| 4,965,288 A | 10/1990 | Palfreyman et al. |
| 5,021,456 A | 6/1991 | Palfreyman et al. |
| 5,059,714 A | 10/1991 | Palfreyman et al. |
| 5,182,297 A | 1/1993 | Palfreyman et al. |
| 5,252,608 A | 10/1993 | Palfreyman et al. |
| 2008/0293969 A1 | 11/2008 | Karimi et al. |
| 2009/0053224 A1 | 2/2009 | Smith et al. |
| 2011/0044907 A1 | 2/2011 | Marshall |

FOREIGN PATENT DOCUMENTS

| | | | |
|---|---|---|---|
| WO | WO 2003097612 A1 | 11/2003 | |
| WO | WO 2006053555 A2 | 5/2006 | |
| WO | WO 2007120528 A2 | 10/2007 | |
| WO | WO 2009/066152 A2 * | 5/2009 | |

(Continued)

OTHER PUBLICATIONS

Lysyl oxidase [online], retrieved from the internet on Nov. 2, 2023. URL: https://en.wikipedia.org/wiki/Lysyl_oxidase.*
Lala, et al. Cancer and Metastasis Reviews 17:91-106, 1998.*
Golub, et al. Science 286, 531 (1999).*
Cancer [online], retrieved from the internet on Nov. 2, 2023. URL: https://medlineplus.gov/cancer.html.*
International Preliminary Report on Patentability issued Jun. 12, 2020 in connection with PCT International Application No. PCT/AU2019/050811.
Baker et al. "Lysyl Oxidase Plays a Critical Role in Endothelial Cell Stimulation to Drive Tumor Angiogenesis." Cancer Res., 2013, vol. 73(2), pp. 583-594.
Bredell et al. "Current relevance of hypoxia in head and neck Cancer," Oncotarget, 2016, vol. 7, No. 31, pp. 50781-50804.
Chanoki, M. et al. "Increased expression of lysyl oxidase in skin wwith scleroderma." Br J Dermatol, 1995, vol. 133, pp. 710-715 (Exhibit 19).

(Continued)

Primary Examiner — Shawquia Jackson
(74) Attorney, Agent, or Firm — Gary J. Gershik

(57) ABSTRACT

The present invention relates to novel compounds which are capable of inhibiting certain amine oxidase enzymes. These compounds are useful for treatment of a variety of indications, e.g., fibrosis, cancer and/or angiogenesis in human subjects as well as in pets and livestock. In addition, the present invention relates to pharmaceutical compositions containing these compounds, as well as various uses thereof.

18 Claims, 15 Drawing Sheets

(56) References Cited

FOREIGN PATENT DOCUMENTS

| WO | WO 2013163675 A1 | 11/2013 |
|---|---|---|
| WO | WO 2016144702 A1 | 9/2016 |
| WO | WO 2016144703 A1 | 9/2016 |
| WO | WO 2017003862 A1 | 1/2017 |
| WO | WO 2017015221 A1 | 1/2017 |
| WO | WO 2017136870 A1 | 8/2017 |
| WO | WO 2017136871 A1 | 8/2017 |
| WO | WO 2017141049 A1 | 8/2017 |
| WO | WO 2018048930 A1 | 3/2018 |
| WO | WO 2018157190 A1 | 9/2018 |
| WO | WO 2019073251 A1 | 4/2019 |

OTHER PUBLICATIONS

Counts, D. F. et al. "Collagen lysyl oxidase activity in the lung decreases during bleomycin induced lung fibrosis." J Pharmacol Exp Ther, 1981, vol. 219, No. 3, pp. 675-678 (Exhibit 20).

Cox et al. "LOX-mediated collagen crosslinking is responsible for fibrosisenhanced metastasis." Cancer Res., 2013, vol. 73(6), pp. 1721-1732.

Cox et al. "The hypoxic cancer secretome induces pre-metastatic bone lesions through lysyl oxidase." Nature, 2015, vol. 522 (7554), pp. 106-110.

Da Silva et al. "LOX Expression and Functional Analysis in Astrocytomas and Impact of IDH1 Mutation." PLoS One, 2015, vol. 10 (3), e0119781.

DeBry et al. "Incidence of Late-Onset Bleb-Related Complications Following Trabeculectomy With Mitomycin." Arch. Ophthalmol., 2002, vol. 120, pp. 297-300.

Di Donato, A. et al. "Lysyl oxidase expression and collagen cross-linking during chronic adriamycin nephropathy." Nephron, 1997, vol. 76, pp. 192-200.

Eliades et al. "Control of Megakaryocyte Expansion and Bone Marrow Fibrosis by Lysyl Oxidase." J. Biol. Chem., 2011, vol. 286, No. 31, pp. 27630-27638.

Erler et al. "Lysyl oxidase is essential for hypoxia-induced metastasis." Nature, 2006, vol. 440 (7088), pp. 1222-1226.

Foot et al. "The discovery and development of selective 3-fluoro-4-aryloxyallylamine inhibitors of the amine oxidase activity of semicarbazide-sensitive amine oxidase/vascular adhesion protein-1 (SSAO/VAP-1) ." Bioorg. Med. Chem. Lett. , 2012, vol. 22, pp. 3935-3940.

Halberg, N. et al. "Hypoxia inducible factor 1α induces fibrosis land insulin resistance in white adipose tissue." Cell Biol, 2009, vol. 29, No. 16, pp. 4467-4483.

Holt et. "A peroxidase-coupled continuous absorbance plate-reader assay for flavin monoamine oxidases, copper-containing amine oxidases and related enzymes." Nat. Protoc., 2006, vol. 1, No. 5, pp. 2498-2505.

Hong et al., "Regulation of Lysyl Oxiades, Collagen, and Connective Tissue Growth Factor by TGF-beta1 and Detection in Human Gingiva." Lab. Invest, 1999, vol. 79, No. 12, pp. 1655-1667.

Huang et al. "Lysyl oxidase enzymes mediate TGF-β1-induced fibroticphenotypes in human skin-like tissues." Lab. Invest., 2019, vol. 99, pp. 514-527.

Kagan, H. M. and Li, W. "Lysyl oxidase: properties, specificity, andbiological roles inside and outside of the cell." J Cell Biochem, 2003, vol. 88, pp. 660-672.

Kagan, H. M. et al. "Changes in aortic lysyl oxidase activity in diet induced atherosclerosis in the rabbit." Arteriosclerosis, 1981, vol. 1, pp. 287-291.

Kagan, H.M. "Lysyl oxidase; Mechanism, regulation and relationship to liver fibrosis." Path. Res. Pract., 1994, vol. 190, pp. 910-919.

Keiser et al., "Studies on bega-aminopropionitrile in patients with scleroderma." Clin. Pharmacol. Ther., 1967, pp. 593-602.

Khaw et al. "Growth factor antibody may safely reduce postop ocularscarring." Ocular Surgery News U. S. Edition, Oct. 1, 2002.

Kirschmann et al. "A Molecular Role for Lysyl Oxidase in Breast Cancer Invasion." Cancer Res., 2002, vol. 62 (15), pp. 4478-4483.

Korenaga et al. "Smoking may cause genetic alterations at 5q22.2~q23.1 in clear-cell renal cell carcinoma." Cancer Genet Cytogenet, 2005, vol. 163 (1), pp. 7-11.

Lai et al. "FAK-ERK activation in cell/matriz adhesion induced by the loss of apolipoprotein E stimulates the malignant progression of ovarian cancer." J. Exp. Clin. Cancer Res., 2018, vol. 37:32.

Le Calve et al. "Lysyl oxidase family activity promotes resistance of pancreatic ductal adenocarcinoma to chemotherapy by limiting the intratumoral anticancer drug distribution." Oncotarget, 2016, vol. 7, No. 22, pp. 32100-32112.

LeBleu et al. "A peek into cancer-associated fibroblasts: origins, functions and translational impact." Dis. Model. Mech., 2018, vol. 11.

Lefevre et al. "Synovial fibroblasts spread rheumatoid arthritis to unaffected joints." Nat. Med., 2009, vol. 15, No. 12, pp. 1414-1420.

Lopez, B. et al. "Role of lysyl oxidase in myocardial fibrosis: from basic science to clinical aspects." Am J Physiol Heart Circ Physiol, 2010, vol. 299, pp H1-H9.

Madar et al. "'Cancer associated fibroblasts'—more than meets the eye." Trends Mol. Med., 2013, vol. 19, No. 8, pp. 447-453.

Miller et al., "Targeting the LOX/hypoxia axis reverses many of the features that make pancreatic cancer deadly: inhibition of LOX abrogates metastasis and enhances drug efficacy." EMBO Mol. Med., 2015, vol. 7(8), pp. 1063-1076.

Nave et al. "Lysyl Oxidases Play a Casual Role in Vascular Remodeling in Clinical and Experimental Pulmonary Arterial Hypertension," Arterioscler. Thromb. Vasc. Biol., 2014, vol. 34, pp. 1446-1458.

Rachman-Tzemah et al., "Blocking Surgically Induced Lysyl Oxidase Activity Reduces the Risk of Lung Metastases." Cell. Rep., 2017, vol. 19 (4), pp. 774-784.

Remst et al. "Gene Expression Analysis of Murine and Human Osteoarthritis Synovium Reveals Elevation of Transforming Growth Factor beta-Responsive Genes in Osteoarthritis-Related Fibrosis." Arthritis and Rhematology, 2014, vol. 66, No. 3, pp. 647 656.

Rossow et al. "LOX-catalyzed collagen stabilization is a proximal cause for intrinsic resistance to chemotherapy." Oncogene, 2018, vol. 37 (36), pp. 4921-4940.

Saito et al. "Aberrant Collagen Cross-linking in Human Oral Squamous Cell Carcinoma." J. Dent. Res., 2019, vol. 98 (5), pp. 517-525.

Siddikiuzzaman et al. "Lysyl oxidase: a potential target for cancer therapy." Inflammapharmacol, 2011, vol. 19, pp. 117-129.

Siegel, R. C. et al. "Biochemical and immunochemical study of lysyl oxidase in experimental hepatic fibrosis in the rat." Proc. Natl. Acad. Sci. USA, 1978, vol. 75, No. 6, pp. 2945-2949.

Stewart et al. "Analysis of hypoxia-associated gene expression in prostate cancer: lysyl oxidase and glucose transporter-1 expression correlate with Gleason score." Oncol. Rep., 2008, vol. 20, pp. 1561-1567.

Sume et al. "Epithelial to Mesenchymal Transition in Gingival Overgrowth." American Journal of Pathology, 2010, vol. 177, No. 1, pp. 208-218.

Tang et al. "Reaction of Aortic Lysyl Oxidase with beta-Aminopropionitrile." J. Biol. Chem., 1983, vol. 258, No. 7, pp. 4331-4338.

Tang et al., "Lysyl oxidase drives tumour progression by trapping EGF receptors at the cell surface." Nat. Commun., 2017, vol. 18(8).

Trackman, P.C. and Kantarci, A. "Connective Tissue Metabolism and Gingival Overgrowth." Crit. Rev. Oral. Biol. 2004, vol. 15(3), pp. 165-175.

Wang et al. "Association between Lysyl Oxidase G473A Polymorphism and Ovarian Cancer in the Han Chinese Population." J. Int. Med. Res., 2012, vol. 40 (3), pp. 917-923.

Wang et al. "Lysyl oxidase is involved in synovial hyperplasia and angiogenesis in rats with collagen-induced arthritis." Mol. Med. Rep., 2017, vol. 16, 6736-6742.

Woznick, A. R. et al. "Lysyl oxidase expression in bronchogenic carcinoma." Am J Surg, 2005, vol. 189, pp. 297-301.

Wu et al., "Lysyl Oxidase G473A Polymorphism Is Associated with Increased Risk of Ovarian Cancer." Genet Test Mol Biomarkers, 2012, vol. 16, No. 8, pp. 915-919.

(56) References Cited

OTHER PUBLICATIONS

Yang et al. "Inactivation of lysyl oxidase by β-aminopropionitrile jinhibits hypoxia-induced invasion and migration of cervical cancer cells." Oncol. Rep., 2013, vol. 29 (2), pp. 541-548.

Yoshida et al. "Quantitative Evaluation of Collagen Crosslinks and Corresponding Tensile Mechanical Properties in Mouse Cervical Tissue during Normal Pregnancy." PLoS One, 2014, vol. 9, issue 11, e112391.

Office Action, including English Language Translation, issued Jul. 6, 2023 in connection with corresponding Japanese Patent Application No. JP 2021-505981.

Ping Sun, Study of the role of SSAO/VAP-1 in OGD conditions using SSAO/VAP-1 expressing HUVEC and human brain endothelial cells (hCMEC/D3) a s experimental models of ischemic stroke, and its possible nexus with Alzheimer's disease [online], Jul. 22, 2015, pp. vii-xiv, 3-5.

Yang et al. "Uric acid increases fibronectin synthesis through upregulation of lysyl oxidase expression in rat renal tubular epithelial cells" Am J Physiol Renal Physiol (2010), 299:F336-F346.

Higgins et al. "Hypoxia promotes fibrogenesis in vivo via HIF-1 stimulation of epithelial-to-mesenchymal transition" J Clin Invest. (2007), 117(12):3810-3820.

Cheng et al. "Lysyl oxidase promotes bleomycin-induced lung fibrosis through modulating inflammation" Journal of Molecular Cell Biology (2014), 6(6):506-515.

Chien et al. "Serum lysyl oxidase-like 2 levels and idiopathic pulmonary fibrosis disease progression" Eur Respir J (2014) 43:1430-1438.

\* cited by examiner

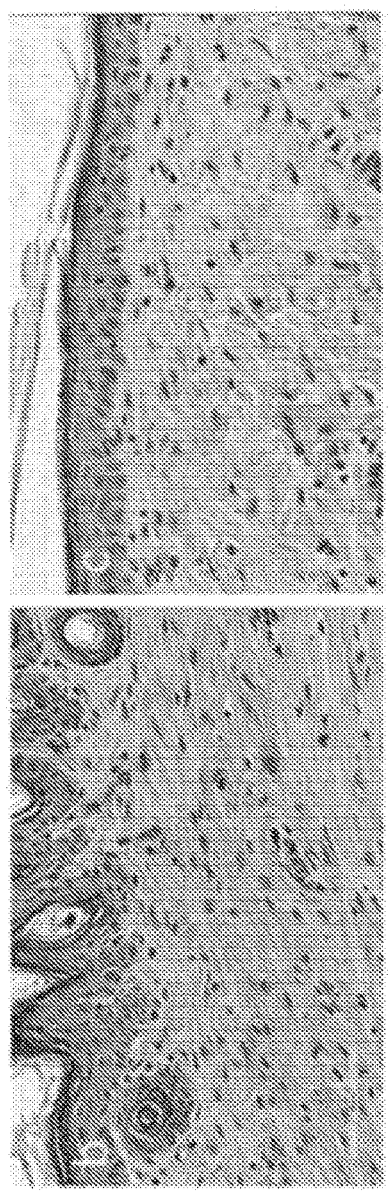
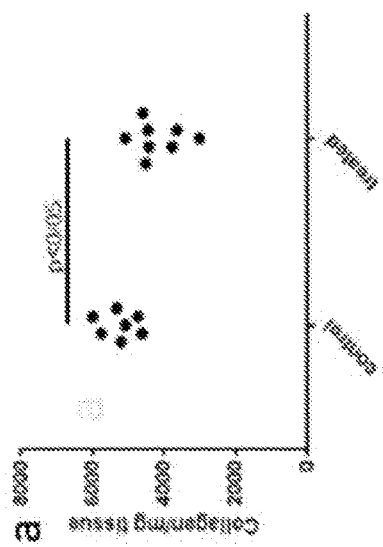
Figure 3(a-c)

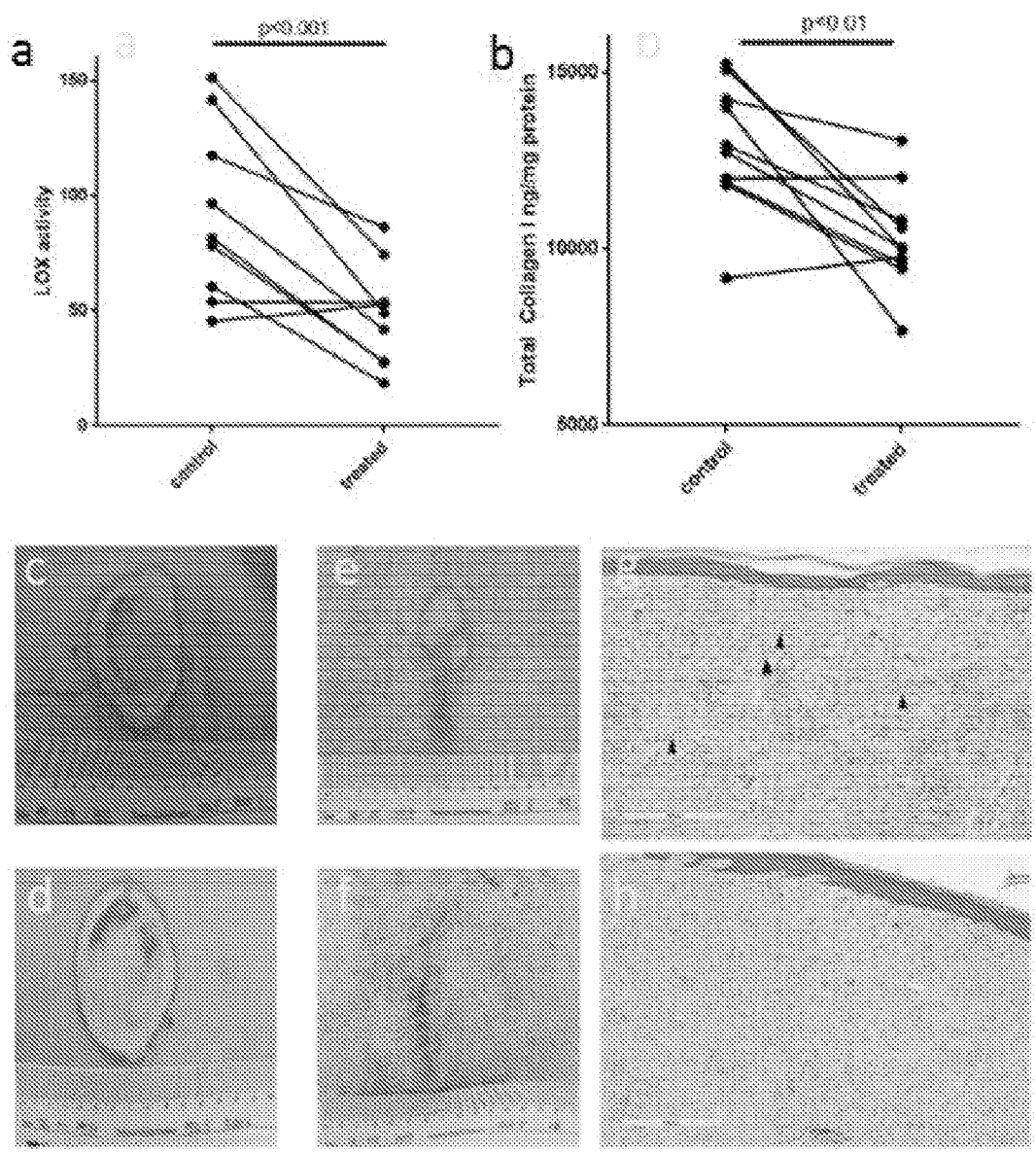
Figure 4(a-h)

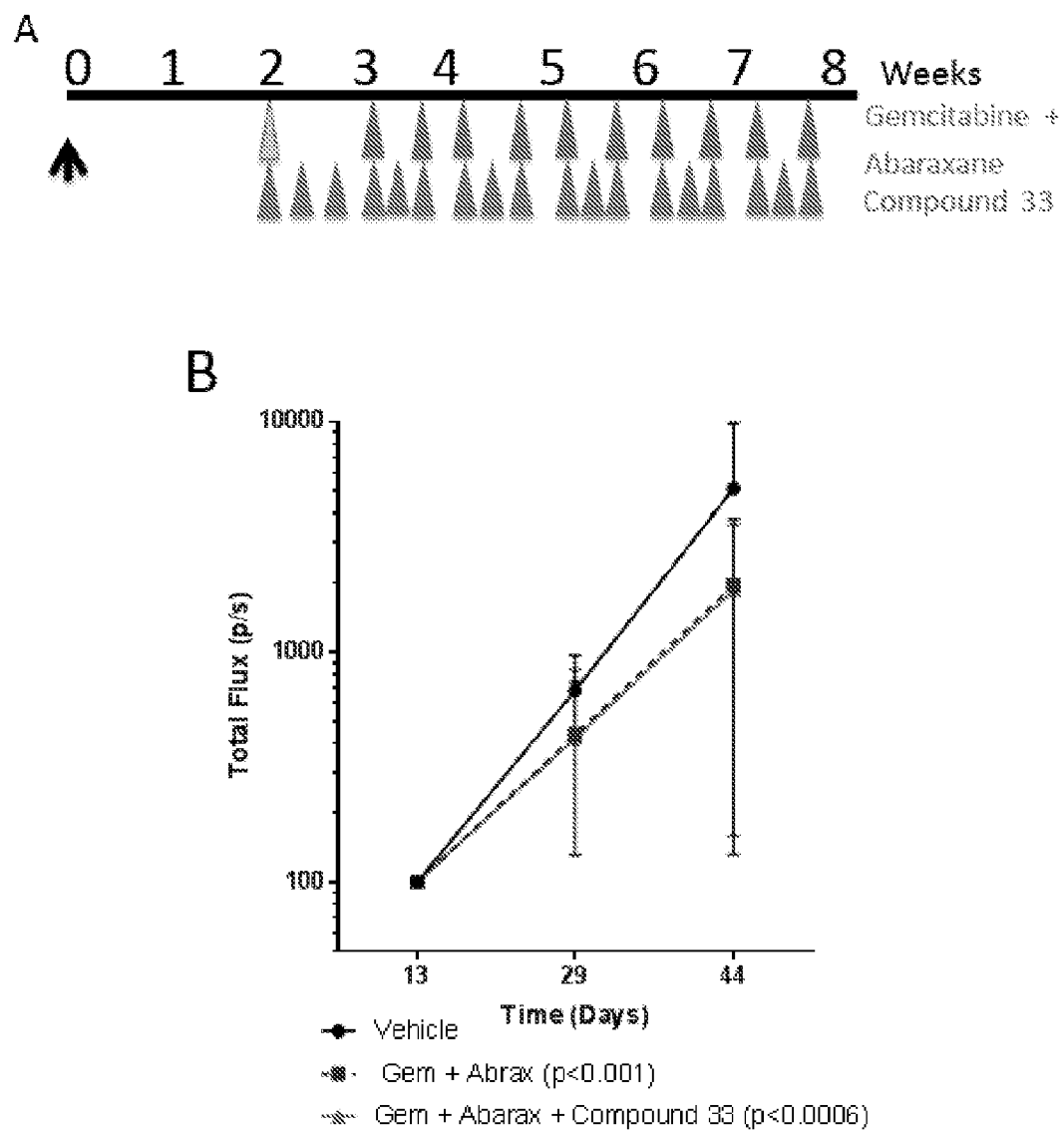
Figure 5(a-b)

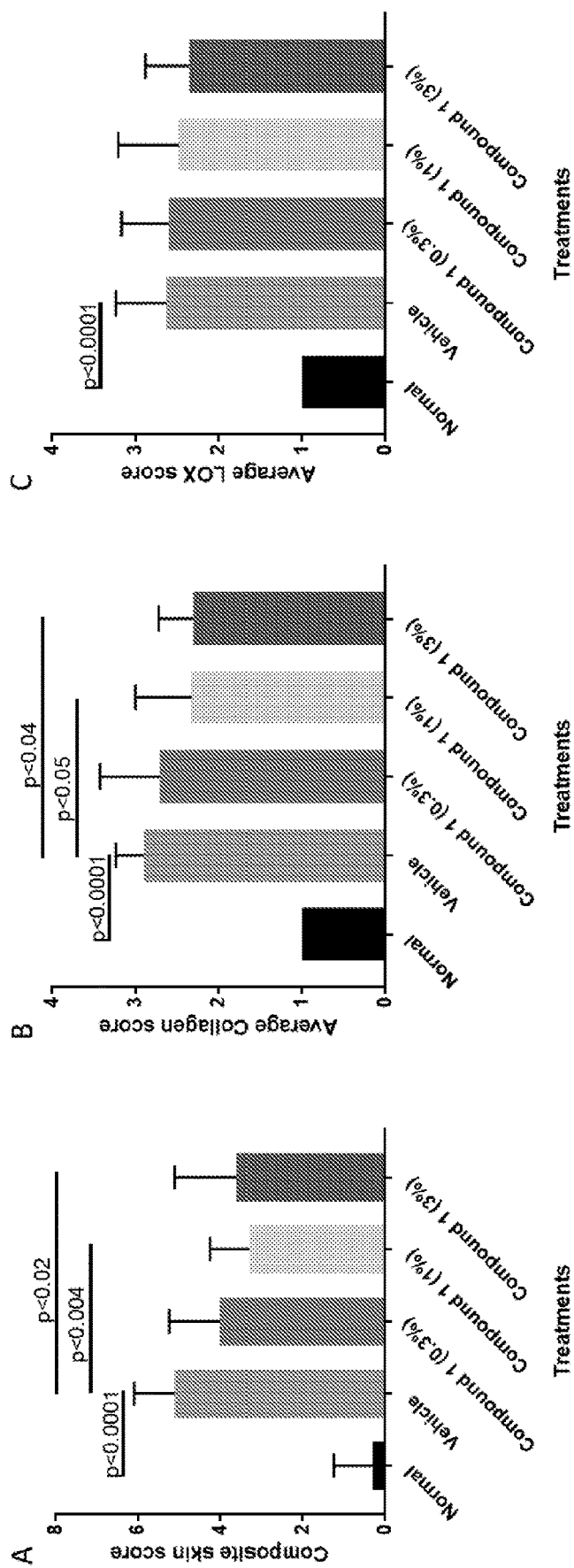
Figure 6(a-c)

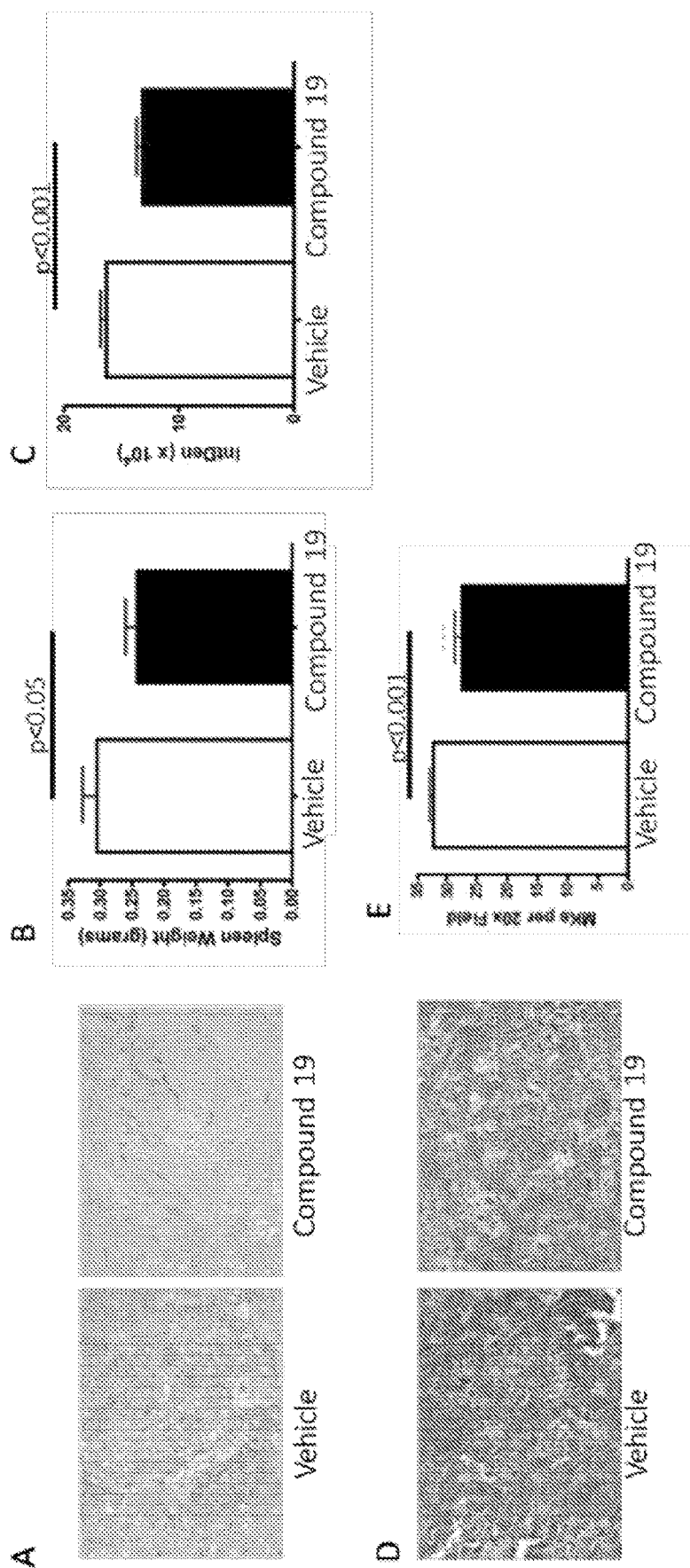
Figure 7(a-e)

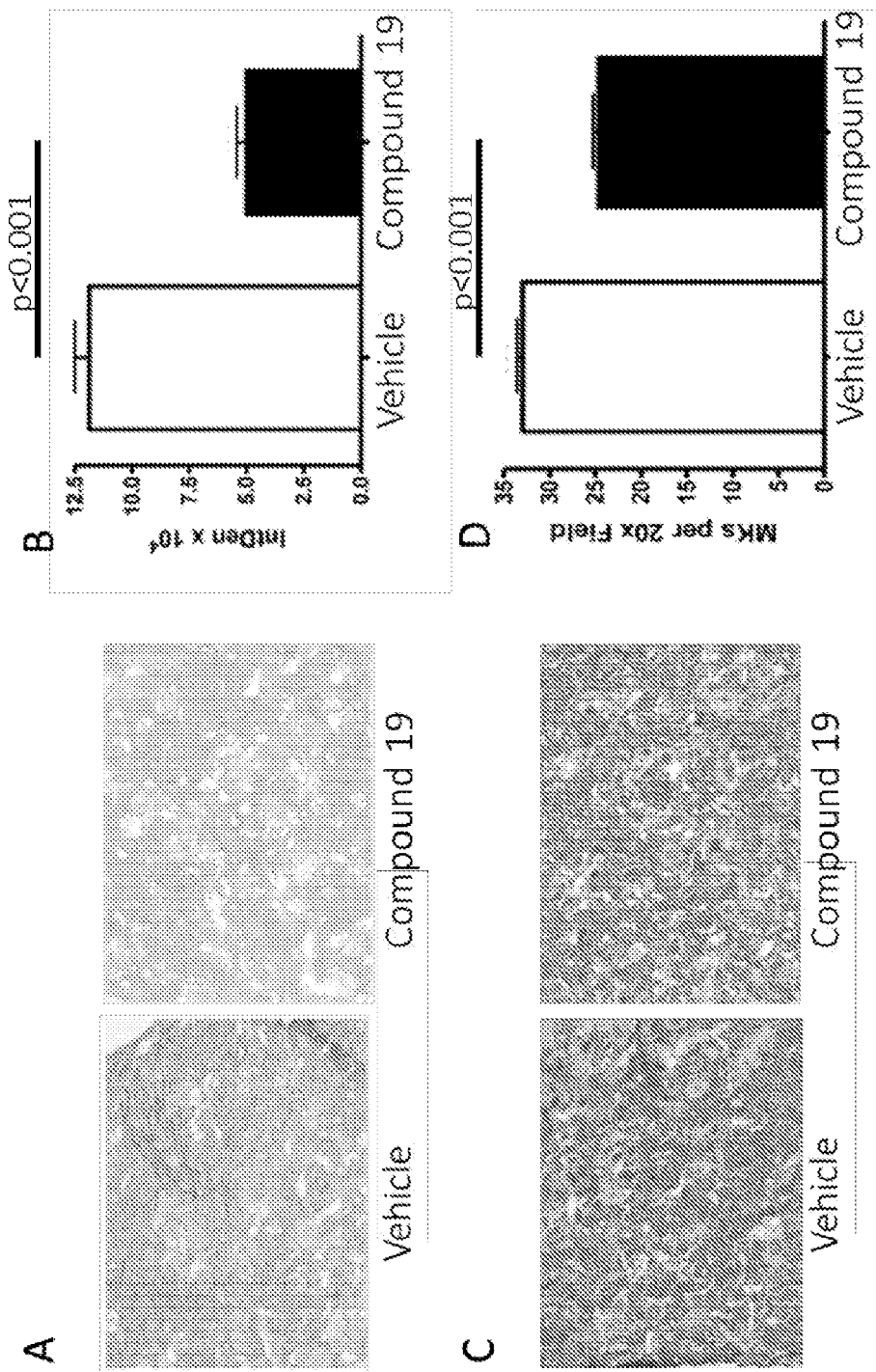
Figure 8(a-d)

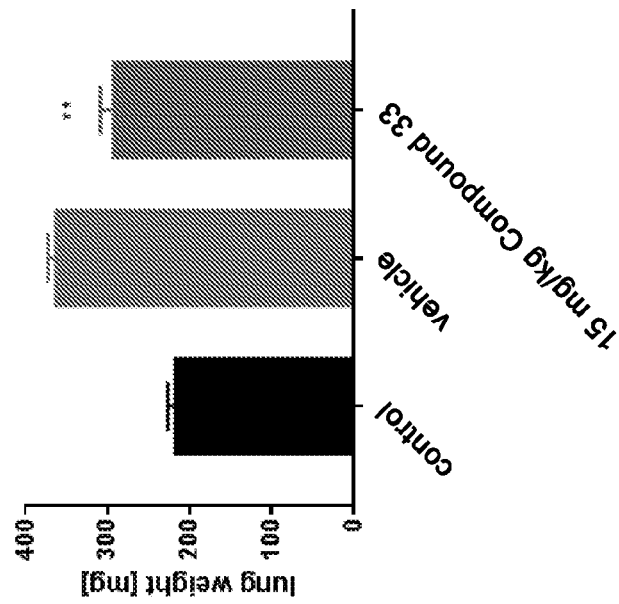
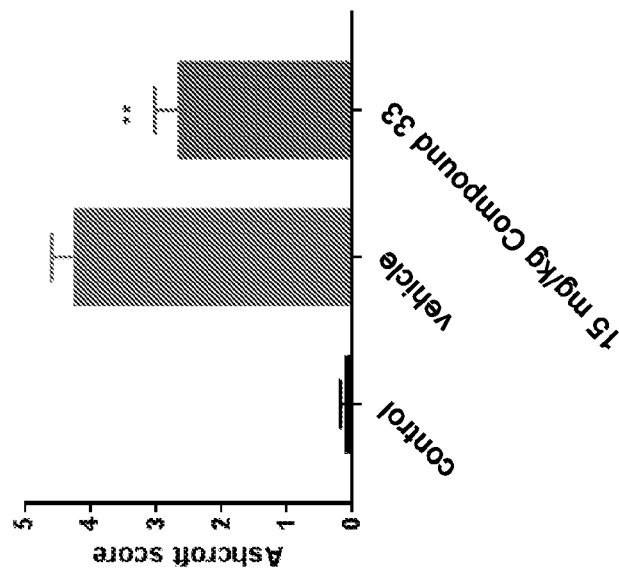
Figure 10

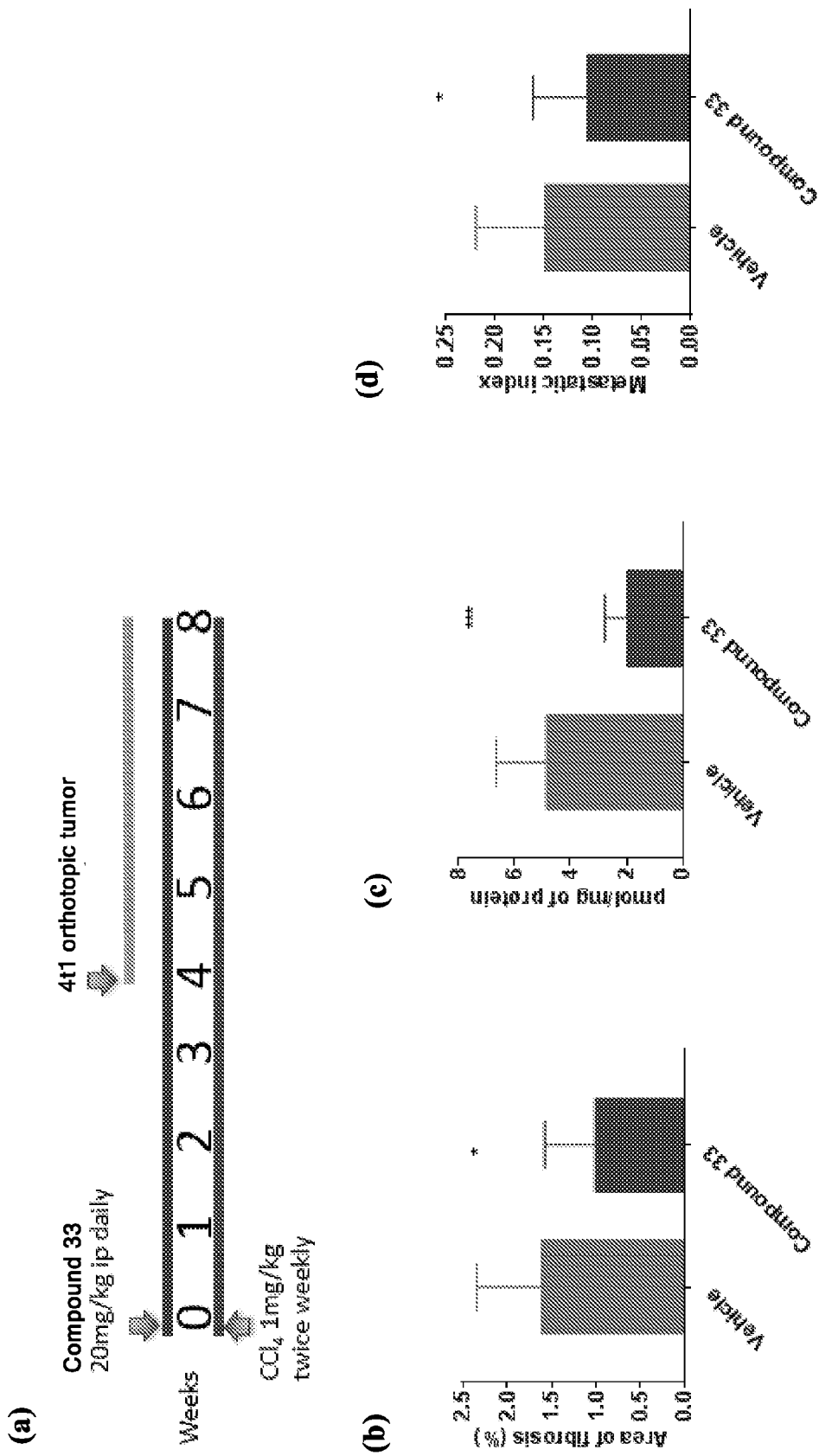
Figure 11(a-d)

HALOALLYLAMINE SULFONE DERIVATIVE INHIBITORS OF LYSYL OXIDASES AND USES THEREOF

RELATED APPLICATIONS

This application is a § 371 national stage of PCT International Application No. PCT/AU2019/050811, filed Aug. 2, 2019, claiming priority of Australian Provisional Patent Application No. 2018902829, filed Aug. 3, 2018, the contents of each of which are hereby incorporated by reference into this application.

TECHNICAL FIELD

The present invention relates to novel compounds which are capable of inhibiting certain amine oxidase enzymes. These compounds are useful for treatment of a variety of indications, e.g., fibrosis, cancer and/or angiogenesis in human subjects as well as in pets and livestock. In addition, the present invention relates to pharmaceutical compositions containing these compounds, as well as various uses thereof.

BACKGROUND

The enzymes are lysyl oxidase (LOX), the first family member to be described and LOX-like1 (LOXL1), LOXL2, LOXL3, and LOXL4 (*J Cell Biochem* 2003; 88: 660-672). Lysyl oxidase isoenzymes are copper-dependent amine oxidases which initiate the covalent cross-linking of collagen and elastin. A major function of lysyl oxidase isoenzymes is to facilitate the cross-linking of collagen and elastin by the oxidative deamination of lysine and hydroxylysine amino acid side chains to aldehydes which spontaneously react with neighbouring residues. The resulting cross-linked strands contribute to extracellular matrix (ECM) stability and render it less susceptible to proteolytic degradation by enzymes such as matrix metalloproteases (MMPs). The activity of lysyl oxidase enzymes is crucial for the maintenance of normal tensile and elastic features of connective tissue of many organ systems of the body.

Lysyl oxidase isoenzymes belong to a larger group of amine oxidases which include flavin-dependent and copper-dependent oxidases which are described by the nature of the catalytic co-factor. Flavin-dependent enzymes include monoamine oxidase-A (MAO-A), monoamine oxidase-B (MAO-B), polyamine oxidase and lysine demethylase (LSD1), and the copper-dependent enzymes including semicarbazide sensitive amine oxidase (vascular adhesion protein-1, SSAO/VAP-1), retinal amine oxidase, diamine oxidase and the lysyl oxidase isoenzymes. The copper-dependent amine oxidases have a second co-factor which varies slightly from enzyme to enzyme. In SSAO/VAP-1 it is an oxidized tyrosine residue (TPQ, oxidized to a quinone), whereas in the lysyl oxidase isoenzymes the TPQ has been further processed by addition of a neighbouring lysine residue (to form LTQ) (*J Cell Biochem* 2003; 88: 660-672).

Lysyl oxidase isoenzymes exhibit different in vivo expression patterns, which suggests that specific isoenzymes will have specific biological roles. Catalytically active forms of LOX have been identified in the cytosolic and nuclear compartments and research is in progress to define their roles in these compartments. LOX itself, for example, plays a major role in epithelial-to-mesenchymal transition (EMT), cell migration, adhesion, transformation and gene regulation. Different patterns of LOX expression/activity have been associated with distinct pathological processes including fibrotic diseases, Alzheimer's disease and other neurodegenerative processes, as well as tumour progression and metastasis (*Am J Surg* 2005; 189: 297-301).

Directed replacement of dead or damaged cells with connective tissue after injury represents a survival mechanism that is conserved throughout evolution and appears to be most pronounced in humans, serving a valuable role following traumatic injury, infection or diseases. Progressive scarring can occur following more chronic and/or repeated injuries that causes impaired function to parts or the entire affected organ. A variety of causes, such as chronic infections, chronic exposure to alcohol and other toxins, autoimmune and allergic reactions or surgery, radio- and chemotherapy can all lead to fibrosis. This pathological process, therefore, can occur in almost any organ or tissue of the body and, typically, results from situations persisting for several weeks or months in which inflammation, tissue destruction and repair occur simultaneously. In this setting, fibrosis most frequently affects the lungs, liver, skin, kidneys and cardiovascular system.

Liver fibrosis for example can occur as a complication of haemochromatosis, Wilson's disease, alcoholism, schistosomiasis, viral hepatitis, bile duct obstruction, exposure to toxins and metabolic disorders. Liver fibrosis is characterized by the accumulation of extracellular matrix that can be distinguished qualitatively from that in normal liver. This fibrosis can progress to cirrhosis, liver failure, cancer and eventually death (*Pathology—Research and Practice* 1994; 190: 910-919).

Fibrotic tissues can accumulate in the heart and blood vessels as a result of hypertension, hypertensive heart disease, atherosclerosis and myocardial infarction where the accumulation of extracellular matrix or fibrotic deposition results in stiffening of the vasculature and stiffening of the cardiac tissue itself (*Am J Physiol Heart Circ Physiol* 2010; 299: H1-H9).

Pulmonary arterial hypertension (PAH) is a rare and rapidly lethal condition characterised by elevated pulmonary arterial pressure and caused by increased pulmonary vascular resistance. Although a heterogeneous condition with a wide range of causes, there is increasing recognition that PAH is associated with other diseases such as connective-tissue disease and scleroderma. Pathological hallmarks of PAH include vascular wall remodelling with excessive extracellular matrix (ECM) deposition and cross-linking. Lysyl oxidases are dysregulated in pulmonary vasculature of patients with idiopathic pulmonary arterial hypertension (IPAH) and contribute to the persistence of ECM components and improper collagen and elastin remodelling through cross-linking (*Arterioscler. Thromb Vasc. Biol.* 2014; 34: 1446-1458). Prognosis for patients with PAH is poor. Targeting the lysyl oxidases pharmacologically could provide therapeutic intervention where few or none currently exist.

A strong association between fibrosis and increased lysyl oxidase activity has been demonstrated. For example, in experimental hepatic fibrosis in rat (*Proc. Natl. Acad. Sci. USA* 1978; 75: 2945-2949), in models of lung fibrosis (*J Pharmacol Exp Ther* 1981; 219: 675-678), in arterial fibrosis (*Arteriosclerosis* 1981; 1: 287-291), in dermal fibrosis (*Br J Dermatol* 1995; 133: 710-715) and in adriamycin-induced kidney fibrosis in rat (*Nephron* 1997; 76: 192-200). Of these experimental models of human disease, the most striking increases in enzyme activity were seen in the rat model of $CCl_4$-induced liver fibrosis. In these studies, the low level of enzyme activity in the healthy liver increased 15- to 30-fold in fibrotic livers.

In humans, there is also a significant association between lysyl oxidase activity measured in the plasma and liver fibrosis progression. Lysyl oxidase activity level is normally low in the serum of healthy subjects, but significantly increased in chronic active hepatitis and even more in cirrhosis. Therefore, lysyl oxidase might serve as a marker of internal fibrosis.

Lysyl oxidase isoenzymes are highly regulated by Hypoxia-Inducible Factor 1α (HIF-1α) and TGF-β, the two most prominent growth factors that cause fibrosis (*Cell Biol* 2009; 29: 4467-4483). Collagen cross-linking occurs in every type of fibrosis, hence a lysyl oxidase isoenzyme inhibitor could be used in idiopathic pulmonary fibrosis, scleroderma, kidney or liver fibrosis.

In normal wound healing, granulation tissue formation is a short-lived process, providing a scaffold for re-epithelialisation and repair. Subsequently, the tissue is remodelled and a normotrophic scar is formed. However, after an injury, humans cannot regenerate normal skin. Instead, the repair (or healing) process leads to scar formation (cicatrisation). Scars are both aesthetically and functionally inferior to skin. Scars are a chronic problem and excessive or hypertrophic scarring and its accompanying aesthetic, functional and psychological sequelae remain key challenges for the treatment of deep skin injury and burns. A key factor in the poor appearance and pliability of scars, in particular hypertrophic scars, are the changes to collagen in the dermal layer. In scar tissue the collagen (predominantly Collagen I) is more densely packed and closely aligned in parallel bundles. In normal skin, collagen is not densely packed and is more of a 'basket-weave' structure. These alterations, both in structure and quantity of collagen, largely underlie the poor appearance of scar and lead to loss of pliability, discomfort and functional problems.

Dermal fibrosis, or excessive scarring of the skin, is a consequence of exaggerated healing response and is characterized by disproportionate fibroblast proliferation and extracellular matrix (ECM) production in the dermis. Clinically, dermal fibrosis manifests as thickened, tightened and hardened areas of the skin. The spectrum of fibrotic skin disorders is wide, including, but not limited to: hypertrophic scarring, keloids, scleroderma (diffuse and limited subtypes), scleredema (Buschke disease), systemic amyloidosis, lipodermatosclerosis, progeroid disorders, stiff skin syndrome, Dupuytren's contracture, nephrogenic fibrosing dermopathy (NFD), mixed connective tissue disease, scleromyxedema, graft-versus-host disease (GVHD) and eosinophilic fasciitis. Although each of these disorders has its own etiology and clinical characteristics, all involve excessive collagen production, and altered collagen remodelling. One possible mechanism for altered ECM remodelling is through covalent cross-linking. This directly implicates the LOX family of enzymes in the pathogenesis of cutaneous fibrosis (*Laboratory investigation* 2019; 99: 514-527). LOX and LOXL1-4 expression is elevated in scar fibroblasts compared to normal skin fibroblasts, with LOX and LOXL1 being the dominant isoforms found in skin tissue.

Studies involving two complimentary, in-vitro skin-like models—human skin equivalent (hSEs), and self-assembled stromal tissues identified LOXL4 as the key isoform mediating TGF-beta induced fibrotic phenotypes (*Lab. Invest.* 2019; 99: 514-527).

Scarring processes are a considerable problem and challenge in the eye and surrounding structures. Ocular scarring plays a major role in either primary disease (e.g. corneal and conjunctival scarring) or treatment failure (e.g. postoperative trabeculectomy) (*Ocular Surgery News* U.S. Edition, Oct. 1, 2002).

Glaucoma is a disease in which the optic nerve is being damaged, leading to progressive and irreversible loss of vision. Elevated intraocular pressure (TOP) is one of the major risk factors for the development and progression of glaucoma. Most treatments for glaucoma are targeted at lowering the intraocular pressure, either by decreasing the formation of aqueous fluid in the eye, or, as in the case of glaucoma filtration surgery, by increasing the outflow of fluid from the eye. Trabeculectomy—the current gold standard for the management of IOP—is a filtering surgery where an ostium is created into the anterior chamber from underneath a partial thickness scleral flap to allow for aqueous flow out of the eye. Post-operative scarring is the main cause of treatment failure. The antimetabolites mitomycin-C (MMC) and 5-fluorouracil (5-FU) are used in current clinical practice to help limit post-operative ocular scar tissue formation. While these agents have been shown to improve the IOP outcome of filtration surgery, they do so in a non-selective manner and are associated with significant side effects (*Arch. Ophthalmol.* 2002; 120: 297-300). Safer, more targeted, anti-fibrotic agents are needed.

Gingival fibromatosis is a rare and heterogeneous group of disorders that develop as slow progressive, local or diffuse, fibrous enlargements of keratinized gingiva (gingival overgrowth or enlargement). In severe cases, the excess tissue may cover the crowns of the teeth, thus causing masticatory, aesthetic, phonetic, functional and periodontal problems. Gingival overgrowth may be inherited, of idiopathic origin, associated with inflammatory diseases of the oral cavity, or associated with other systemic diseases. However, the majority of cases are due to side-effects of systemic medications such as the anti-seizure drug phenytoin, the immunosuppressant cyclosporin A, and certain anti-hypertensive dihydropyridine anti-calcium-channel-blockers, in particular nifedipine (*crit rev oral biol* 2004; 15: 165-175). The pathological manifestation of gingival overgrowth comprises excessive accumulation of extracellular matrix proteins, of which Collagen I is the most predominant. One recognized concept of mechanism for drug induced gingival overgrowth is EMT, a process in which interaction of gingival cells and the extracellular matrix are weakened as epithelial cells transdifferentiate into fibrogenic fibroblast-like cells (*AJP* 2010; 177: 208-218). The damaged epithelium, basement membrane and underlying stroma result in TGF-stimulation of lysyl oxidase enzyme activity and contribute to connective tissue fibrosis (Lab Invest 1999; 79: 1655-1667).

The rationale for the consistent and strong inhibition of fibrosis by lysyl oxidase isoenzyme blockers is that the lack of cross-linking activity renders the collagen susceptible to degradation by proteolytic enzymes such as MMPs. Hence, any type of fibrosis should be reversed by treatment with lysyl oxidase isoenzyme inhibitors. Given the varied involvement of all lysyl oxidase isoenzymes in fibrosis, an inhibitor that demonstrates sustained, strong inhibition of all lysyl oxidase isoenzymes, i.e. a pan LOX inhibitor, should be most efficacious.

Rheumatoid Arthritis (RA) is a systemic autoimmune disorder characterized by chronic, painful inflammation of the lining of the joints. In some people, however, the condition can progress to involve painful swelling and inflammation of the surrounding tissue, and other body systems, including the skin, eyes, lungs, heart and blood vessels. Rheumatoid arthritis is thus a painful and debilitating disease that can result in substantial loss of function and mobility in the hands, wrists and feet. Active rheumatoid arthritis emanates from a few joints, but can subsequently progress to affect multiple joints. Synovial hyperplasia, involving infiltrated immune cells and resident synovial fibroblasts (SFs), is a typical feature of RA. Rheumatoid arthritis synovial fibroblasts (RASFs) are the most common cell type at sites of invasion and are the main culprit in joint destruction. Activated RASFs are able to transmigrate and, as such, have been implicated in the spread of arthritis between joints. Cytokines from the infiltrated immune cells induce activation and proliferation of synovial fibroblasts. These activated SFs in turn generate the pathogenic stroma to perpetuate chronic inflammation, ultimately leading to cartilage and bone destruction. By implanting RASFs together with human cartilage into severe combined immunodeficient mice, it has been demonstrated that activated RASFs migrate in vivo, spreading the disease to the sites of implanted human cartilage. Furthermore, whilst RASFs actively degrade cartilage, controls implanted with synovial fibroblasts from osteoarthritis (OA) patients and cutaneous fibroblasts from healthy donors did not (*Nat. Med.* 2009; 15: 1414-1420). RASFs differ from unactivated, healthy fibroblasts by their morphology and gene expression. RASFs are characterised by the expression of antiapoptotic, proto-oncogenes and lack of expression of tumor suppressor genes. The production of pro-inflammatory cytokines and chemokines by RASFs further enable attraction of immune cells to the synovium. Furthermore, the production of matrix metalloprotease (MMP) enzymes promotes invasion into and destruction of cartilage.

The type II collagen-induced arthritis (CIA) model is a commonly used animal model for RA as it recapitulates well the signature immunological, pathological and arthritic presentations observed in RA in humans. In CIA rats, high expressions levels of LOX in the synovial membranes, synovial fluid and serum have been demonstrated. Inhibition of LOX with beta-aminopropionitrile (BAPN; a pan LOX inhibitor) was found to attenuate inflammation, synovial hyperplasia, angiogenesis and expression of MMP-2 and MMP-9, indicating that LOX promotes synovial hyperplasia and angiogenesis in CIA rats. Furthermore, knockdown of LOXL2 and antibodies against LOXL2 attenuated collagen deposition, proliferation and invasion of RASF (*Mol. Med. Rep.* 2017: 6736-6742).

Whilst there is no cure for RA, there are a number of treatments available that alleviate symptoms and modify disease progression. However, such treatments come with significant side effects associated, in part, with the suppression of the immune system. Selective drugs that target RASF would represent more useful therapy for RA.

Osteoarthritis (OA) is a disease characterised by degeneration of joint cartilage and underlying bone. Predominantly resulting from "wear and tear", OA causes pain and stiffening of the joint. The most commonly affected joints are those of the fingers, knees, back and hips. Unlike other forms of arthritis (such as RA), osteoarthritis only affects the joints. Often, joints on one side of the body are affected more than those on the other. OA is a progressive and debilitating disease that can have a significant impact on work and normal daily activities.

Synovial fibrosis is a key contributor to OA, and is a manifestation of fibroblast proliferation and an imbalance in collagen synthesis and collagen degradation. This imbalance leads to excessive deposition of collagen into the extracellular matrix (ECM) and results in thickening and stiffening of the synovial membrane.

Genes encoding a number of the lysyl oxidase family of enzymes including LOX, LOXL2, LOXL3 and LOXL4 have been shown to be highly expressed in mice with experimental OA, and humans with end-stage OA (*Arthritis and Rheumatology* 2014; 66: 647-656).

Given the varied contribution of many of the members of the lysyl oxidase family of enzymes to the development of both rheumatoid arthritis and osteoarthritis, a pan LOX inhibitor may provide for a potentially more efficacious therapy.

BAPN is a widely used, nonselective mechanism-based, irreversible lysyl oxidase inhibitor. Since the 1960s BAPN has been used in animal studies (mainly rat, mouse and hamster) and has been efficacious in reducing collagen content in various models (e.g. $CCl_4$, bleomycin, quartz, cancer) and tissues (e.g. liver, lung and dermis) (*J Cell Biochem* 2003; 88: 660-672). However, studies in human patients with scleroderma, found BAPN to be poorly tolerated and highlights the need for safer alternatives (*Clin. Pharmacol. Ther.* 1967: 593-602).

Lysyl oxidase catalysed collagen cross-linking can proceed via two pathways: the allysine and hydroxyallysine pathways. In the hydroxyallysine pathway, immature divalent crosslinks are formed first, including dehydro-dihydroxylysinonorleucine (deH-DHLNL) and dehydro-hydroxylysinonorleucine (deH-HLNL), and then further progress (via lysyl oxidase independent reactions) to mature trivalent crosslinks, between three collagen molecules to form deoxypyridinoline (DPD) and pyridinoline (PYD). These mature and immature crosslinks can be measured by LC-MS/MS (*PLoS One* 2014; 9 (11), e112391).

Lysyl oxidase isoenzymes are not only involved in the cross-linking of elastin and collagen during wound healing and fibrosis, but also regulate cell movement and signal transduction. Its intracellular and intranuclear function is associated with gene regulation and can lead to tumourigenesis and tumour progression (*Inflammapharmacol* 2011; 19: 117-129). Both down and upregulation of lysyl oxidase isoenzymes in tumour tissues and cancer cell lines have been described, suggesting a dual role for lysyl oxidase isoenzymes and LOX pro-peptide as a metastasis promoter gene as well as a tumour suppressor gene.

In addition to its role in tissue remodelling, the LOX isoenzymes also play a critical role in primary cancer and metastasis. Tumour growth is associated with a reactive stroma, which is predominantly composed of fibroblasts; termed cancer associated fibroblasts (CAFs). Mice subcutaneously inoculated with an equal mixture of tumour and CAFs cells are known to have a faster growth rate and higher incidence of metastases (*Trends Mol Med.* 2013; 19(8): 447-453). CAF knockout models have shown to be pro-tumorigenic, however this is quite an abstract scenario when comparing to a patient's tumour microenvironment. CAFs have been shown to have an increased expression of LOXs compared to normal fibroblasts (*Dis Model Mech.* 2018; 11 (4)). Utilising a LOX inhibitor in a cancer setting potentially will affect both the tumour and stromal compartment to assist in decreasing tumour growth and metastasis.

Emerging evidence suggests an association between idiopathic pulmonary fibrosis and lung cancer, however, more studies are needed. Chemical or irradiation induced fibrosis in both, lung and liver mouse models causes an increase in alpha smooth muscle actin (a marker of fibroblasts), LOX expression and metastatic tumour growth, which is reversed by a LOX antibody (*Cancer Res.* 2013; 73 (6): 1721-1732).

To date, an increase in lysyl oxidase isoenzymes mRNA and/or protein has been observed in breast, CNS cancer cell lines, head and neck squamous cell, esophageal, kidney, lung, prostatic, clear cell renal cell and lung carcinomas, ovarian, uterine, melanoma and osteosarcoma patient samples from The Cancer Genome Atlas (TCGA). Shown in Table 1 is the TCGA patient gene expression data for the LOX family A plus symbol indicates higher than the average gene expression within this dataset.

TABLE 1

TCGA patient gene expression data for the LOX family

| Cancer | LOX | LOXL1 | LOXL2 | LOXL3 | LOXL4 | Number of patient samples |
|---|---|---|---|---|---|---|
| Breast invasive carcinoma | + | + | + | + | | 1212 |
| Esophageal carcinoma | + | + | + | | | 196 |
| Glioblastoma multiforme | | | + | + | | 171 |
| Head & neck squamous cell carcinoma | + | + | + | | | 566 |
| Kidney renal clear carcinoma | + | | + | | + | 606 |
| Kidney renal papillary cell carcinoma | | + | | | + | 323 |
| Lung squamous cell carcinoma | + | + | + | | + | 552 |
| Mesothelioma | + | + | + | + | + | 87 |
| Ovarian serous cystadenocarcinoma | + | + | | + | + | 307 |
| Pancreatic adenocarcinoma | + | + | + | + | + | 183 |
| Pheochromocytoma and paraganglioma | | | + | + | | 187 |
| Sarcoma | + | + | + | + | | 265 |
| Skin cutaneous melanoma | + | | | + | + | 473 |
| Uterine carcinoma | + | + | + | + | + | 57 |
| Uterine corpus endometrial carcinoma | | + | | | | 201 |

Statistically significant clinical correlations between lysyl oxidase isoenzymes expression and tumour progression have been observed in breast, head and neck squamous cell, myelofibrosis, prostatic, pancreatic, ovarian, and clear cell renal cell carcinomas. The role of lysyl oxidase isoenzymes in tumour progression has been most extensively studied in breast cancer using in vitro models of migration/invasion and in in vivo tumourigenesis and metastasis mouse models (*Nature.* 2006; 440 (7088): 1222-1226). Increased lysyl oxidase isoenzymes expression was found in hypoxic patients, and was associated with negative estrogen receptor status (ER−), decreased overall survival in ER− patients and node-negative patients who did not receive adjuvant systemic treatment, as well as shorter bone metastasis-free survival in ER− patients and node negative patients; in vivo models demonstrated that the LOX inhibitors have potential in breast cancer patients with bone metastasis, by modulating bone homeostasis independent of RANKL (*Nature.* 2015; 522 (7554): 106-110). Lysyl oxidase isoenzymes mRNA was demonstrated to be upregulated in invasive and metastatic cell lines (MDA-MB-231 and Hs578T), as well as in more aggressive breast cancer cell lines and distant metastatic tissues compared with primary cancer tissues (*Cancer Res.* 2002; 62 (15): 4478-4483).

Pathogenic processes in primary myelofibrosis involve a primary megakaryocyte-weighted clonal myeloproliferation and paraneoplastic stromal reaction that includes bone marrow fibrosis, osteosclerosis, angiogenesis, and extramedullary hematopoiesis. The bone marrow reaction includes excess deposition of extracellular matrix proteins such as fibrillary collagen, hypocellularity, activation and recruitment of bone marrow fibroblasts, excessive cytokine and growth factor production, and other changes that result in a reduction in hematopoietic capacity. Secondary myelofibrosis can result from polycythaemia rubra vera or essential thrombocytosis. In myelofibrosis, disease progression correlates with increased numbers of megakaryocytes, which overexpress LOX. In a GATA 1 low mouse model of myelofibrosis, disease progression (including increase in megakaryocytes number, fibrosis and spleen size), were significantly attenuated by a pan LOX inhibitor (*J Biol Chem.* 2011; 286(31): 27630-27638).

In most tumor types, the first line of treatment is surgical resection. A wound healing response is initiated by surgery and may correlate with an increase in metastatic spread. Breast cancer models have shown that abdominal surgery increases lung metastasis. Furthermore, it was shown to be caused by systemic LOX. Injection of plasma, collected from abdominal surgery mice (which contained LOX), into tumour bearing mice resulted in an increase in lung metastasis. The surgery induced systemic LOX was blocked by BAPN, reducing metastasis and increasing survival (*Cell Rep.* 2017; 19 (4): 774-784).

In colon, breast cancer and melanoma models, tumor associated endothelial cells have been shown to have an increased expression of LOX, which stimulates angiogenesis and tumour growth (*Cancer Res.* 2015; 73(2): 583-594).

In pancreatic, breast, lung, ovarian and colon cancer patients, high collagen content has been correlated with high LOX gene expression, chemotherapy resistance and significantly decreased survival (*Oncogene.* 2018; 37(36) 4921-4940, *EMBO Mol Med.* 2015; 7(8) 1063-1076, *Oncotarget.* 2016; 7(22) 32100-32112). LOX inhibitors (both BAPN and a LOX antibody) and standard of care chemotherapies were combined in desmoplastic tumour mouse models to lower the tumour interstitial pressure causing expansion of vessels (*Oncotarget.* 2016; 7(22) 32100-32112). The increased vascular flow increases the concentration of the chemotherapeutic agent at the site of the primary tumour, which leads to a lower metastatic load and increased survival (*Oncotarget.* 2016 May 31; 7(22) 32100-32112).

In head and neck squamous cell carcinomas, increased lysyl oxidase isoenzyme expression was found in association with CA-IX, a marker of hypoxia, and was associated with decreased cancer specific survival, decreased overall survival and lower metastasis-free survival (*Oncotarget.* 2016; 7(31): 50781-50804). In oral squamous cell carcinoma, lysyl oxidase isoenzyme mRNA expression was upregulated compared to normal mucosa.

Gene expression profiling of gliomas identified overexpressed lysyl oxidase isoenzyme as part of a molecular signature indicative of invasion, and associated with higher-grade tumours that are strongly correlated with poor patient survival (*PloS ONE.* 2015 Mar. 19; 10(3) e0119781). Lysyl oxidase isoenzyme protein expression was increased in glioblastoma and astrocytoma tissues, and in invasive U343 and U251 cultured astrocytoma cells.

In tissues, lysyl oxidase isoenzyme mRNA was upregulated in prostate cancer compared to benign prostatic hypertrophy, correlated with Gleason score, and associated with both high grade and short time to recurrence (*Oncol Rep* 2008; 20: 1561-1567).

In clear cell RCC, smoking was associated with allelic imbalances at chromosome 5q23.1, where the LOX gene is localized, and may involve duplication of the gene (*Cancer Genet Cytogenet.* 2005; 163(1)7: 7-11).

SiHa cervical cancer cells demonstrated increased invasion in vitro under hypoxic/anoxic conditions; this was repressed by inhibition of extracellular catalytically active lysyl oxidase activity by treatment with BAPN as well as LOX antisense oligos, LOX antibody, LOX shRNA or an extracellular copper chelator (*Oncol Rep.* 2013; 29 (2), 541-548).

In ovarian cancer genetically engineered mouse models (ApoE knockout) a desmoplastic tumour with increased LOX gene expression is formed. Treatment with BAPN significantly increased survival and decreased lung metastasis (*J Exp Clin Cancer Res.* 2018; 37: 32). Certain tumours from patients with ovarian cancer have a single nucleotide polymorphism of the LOX gene, G473A. Two independent studies have shown that people with the G473A polymorphism expressed have increased chances of developing ovarian cancer (*J Int Med Res.* 2012; 40(3): 917-923; Genet Test Mol Biomarkers. 2012; 16 (8): 915-919).

In primary human oral squamous cell carcinoma (OSCC), levels of lysyl oxidase enzyme (in particular LOX and LOXL2) and lysyl hydroxylase expression are significantly increased, and markedly elevated in late-stage, regional lymph node metastasis (RLNM)-positive tumors. Both reducible, or immature, cross-links (deH-DHLNL and deH-HLNL) and non-reducible, or mature cross-links (DPD and PYD) are significantly elevated in OSCCs compared to normal tissues (*J Dent Res* 2019; 98(5): 517-525).

The findings described herein, provide a strong rationale for combination therapies involving LOX isoenzyme inhibitors and anti-tumor therapy in patients.

More recently, CCT365623 a reversible pan LOX inhibitor has been utilised in a breast cancer model (MMTV-PyMT) to reduce metastasis and increase survival (*Nat Commun.* 2017; 18 (8): 14909).

The scientific and patent literature describes small molecule inhibitors of lysyl oxidase isoenzymes and antibodies of LOX and LOXL2 with therapeutic effects in animal models of fibrosis and cancer metastasis. Some known MAO inhibitors also are reported to inhibit lysyl oxidase isoenzyme (e.g., the MAO-B inhibitor Mofegiline illustrated below). This inhibitor is a member of the haloallylamine family of MAO inhibitors; the halogen in Mofegiline is fluorine. Fluoroallylamine inhibitors are described in U.S. Pat. No. 4,454,158. There are issued patents claiming fluoroallylamines and chloroallylamines, for example MDL72274 (illustrated below) as inhibitors of lysyl oxidase (U.S. Pat. Nos. 4,943,593; 4,965,288; 5,021,456; 5,059,714; 5,182,297; 5,252,608). Many of the compounds claimed in these patents are also reported to be potent MAO-B and SSAO/VAP-1 inhibitors.

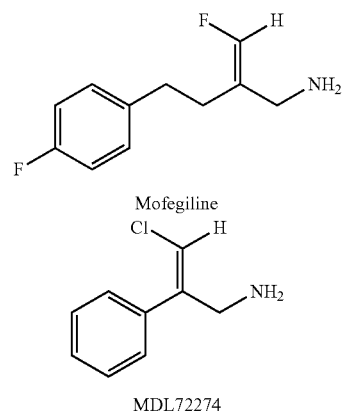

Mofegiline

MDL72274

Additional fluoroallylamine inhibitors are described U.S. Pat. No. 4,699,928. Other examples structurally related to Mofegiline can be found in WO 2007/120528.

WO 2009/066152 discloses a family of 3-substituted 3-haloallylamines that are inhibitors of SSAO/VAP-1 useful as treatment for a variety of indications, including inflammatory disease. None of these documents specifically disclose the fluoroallylamine compounds of formula (I) according to the present invention.

Antibodies to LOX and LOXL2 have been disclosed in US 2009/0053224 with methods to diagnostic and therapeutic applications. Anti-LOX and anti-LOXL2 antibodies can be used to identify and treat conditions such as a fibrotic condition, angiogenesis, or to prevent a transition from an epithelial cell state to a mesenchymal cell state: US 2011/0044907.

WO 2017/136871 and WO 2017/136870 disclose haloallylamine indole and azaindole derivative inhibitors of lysyl oxidases and uses thereof.

WO 2018/157190 disclose haloallylamine pyrazole derivative inhibitors of lysyl oxidases and uses thereof.

WO 2017/141049 and WO 2019/073251 disclose families of methylamine and bridged homopiperazine derivatives respectively as lysyl oxidase inhibitors and their use in the treatment of cancer and diseases associated with fibrosis.

WO 2003/097612, WO 2006/053555, and US 2008/0293936 disclose another class of lysyl oxidase inhibitors.

WO 2018/048930, WO 2017/015221, WO 2017/003862, WO 2016/144702 and WO 2016/144703 disclose further LOXL2 inhibitors.

SUMMARY

The present invention provides substituted fluoroallylamine compounds that inhibit lysyl oxidase (LOX), lysyl oxidase-like2 (LOXL2) and other lysyl oxidase isoenzymes. Surprisingly, modification of 3-substituted-3-fluoroallylamine structures described previously has led to the discovery of novel compounds that are potent inhibitors of the human LOX and LOXL isoenzymes. Furthermore, certain of these novel compounds also selectively inhibit certain LOX and LOXL isoenzymes with respect to the other enzymes in the amine oxidase family.

A first aspect of the invention provides for a compound of Formula I:

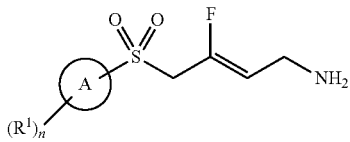

Formula I or a stereoisomer, pharmaceutically acceptable salt, polymorphic form, solvate, hydrate or tautomeric form thereof; wherein:

A is aryl or heteroaryl;

each $R^1$ is independently selected from the group consisting of X—$R^2$, halogen, deuterium, $C_{1-6}$alkyl, O—$C_{1-6}$alkyl, aryl, heteroaryl, cycloalkyl, heterocycloalkyl, —CN, —C(O)O$R^3$, —C(O)N$R^4R^5$, —S(O)$_2$N$R^4R^5$, —S(O)$_2R^6$, —N$R^8$C(O)$R^9$, and —N$R^8$S(O)$_2R^9$; wherein each $C_{1-6}$alkyl, aryl, heteroaryl, cycloalkyl and heterocycloalkyl is optionally substituted by one or more substituents selected from the group consisting of halogen, —OH, —SO$_2$CH$_3$, —$C_{1-4}$alkyl, —O—$C_{1-4}$alkyl, —CF$_3$, —CH$_2$CF$_3$ and —O—CF$_3$;

X is selected from the group consisting of O, CH$_2$, OCH$_2$, CH$_2$O, CH$_2$S(O)$_2$, CONH and NHCO;

$R^2$ is selected from the group consisting of cycloalkyl, heterocycloalkyl, aryl and heteroaryl; wherein each $R^2$ is optionally substituted by one or more $R^7$;

$R^3$ is selected from the group consisting of hydrogen, $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —SO$_2$CH$_3$, —$C_{1-4}$alkyl, —O—$C_{1-4}$alkyl, —CF$_3$, —CH$_2$CF$_3$ and —O—CF$_3$;

$R^4$ and $R^5$ are independently selected from the group consisting of hydrogen, $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —SO$_2$CH$_3$, —$C_{1-4}$alkyl, —O—$C_{1-4}$alkyl, —CF$_3$, —CH$_2$CF$_3$ and —O—CF$_3$; or $R^4$ and $R^5$ when attached to the same nitrogen atom are combined to form a 4- to 7-membered ring having from 0 to 1 additional heteroatoms as ring members;

$R^6$ is selected from the group consisting of $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —$C_{1-4}$alkyl, —O—$C_{1-4}$alkyl, —CF$_3$, —CH$_2$CF$_3$, and —O—CF$_3$;

$R^7$ is selected from the group consisting of halogen, OH, $C_{1-6}$alkyl, O—$C_{1-6}$alkyl, $C_{3-7}$cycloalkyl, —C(O)O$R^3$, —C(O)N$R^4R^5$, —N$R^4$C(O)$R^6$, —S(O)$_2$N$R^4R^5$, —N$R^4$S(O)$_2R^6$ and —S(O)$_2R^6$; wherein each $C_{1-6}$alkyl is optionally substituted by one or more substituents selected from the group consisting of halogen and —OH;

$R^8$ is hydrogen or $C_{1-6}$alkyl;

$R^9$ is selected from the group consisting of $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —$C_{1-4}$alkyl, —O—$C_{1-4}$alkyl, —CF$_3$, —CH$_2$CF$_3$, and —O—CF$_3$; or $R^8$ and $R^9$ are combined to form a 5- to 7-membered ring having from 0 to 1 additional heteroatoms as ring members; and n is 0, 1, 2, 3, 4, 5 or 6.

A second aspect of the invention provides for a pharmaceutical composition comprising a compound according to the first aspect of the invention, or a pharmaceutically acceptable salt or solvate thereof, and at least one pharmaceutically acceptable excipient, carrier or diluent.

A third aspect of the invention provides for a method of inhibiting the amine oxidase activity of any one of LOX, LOXL1, LOXL2, LOXL3 or LOXL4 in a subject in need thereof, comprising administering to the subject an effective amount of a compound according to the first aspect of the invention, or a pharmaceutically acceptable salt or solvate thereof, or a pharmaceutical composition according to the second aspect of the invention.

A fourth aspect of the invention provides for a method of treating a condition associated with any one of LOX, LOXL1, LOXL2, LOXL3 or LOXL4 protein, comprising administering to a subject in need thereof a therapeutically effective amount of compound according to the first aspect of the invention, or a pharmaceutically acceptable salt or solvate thereof, or a pharmaceutical composition according to the second aspect of the invention.

A fifth aspect of the invention provides for use of a compound according to the first aspect of the invention, or a pharmaceutically acceptable salt or solvate thereof, for the manufacture of a medicament for treating a condition associated with any one of LOX, LOXL1, LOXL2, LOXL3 or LOXL4 protein.

A sixth aspect of the invention provides for a compound according to the first aspect of the invention, or a pharmaceutically acceptable salt or solvate thereof, for use in treating a condition associated with any one of LOX, LOXL1, LOXL2, LOXL3 or LOXL4 protein.

In one embodiment of the methods and uses of the present invention the condition is selected from fibrosis, cancer and angiogenesis.

Contemplated herein is combination therapy in which the methods further comprise co-administering additional therapeutic agents that are used for the treatment of cancer, fibrosis, angiogenesis, inflammation, hypertension, immunosuppression and metabolic conditions.

Definitions

The following are some definitions that may be helpful in understanding the description of the present invention. These are intended as general definitions and should in no way limit the scope of the present invention to those terms alone, but are put forth for a better understanding of the following description.

Unless the context requires otherwise or specifically states to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

As used herein, the term "alkyl" includes within its meaning monovalent ("alkyl") and divalent ("alkylene") straight chain or branched chain saturated hydrocarbon radicals having from 1 to 6 carbon atoms, e.g., 1, 2, 3, 4, 5 or 6 carbon atoms. The straight chain or branched alkyl group is attached at any available point to produce a stable compound. For example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, and the like.

The term "alkoxy" or "alkyloxy" as used herein refers to straight chain or branched alkyloxy (i.e, O-alkyl) groups, wherein alkyl is as defined above. Examples of alkoxy groups include methoxy, ethoxy, n-propoxy, and isopropoxy.

The term "cycloalkyl" as used herein includes within its meaning monovalent ("cycloalkyl") and divalent ("cycloalkylene") saturated, monocyclic, bicyclic, polycyclic or fused analogs. In the context of the present disclosure the cycloalkyl group may have from 3 to 10 carbon atoms. A fused analog of a cycloalkyl means a monocyclic ring fused to an aryl or heteroaryl group in which the point of attachment is on the non-aromatic portion. Examples of cycloalkyl and fused analogs thereof include cyclopropyl, cyclobutyl, cyclopentyl, cyclohexyl, cycloheptyl, tetrahydronaphthyl, decahydronaphthyl, indanyl, adamantyl and the like.

The term "aryl" or variants such as "arylene" as used herein refers to monovalent ("aryl") and divalent ("arylene") single, polynuclear, conjugated and fused analogs of aromatic hydrocarbons having from 6 to 10 carbon atoms. A fused analog of aryl means an aryl group fused to a monocyclic cycloalkyl or monocyclic heterocyclyl group in which the point of attachment is on the aromatic portion. Examples of aryl and fused analogs thereof include phenyl, naphthyl, indanyl, indenyl, tetrahydronaphthyl, 2,3-dihydrobenzofuranyl, tetrahydrobenzopyranyl, 1,4-benzodioxanyl, and the like. A "substituted aryl" is an aryl that is independently substituted, with one or more, preferably 1, 2 or 3 substituents, attached at any available atom to produce a stable compound.

The term "alkylaryl" as used herein, includes within its meaning monovalent ("aryl") and divalent ("arylene"), single, polynuclear, conjugated and fused aromatic hydrocarbon radicals attached to divalent, saturated, straight or branched chain alkylene radicals. Examples of alkylaryl groups include benzyl.

The term "heteroaryl" and variants such as "heteroaromatic group" or "heteroarylene" as used herein, includes within its meaning monovalent ("heteroaryl") and divalent ("heteroarylene"), single, polynuclear, conjugated and fused heteroaromatic radicals having from 5 to 10 atoms, wherein 1 to 4 ring atoms, or 1 to 2 ring atoms are heteroatoms independently selected from O, N, NH and S. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. The heteroaromatic group may be $C_{1-9}$ heteroaromatic. A fused analog of heteroaryl means a heteroaryl group fused to a monocyclic cycloalkyl or monocyclic heterocyclyl group in which the point of attachment is on the aromatic portion. Examples of heteroaryl groups and fused analogs thereof include pyrazolyl, pyridyl, oxazolyl, oxadiazolyl, thiadiazolyl, tetrazolyl, triazinyl, thienyl, benzoxazolyl, benzothiazolyl, benzimidazolyl, benzofuranyl, benzothiophenyl, furo (2,3-b)pyridyl, indolyl, isoquinolyl, imidazopyridyl, pyrimidinyl, pyridazinyl, pyrazinyl, pyridonyl, phenanthrolinyl, quinolyl, isoquinolinyl, imidazolinyl, thiazolinyl, pyrrolyl, furanyl, thiophenyl, oxazolyl, isoxazolyl, isothiazolyl, triazolyl, and the like. "Nitrogen containing heteroaryl" refers to heteroaryl wherein any heteroatoms are N. A "substituted heteroaryl" is a heteroaryl that is independently substituted, with one or more, preferably 1, 2 or 3 substituents, attached at any available atom to produce a stable compound.

The term "heterocyclyl" and variants such as "heterocycloalkyl" as used herein, includes within its meaning monovalent ("heterocyclyl") and divalent ("heterocyclylene"), saturated or partially saturated (non-aromatic), monocyclic, bicyclic, polycyclic or fused hydrocarbon radicals having from 3 to 10 ring atoms, wherein from 1 to 4, or from 1 to 2, ring atoms are heteroatoms independently selected from O, N, NH, or S, SO or $SO_2$, in which the point of attachment may be carbon or nitrogen. A fused analog of heterocyclyl means a monocyclic heterocycle fused to an aryl or heteroaryl group in which the point of attachment is on the non-aromatic portion. The heterocyclyl group may be $C_{3-8}$ heterocyclyl. The heterocycloalkyl group may be $C_{3-6}$ heterocyclyl. The heterocyclyl group may be $C_{3-5}$ heterocyclyl. Examples of heterocyclyl groups and fused analogs thereof include pyrrolidinyl, thiazolidinyl, piperidinyl, piperazinyl, imidazolidinyl, 2,3-dihydrofuro(2,3-b)pyridyl, benzoxazinyl, tetrahydroquinolinyl, tetrahydroisoquinolinyl, dihydroindolyl, quinuclidinyl, azetidinyl, morpholinyl, tetrahydrothiophenyl, tetrahydrofuranyl, tetrahydropyranyl, and the like. The term also includes partially unsaturated monocyclic rings that are not aromatic, such as 2- or 4-pyridones attached through the nitrogen or N-substituted uracils.

The term "halogen" or variants such as "halide" or "halo" as used herein refers to fluorine, chlorine, bromine and iodine.

The term "heteroatom" or variants such as "hetero-" or "heterogroup" as used herein refers to O, N, NH and S.

In general, "substituted" refers to an organic group as defined herein (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents.

The term "optionally substituted" as used herein means the group to which this term refers may be unsubstituted, or may be substituted with one or more groups independently selected from alkyl, alkenyl, alkynyl, cycloalkyl, cycloalkenyl, heterocycloalkyl, halo, haloalkyl, hydroxyl, hydroxyalkyl, alkoxy, thioalkoxy, alkenyloxy, haloalkoxy, $NO_2$, NH(alkyl), N(alkyl)$_2$, alkylamino, dialkylamino, acyl, alkenoyl, alkynoyl, acylamino, diacylamino, acyloxy, alkylsulfonyl, alkylsulfonyloxy, sulfonamido, heterocycloxy, heterocycloamino, haloheterocycloalkyl, alkylsulfenyl, alkylcarbonyloxy, phosphorus-containing groups such as phosphono and phosphinyl, aryl, heteroaryl, alkylaryl, aralkyl, alkylheteroaryl, cyano, $CO_2H$, $CO_2$alkyl, C(O)NH$_2$, —C(O)NH(alkyl), and —C(O)N(alkyl)$_2$. Preferred substituents include halogen, $C_1$-$C_6$alkyl, $C_1$-$C_6$haloalkyl, $C_1$-$C_6$alkoxy, hydroxy($C_{1-6}$)alkyl, $C_3$-$C_6$cycloalkyl, C(O)OH, NHC(O)$C_1$-$C_4$alkyl, C(O)$C_1$-$C_4$alkyl, $NH_2$, $NHC_1$-$C_4$alkyl, N($C_1$-$C_4$alkyl)$_2$, $SO_2$($C_1$-$C_4$alkyl), OH and CN. Particularly preferred substituents include $C_{1-4}$alkyl, $C_{1-4}$alkoxy, $SO_2$($C_1$-$C_4$alkyl), halogen, OH, hydroxy($C_{1-3}$)alkyl (e.g. C($CH_3$)$_2$OH), and $C_{1-3}$haloalkyl (e.g. $CF_3$, $CH_2CF_3$).

The present invention includes within its scope all stereoisomeric and isomeric forms of the compounds disclosed herein, including all diastereomeric isomers, racemates, enantiomers and mixtures thereof. It is also understood that the compounds described by Formula I may be present as E and Z isomers, also known as cis and trans isomers. Thus, the present disclosure should be understood to include, for example, E, Z, cis, trans, (R), (S), (L), (D), (+), and/or (−) forms of the compounds, as appropriate in each case. Where a structure has no specific stereoisomerism indicated, it should be understood that any and all possible isomers are encompassed. Compounds of the present invention embrace all conformational isomers. Compounds of the present invention may also exist in one or more tautomeric forms, including both single tautomers and mixtures of tautomers. Also included in the scope of the present invention are all polymorphs and crystal forms of the compounds disclosed herein.

The present invention includes within its scope isotopes of different atoms. Any atom not specifically designated as a particular isotope is meant to represent any stable isotope of that atom. Thus, the present disclosure should be understood to include deuterium and tritium isotopes of hydrogen.

All references cited in this application are specifically incorporated by cross-reference in their entirety. Reference to any such documents should not be construed as an admission that the document forms part of the common general knowledge or is prior art.

In the context of this specification the term "administering" and variations of that term including "administer" and "administration", includes contacting, applying, delivering or providing a compound or composition of the invention to an organism, or a surface by any appropriate means. In the context of this specification, the term "treatment", refers to any and all uses which remedy a disease state or symptoms, prevent the establishment of disease, or otherwise prevent, hinder, retard, or reverse the progression of disease or other undesirable symptoms in any way whatsoever.

In the context of this specification the term "topical administration" or variations on that term including "topical application" includes within its meaning applying, contacting, delivering or providing a compound or composition of the invention to the skin, or localized regions of the body.

In the context of this specification the term "local administration" or variations on that term including "local application" includes within its meaning applying, contacting, delivering or providing a compound or composition of the invention to the skin, or localized regions of the body.

In the context of this specification the term "effective amount" includes within its meaning a sufficient but non-toxic amount of a compound or composition of the invention to provide a desired effect. Thus, the term "therapeutically effective amount" includes within its meaning a sufficient but non-toxic amount of a compound or composition of the invention to provide the desired therapeutic effect. The exact amount required will vary from subject to subject depending on factors such as the species being treated, the sex, age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

BRIEF DESCRIPTION OF THE FIGURES

FIG. 3(a) Shows reduction in collagen in mouse scar tissue after injury when treated with topical Compound 1.

FIG. 3(b) Histology shows thick parallel collagen bundles in control scar tissue.

FIG. 3(c) Tissue treated with Compound 1 shows decreased density of bundles and more 'normal' structure of collagen.

FIG. 4(a-b) shows reduction in LOX activity and total collagen after daily topical treatment for 4 weeks with 3% Compound 1 solution versus control.

FIG. 4(c-f) Gross morphology shows similar wounds at time of injury (c, control; d, treated) and at time of euthanasia treated wounds appear more healed (e, control, f treated).

FIG. 4(g-h) Histology shows thick collagen bands in untreated scar tissue (highlighted by arrows, g). This appears to be reduced in treated tissue (h).

FIG. 6(a-c) Histological analysis of Sclerosis mouse skin model with topical treatment with Compound 1. A. Composite skin score. B. Average Collagen score. C. Average LOX score.

FIG. 7(a-e) Analysis of the spleen from primary Myelofibrosis model (GATA-1low) treated with Compound 19. A. Gomori silver stain of spleen. B. Spleen weight. C. Quantification Spleen reticulin fibrosis. D. H&E stain image of spleen. E. Quantification of the Megakaryocytes in the spleen.

FIG. 8(a-d) Analysis of the bone marrow from primary Myelofibrosis model (GATA-1low) treated with Compound 19. A. Gomori silver stain of bone marrow. B. Quantification bone marrow reticulin fibrosis. C. H&E stain image of bone marrow. D. Quantification of the Megakaryocytes in the bone marrow.

FIG. 10 depicts the ability of Compound 33 to reduce bleomycin-induced lung fibrosis (Ashcroft score) and weight gain.

FIG. 11(a-d) depicts the ability of Compound 33 to reduce fibrosis associated metastasis in a $CCl_4$ induced mouse liver fibrosis model with orthotopically injected breast cancer cell line (4t). (a) Schematic of the study design; (b) clinical measure of liver fibrosis; (c) concentration of cross-links in the liver; (d) measurement of liver metastasis.

DETAILED DESCRIPTION

Figures 1A, 1B:
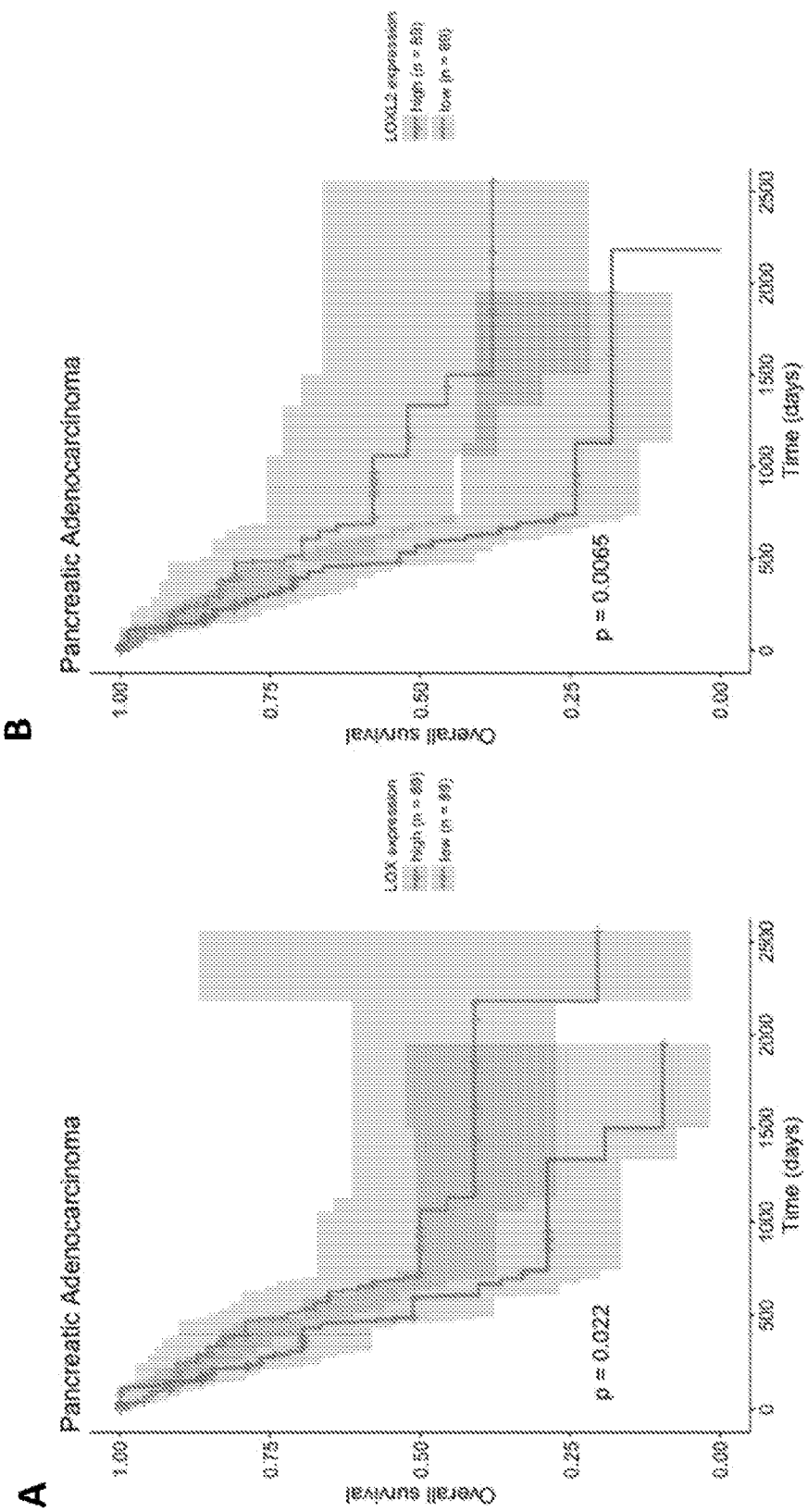
FIGS. 1(a) and 1(b) depict survival curves comparing high and low gene expression in pancreatic adenocarcinoma patients based on the TCGA dataset. A. LOX gene expression. B. LOXL2 gene expression.

The present invention relates to substituted fluoroallylamine derivatives which may inhibit lysyl oxidase (LOX), lysyl oxidase-like2 (LOXL2) and other lysyl oxidase isoenzymes. In particular the present invention relates to substituted fluoroallylamine derivatives with a sulfone linker.

In particular the present invention relates to compounds of Formula I:

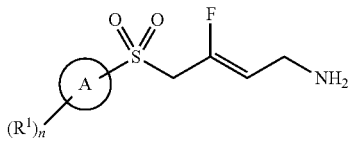

Formula I or a stereoisomer, pharmaceutically acceptable salt, polymorphic form, solvate, hydrate or tautomeric form thereof; wherein:

A is aryl or heteroaryl;

each $R^1$ is independently selected from the group consisting of X—$R^2$, halogen, deuterium, $C_{1-6}$alkyl, O—$C_{1-6}$alkyl, aryl, heteroaryl, cycloalkyl, heterocycloalkyl, —CN, —C(O)O$R^3$, —C(O)N$R^4R^5$, —S(O)$_2$N$R^4R^5$, —S(O)$_2R^6$, —N$R^8$C(O)$R^9$, and —N$R^8$S(O)$_2R^9$; wherein each $C_{1-6}$alkyl, aryl, heteroaryl, cycloalkyl and heterocycloalkyl is optionally substituted by one or more substituents selected from the group consisting of halogen, —OH, —SO$_2$CH$_3$, —$C_{1-4}$alkyl, —O—$C_{1-4}$alkyl, —CF$_3$, —CH$_2$CF$_3$ and —O—CF$_3$;

X is selected from the group consisting of O, CH$_2$, OCH$_2$, CH$_2$O, CH$_2$S(O)$_2$, CONH and NHCO;

$R^2$ is selected from the group consisting of cycloalkyl, heterocycloalkyl, aryl and heteroaryl; wherein each $R^2$ is optionally substituted by one or more $R^7$;

$R^3$ is selected from the group consisting of hydrogen, $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —SO$_2$CH$_3$, —$C_{1-4}$alkyl, —O—$C_{1-4}$alkyl, —CF$_3$, —CH$_2$CF$_3$ and —O—CF$_3$;

$R^4$ and $R^5$ are independently selected from the group consisting of hydrogen, $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —SO$_2$CH$_3$, —$C_{1-4}$alkyl, —O—$C_{1-4}$alkyl, —CF$_3$, —CH$_2$CF$_3$ and —O—CF$_3$; or $R^4$ and $R^5$ when attached to the same nitrogen atom are combined to form a 4- to 7-membered ring having from 0 to 1 additional heteroatoms as ring members;

$R^6$ is selected from the group consisting of $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —$C_{1-4}$alkyl, —O—$C_{1-4}$alkyl, —CF$_3$, —CH$_2$CF$_3$, and —O—CF$_3$;

$R^7$ is selected from the group consisting of halogen, —OH, $C_{1-6}$alkyl, O—$C_{1-6}$alkyl, $C_{3-7}$cycloalkyl, —C(O)O$R^3$, —C(O)N$R^4R^5$, —N$R^4$C(O)$R^6$, —S(O)$_2$N$R^4R^5$, —N$R^4$S(O)$_2R^6$ and —S(O)$_2R^6$; wherein each $C_{1-6}$alkyl is optionally substituted by one or more substituents selected from the group consisting of halogen and —OH;

$R^8$ is hydrogen or $C_{1-6}$alkyl;

$R^9$ is selected from the group consisting of $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —$C_{1-4}$alkyl, —O—$C_{1-4}$alkyl, —CF$_3$, —CH$_2$CF$_3$, and —O—CF$_3$; or $R^8$ and $R^9$ are combined to form a 5- to 7-membered ring having from 0 to 1 additional heteroatoms as ring members; and n is 0, 1, 2, 3, 4, 5 or 6.

In one embodiment of compounds of the present invention, A is selected from aryl and heteroaryl. In another embodiment of compounds of the present invention, A is selected from the group consisting of phenyl, naphthyl, pyridinyl, quinolinyl, benzothiazolyl and indolyl. In a further embodiment of compounds of the present invention, A is selected from the group consisting of

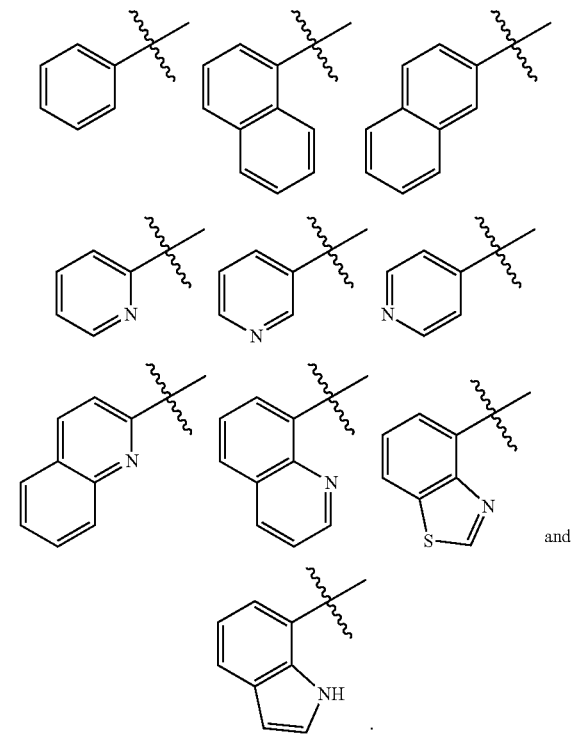

and

In a still further embodiment of compounds of the present invention, A is selected from the group consisting of

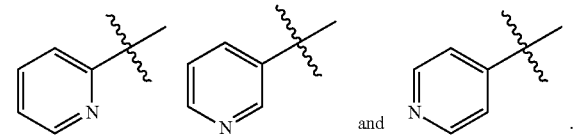 [SMILES: *c1ccccn1 ; *c1cccnc1 ; *c1ccncc1]

and

In a further embodiment, A is selected from the group consisting of

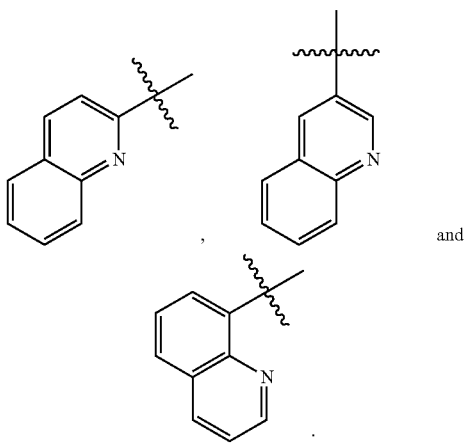

In a still further embodiment, A is

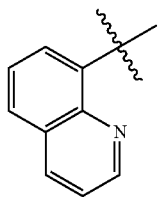

In another embodiment, A is phenyl. In a further embodiment, A is heteroaryl.

In one embodiment of compounds of the present invention, $R^1$ is independently selected from the group consisting of X—$R^2$, halogen, deuterium, $C_{1-6}$alkyl, O—$C_{1-6}$alkyl, aryl, heteroaryl, cycloalkyl, heterocycloalkyl, —CN, —C(O)O$R^3$, —C(O)N$R^4R^5$, —S(O)$_2$N$R^4R^5$, —S(O)$_2R^6$, —N$R^8$C(O)$R^9$, and —N$R^8$S(O)$_2R^9$; wherein each $C_{1-6}$alkyl, aryl, heteroaryl, cycloalkyl and heterocycloalkyl is optionally substituted by one or more substituents selected from the group consisting of halogen, —OH, —SO$_2$CH$_3$, —$C_{1-4}$alkyl, —O—$C_{1-4}$alkyl, —CF$_3$, —CH$_2$CF$_3$ and —O—CF$_3$. In another embodiment of compounds of the present invention, each $R^1$ is independently selected from the group consisting of —X—$R^2$, $C_{1-6}$alkyl, $C_{1-6}$haloalkyl, —C(O)O$R^3$, —C(O)N$R^4R^5$, —S(O)$_2$N$R^4R^5$, —S(O)$_2R^6$. In a further embodiment of compounds of the present invention, each $R^1$ is independently selected from the group consisting of halogen, $C_{1-6}$alkyl, $C_{1-6}$haloalkyl, and —S(O)$_2R^6$. In one embodiment of compounds of the present invention, at least one of $R^1$ is X—$R^2$. In another embodiment of compounds of the present invention, one of $R^1$ is X—$R^2$.

In one embodiment of compounds of present invention, X is selected from the group consisting of O, CH$_2$, OCH$_2$, CH$_2$O, CH$_2$S(O)$_2$, CONH and NHCO. In another embodiment of compounds of the present invention, X is selected from the group consisting of O, CH$_2$, OCH$_2$, CONH and NHCO. In another embodiment of compounds of the present invention, X is selected from the group consisting of O, OCH$_2$ and CONH. In a further embodiment of compounds of the present invention, X is selected from the group consisting of O, CH$_2$ and OCH$_2$. In another embodiment of compounds of the present invention, X is selected from the group consisting of CONH and NHCO. In a further embodiment of compounds of the present invention, X is O. In another embodiment of compounds of the present invention, X is OCH$_2$. In a further embodiment of compounds of the present invention, X is CONH.

In one embodiment of compounds of the present invention, $R^2$ is selected from the group consisting of cycloalkyl, heterocycloalkyl, aryl and heteroaryl where each $R^2$ is optionally substituted by one or more $R^7$. In another embodiment of compounds of the present invention, $R^2$ is selected from the group consisting of aryl and cycloalkyl where each $R^2$ is optionally substituted by one or more $R^7$. In a further embodiment of compounds of the present invention, $R^2$ is cycloalkyl where each $R^2$ is optionally substituted by one or more $R^7$. In another embodiment of compounds of the present invention, $R^2$ is aryl optionally substituted by one or more $R^7$. In another embodiment of compounds of the present invention, $R^2$ is phenyl substituted by one $R^7$. In another embodiment of compounds of the present invention, $R^2$ is adamantyl or phenyl where each $R^2$ is optionally substituted by one or more $R^7$. In another embodiment, $R^2$ is adamantyl or phenyl optionally substituted by —S(O)$_2$N$R^4R^5$. In a further embodiment $R^2$ is adamantyl. In another embodiment, $R^2$ is phenyl optionally substituted by —S(O)$_2$N$R^4R^5$.

In one embodiment of compounds of the present invention, $R^2$ is substituted by one $R^7$. In another embodiment of compounds of the present invention, $R^2$ is substituted by two $R^7$. In a further embodiment of compounds of the present invention, $R^2$ is substituted by three $R^7$. In another embodiment of compounds of the present invention, $R^2$ is substituted by four or five $R^7$.

In one embodiment of compounds of the present invention, $R^3$ is selected from the group consisting of hydrogen, $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —SO$_2$CH$_3$, —$C_{1-4}$alkyl, —O—$C_{1-4}$alkyl, —CF$_3$, —CH$_2$CF$_3$ and —O—CF$_3$. In another embodiment of compounds of the present invention, $R^3$ is hydrogen. In a further embodiment of compounds of the present invention, $R^3$ is $C_{1-6}$alkyl or $C_{3-7}$cycloalkyl. In a still further embodiment of compounds of the present invention, $R^3$ is hydrogen or $C_{1-6}$alkyl. In another embodiment of compounds of the present invention, $R^3$ is $C_{1-6}$alkyl. In a further embodiment of compounds of the present invention, $R^3$ is methyl or ethyl. In another embodiment of compounds of the present invention, $R^3$ is selected from the group consisting of hydrogen, methyl and ethyl.

In one embodiment of compounds of the present invention, $R^4$ and $R^5$ are independently selected from the group consisting of hydrogen, $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —SO$_2$CH$_3$, —$C_{1-4}$alkyl, —O—$C_{1-4}$alkyl, —CF$_3$, —CH$_2$CF$_3$ and —O—CF$_3$. In another embodiment of compounds of the present invention, $R^4$ and $R^5$ are independently selected from the group consisting of hydrogen and $C_{1-6}$alkyl. In another embodiment of compounds of the present invention, $R^4$ and $R^5$ are hydrogen. In a further embodiment of the present invention, $R^4$ and $R^5$ are $C_{1-6}$alkyl. In another embodiment of compounds of the present invention, $R^4$ and $R^5$ are both methyl. In a further embodiment of compounds of the present invention, $R^4$ and $R^5$ are both isopropyl. In one embodiment of compounds of the present invention, $R^4$ is hydrogen and $R^5$ is isopropyl. In a further embodiment of compounds of the present invention, $R^4$ and $R^5$ are independently selected from the group consisting of hydrogen and $C_{3-7}$cycloalkyl. In one embodiment of the present invention, $R^4$ is hydrogen and $R^5$ is $C_{1-6}$alkyl. In one embodiment of compounds of the present invention, $R^4$ is hydrogen and $R^5$ is methyl. In a further embodiment of compounds of the present invention, $R^4$ is hydrogen and $R^5$ is $C_{3-7}$cycloalkyl.

In one embodiment of compounds of the present invention, $R^4$ and $R^5$ when attached to the same nitrogen atom are combined to form a 4- to 7-membered ring having from 0 to 1 additional heteroatoms as ring members. In a further embodiment, $R^4$ and $R^5$ when attached to the same nitrogen atom are combined to form a 4- to 7-membered ring having 1 additional heteroatom as ring members. In another embodiment, $R^4$ and $R^5$ when attached to the same nitrogen atom are combined to form a 4- to 7-membered ring having 0 additional heteroatoms as ring members.

In one embodiment of compounds of the present invention, $R^6$ is selected from the group consisting of $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —$C_{1-4}$alkyl, —O—$C_{1-4}$alkyl, —$CF_3$, —$CH_2CF_3$, and —O—$CF_3$. In another embodiment, $R^6$ is selected from the group consisting of $C_{1-6}$alkyl and $C_{3-7}$cycloalkyl. In another embodiment, $R^6$ is $C_{1-6}$alkyl. In a further embodiment, $R^6$ is $C_{3-7}$cycloalkyl.

In one embodiment of compounds of the present invention, $R^7$ is selected from the group consisting of halogen, —OH, $C_{1-6}$alkyl, O—$C_{1-6}$alkyl, $C_{3-7}$cycloalkyl, —C(O)OR^3, —C(O)NR^4R^5, —NR^4C(O)R^6, —S(O)_2NR^4R^5, —NR^4S(O)_2R^6$ and —$S(O)_2R^6$; wherein each $C_{1-6}$alkyl is optionally substituted by one or more substituents selected from the group consisting of halogen and —OH. In another embodiment of compounds of the present invention, $R^7$ is selected from the group consisting of halogen, $C_{1-6}$alkyl, —$C(O)NR^4R^5$, —$S(O)_2NR^4R^5$ and —$S(O)_2R^6$. In a further embodiment of compounds of the present invention, $R^7$ is selected from the group consisting of —$C(O)NR^4R^5$, —$S(O)_2NR^4R^5$ and —$S(O)_2R^6$. In another embodiment of compounds of the present invention, $R^7$ is —$S(O)_2NR^4R^5$. In a further embodiment of the present invention, $R^7$ is —$S(O)_2N(CH_3)_2$.

In one embodiment of compounds of the present invention, $R^8$ hydrogen or $C_{1-6}$alkyl. In another embodiment of compounds of the present invention, $R^8$ is hydrogen. In a further embodiment of compounds of the present invention, $R^8$ is selected from the group consisting of hydrogen, methyl and ethyl. In another embodiment of compounds of the present invention, $R^8$ is hydrogen or methyl.

In one embodiment of compounds of the present invention, $R^9$ is selected from the group consisting of $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —$C_{1-4}$alkyl, —O—$C_{1-4}$alkyl, —$CF_3$, —$CH_2CF_3$, and —O—$CF_3$. In another embodiment, $R^9$ is selected from the group consisting of $C_{1-6}$alkyl and $C_{3-7}$cycloalkyl. In another embodiment, $R^9$ is $C_{1-6}$alkyl. In a further embodiment, $R^9$ is $C_{3-7}$cycloalkyl.

In one embodiment of compounds of the present invention, $R^8$ and $R^9$ are combined to form a 5- to 7-membered ring having from 0 to 1 additional heteroatoms as ring members. In a further embodiment, $R^8$ and $R^9$ are combined to form a 5- to 7-membered ring having 1 additional heteroatom as ring members. In another embodiment, $R^8$ and $R^9$ are combined to form a 5- to 7-membered ring having 0 additional heteroatoms as ring members.

In one of embodiment of compounds of the present invention, n is 0, 1, 2, 3, 4 or 5. In another embodiment of compounds of the present invention, n is 0. In a further embodiment of compounds of the present invention, n is 0, 1 or 2. In another embodiment of compounds of the present invention, n is 1, 2 or 3. In another embodiment of compounds of the present invention n is 1 or 2. In a further embodiment of compounds of the present invention, n is 1. In another embodiment of compounds of the present invention, n is 2. In a further embodiment of compounds of the present invention, n is 3. In another embodiment of compounds of the present invention, n is 4. In a further embodiment of compounds of the present invention, n is 5. In another embodiment of compounds of the present invention, n is 6.

In one embodiment, the present invention also relates to compounds of Formula Ia:

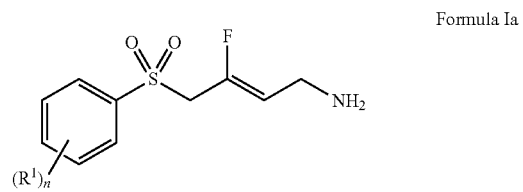

Formula Ia or a stereoisomer, pharmaceutically acceptable salt, polymorphic form, solvate, hydrate or tautomeric form thereof; wherein:

each $R^1$ is independently selected from the group consisting of X—$R^2$, halogen, $C_{1-6}$alkyl, O—$C_{1-6}$alkyl, aryl, heteroaryl, cycloalkyl, heterocycloalkyl, —CN, —$C(O)OR^3$, —$C(O)NR^4R^5$, —$S(O)_2NR^4R^5$, —$S(O)_2R^6$, —$NR^8C(O)R^9$, and —$NR^8S(O)_2R^9$; wherein each $C_{1-6}$alkyl, aryl, heteroaryl and cycloalkyl, heterocycloalkyl is optionally substituted by one or more substituents selected from the group consisting of halogen, —OH, —$SO_2CH_3$, —$C_{1-4}$alkyl, —O—$C_{1-4}$alkyl, —$CF_3$, —$CH_2CF_3$ and —O—$CF_3$;

X is selected from the group consisting of O, $CH_2$, $OCH_2$, $CH_2O$, $CH_2S(O)_2$, CONH and NHCO;

$R^2$ is selected from the group consisting of cycloalkyl, heterocycloalkyl, aryl and heteroaryl; wherein each $R^2$ is optionally substituted by one or more $R^7$;

$R^3$ is selected from the group consisting of hydrogen, $C_{1-6}$alkyl and $C_{3-7}$cycloalkyl;

$R^4$ and $R^5$ are independently selected from the group consisting of hydrogen, $C_{1-6}$alkyl and $C_{3-7}$cycloalkyl; or $R^4$ and $R^5$ when attached to the same nitrogen atom are combined to form a 4- to 7-membered ring having from 0 to 1 additional heteroatoms as ring members;

$R^6$ is selected from the group consisting of $C_{1-6}$alkyl and $C_{3-7}$cycloalkyl;

$R^7$ is selected from the group consisting of halogen, —OH, $C_{1-6}$alkyl, O—$C_{1-6}$alkyl, $C_{3-7}$cycloalkyl, —$C(O)OR^3$, —$C(O)NR^4R^5$, —$NR^4C(O)R^6$, —$S(O)_2NR^4R^5$, —$NR^4S(O)_2R^6$ and —$S(O)_2R^6$; wherein each $C_{1-6}$alkyl is optionally substituted by one or more substituents selected from the group consisting of halogen and —OH;

$R^8$ is hydrogen or $C_{1-6}$alkyl;

$R^9$ is selected from the group consisting of $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —$C_{1-4}$alkyl, —O—$C_{1-4}$alkyl, —$CF_3$, —$CH_2CF_3$, and —O—$CF_3$; or $R^8$ and $R^9$ are combined to form a 5- to 7-membered ring having from 0 to 1 additional heteroatoms as ring members; and n is 0, 1, 2 or 3.

In one embodiment, the present invention also relates to compounds of Formula Ib:

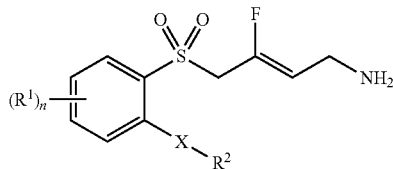

Formula Ib or a pharmaceutically acceptable salt or solvate thereof; wherein:

each $R^1$ is independently selected from the group consisting of halogen, $C_{1-6}$alkyl, O—$C_{1-6}$alkyl, aryl, heteroaryl, cycloalkyl, heterocycloalkyl, —CN, —C(O)OR$^3$, —C(O)NR$^4$R$^5$, —S(O)$_2$NR$^4$R$^5$, —S(O)$_2$R$^6$, —NR$^8$C(O)R$^9$, and —NR$^8$S(O)$_2$R$^9$; wherein each $C_{1-6}$alkyl, aryl, heteroaryl, cycloalkyl and heterocycloalkyl is optionally substituted by one or more substituents selected from the group consisting of halogen, —OH, —SO$_2$CH$_3$, —$C_{1-4}$alkyl, —O—$C_{1-4}$alkyl, —CF$_3$, —CH$_2$CF$_3$ and —O—CF$_3$;

X is selected from the group consisting of O, CH$_2$, OCH$_2$, CH$_2$O, CH$_2$S(O)$_2$, CONH and NHCO;

$R^2$ is selected from the group consisting of cycloalkyl, heterocycloalkyl, aryl and heteroaryl; wherein each $R^2$ is optionally substituted by one or more $R^7$;

$R^3$ is selected from the group consisting of hydrogen, $C_{1-6}$alkyl and $C_{3-7}$cycloalkyl;

$R^4$ and $R^5$ are independently selected from the group consisting of hydrogen, $C_{1-6}$alkyl and $C_{3-7}$cycloalkyl; or $R^4$ and $R^5$ when attached to the same nitrogen atom are combined to form a 4- to 7-membered ring having from 0 to 1 additional heteroatoms as ring members;

$R^6$ is selected from the group consisting of $C_{1-6}$alkyl and $C_{3-7}$cycloalkyl $R^7$ is selected from the group consisting of halogen, —OH, $C_{1-6}$alkyl, O—$C_{1-6}$alkyl, $C_{3-7}$cycloalkyl, —C(O)OR$^3$, —C(O)NR$^4$R$^5$, —NR$^4$C(O)R$^6$, —S(O)$_2$NR$^4$R$^5$, —NR$^4$S(O)$_2$R$^6$ and —S(O)$_2$R$^6$; wherein each $C_{1-6}$alkyl is optionally substituted by one or more substituents selected from the group consisting of halogen and —OH;

$R^8$ is hydrogen or $C_{1-6}$alkyl;

$R^9$ is selected from the group consisting of $C_{1-6}$alkyl and $C_{3-7}$cycloalkyl wherein each $C_{1-6}$alkyl and $C_{3-7}$cycloalkyl is optionally substituted by one or more substituents selected from the group consisting of halogen, —OH, —$C_{1-4}$alkyl, —O—$C_{1-4}$alkyl, —CF$_3$, —CH$_2$CF$_3$, and —O—CF$_3$; or $R^8$ and $R^9$ are combined to form a 5- to 7-membered ring having from 0 to 1 additional heteroatoms as ring members; and n is 0, 1 or 2.

In one embodiment of compounds of Formula Ib of the invention, X is selected from the group consisting of 0, OCH$_2$ and CONH; $R^2$ is selected from the group consisting of adamantyl and phenyl; wherein each $R^2$ is optionally substituted by one or more $R^7$; $R^4$ and $R^5$ are independently selected from the group consisting of hydrogen and $C_{1-6}$alkyl; $R^7$ is —S(O)$_2$NR$^4$R$^5$; and n is 0.

In another embodiment, the present invention also relates to compounds of Formula Ic:

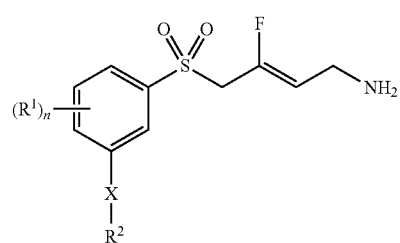

Formula Ic or a pharmaceutically acceptable salt or solvate thereof; wherein:

each $R^1$ is independently selected from the group consisting of halogen, $C_{1-6}$alkyl, —O—$C_{1-6}$alkyl, aryl, heteroaryl, cycloalkyl, heterocycloalkyl, —CN, —C(O)OR$^3$, —C(O)NR$^4$R$^5$, —S(O)$_2$NR$^4$R$^5$, —S(O)$_2$R$^6$, —NR$^8$C(O)R$^9$, and —NR$^8$S(O)$_2$R$^9$; wherein each $C_{1-6}$alkyl, aryl, heteroaryl, cycloalkyl and heterocycloalkyl is optionally substituted by one or more substituents selected from the group consisting of halogen, —OH, —SO$_2$CH$_3$, —$C_{1-4}$alkyl, —O—$C_{1-4}$alkyl, —CF$_3$, —CH$_2$CF$_3$ and —O—CF$_3$;

X is selected from the group consisting of O, CH$_2$, OCH$_2$, CH$_2$O, CH$_2$S(O)$_2$, CONH and NHCO;

$R^2$ is selected from the group consisting of cycloalkyl, heterocycloalkyl, aryl and heteroaryl; wherein each $R^2$ is optionally substituted by one or more $R^7$;

$R^3$ is selected from the group consisting of hydrogen, $C_{1-6}$alkyl and $C_{3-7}$cycloalkyl;

$R^4$ and $R^5$ are independently selected from the group consisting of hydrogen, $C_{1-6}$alkyl and $C_{3-7}$cycloalkyl; or $R^4$ and $R^5$ when attached to the same nitrogen atom are combined to form a 4- to 7-membered ring having from 0 to 1 additional heteroatoms as ring members;

$R^6$ is selected from the group consisting of $C_{1-6}$alkyl and $C_{3-7}$cycloalkyl;

$R^7$ is selected from the group consisting of halogen, —OH, $C_{1-6}$alkyl, O—$C_{1-6}$alkyl, $C_{3-7}$cycloalkyl, —C(O)OR$^3$, —C(O)NR$^4$R$^5$, —NR$^4$C(O)R$^6$, —S(O)$_2$NR$^4$R$^5$, —NR$^4$S(O)$_2$R$^6$ and —S(O)$_2$R$^6$; wherein each $C_{1-6}$alkyl is optionally substituted by one or more substituents selected from the group consisting of halogen and —OH;

$R^8$ is hydrogen or $C_{1-6}$alkyl;

$R^9$ is selected from the group consisting of $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —$C_{1-4}$alkyl, —O—$C_{1-4}$alkyl, —CF$_3$, —CH$_2$CF$_3$, and —O—CF$_3$; or $R^8$ and $R^9$ are combined to form a 5- to 7-membered ring having from 0 to 1 additional heteroatoms as ring members; and n is 0, 1 or 2.

In one embodiment of compounds of Formula Ic of the invention, X is selected from the group consisting of OCH$_2$ and CONH; $R^2$ is selected from the group consisting of adamantyl and phenyl; wherein each $R^2$ is optionally substituted by one or more $R^7$; $R^4$ and $R^5$ are independently selected from the group consisting of hydrogen and $C_{1-6}$alkyl; $R^7$ is —S(O)$_2$NR$^4$R$^5$; and n is 0.

In another embodiment, the present invention also relates to compounds of Formula Id:

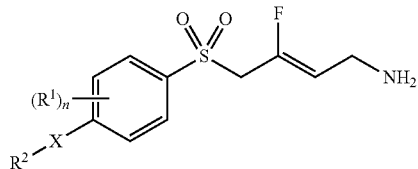

Formula Id or a pharmaceutically acceptable salt or solvate thereof; wherein:

each $R^1$ is independently selected from the group consisting of halogen, $C_{1-6}$alkyl, O—$C_{1-6}$alkyl, aryl, heteroaryl, cycloalkyl, heterocycloalkyl, —CN, —C(O)O$R^3$, —C(O)N$R^4R^5$, —S(O)$_2$N$R^4R^5$, —S(O)$_2R^6$, —N$R^8$C(O)$R^9$, and —N$R^8$S(O)$_2R^9$; wherein each $C_{1-6}$alkyl, aryl, heteroaryl, cycloalkyl and heterocycloalkyl is optionally substituted by one or more substituents selected from the group consisting of halogen, —OH, —SO$_2$CH$_3$, —$C_{1-4}$alkyl, —O—$C_{1-4}$alkyl, —CF$_3$, —CH$_2$CF$_3$ and —O—CF$_3$;

X is selected from the group consisting of O, CH$_2$, OCH$_2$, CONH and NHCO;

$R^2$ is selected from the group consisting of cycloalkyl, heterocycloalkyl, aryl and heteroaryl; wherein each $R^2$ is optionally substituted by one or more $R^7$;

$R^3$ is selected from the group consisting of hydrogen, $C_{1-6}$alkyl and $C_{3-7}$cycloalkyl;

$R^4$ and $R^5$ are independently selected from the group consisting of hydrogen, $C_{1-6}$alkyl and $C_{3-7}$cycloalkyl; or $R^4$ and $R^5$ when attached to the same nitrogen atom are combined to form a 4- to 7-membered ring having from 0 to 1 additional heteroatoms as ring members;

$R^6$ is selected from the group consisting of $C_{1-6}$alkyl and $C_{3-7}$cycloalkyl;

$R^7$ is selected from the group consisting of halogen, —OH, $C_{1-6}$alkyl, O—$C_{1-6}$alkyl, $C_{3-7}$cycloalkyl, —C(O)O$R^3$, —C(O)N$R^4R^5$, —N$R^4$C(O)$R^6$, —S(O)$_2$N$R^4R^5$, —N$R^4$S(O)$_2R^6$ and —S(O)$_2R^6$; wherein each $C_{1-6}$alkyl is optionally substituted by one or more substituents selected from the group consisting of halogen and —OH;

$R^8$ is hydrogen or $C_{1-6}$alkyl;

$R^9$ is selected from the group consisting of $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —$C_{1-4}$alkyl, —O—$C_{1-4}$alkyl, —CF$_3$, —CH$_2$CF$_3$, and —O—CF$_3$; or $R^8$ and $R^9$ are combined to form a 5- to 7-membered ring having from 0 to 1 additional heteroatoms as ring members; and n is 0, 1 or 2.

In one embodiment of compounds of Formula Id of the invention, X is selected from the group consisting of OCH$_2$ and CONH; $R^2$ is selected from the group consisting of adamantyl and phenyl; wherein each $R^2$ is optionally substituted by one or more $R^7$; $R^4$ and $R^5$ are independently selected from the group consisting of hydrogen and $C_{1-6}$alkyl; $R^7$ is —S(O)$_2$N$R^4R^5$; and n is 0.

In another embodiment, the present invention also relates to compounds of Formula Ie:

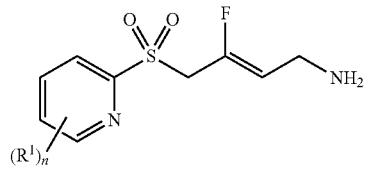

Formula Ie or a pharmaceutically acceptable salt or solvate thereof; wherein:

each $R^1$ is independently selected from the group consisting of halogen, $C_{1-6}$alkyl, O—$C_{1-6}$alkyl, aryl, heteroaryl, cycloalkyl, heterocycloalkyl, —CN, —C(O)O$R^3$, —C(O)N$R^4R^5$, —S(O)$_2$N$R^4R^5$, —S(O)$_2R^6$, —N$R^8$C(O)$R^9$, and —N$R^8$S(O)$_2R^9$; wherein each $C_{1-6}$alkyl, aryl, heteroaryl, cycloalkyl and heterocycloalkyl is optionally substituted by one or more substituents selected from the group consisting of halogen, —OH, —SO$_2$CH$_3$, —$C_{1-4}$alkyl, —O—$C_{1-4}$alkyl, —CF$_3$, —CH$_2$CF$_3$ and —O—CF$_3$;

$R^3$ is selected from the group consisting of hydrogen, $C_{1-6}$alkyl and $C_{3-7}$cycloalkyl;

$R^4$ and $R^5$ are independently selected from the group consisting of hydrogen, $C_{1-6}$alkyl and $C_{3-7}$cycloalkyl; or $R^4$ and $R^5$ when attached to the same nitrogen atom are combined to form a 4- to 7-membered ring having from 0 to 1 additional heteroatoms as ring members;

$R^6$ is selected from the group consisting of $C_{1-6}$alkyl and $C_{3-7}$cycloalkyl;

$R^8$ is hydrogen or $C_{1-6}$alkyl;

$R^9$ is selected from the group consisting of $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —$C_{1-4}$alkyl, —O—$C_{1-4}$alkyl, —CF$_3$, —CH$_2$CF$_3$, and —O—CF$_3$; or $R^8$ and $R^9$ are combined to form a 5- to 7-membered ring having from 0 to 1 additional heteroatoms as ring members; and n is 0, 1 or 2.

In another embodiment, the present invention also relates to compounds of Formula If:

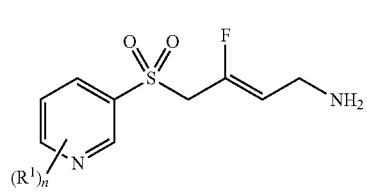

Formula If or a pharmaceutically acceptable salt or solvate thereof; wherein:

each $R^1$ is independently selected from the group consisting of halogen, $C_{1-6}$alkyl, O—$C_{1-6}$alkyl, aryl, heteroaryl, cycloalkyl, heterocycloalkyl, —CN, —C(O)O$R^3$, —C(O)N$R^4R^5$, —S(O)$_2$N$R^4R^5$, —S(O)$_2R^6$, —N$R^8$C(O)$R^9$, and —N$R^8$S(O)$_2R^9$; wherein each $C_{1-6}$alkyl, aryl, heteroaryl, cycloalkyl and heterocycloalkyl is optionally substituted by one or more substituents selected from the group consisting of halogen, —OH, —SO$_2$CH$_3$, —$C_{1-4}$alkyl, —O—$C_{1-4}$alkyl, —CF$_3$, —CH$_2$CF$_3$ and —O—CF$_3$;

$R^3$ is selected from the group consisting of hydrogen, $C_{1-6}$alkyl and $C_{3-7}$cycloalkyl;

$R^4$ and $R^5$ are independently selected from the group consisting of hydrogen, $C_{1-6}$alkyl and $C_{3-7}$cycloalkyl; or $R^4$ and $R^5$ when attached to the same nitrogen atom are combined to form a 4- to 7-membered ring having from 0 to 1 additional heteroatoms as ring members;

$R^6$ is selected from the group consisting of $C_{1-6}$alkyl and $C_{3-7}$cycloalkyl;

$R^8$ is hydrogen or $C_{1-6}$alkyl;

$R^9$ is selected from the group consisting of $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —$C_{1-4}$alkyl, —O—$C_{1-4}$alkyl, —$CF_3$, —$CH_2CF_3$, and —O—$CF_3$; or $R^8$ and $R^9$ are combined to form a 5- to 7-membered ring having from 0 to 1 additional heteroatoms as ring members; and n is 0, 1 or 2.

In another embodiment, the present invention also relates to compounds of Formula Ig:

Formula Ig or a pharmaceutically acceptable salt or solvate thereof; wherein:

each $R^1$ is independently selected from the group consisting of halogen, $C_{1-6}$alkyl, O—$C_{1-6}$alkyl, aryl, heteroaryl, cycloalkyl, heterocycloalkyl, —CN, —C(O)O$R^3$, —C(O)N$R^4R^5$, —S(O)$_2$N$R^4R^5$, —S(O)$_2R^6$, —$NR^8$C(O)$R^9$, and —$NR^8$S(O)$_2R^9$; wherein each $C_{1-6}$alkyl, aryl, heteroaryl, cycloalkyl and heterocycloalkyl is optionally substituted by one or more substituents selected from the group consisting of halogen, —OH, —$SO_2CH_3$, —$C_{1-4}$alkyl, —O—$C_{1-4}$alkyl, —$CF_3$, —$CH_2CF_3$ and —O—$CF_3$;

$R^3$ is selected from the group consisting of hydrogen, $C_{1-6}$alkyl and $C_{3-7}$cycloalkyl;

$R^4$ and $R^5$ are independently selected from the group consisting of hydrogen, $C_{1-6}$alkyl and $C_{3-7}$cycloalkyl; or $R^4$ and $R^5$ when attached to the same nitrogen atom are combined to form a 4- to 7-membered ring having from 0 to 1 additional heteroatoms as ring members;

$R^6$ is selected from the group consisting of $C_{1-6}$alkyl and $C_{3-7}$cycloalkyl;

$R^8$ is hydrogen or $C_{1-6}$alkyl;

$R^9$ is selected from the group consisting of $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —$C_{1-4}$alkyl, —O—$C_{1-4}$alkyl, —$CF_3$, —$CH_2CF_3$, and —O—$CF_3$; or $R^8$ and $R^9$ are combined to form a 5- to 7-membered ring having from 0 to 1 additional heteroatoms as ring members; and n is 0, 1 or 2:

In another embodiment of compounds of Formula Ie, If and Ig of the invention, each $R^1$ is a $C_{1-6}$alkyl and n is 0 or 1.

In another embodiment of compounds of Formula I of the invention, each $R^1$ is independently selected from the group consisting of halogen, $C_{1-6}$alkyl, $C_{1-6}$haloalkyl, $C_{1-6}$alkyloxy, $C_{1-6}$haloalkoxy, —CN, —C(O)O$R^3$, —C(O)N$R^4R^5$, —$NR^4$C(O)$R^6$, —S(O)$_2$N$R^4R^5$, —$NR^4$S(O)$_2R^6$ and —S(O)$_2R^6$; $R^3$ is selected from the group consisting of hydrogen, optionally substituted $C_{1-6}$alkyl and optionally substituted $C_{3-7}$cycloalkyl; $R^4$ and $R^5$ are independently selected from the group consisting of hydrogen, optionally substituted $C_{1-6}$alkyl and optionally substituted $C_{3-7}$cycloalkyl; or $R^4$ and $R^5$ when attached to the same nitrogen atom are combined to form a 4- to 7-membered ring having from 0 to 1 additional heteroatoms as ring members; $R^6$ is selected from the group consisting of optionally substituted $C_{1-6}$alkyl, optionally substituted $C_{3-7}$cycloalkyl and optionally substituted $C_{1-6}$haloalkyl; and n is 0, 1, 2 or 3.

In another embodiment of compounds of Formula I of the invention, each $R^1$ is independently selected from the group consisting of halogen, $C_{1-6}$alkyl, $C_{1-6}$haloalkyl, and —S(O)$_2R^6$; $R^6$ is $C_{1-6}$alkyl; and n is 0, 1 or 2.

In another embodiment of compounds of Formula I of the invention, each $R^1$ is independently selected from the group consisting of chlorine, fluorine, methyl, isopropyl, $OCH_3$, phenyl and $SO_2CH_3$; and n is 1 or 2.

In a further embodiment of compounds of Formula I of the invention, A is and n is O.

In the context of the present disclosure, any one or more aspect(s) or embodiment(s) may be combined with any other aspect(s) or embodiment(s).

Exemplary compounds according to the present invention include the compounds set forth in Table 2:

TABLE 2

| 1 | | (Z)-3-fluoro-4-(phenylsulfonyl)but-2-en-1-amine |
|---|---|---|

TABLE 2-continued

| | | |
|---|---|---|
| 2 | | (Z)-4-((3,5-bis(trifluoromethyl)phenyl)sulfonyl)-3-fluorobut-2-en-1-amine |
| 3 | | (Z)-3-fluoro-4-((4-(methylsulfonyl)phenyl)sulfonyl)but-2-en-1-amine |
| 4 | | N-((1R,3R,5S)-adamantan-1-yl)-4-(((Z)-4-amino-2-fluorobut-2-en-1-yl)sulfonyl)benzamide |
| 5 | | (Z)-4-((2-((4-amino-2-fluorobut-2-en-1-yl)sulfonyl)phenoxy)methyl)-N,N-dimethylbenzenesulfonamide |
| 6 | | (Z)-4-(2-((4-amino-2-fluorobut-2-en-1-yl)sulfonyl)phenoxy)-N,N-dimethylbenzenesulfonamide |
| 7 | | (Z)-4-((2-(benzyloxy)phenyl)sulfonyl)-3-fluorobut-2-en-1-amine |

TABLE 2-continued
| | | |
|---|---|---|
| 8 | 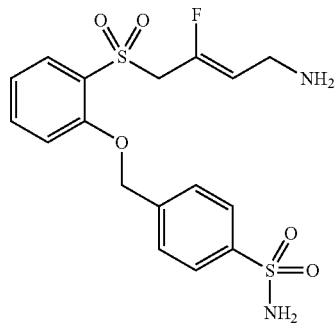 [SMILES: NC/C=C(\F)CS(=O)(=O)c1ccccc1OCc1ccc(S(N)(=O)=O)cc1] | (Z)-4-((2-((4-amino-2-fluorobut-2-en-1-yl)sulfonyl)phenoxy)methyl)benzenesulfonamide |
| 9 | 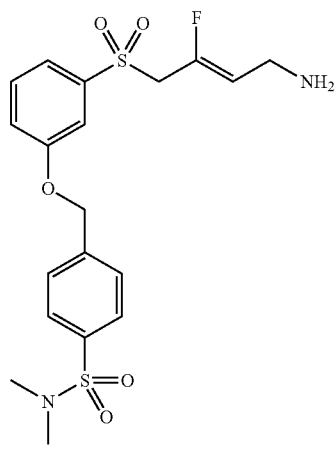 [SMILES: CN(C)S(=O)(=O)c1ccc(COc2cccc(S(=O)(=O)C/C(F)=C/CN)c2)cc1] | (Z)-4-((3-((4-amino-2-fluorobut-2-en-1-yl)sulfonyl)phenoxy)methyl)-N,N-dimethylbenzenesulfonamide |
| 10 | 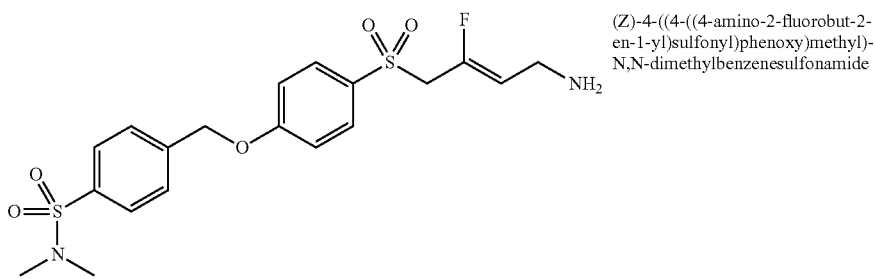 | (Z)-4-((4-((4-amino-2-fluorobut-2-en-1-yl)sulfonyl)phenoxy)methyl)-N,N-dimethylbenzenesulfonamide |
| 11 | 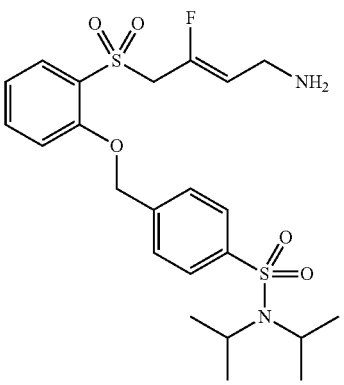 [SMILES: CC(C)N(C(C)C)S(=O)(=O)c1ccc(COc2ccccc2S(=O)(=O)C/C(F)=C/CN)cc1] | (Z)-4-((2-((4-amino-2-fluorobut-2-en-1-yl)sulfonyl)phenoxy)methyl)-N,N-diisopropylbenzenesulfonamide |

TABLE 2-continued
| | | |
|---|---|---|
| 12 | 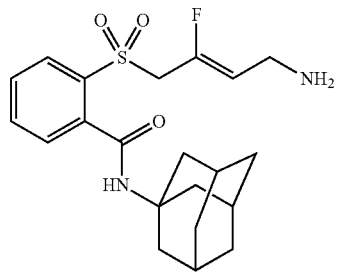 [SMILES: NC/C=C(\F)CS(=O)(=O)c1ccccc1C(=O)NC12CC3CC(CC(C3)C1)C2] | N-((1S,3R,5S)-adamantan-1-yl)-2-(((Z)-4-amino-2-fluorobut-2-en-1-yl)sulfonyl)benzamide |
| 13 | 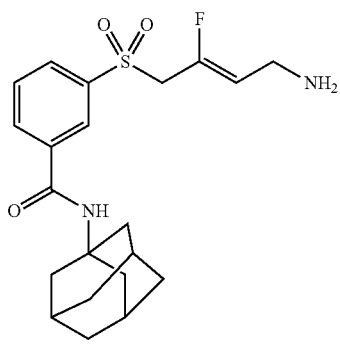 [SMILES: NC/C=C(\F)CS(=O)(=O)c1cccc(C(=O)NC23CC4CC(CC(C4)C2)C3)c1] | N-((1S,3R,5S)-adamantan-1-yl)-3-(((Z)-4-amino-2-fluorobut-2-en-1-yl)sulfonyl)benzamide |
| 14 | 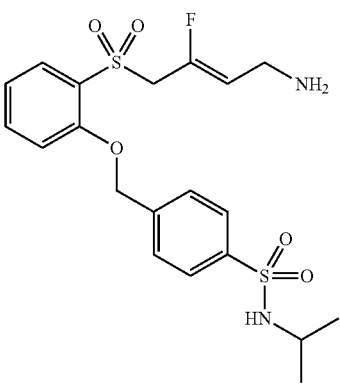 [SMILES: CC(C)NS(=O)(=O)c1ccc(COc2ccccc2S(=O)(=O)C/C(F)=C/CN)cc1] | (Z)-4-((2-((4-amino-2-fluorobut-2-en-1-yl)sulfonyl)phenoxy)methyl)-N-isopropylbenzenesulfonamide |
| 15 | 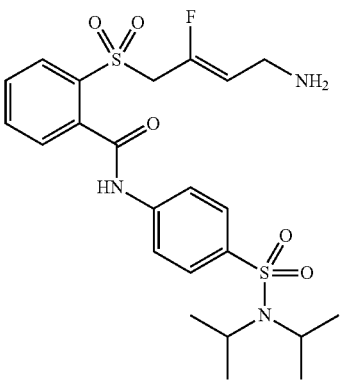 [SMILES: CC(C)N(C(C)C)S(=O)(=O)c1ccc(NC(=O)c2ccccc2S(=O)(=O)C/C(F)=C/CN)cc1] | (Z)-2-((4-amino-2-fluorobut-2-en-1-yl)sulfonyl)-N-(4-(N,N-diisopropylsulfamoyl)phenyl)benzamide |

TABLE 2-continued

| 16 | 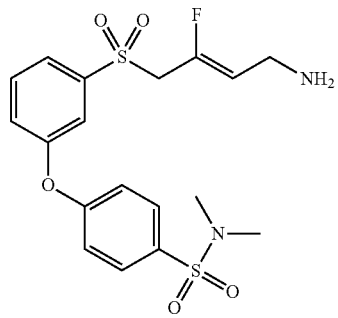 [SMILES: CN(C)S(=O)(=O)c1ccc(Oc2cccc(S(=O)(=O)C/C(F)=C/CN)c2)cc1] | (Z)-4-(3-(4-amino-2-fluorobut-2-enylsulfonyl)phenoxy)-N,N-dimethylbenzenesulfonamide |
| 17 | 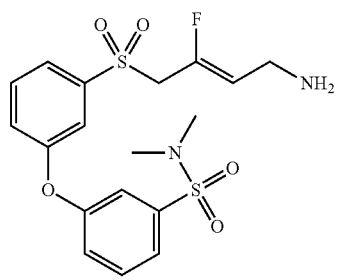 [SMILES: CN(C)S(=O)(=O)c1cccc(Oc2cccc(S(=O)(=O)C/C(F)=C/CN)c2)c1] | (Z)-3-(3-(4-amino-2-fluorobut-2-enylsulfonyl)phenoxy)-N,N-dimethylbenzenesulfonamide |
| 18 | 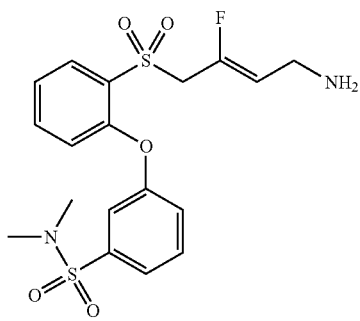 [SMILES: CN(C)S(=O)(=O)c1cccc(Oc2ccccc2S(=O)(=O)C/C(F)=C/CN)c1] | (Z)-3-(2-(4-amino-2-fluorobut-2-enylsulfonyl)phenoxy)-N,N-dimethylbenzenesulfonamide |
| 19 | 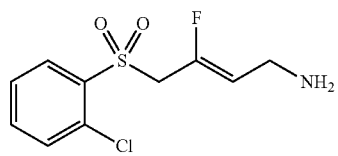 [SMILES: NC/C=C(\F)CS(=O)(=O)c1ccccc1Cl] | (Z)-4-(2-chlorophenylsulfonyl)-3-fluorobut-2-en-1-amine |
| 20 | 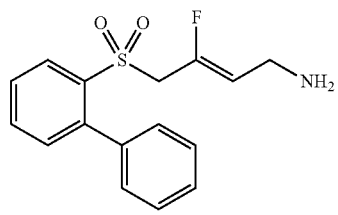 [SMILES: NC/C=C(\F)CS(=O)(=O)c1ccccc1-c1ccccc1] | (Z)-4-(biphenyl-2-ylsulfonyl)-3-fluorobut-2-en-1-amine |
| 21 | 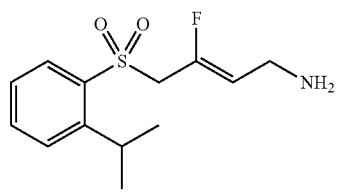 [SMILES: CC(C)c1ccccc1S(=O)(=O)C/C(F)=C/CN] | (Z)-3-fluoro-4-(2-isopropylphenylsulfonyl)but-2-en-1-amine |

TABLE 2-continued

| | | |
|---|---|---|
| 22 | | (Z)-3-fluoro-4-(2-methoxyphenylsulfonyl)but-2-en-1-amine |
| 23 | | (Z)-3-fluoro-4-(naphthalen-1-ylsulfonyl)but-2-en-1-amine |
| 24 | | (Z)-3-fluoro-4-(naphthalen-2-ylsulfonyl)but-2-en-1-amine |
| 25 | | (Z)-4-(2,4-dichlorophenylsulfonyl)-3-fluorobut-2-en-1-amine |
| 26 | | (Z)-4-(3-chlorophenylsulfonyl)-3-fluorobut-2-en-1-amine |
| 27 | | (Z)-4-(4-chlorophenylsulfonyl)-3-fluorobut-2-en-1-amine |
| 28 | | (Z)-4-(3,5-dichlorophenylsulfonyl)-3-fluorobut-2-en-1-amine |
| 29 | | (Z)-3-fluoro-4-(pyridin-4-ylsulfonyl)but-2-en-1-amine |

TABLE 2-continued

| # | Structure | Name |
|---|---|---|
| 30 | pyridin-2-yl-SO₂-CH₂-C(F)=CH-CH₂-NH₂ | (Z)-3-fluoro-4-(pyridin-2-ylsulfonyl)but-2-en-1-amine |
| 31 | pyridin-3-yl-SO₂-CH₂-C(F)=CH-CH₂-NH₂ | (Z)-3-fluoro-4-(pyridin-3-ylsulfonyl)but-2-en-1-amine |
| 32 | quinolin-2-yl-SO₂-CH₂-C(F)=CH-CH₂-NH₂ | (Z)-3-fluoro-4-(quinolin-2-ylsulfonyl)but-2-en-1-amine |
| 33 | quinolin-8-yl-SO₂-CH₂-C(F)=CH-CH₂-NH₂ | (Z)-3-fluoro-4-(quinolin-8-ylsulfonyl)but-2-en-1-amine |
| 34 | 5-isopropylpyridin-2-yl-SO₂-CH₂-C(F)=CH-CH₂-NH₂ | (Z)-3-fluoro-4-(5-isopropylpyridin-2-ylsulfonyl)but-2-en-1-amine |
| 35 | 5-methylpyridin-2-yl-SO₂-CH₂-C(F)=CH-CH₂-NH₂ | (Z)-3-fluoro-4-(5-methylpyridin-2-ylsulfonyl)but-2-en-1-amine |
| 36 | 6-methylpyridin-2-yl-SO₂-CH₂-C(F)=CH-CH₂-NH₂ | (Z)-3-fluoro-4-(6-methylpyridin-2-ylsulfonyl)but-2-en-1-amine |
| 37 | 2-fluorophenyl-SO₂-CH₂-C(F)=CH-CH₂-NH₂ | (Z)-3-fluoro-4-(2-fluorophenylsulfonyl)but-2-en-1-amine |
| 38 | 3-fluorophenyl-SO₂-CH₂-C(F)=CH-CH₂-NH₂ | (Z)-3-fluoro-4-(3-fluorophenylsulfonyl)but-2-en-1-amine |

TABLE 2-continued

| | | |
|---|---|---|
| 39 | | (Z)-3-fluoro-4-(4-fluorophenylsulfonyl)but-2-en-1-amine |
| 40 | | (Z)-3-fluoro-4-(o-tolylsulfonyl)but-2-en-1-amine |
| 41 | | (Z)-3-fluoro-4-(m-tolylsulfonyl)but-2-en-1-amine |
| 42 | | (Z)-3-fluoro-4-tosylbut-2-en-1-amine |
| 43 | | (Z)-3-fluoro-4-(3-methylpyridin-2-ylsulfonyl)but-2-en-1-amine |
| 44 | | (Z)-3-fluoro-4-(2-methylpyridin-4-ylsulfonyl)but-2-en-1-amine |
| 45 | | (Z)-3-fluoro-4-(2-isopropylpyridin-3-ylsulfonyl)but-2-en-1-amine |
| 46 | | (Z)-3-fluoro-4-(6-methylpyridin-3-ylsulfonyl)but-2-en-1-amine |
| 47 | | (Z)-3-fluoro-4-(2-methylpyridin-3-ylsulfonyl)but-2-en-1-amine |
| 48 | | (Z)-3-fluoro-4-(4-methylpyridin-3-ylsulfonyl)but-2-en-1-amine |

TABLE 2-continued

| | | |
|---|---|---|
| 49 | 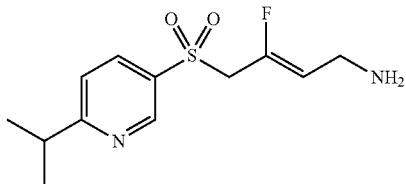 [SMILES: CC(C)c1ccc(S(=O)(=O)C/C(F)=C/CN)cn1] | (Z)-3-fluoro-4-(6-isopropylpyridin-3-ylsulfonyl)but-2-en-1-amine |
| 50 | 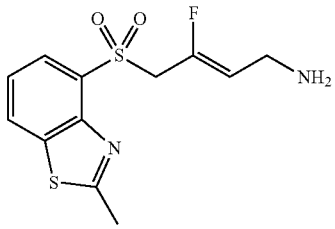 [SMILES: Cc1nc2c(S(=O)(=O)C/C(F)=C/CN)cccc2s1] | (Z)-3-fluoro-4-((2-methylbenzo[d]thiazol-4-yl)sulfonyl)but-2-en-1-amine |
| 51 | 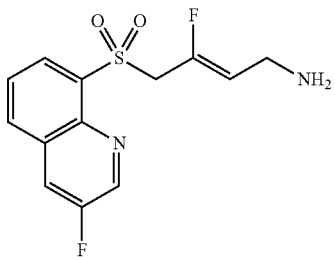 [SMILES: NC/C=C(\F)CS(=O)(=O)c1cccc2cc(F)cnc12] | (Z)-3-fluoro-4-((3-fluoroquinolin-8-yl)sulfonyl)but-2-en-1-amine |
| 52 | 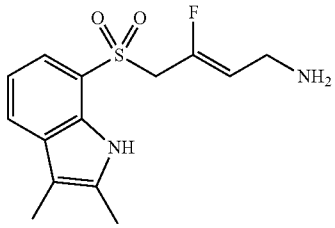 [SMILES: Cc1[nH]c2c(S(=O)(=O)C/C(F)=C/CN)cccc2c1C] | (Z)-4-((2,3-dimethyl-1H-indol-7-yl)sulfonyl)-3-fluorobut-2-en-1-amine |
| 53 | 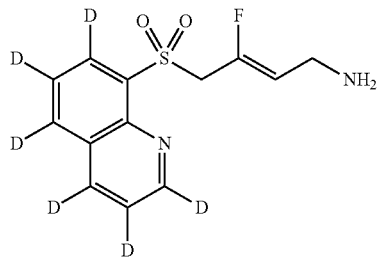 [SMILES: [2H]c1nc2c(S(=O)(=O)C/C(F)=C/CN)c([2H])c([2H])c([2H])c2c([2H])c1[2H]] | (Z)-3-fluoro-4-((quinolin-8-yl-$d_6$)sulfonyl)but-2-en-1-amine |

In one embodiment, the compound of the present invention is selected from the group consisting of

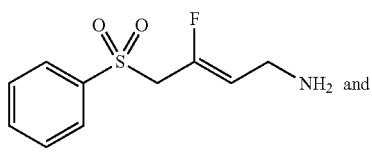 and

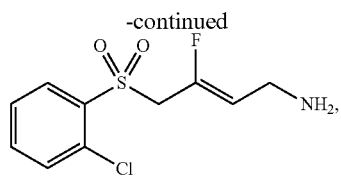

or a pharmaceutically acceptable salt or solvate thereof. In another embodiment, the compound of the present invention is

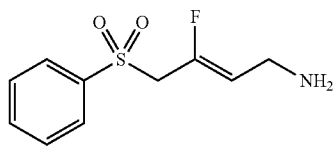 [SMILES: NC/C=C(\F)CS(=O)(=O)c1ccccc1]

or a pharmaceutically acceptable salt or solvate thereof. In a further embodiment, the compound of the present invention is

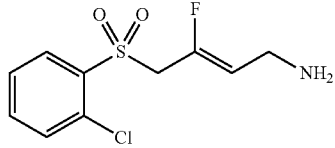 [SMILES: NC/C=C(\F)CS(=O)(=O)c1ccccc1Cl]

or a pharmaceutically acceptable salt or solvate thereof.

In one embodiment, the compound of the present invention is selected from the group consisting of

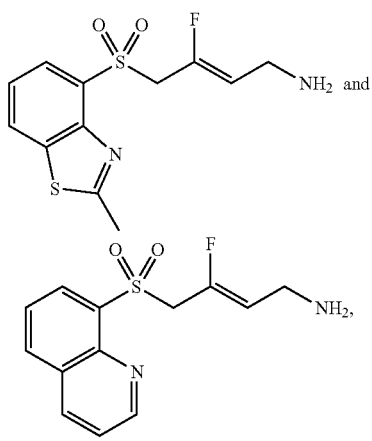

or a pharmaceutically acceptable salt or solvate thereof. In another embodiment, the compound of the present invention is

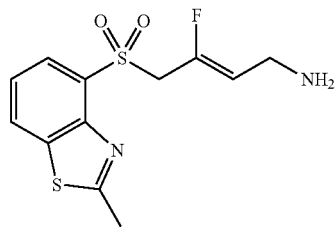 [SMILES: Cc1nc2c(S(=O)(=O)C/C(F)=C/CN)cccc2s1]

or a pharmaceutically acceptable salt or solvate thereof. In a further embodiment, the compound of the present invention is

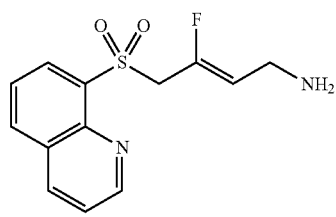

or a pharmaceutically acceptable salt or solvate thereof.

Preparation of Compounds of Formula I

Compounds of Formula I can be readily prepared by those skilled in the art using methods and materials known in the art and with reference to standard textbooks, such as "Advanced Organic Chemistry" by Jerry March (third edition, 1985, John Wiley and Sons) or "Comprehensive Organic Transformations" by Richard C. Larock (1989, VCH Publishers).

Compounds of Formula I may be synthesised as described below. The following schemes provide an overview of representative non-limiting embodiments of the invention. Those skilled in the art will recognize that analogues of Formula I, including different isomeric forms, may also be prepared from the analogous starting materials.

Scheme 1:

The preparation of compounds described by Formula Ib wherein X is —OCH$_2$— is described in Scheme 1 below. A person skilled in the art will recognise that compounds described by Formulae Ic, Id, Ie, If and Ig can be prepared by employing analogous synthetic methodologies with suitable starting materials.

Scheme 1

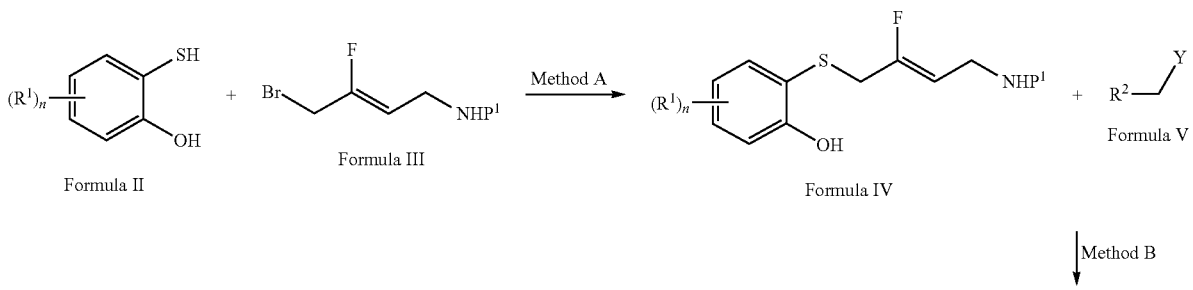

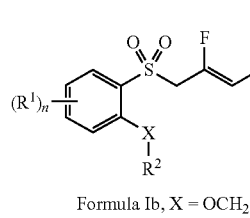

Formula Ib, X = OCH₂

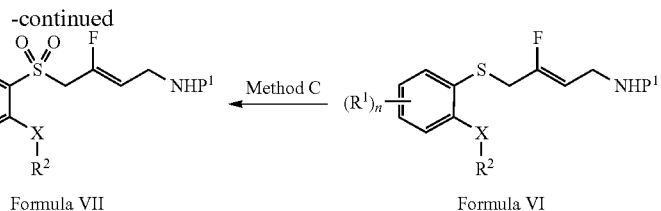

Formula VII    Formula VI

P¹ is a functional group used to protect a nitrogen functionality. Examples of P¹ are carbamate forming groups such as the tert-butyloxycarbonyl (BOC), the 9-fluorenylmethyloxy-carbonyl (FMOC), and the benzyloxycarbonyl (CBZ) groups.

In general Scheme 1 the R¹-substituted hydroxythiophenol starting material described by Formula II can be obtained from commercial sources or can be prepared by many methods well known in the art. Whilst there are many ways to achieve the reaction described by Method A, one convenient protocol involves reaction of compounds described by Formulae II and III with a base such as potassium carbonate in a solvent such as N,N-dimethylformamide at ambient temperature for several hours. Following standard extraction and purification methods the product described by Formula IV can be obtained in good yield and purity.

Whilst there are many ways to achieve the reaction described by Method B, one convenient protocol involves reaction of compounds described by Formulae IV and V (in which Y is an appropriate leaving group, such as Br, I, OTs and OMs) with a base such as potassium carbonate in a solvent such as N,N-dimethylformamide at ambient temperature for several hours. The product described by Formula VI can be recovered by standard work up procedures.

One convenient protocol for the conversion of compounds described by Formula VI to those described by Formula VII is Method C which involves treatment of a solution of a compound described by Formula VI and a base such as sodium hydrogen carbonate in a solvent such as dichloromethane with an oxidising agent such as mCPBA (3-chloroperoxybenzoic acid) at temperatures between 0° C. and ambient for several hours. The product described by Formula VII can be recovered by standard work-up procedures.

There are many, well established, chemical procedures for the deprotection of the compounds described by Formula VII to the compounds described by Formula Ib (Method D). For example if P¹ is a BOC protecting group, compounds described by Formula VII can be treated with an acidic substance such as dry hydrogen chloride in a solvent such as diethyl ether to furnish the compounds described by Formula Ib as the hydrochloride salts. In general, the free amino compounds are converted to acid addition salts for ease of handling and for improved chemical stability. Examples of acid addition salts include but are not limited to hydrochloride, hydrobromide, 2,2,2-trifluoroacetate and methanesulfonate salts.

Scheme 2:

The preparation of compounds described by Formula Ib wherein X is —CONH— is described in Scheme 2 below. A person skilled in the art will recognise that compounds described by Formulae Ic, Id, Ie, If and Ig can be prepared by employing analogous synthetic methodologies with suitable starting materials.

Scheme 2

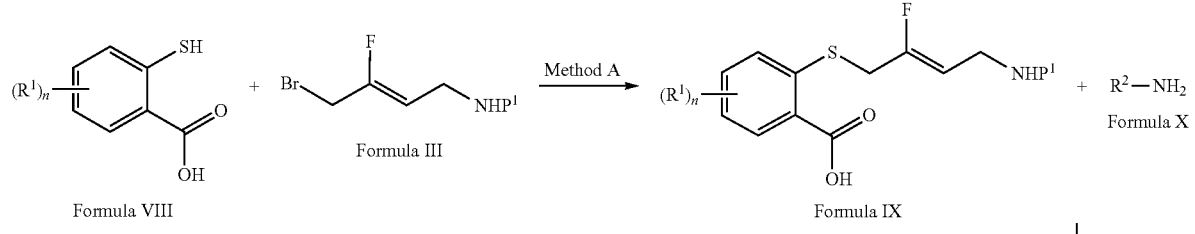

Formula VIII    Formula III    Formula IX    Formula X

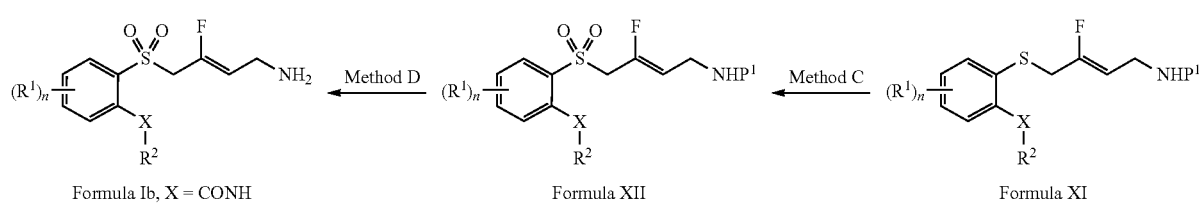

Formula Ib, X = CONH    Formula XII    Formula XI

In general Scheme 2 the $R^1$-substituted mercaptobenzoic acid starting material can be obtained from commercial sources or can be prepared by many methods well known in the art.

Compounds described by Formula XI can be prepared by the reaction of an appropriately substituted benzoic acid fragment (described by Formula IX) with an amine fragment (Formula X) in the presence of a suitable coupling reagent (such as HATU) and a base (such as triethylamine) in as solvent such as N,N-dimethylformamide at ambient temperature for several hours (Method E). The product described by Formula XI can be recovered by standard work-up procedures.

Scheme 3:

The preparation of compounds described by Formula Ib wherein X is —O— is described in Scheme 3 below. A person skilled in the art will recognise that compounds described by Formulae Ic, Id, Ie, If and Ig can be prepared by employing analogous synthetic methodologies with suitable starting materials.

Scheme 3

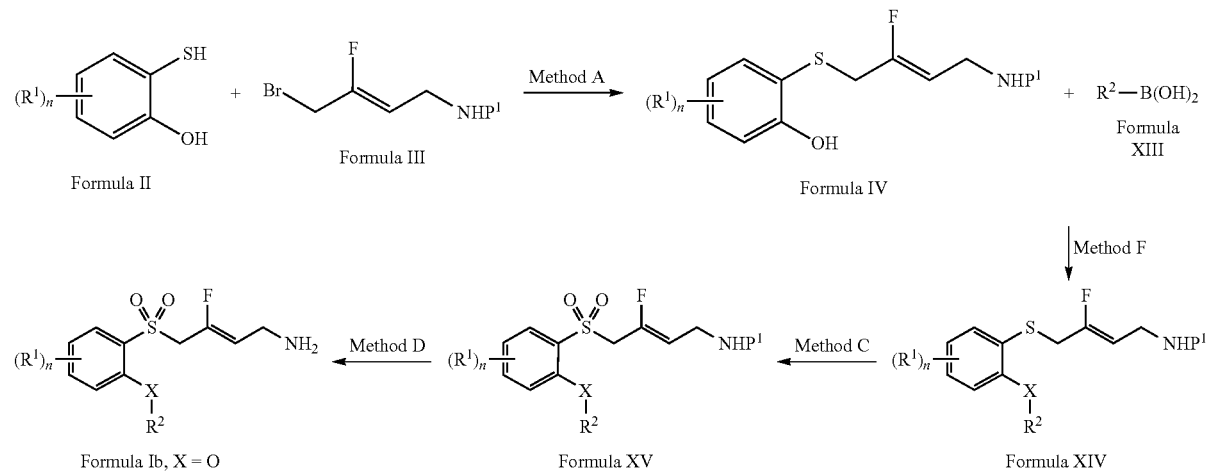

In general Scheme 3 the $R^1$-substituted hydroxythiophenol starting material can be obtained from commercial sources or can be prepared by many methods well known in the art.

A modification of the copper-catalysed Ullmann reaction can be employed to couple the compounds described by Formulae IV and XIII (Method F). There are numerous variants of this type of reaction described in the literature, with one example being the Chan-Evans-Lam modification. Compounds described by Formulae IV and XIII, in the presence of pyridine, can be dissolved in a solvent such as dichloromethane and then treated with copper (II) acetate at ambient temperature for several hours. Following standard extraction and purification methods, the coupled product described by Formula XIV can be obtained in good yield and purity.

Scheme 4:

The preparation of compounds described by Formula Ia is described in Scheme 4 below.

Scheme 4

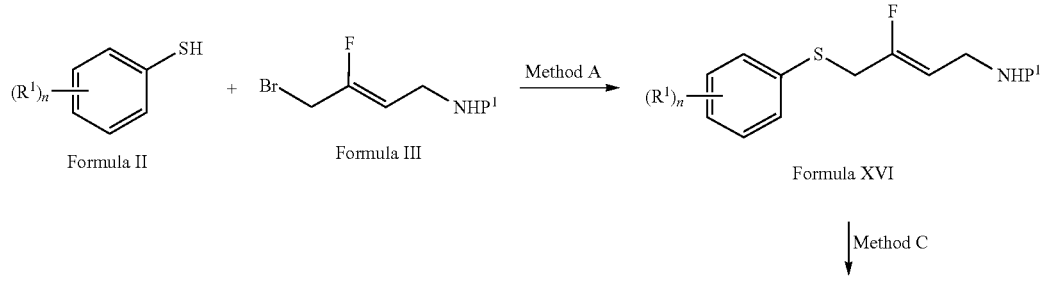

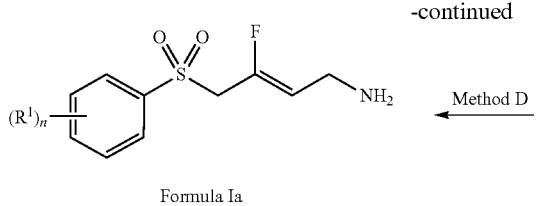

Formula Ia

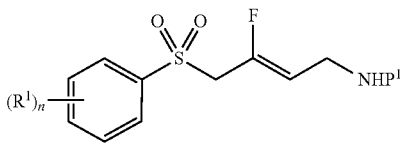

Formula XVII

In general Scheme 4 the $R^1$-substituted thiol starting material can be obtained from commercial sources or can be prepared by many methods well known to persons skilled in the art.

Scheme 5:

The preparation of compounds described by Formula Ia is described in Scheme 5 below.

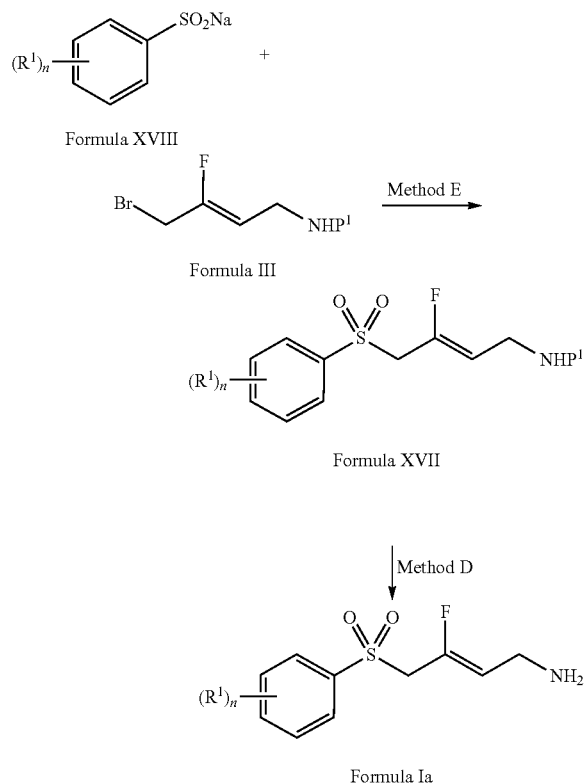

In general Scheme 5 the $R^1$-substituted aryl sulfinate starting material described by formula XVIII can be obtained from commercial sources or can be prepared by many methods well known to persons skilled in the art. One convenient protocol for achieving the conversion described by Method E involves reaction of compounds described by Formulae XVIII and III with a base such as potassium carbonate in a solvent such as N,N-dimethylformamide at ambient temperature for several hours. Following standard extraction and purification methods the product described by Formula XVII can be obtained in good yield and purity A person skilled in the art will appreciate that compounds of Formula I where A is a heteroaryl can be prepared by procedures analogous to those described above.

Cis/trans (E/Z) isomers may be separated by conventional techniques well known to those skilled in the art, for example, chromatography and fractional crystallisation.

Therapeutic Uses and Formulations

Another aspect of the present invention relates to a pharmaceutical composition comprising a compound of Formula I, or a pharmaceutically acceptable salt or stereoisomer thereof, together with a pharmaceutically acceptable diluent, excipient or adjuvant.

The present invention also relates to use of the compounds of Formula I in therapy, in particular to inhibit members of the lysyl oxidase family members, LOX, LOXL1, LOXL2, LOXL3 and LOXL4. In one embodiment, the invention provides for the selective inhibition of specific lysyl oxidase isoenzymes. In another embodiment, the invention provides for the simultaneous inhibition of 2, 3 or 4 LOX isoenzymes. The relative inhibitory potencies of the compounds can be determined by the amount needed to inhibit the amine oxidase activity of LOX, LOXL1, LOXL2, LOXL3 and LOXL4 in a variety of ways, e.g., in an in vitro assay with recombinant or purified human protein or with recombinant or purified non-human enzyme, in cellular assays expressing normal rodent enzyme, in cellular assays which have been transfected with human protein, in in vivo tests in rodent and other mammalian species, and the like.

In one embodiment, the compounds of the present invention are long lasting inhibitors of the lysyl oxidase family members LOX, LOXL1, LOXL2, LOXL3 and LOXL4. In one embodiment, the compounds of the present invention are long lasting inhibitors of the LOX or LOXL1-4 enzymes if the inhibition continues to be greater than 50% of the LOX or LOXL1-4 enzymes' activity after the compound concentration has been reduced below the IC50. In one embodiment, the compounds of the present invention show sustained inhibition of the LOX or LOXL1-4 enzymes over a period of 24 hours. In one embodiment, the compounds of the present invention are irreversible inhibitors of the lysyl oxidase family members LOX, LOXL1, LOXL2, LOXL3 and LOXL4.

Accordingly, a further aspect of the invention is directed to a method of inhibiting the amine oxidase activity of any one of LOX, LOXL1, LOXL2, LOXL3 or LOXL4 in a subject in need thereof, comprising administering to the subject an effective amount of a compound of Formula I, or a pharmaceutically acceptable salt or solvate thereof, or a pharmaceutical composition thereof.

In one embodiment, the present invention is directed to a method of inhibiting the amine oxidase activity of LOXL2. In another embodiment, the present invention is directed towards inhibiting the amine oxidase activity of LOX and LOXL2. In a further embodiment, the present invention is directed to a method of inhibiting the amine oxidase activity of LOX.

As discussed previously, LOX and LOXL1-4 enzymes are members of a large family of flavin-dependent and copper-dependent amine oxidases, which includes SSAO/VAP-1, monoamine oxidase-B (MAO-B) and diamine oxidase (DAO). In one embodiment, compounds of the present invention selectively inhibit members of the lysyl oxidase isoenzyme family with respect to SSAO/VAP-1, MAO-B, DAO and other members of the amine oxidase family.

The present invention also discloses methods to use the compounds described by Formula I to inhibit one or more lysyl oxidase isoenzymes (LOX, LOXL1, LOXL2, LOXL3 and LOXL4) in patients suffering from a fibrotic disease, and methods to treat fibrotic diseases. Furthermore, the present invention discloses methods to use the compounds described by Formula I to inhibit one or more lysyl oxidase isoenzymes (LOX, LOXL1, LOXL2, LOXL3 and LOXL4) in patients suffering from cancer, including metastatic cancer, and methods to treat cancer and metastatic cancer.

In a further aspect of the invention there is provided a method of treating a condition associated with any one of LOX, LOXL1, LOXL2, LOXL3 or LOXL4 protein, comprising administering to a subject in need thereof a therapeutically effective amount of compound of Formula I, or a pharmaceutically acceptable salt or solvate thereof, or a pharmaceutical composition thereof.

In another aspect there is a provided a method of treating a condition modulated by any one of LOX, LOXL1, LOXL2, LOXL3 or LOXL4, comprising administering to a subject in need thereof a therapeutically effective amount of compound of Formula I, or a pharmaceutically acceptable salt or solvate thereof, or a pharmaceutical composition thereof.

In one embodiment, of the methods of the present invention, the condition is selected from the group consisting of fibrosis, cancer and angiogenesis.

In another aspect, the present invention provides a method for decreasing extracellular matrix formation by treating human subjects, pets and livestock with fluoroallylamine inhibitors of lysyl oxidase isoenzyme family of Formula I as described herein.

The above-described methods are applicable wherein the condition is fibrosis. As employed here "fibrosis" includes such diseases as cystic fibrosis, idiopathic pulmonary fibrosis, liver fibrosis, kidney fibrosis, scleroderma, radiation-induced fibrosis, Peyronie's disease, scarring and other diseases where excessive fibrosis contributes to disease pathology.

In one embodiment, the fibrosis is selected from the group consisting of mediastinal fibrosis, myelofibrosis, retroperitoneal fibrosis, progressive massive fibrosis, nephrogenic systemic fibrosis, Crohn's Disease, keloid, systemic sclerosis, arthrofibrosis, Dupuytren's contracture, adhesive capsulitis, fibrosis of the pancreas, fibrosis of the intestine, liver fibrosis, lung fibrosis, kidney fibrosis, cardiac fibrosis, fibrostenosis, cystic fibrosis, idiopathic pulmonary fibrosis, radiation-induced fibrosis, Peyronie's disease and scleroderma or is associated with respiratory disease, abnormal wound healing and repair, scarring, hypertrophic scarring/keloids, scarring post surgery, cardiac arrest and all conditions where excess or aberrant deposition of fibrous material is associated with disease, injury, implants or surgery. In another embodiment, the fibrosis is selected from the group consisting of liver fibrosis, lung fibrosis, kidney fibrosis, cardiac fibrosis, scarring and scleroderma. In a further embodiment the fibrosis is selected from the group consisting of myelofibrosis, systemic sclerosis, liver fibrosis, lung fibrosis, kidney fibrosis, cardiac fibrosis and radiation induced fibrosis.

In one embodiment, kidney fibrosis includes, but is not limited to, diabetic nephropathy, vesicoureteral reflux, tubulointerstitial renal fibrosis, glomerulonephritis or glomerular nephritis, including focal segmental glomerulosclerosis and membranous glomerulonephritis, IgA nephropathy and mesangiocapillary glomerular nephritis. In one embodiment, liver fibrosis results in cirrhosis, and includes associated conditions such as chronic viral hepatitis, non-alcoholic fatty liver disease (NAFLD), alcoholic steatohepatitis (ASH), non-alcoholic steatohepatitis (NASH), primary biliary cirrhosis (PBC), biliary cirrhosis, and autoimmune hepatitis.

In one embodiment, the fibrosis is selected from keloid, scarring, ocular scarring, hypertrophic scarring, scleroderma, Dupuytren's contracture and Peyronie's disease. In one embodiment, the hypertrophic scarring results from a burn. In one embodiment, the hypertrophic scarring is caused by external injuries. In another embodiment, the hypertrophic scarring is caused by surgical procedures. In one embodiment, the keloid is caused by external injuries. In another embodiment, the keloid is caused by surgical procedures. In a further embodiment, the keloid is a result of a skin injury caused by acne, burns, chicken pox, ear piercing, scratches, surgical cuts or vaccination sites.

The above-described methods are also applicable wherein the condition is a proliferative disease for example cancer. In one embodiment, the cancer is selected from the group consisting of lung cancer; breast cancer; colorectal cancer; anal cancer; pancreatic cancer; prostate cancer; ovarian carcinoma; liver and bile duct carcinoma; esophageal carcinoma; mesothelioma, non-Hodgkin's lymphoma; bladder carcinoma; carcinoma of the uterus; glioma, glioblastoma, medullablastoma, and other tumours of the brain; myelofibrosis, kidney cancer; cancer of the head and neck; cancer of the stomach; multiple myeloma; testicular cancer; germ cell tumour; neuroendocrine tumour; cervical cancer; oral cancer, carcinoids of the gastrointestinal tract, breast, and other organs; signet ring cell carcinoma; mesenchymal tumours including sarcomas, fibrosarcomas, haemangioma, angiomatosis, haemangiopericytoma, pseudoangiomatous stromal hyperplasia, myofibroblastoma, fibromatosis, inflammatory myofibroblastic tumour, lipoma, angiolipoma, granular cell tumour, neurofibroma, schwannoma, angiosarcoma, liposarcoma, rhabdomyosarcoma, osteosarcoma, leiomyoma or a leiomyosarcoma.

In one embodiment, the cancer is selected from the group consisting of breast cancer, head and neck squamous cell carcinoma, brain cancer, prostate cancer, renal cell carcinoma, liver cancer, lung cancer, oral cancer, cervical cancer and tumour metastasis.

In one embodiment, lung cancer includes lung adenocarcinoma, squamous cell carcinoma, large cell carcinoma, bronchoalveolar carcinoma, non-small-cell carcinoma, small cell carcinoma and mesothelioma. In one embodiment, breast cancer includes ductal carcinoma, lobular carcinoma, inflammatory breast cancer, clear cell carcinoma, and mucinous carcinoma. In one embodiment, colorectal cancer includes colon cancer and rectal cancer. In one embodiment, pancreatic cancer includes pancreatic adenocarcinoma, islet cell carcinoma and neuroendocrine tumours.

In one embodiment, ovarian carcinoma includes ovarian epithelial carcinoma or surface epithelial-stromal tumour including serous tumour, endometrioid tumour and mucinous cystadenocarcinoma, and sex-cord-stromal tumour. In one embodiment liver and bile duct carcinoma includes hepatocelluar carcinoma, cholangiocarcinoma and hemangioma. In one embodiment, esophageal carcinoma includes esophageal adenocarcinoma and squamous cell carcinoma. In one embodiment, carcinoma of the uterus includes endometrial adenocarcinoma, uterine papillary serous carcinoma, uterine clear-cell carcinoma, uterine sarcomas and leiomyosarcomas and mixed mullerian tumours. In one embodiment, kidney cancer includes renal cell carcinoma, clear cell carcinoma and Wilm's tumour. In one embodiment, cancer of the head and neck includes squamous cell carcinomas. In one embodiment, cancer of the stomach includes stomach adenocarcinoma and gastrointestinal stromal tumour.

In one embodiment, the cancer is selected from the group consisting of colon cancer, ovarian cancer, lung cancer, esophageal carcinoma, breast cancer and prostate cancer. In one embodiment, the cancer is selected from the group consisting of pancreatic cancer, liver cancer, breast cancer, myelofibrosis and mesothelioma.

In one embodiment, the compounds of the invention may be for use in the treatment of a non-metastatic cancer. In another embodiment, the compounds of the invention may be for use in the treatment of metastatic cancer. In a further embodiment, the compounds of the present invention may be for use in the prevention or treatment of tumour metastasis.

The above-described methods are applicable wherein the condition is angiogenesis.

In one embodiment of the methods of the present invention, the subject is selected from the group consisting of humans, pets and livestock. In another embodiment of the methods of the present invention, the subject is a human.

A further aspect of the invention provides for use of a compound of Formula I, or a pharmaceutically acceptable salt or solvate thereof, for the manufacture of a medicament for treating a condition associated with any one of LOX, LOXL1, LOXL2, LOXL3 or LOXL4 protein.

Another aspect of the invention provides for use of a compound of Formula I, or a pharmaceutically acceptable salt or solvate thereof, for the manufacture of a medicament for treating a condition modulated by any one of LOX, LOXL1, LOXL2, LOXL3 or LOXL4.

Pharmaceutical and/or Therapeutic Formulations

In another embodiment of the present invention, there are provided compositions comprising a compound having Formula I and at least one pharmaceutically acceptable excipient, carrier or diluent thereof. The compound(s) of Formula I may also be present as suitable salts, including pharmaceutically acceptable salts.

The phrase "pharmaceutically acceptable carrier" refers to any carrier known to those skilled in the art to be suitable for the particular mode of administration. In addition, the compounds may be formulated as the sole pharmaceutically active ingredient in the composition or may be combined with other active ingredients.

The phrase "pharmaceutically acceptable salt" refers to any salt preparation that is appropriate for use in a pharmaceutical application. By pharmaceutically acceptable salt it is meant those salts which, within the scope of sound medical judgement, are suitable for use in contact with the tissues of humans and lower animals without undue toxicity, irritation, allergic response and the like, and are commensurate with a reasonable benefit/risk ratio. Pharmaceutically acceptable salts are well known in the art and include acid addition and base salts. Hemisalts of acids and bases may also be formed. Pharmaceutically acceptable salts include amine salts of mineral acids (e.g., hydrochlorides, hydrobromides, sulfates, and the like); and amine salts of organic acids (e.g., formates, acetates, lactates, malates, tartrates, citrates, ascorbates, succinates, maleates, butyrates, valerates, fumarates, and the like).

For compounds of formula (I) having a basic site, suitable pharmaceutically acceptable salts may be acid addition salts. For example, suitable pharmaceutically acceptable salts of such compounds may be prepared by mixing a pharmaceutically acceptable acid such as hydrochloric acid, sulfuric acid, methanesulfonic acid, succinic acid, fumaric acid, maleic acid, benzoic acid, phosphoric acid, acetic acid, oxalic acid, carbonic acid, tartaric acid, or citric acid with the compounds of the invention.

S. M. Berge et al. describe pharmaceutically acceptable salts in detail in *J. Pharmaceutical Sciences*, 1977, 66:1-19. The salts can be prepared in situ during the final isolation and purification of the compounds of the invention, or separately by reacting the free base function with a suitable organic acid. Representative acid addition salts include acetate, adipate, alginate, ascorbate, asparate, benzenesulfonate, benzoate, bisulfate, borate, butyrate, camphorate, camphorsulfonate, citrate, digluconate, cyclopentanepropionate, dodecylsulfate, ethanesulfonate, fumarate, glucoheptonate, glycerophosphate, hemisulfate, heptonate, hexanoate, hydrobromide, hydrochloride, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, 3-phenylpropionate, phosphate, picrate, pivalate, propionate, stearate, succinate, sulfate, tartrate, toluenesulfonate, undecanoate, valerate salts, and the like. Suitable base salts are formed from bases that form non-toxic salts. Examples include the arginine, benzathine, calcium, choline, diethylamine, diolamine, glycine, lysine, magnesium, meglumine, olamine, potassium, sodium, tromethamine and zinc salts. Representative alkali or alkaline earth metal salts include sodium, lithium potassium, calcium, magnesium, and the like, as well as non-toxic ammonium, quaternary ammonium, and amine cations, including, but not limited to ammonium, tetramethylammonium, tetraethylammonium, dimethylamine, trimethylamine, triethylamine, ethylamine, triethanolamine and the like.

Pharmaceutically acceptable salts of compounds of formula I may be prepared by methods known to those skilled in the art, including for example:
  (i) by reacting the compound of formula I with the desired acid or base;
  (ii) by removing an acid- or base-labile protecting group from a suitable precursor of the compound of formula I or by ring-opening a suitable cyclic precursor, for example, a lactone or lactam, using the desired acid or base; or
  (iii) by converting one salt of the compound of formula I to another by reaction with an appropriate acid or base or by means of a suitable ion exchange column.

The above reactions (i)-(iii) are typically carried out in solution. The resulting salt may precipitate out and be collected by filtration or may be recovered by evaporation of the solvent. The degree of ionisation in the resulting salt may vary from completely ionised to almost non-ionised.

Thus, for instance, suitable pharmaceutically acceptable salts of compounds according to the present invention may be prepared by mixing a pharmaceutically acceptable acid such as hydrochloric acid, sulfuric acid, methanesulfonic acid, succinic acid, fumaric acid, maleic acid, benzoic acid, phosphoric acid, acetic acid, carbonic acid, tartaric acid, or citric acid with the compounds of the invention. Suitable pharmaceutically acceptable salts of the compounds of the present invention therefore include acid addition salts.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when the solvent is water.

In one embodiment, the compounds of Formula I may be administered in the form of a "prodrug". The phrase "prodrug" refers to a compound that, upon in vivo administration, is metabolized by one or more steps or processes or otherwise converted to the biologically, pharmaceutically or therapeutically active form of the compound. Prodrugs can be prepared by modifying functional groups present in the compound in such a way that the modifications are cleaved, either in routine manipulation or in vivo, to a compound described herein. For example, prodrugs include compounds of the present invention wherein a hydroxy, amino, or carbohydrate group is bonded to any group that, when administered to a mammalian subject, can be cleaved to form a free hydroxyl, free amino, or free carboxylic acid group, respectively. Representative prodrugs include, for example, amides, esters, enol ethers, enol esters, acetates, formates, benzoate derivatives, and the like of alcohol and amine functional groups in the compounds of the present invention. The prodrug form can be selected from such functional groups as —C(O)alkyl, —C(O)cycloalkyl, —C(O)aryl, —C(O)-arylalkyl, C(O)heteroaryl, —C(O)-heteroarylalkyl, or the like. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

Compositions herein comprise one or more compounds provided herein. The compounds are, in one embodiment, formulated into suitable pharmaceutical preparations such as solutions, suspensions, tablets, creams, gels, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., *Ansel Introduction to Pharmaceutical Dosage Forms*, Fourth Edition 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders to be treated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated from there for dosages for humans.

The concentration of active compound in the pharmaceutical composition will depend on absorption, distribution, inactivation and elimination rates of the active compound, the physicochemical characteristics of the compound, the dosage schedule, and amount administered as well as other factors known to those of skill in the art.

In one embodiment, a therapeutically effective dosage should produce a serum concentration of active ingredient of from about 0.1 ng/mL to about 50-100 µg/mL. The pharmaceutical compositions, in another embodiment, should provide a dosage of from about 0.001 mg to about 2000 mg of compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

Dosing may occur at intervals of minutes, hours, days, weeks, months or years or continuously over any one of these periods. Suitable dosages lie within the range of about 0.1 ng per kg of body weight to 0.1 g per kg of body weight per dosage. The dosage is preferably in the range of 10 µg to 0.1 g per kg of body weight per dosage, such as is in the range of 0.1 mg to 0.01 g per kg of body weight per dosage. Suitably, the dosage is in the range of 10 µg to 50 mg per kg of body weight per dosage, such as 10 µg to 20 mg per kg of body weight per dosage, or 10 µg to 10 mg per kg of body weight per dosage. Other suitable dosages may be in the range of 0.1 mg to 25 mg per kg of body weight, including 0.1 mg to 10, 20, 50 or 100 mg per kg of body weight per dosage.

Alternatively, an effective dosage may be up to about 10 mg/cm$^2$, or it may be up to about 1 mg/cm$^2$, about 0.5 mg/cm$^2$, about 0.2 mg/cm$^2$, about 0.1 mg/cm$^2$, about 0.05 mg/cm$^2$, about 0.02 mg/cm$^2$, or about 0.01 mg/cm$^2$. It may be, for example, in the range from about 10 µg/cm$^2$ to about 1 mg/cm$^2$, about 10 µg/cm$^2$ to about 0.1 mg/cm$^2$, about 10 µg/cm$^2$ to about 0.01 mg/cm$^2$, about 10 µg/cm$^2$ to about 500 µg/cm$^2$, about 10 µg/cm$^2$ to about 200 µg/cm$^2$, about 10 µg/cm$^2$ to about 100 µg/cm$^2$, about 10 µg/cm$^2$ to about 50 µg/cm$^2$, about 20 µg/cm$^2$ to about 1 mg/cm$^2$, about 50 µg/cm$^2$ to about 1 mg/cm$^2$, about 100 µg/cm$^2$ to about 1 mg/cm$^2$, about 200 µg/cm$^2$ to about 1 mg/cm$^2$, about 500 µg/cm$^2$ to about 1 mg/cm$^2$, about 50 µg/cm$^2$ to about 500 µg/cm$^2$, about 50 µg/cm$^2$ to about 200 µg/cm$^2$, about 100 µg/cm$^2$ to about 500 µg/cm$^2$, or about 200 µg/cm$^2$ to about 500 µg/cm$^2$.

Suitable dosage amounts and dosing regimens can be determined by the attending physician and may depend on the particular condition being treated, the severity of the condition, as well as the general health, age and weight of the subject.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, dissolution in aqueous sodium bicarbonate, formulating the compounds of interest as nanoparticles, and the like. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. The active ingredient may be administered at once, or may be divided into a number of smaller doses to be administered at intervals of time. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoles and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% (wt %) with the balance made up from non-toxic carrier may be prepared. Methods for preparation of these compositions are known to those skilled in the art. The contemplated compositions may contain 0.001%-100% (wt %) active ingredient, in one embodiment 0.1-95% (wt %), in another embodiment 75-85% (wt %).

Modes of Administration

Convenient modes of administration include injection (subcutaneous, intravenous, etc.), oral administration, inhalation, transdermal application, topical creams or gels or powders, vaginal or rectal administration. Depending on the route of administration, the formulation and/or compound may be coated with a material to protect the compound from the action of enzymes, acids and other natural conditions which may inactivate the therapeutic activity of the compound. The compound may also be administered parenterally or intraperitoneally.

Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and ethanol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, olive oil, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation. These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% (vol %) isotonic solutions, pH about 5-7, with appropriate salts.

Compositions for Other Routes of Administration

Other routes of administration, such as transdermal patches, including iontophoretic and electrophoretic devices, vaginal and rectal administration, are also contemplated herein.

Transdermal patches, including iontophoretic and electrophoretic devices, are well known to those of skill in the art. For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Co-Administration with Other Drugs

In accordance with another aspect of the present invention, it is contemplated that compounds of Formula I as described herein may be administered to a subject in need thereof in combination with medication considered by those of skill in the art to be current standard of care for the condition of interest. Such combinations provide one or more advantages to the subject, e.g., requiring reduced dosages to achieve similar benefit, obtaining the desired palliative effect in less time, and the like.

Compounds in accordance with the present invention may be administered as part of a therapeutic regimen with other drugs. It may be desirable to administer a combination of active compounds, for example, for the purpose of treating a particular disease or condition. Accordingly, it is within the scope of the present invention that two or more pharmaceutical compositions, at least one of which contains a compound of Formula (I) according to the present invention, may be combined in the form of a kit suitable for co-administration of the compositions.

In one embodiment of the methods of the present inventions a compound of Formula I may be administered with a second therapeutic agent. In one embodiment the second therapeutic agent may be selected from one or more of the following categories:

(i) Anti-cancer agents such as cis-platin, oxaliplatin, carboplatin, cyclophosphamide, nitrogen mustard, uracil mustard, bendamustin, melphalan, chlorambucil, chlormethine, busulphan, temozolomide, nitrosoureas, ifosamide, pipobroman, triethylene-melamine, triethylene thiophosphoramine, carmustine, lomustine, stroptozocin and dacarbazine, gemcitabine, fosgemcitabine palabenamide, 5-fluorouracil, tegafur, raltitrexed, methotrexate, pemetrexed, leucovorin, cytosine arabinoside, floxuridine, cytarabine, 6-mercaptopurine, 6-thioguanine, fludarabine phosphate, pentostatine, hydroxyurea, trifluridine, trifluracil, adriamycin, bleomycin, doxorubicin, daunomycin, epirubicin, idarubicin, mitomycin-C, dactinomycin, mithramycin, vincristine, vinblastine, vindesine and vinorelbine, taxol, taxotere, eribulin, carfilzomib, bortezomib, etoposide, teniposide, amsacrine, topotecan, irinotecan, mitoxantrone, camptothecin, dactinomycin, daunorubicin, aldoxorubicin, epirubicin, idarubicin, ara-C, paclitaxel (Taxol™), nabpaclitaxel, docetaxel, deoxycoformycin, L-asparaginase, IFN-alpha, azacitidine, decitabine, vorinostat, MS-275, panobinostat, romidepsin, valproic acid, mocetinostat, pracinostat, belinostat, irabectedin, tamoxifen, fulvestrant, toremifene, raloxifene, droloxifene, iodoxyfene, bicalutamide, flutamide, nilutamide, cyproterone acetate, goserelin, leuprorelin, buserelin, progestogens, megestrol acetate, anastrozole, letrozole, vorazole, exemestane, finasteride, navelbene, capecitabine, and droloxafine; and abiraterone, enzalutamide, lanreotide, dasatinib, bosutinib, trastuzumab, pertuzumab, panitumumab, cetuximab, gefitinib, erlotinib, afatinib, vandetanib, osimertinib, rociletinib, lapatinib, imatinib, nilotinib, sorafenib, tipifarnib and lonafarnib, vemurafenib, dabrafenib, trametinib, cobimetinib, ponatinib, palbociclib, everolimus, ruxolitinib, pacritinib, jaktinib, imetelstat, plitidepsin, pevonedistat, ibrutinib, ceritinib, crizotinib, ectinib, cabozantirsib, vismodegib, sonidegib, regorafenib, vandetanib, vatalanib, sunitinib, axitinib, pazopanib, lenvatinib, talimogene laherparepvec, denosumab, obinuluzumab, blinatomumab, dinutuximab, idarucizumab, daratumumab, necitumumab, elotuzumab, olaratumab, alemtuzumab, rituximab, ibritumomab tiuxetan, ofatumumab, peginterferon alpha-2b, aldesleukin, Gardasil, Cervarix, Oncophage, Sipuleucel-T, nivolumab, pembrolizumab, atezolizumab, indoximod, nivolumab, ipilumumab, brentuximab vedotin, irastuzumab emtansine, fludarabine, cladribine, pentostatin, idelalisib, perifosine, birinapant, bortezomib, ixazomib, carfilzomib, marizomib, olaparib, rucaparib, venetoclax, navitoclax, obatoclax, glasdegib, pacrinostat, buparlisib, momelotinib, itacitinib, umbralisib, gusacitinib, tagraxofusp, ribociclib, abemaciclib, niraparib, trabectedin, pofimer, vinflunine, napabucasin, lurbinectedin, tazemetostat, acalabrutinib, levatinib, neratinib, pamiparib, epacadostat, enzastaurin, selinexor, masitinib, evofosfamide, glufosfamide, roxadustat, streptozocin, devimistat, galunisertib, binimetinib, veliparib, entinostat, pexidartinib, talazoparib, entrectinib.

(ii) Anti-inflammatory agents such as meloxicam, feoprofen, oxaprozin, salsalate, etoricoxib, tenoxicam, aspirin, nabumetone, flurbiprofen, mefenamic acid, phenylbutazone, lornoxicam, indomethacin, etodolac, diflunisal, ketoprofen, valdecoxib, tolfenamic acid, piroxicam, sulindac, tolmetin, ketorolac, loxoprofen, acetaminophen, bromfenac, diclofenac, ibuprofen, meclofenamate, nabumetone, naproxen, nepafenac, celecoxib, triamcinolone acetonide, hydrocortisone, hydrocortisone acetate, methylprednisolone, aclomethasone dipropionate, emricasan, BI 1467335, namodenoson, GLPG-1690, terguride.

(iii) Anti-hypertensive agent such as hydrochlorothiazide, chlorthalidone, furosemide, spironolactone, triamterene, amiloride, benazepril, captopril, lisinopril, enalapril, ramipril, fosinopril, moexipril, perindopril, quinapril, trandolapril, losartan, candesartan, valsartan, telmisartan, clonidine, methyldopa, propranolol, nadolol, timolol, pindolol, labetolol, metoprolol, atenolol, esmolol, betaxolol, carvedilol, prazosin, terazosin, doxazosin, phenoxybenzamine, phentolamine, verapamil, diltiazem, nifedipine, felodipine, amlodipine, nimodipine, diazoxide, minoxidil, pinacidil, nicorandil, hydralazine, sodium nitroprusside, bosentan, epoprostenol, iloprost, beraprost, esuberaprost, ralinepag, macitentan, sitaxentan, ambrisentan, riociguat, treprostinil, ubenimex, selexipag, levosimendan, udenafil, tadalafil and sildenafil.

(iv) Anti-fibrotic agent such as pirfenidone, nintedanib, cenicriviroc, selonsertib, lanifibranor, nimacimab, nitrazoxanide, NGM282, apararenone, tipelukast, Actimmune, ponatinib, lenvatinib, dovitinib, lucitanib, danusertinib, brivatinib, erdafitinib, belapectin, PD173074, PD166866, AZD4547, BGJ398, LY2874455, TAS-120, ARQ087, BLU9931, FGF401, BAY-1163877, ENMD-2076, IMCA1, FGF401, DEBIO1347, FIIN-2, GP-369, PRO-001, H3B-6527, BAY1187982, MFGR1877S, FP-1039, BLU554, PRN1371, S49076, SU6668, SU5416, PBI-4050, KD-025.

(v) Anti-angiogenesis agent such as axitinib, bevacizumab, cabozantinib, lenalidomide, lenvatinib, pazopanib, ramucirumab, vandetanib, vatalanib, sunitinib, ziv-aflibercept, thalidomide, pomalidomide, lenalidomide.

(vi) Immunosuppressive agent such as prednisone, budesonide, prednisolone, tofacitinib, cyclosporine, tacrolimus, sirolimus, everolimus, azathioprine, leflunomide, mycophenolate, abatacept, adalimumab, anakinra, certolizumab, etanercept, golimumab, infliximab, ixekizumab, natalizumab, rituximab, secukinumab, tocilizumab, ustekinumab, vedolizumab, basiliximab, daclizumab, dimethyl fumarate, mycophenolate mofetil.

(vii) Metabolic agent such as obeticholic acid, elafibranor, aramchol, seladelpar, MGL-3196, tropifexor, MSDC-0602K, BMS-986036, semaglutide, EDP-305, gemcabene, PF-05221304, PF-06865571, PF-06835919, LIK066, LMB763, vitamin E, acarbose, miglitol, pramlintide, alogliptan, linagliptan, saxagliptin, sitagliptin, albiglutide, dulaglutide, exenatide, liraglutide, lixisenatide, insulin, nateglinide, repaglinide. Metformin, canagliflozin, dapagliflozin, empagliflozin, chlorpropamide, glimepiride, glipizide, glyburide, tolazamide, tolbutamide, rosiglitazone, pioglitazone, atorvastatin, amlodipine, simvastatin, ezetimibe, lovastatin, sitagliptin, cholestyramine, colesevelam, colestipol, fenofibrate, gemfibrozil, fenofibric acid, niacin, icosapent, mipomersen, lomitapide, evolocumab, alirocumab, fluvastatin, pravastatin, rosuvastatin, pitavastatin, simvastatin, cerivastatin, allopurinol, lesinurad, pegloticase, febuxostat, rasburicase, ivacaftor, velaglucerase alfa, imiglucerase, alglucosidase alfa, laronidase, cerliponase alfa, alglucerase, idursulfase, taliglucerase alfa, agalsidase beta, sebelipase alfa, vestronidase alfa, galsulfase, elosulfase alfa, eliglustat, burosumab, migalastat, sapropterin, metreleptin, nitisinone, pegvaliase, asfotase alfa, inotersen, miglustat, orlistat, sodium phenylbutyrate, glycerol phenylbutyrate.

In one embodiment, the compounds of the present invention may be administered in combination with other therapeutic treatments. For example, the compounds of the present invention may be administered in combination with radiotherapy or chemotherapy. In one embodiment, the compounds of the present invention may be administered in combination with one or more additional anti-tumour agent and/or radiotherapy for the treatment of a cancer.

When two or more active ingredients are co-administered, the active ingredients may be administered simultaneously, sequentially or separately. In one embodiment, the compound of Formula I is co-administered simultaneously with a second therapeutic agent. In another embodiment, the compound of Formula I and the second therapeutic agent are administered sequentially. In a further embodiment, the compound of Formula I and the second therapeutic agent are administered separately.

The invention will now be described in greater detail, by way of illustration only, with reference to the following non-limiting examples. The examples are intended to serve to illustrate the invention and should not be construed as limiting the generality of the disclosure of the description throughout this specification.

Experimental: General Methods

Commercially available solvents and reagents were used as received. Where appropriate, reactions were carried out under an argon atmosphere. Reactions were monitored by either analytical thin-layer chromatography (TLC) or by analytical liquid chromatography-mass spectrometry (LCMS) recorded on either a Shimadzu LCMS 2020 instrument or an Agilent LC/MSD 1200 instrument using reverse-phase conditions. Purification of intermediates and final compounds was conducted, where necessary, using column chromatography or preparative HPLC. Normal-phase column chromatography was conducted under medium pressure either on silica gel or on prepacked silica gel cartridges using a flash chromatography system (CombiFlash Rf200, Teledyne Isco systems, USA). Reverse-phase column chromatography was conducted under low pressure on prepacked C18 cartridges using a flash chromatography system (Releveris® X2). Eluents were monitored by UV light ($\lambda$=254/280 nm). $^1$H-NMR and $^{19}$F-NMR spectra were recorded using either a Bruker 300 MHz NMR spectrometer, a Bruker Avance III plus 400 MHz NMR spectrometer or a Varian III plus 300 MHz spectrometer. Chemical shifts ($\delta$) are reported as parts per million (ppm) relative to tetramethylsilane (TMS; internal standard). The following abbreviations are used for multiplicities: s=singlet; br s=broad singlet; d=doublet; t=triplet; q=quartet; m=multiplet; and br m=broad multiplet. Low resolution mass spectra (MS) were obtained as electrospray—atmospheric pressure ionization (ES-API) mass spectra, which were recorded on either a Shimadzu LCMS 2020 instrument or an Agilent LC/MSD 1200 instrument using reverse-phase conditions. All animal experiments performed were conducted in compliance with institutional guidelines and approval from local ethics committees.

Example 1

Preparation of (Z)-tert-butyl (4-bromo-3-fluorobut-2-en-1-yl)carbamate

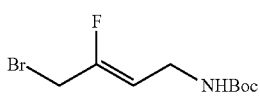

Procedure A: Preparation of tert-butyl 2-oxoethylcarbamate

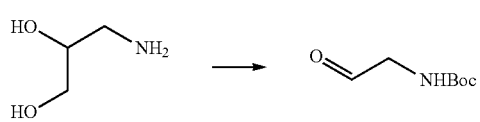 [SMILES: NCC(O)CO ; CC(C)(C)OC(=O)NCC=O]

To a stirring solution of 3-amino-1,2-propanediol (20.0 g, 0.22 mol) in water (200 mL) at 0-5° C. was added di-tert-butyl dicarbonate (55.5 mL, 0.24 mol). After adjusting the alkalinity of the solution to pH-9 by addition of aq. NaOH (6 N), the mixture was left to stir at room temperature (rt) for 18 h. The reaction mixture was cooled to 0-5° C. and then acidified to pH-6 before the addition of sodium metaperiodate (56.3 g, 0.26 mol). The resulting suspension was stirred at rt for 2 h. The mixture was filtered to remove all solids and the filtrate was transferred to a separatory funnel and extracted with ethyl acetate (200 mL). Sodium chloride was added to the aqueous layer until a saturated solution was obtained. The aqueous layer was then extracted further with ethyl acetate (100 mL). The combined organics were dried over Na$_2$SO$_4$ and then concentrated in vacuo to give crude tert-butyl 2-oxoethylcarbamate (45.7 g) as a yellow gum. The crude material was used in the subsequent step without purification.

Procedure B: Preparation of (E)-ethyl 4-(tert-butoxycarbonylamino)-2-fluorobut-2-enoate and (Z)-ethyl 4-(tert-butoxycarbonylamino)-2-fluorobut-2-enoate

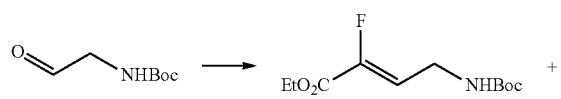

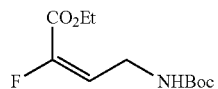

To a stirring suspension of crude tert-butyl 2-oxoethylcarbamate (43.7 g, 0.22 mol) and magnesium sulfate (32.0 g) in acetonitrile (200 mL) at 0° C. under N$_2$ was added sequentially ethyl 2-fluorophosphonoacetate (55.7 mL, 0.27 mol) and 1,8-diazabicyclo[5.4.0]undec-7-ene (32.8 mL, 0.22 mol). The reaction mixture was allowed to warm to rt and stirring was continued for 3 h. After removing the solvent under reduced pressure the residue was taken up in ethyl acetate (200 mL) and then transferred to a separatory funnel. The organics were washed successively with aq. HCl (2 M; 100 mL×2), aq. NaOH (2 M; 100 mL×2) and brine (100 mL). After drying over MgSO$_4$, the organics were concentrated in vacuo to give the crude, desired product as a mixture of E/Z isomers (2:3; 57.0 g). This crude material was progressed to the next step without purification.

Procedure C: Preparation of (E)-tert-butyl 3-fluoro-4-hydroxybut-2-enylcarbamate and (Z)-tert-butyl 3-fluoro-4-hydroxybut-2-enylcarbamate

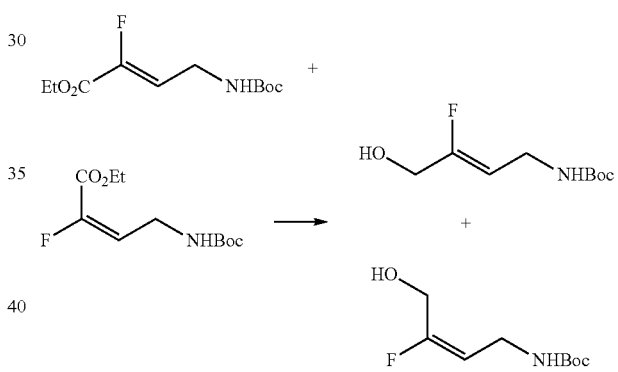

To a stirring solution of crude E/Z-ethyl 4-(tert-butoxycarbonylamino)-2-fluorobut-2-enoate (18.0 g, 72.8 mmol) in THF (150 mL) at 0° C. under N2 was added diisobutylaluminum hydride (1 M in toluene, 182 mL, 182 mmol) dropwise over 45 min. After complete addition, the mixture was left to stir at 0° C. for 3 h. The reaction mixture was transferred to a separatory funnel and added dropwise to a stirring mixture of ice (100 g) and aq. NaOH (2 M; 200 mL). Following addition the mixture was stirred for 2 h. The quenched reaction mixture was extracted with diethyl ether (100 mL×2) and the combined organics were washed with brine (100 mL). After drying over MgSO$_4$ the organics were concentrated in vacuo to give the crude alcohol as a mixture of E/Z isomers. This mixture was purified over silica gel (135 g), eluting with 25% ethyl acetate in n-hexane to give (Z)-tert-butyl 3-fluoro-4-hydroxybut-2-enylcarbamate (6.20 g, 30% over three steps) and (E)-tert-butyl 3-fluoro-4-hydroxybut-2-enylcarbamate (1.85 g, 8.9% over three steps). (E)-tert-butyl 3-fluoro-4-hydroxybut-2-enylcarbamate: $^1$H-NMR (200 MHz; CDCl$_3$) δ ppm: 1.43 (9H, s), 3.72 (2H, dd, J 7.5, 5.4 Hz), 4.25 (2H, d, J 21.5 Hz), 4.85 (1H, br. s), 5.18 (1H, dt, J 19.2, 8.5 Hz). (Z)-tert-butyl 3-fluoro-4-hydroxybut-2-enylcarbamate: $^1$H-NMR (300 MHz;

CDCl₃) δ ppm: 1.46 (9H, s), 3.84 (2H, dd, J 6.2, 6.2 Hz), 4.13 (2H, d, J 13.9 Hz), 4.68 (1H, br. s), 5.03 (1H, dt, J 36.0, 7.1 Hz).

Procedure D: Preparation of (Z)-tert-butyl 4-bromo-3-fluorobut-2-enylcarbamate

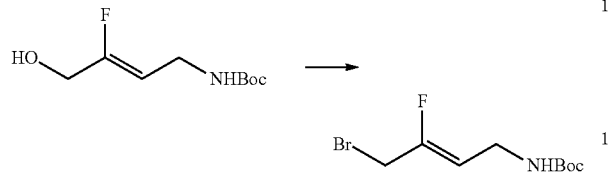

To a stirring solution of (Z)-tert-butyl 3-fluoro-4-hydroxybut-2-enylcarbamate (6.20 g, 30.2 mmol) and triethylamine (6.32 mL, 45.3 mmol) in acetone (100 mL) at 0° C. was added methanesulfonyl chloride (2.81 mL, 36.3 mmol) dropwise. After complete addition the mixture was left to stir at 0° C. for 30 min. After this time, lithium bromide (13.1 g, 0.15 mol) was added portion-wise and the resulting suspension was stirred for a further 2 h. The reaction mixture was filtered to remove all solids and the filtrate was concentrated under reduced pressure. The residue was partitioned between water (50 mL) and CH₂Cl₂ (50 mL) and the aqueous layer was extracted with further CH₂Cl₂ (50 mL×2). The combined organics were dried over Na₂SO₄ and concentrated in vacuo. The crude residue was purified over silica gel (100 g) eluting with n-hexane followed by 25% ethyl acetate in n-hexane to afford (Z)-tert-butyl 4-bromo-3-fluorobut-2-enylcarbamate (7.00 g, 86%) as a colourless solid. ¹H-NMR (300 MHz; CDCl₃) δ ppm: 1.46 (9H, s), 3.85 (2H, dd, J 6.2, 6.2 Hz), 3.93 (2H, d, J 19.5 Hz), 4.66 (1H, br. s), 5.16 (1H, dt, J 34.0, 6.5 Hz).

Example 2

The following compound was prepared according to procedures E, F, G, H and I.

Preparation of (Z)-4-((2-((4-amino-2-fluorobut-2-en-1-yl)sulfonyl)phenoxy)methyl)-N,N-diisopropylbenzenesulfonamide hydrochloride (Compound 11)

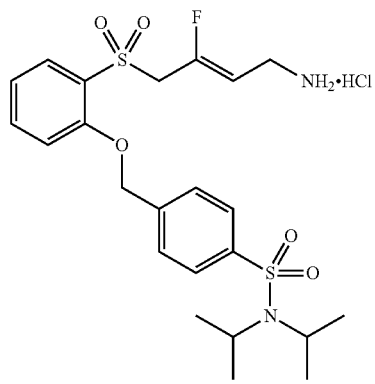

Procedure E: Preparation of 4-(bromomethyl)-N,N-diisopropylbenzenesulfonamide

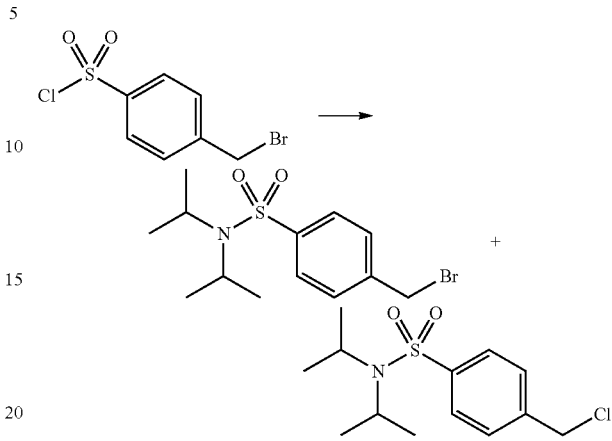

To a stirring solution of 4-(bromomethyl)benzenesulfonyl chloride (500 mg, 1.86 mmol) in CH₂Cl₂ (10 mL) at 0° C. was added diisopropylamine (0.65 mL, 4.63 mmol) dropwise. Following addition the resulting mixture was left to stir at this temperature for 30 min before allowing to warm to rt and stirring for a further 48 h. The reaction mixture was partitioned between aq. HCl (1 M, 20 mL) and CH₂Cl₂ (20 mL). The organic layer was washed with aq. HCl (1 M; 20 mL) and water (20 mL), dried over Na₂SO₄ and concentrated in vacuo to give the title compound (yellow oil, 190 mg) as a mixture with 4-(chloromethyl)-N,N-diisopropylbenzenesulfonamide, which was used as such in the next step.

Procedure F: Preparation of (Z)-tert-butyl (3-fluoro-4-((2-hydroxyphenyl)thio)but-2-en-1-yl)carbamate

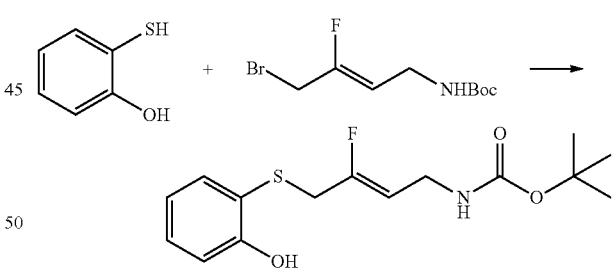

To a solution of 2-mercaptophenol (235 mg, 1.86 mmol) and (Z)-tert-butyl (4-bromo-3-fluorobut-2-en-1-yl)carbamate (500 mg, 1.86 mmol) in acetone (3 mL) at rt was added potassium carbonate (387 mg, 2.70 mmol) and the resulting solution was stirred at rt for 16 h. The reaction mixture was then partitioned between EtOAc (20 mL) and water (20 mL) and the phases separated. The aqueous phase was extracted with EtOAc (20 mL×2) and the organic phases then combined and washed (brine; 20 mL), dried (Na₂SO₄) and concentrated in vacuo to afford (Z)-tert-butyl (3-fluoro-4-((2-hydroxyphenyl)thio)but-2-en-1-yl)carbamate (580 mg, 99%) as a light yellow solid. ¹H-NMR (300 MHz; CDCl₃) δ ppm: 1.45 (9H, s), 3.31 (2H, d, J=19.7 Hz), 3.69 (2H, app. t, J=6.7 Hz), 4.47 (1H, dt, J=34.6, 7.2 Hz), 4.49 (1H, br. s), 6.67 (1H, s), 6.90 (1H, ddd, J=7.6, 7.6 1.3 Hz), 7.02 (1H, dd, J=8.2, 1.2 Hz), 7.31 (1H, ddd, J=8.2, 7.3, 1.6 Hz), 7.45 (1H, dd, J=7.7, 1.7 Hz).

Procedure G: Preparation of (Z)-tert-butyl (4-((2-((4-(N,N-diisopropylsulfamoyl)benzyl)oxy)phenyl)thio)-3-fluorobut-2-en-1-yl)carbamate

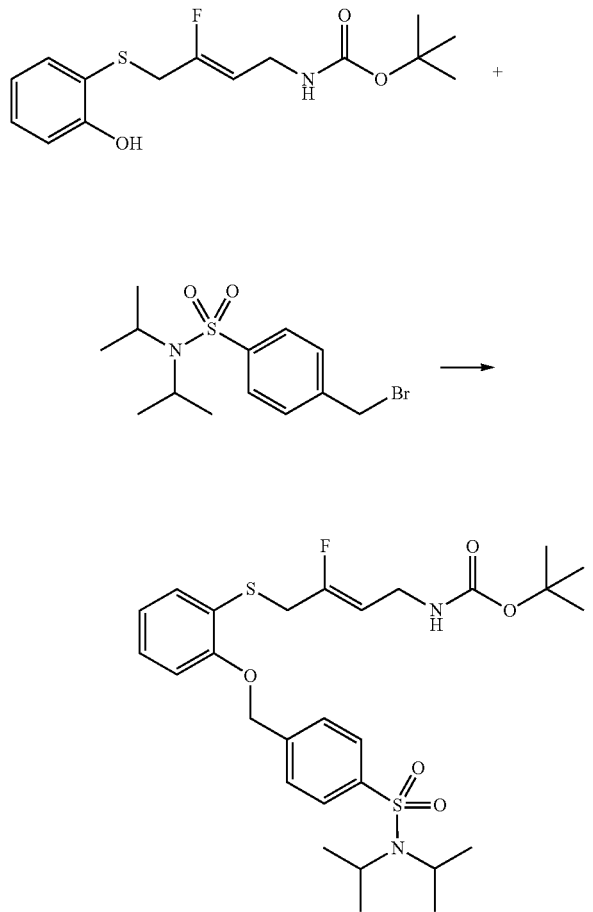

To a stirring solution of (Z)-tert-butyl (3-fluoro-4-((2-hydroxyphenyl)thio)but-2-en-1-yl)carbamate (100 mg, 0.32 mmol) and 4-(bromomethyl)-N,N-diisopropylbenzenesulfonamide (107 mg, 0.32 mmol) in DMF (1 mL) at rt was added potassium carbonate (66 mg, 0.48 mmol). The resulting suspension was stirred at this temperature for 16 h. The reaction mixture was then partitioned between EtOAc (10 mL) and water (10 mL) and the phases separated. The aqueous phase was extracted with EtOAc (10 mL×2) and the organic phases then combined and washed (sat. aq. NH₄Cl then brine), dried (Na₂SO₄) and concentrated in vacuo to afford (Z)-tert-butyl (4-((2-((4-(N,N-diisopropylsulfamoyl)benzyl)oxy)phenyl)thio)-3-fluorobut-2-en-1-yl)carbamate (180 mg, 99%) as a yellow gum that was used in the subsequent step without purification.

Procedure H: Preparation of (Z)-tert-butyl (4-((2-((4-(N,N-diisopropylsulfamoyl)benzyl)oxy)phenyl)sulfonyl)-3-fluorobut-2-en-1-yl)carbamate

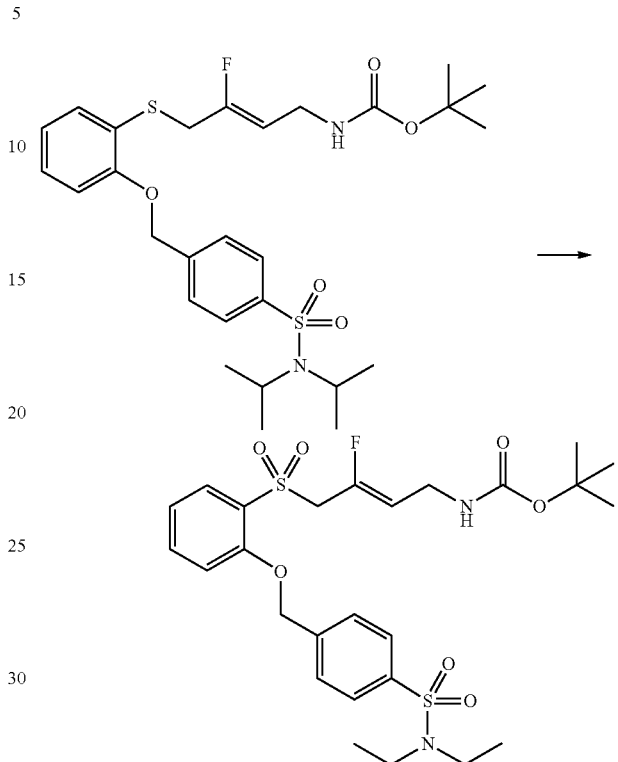

To a stirring suspension of (4-((2-((4-(N,N-diisopropylsulfamoyl)benzyl)oxy)phenyl)thio)-3-fluorobut-2-en-1-yl)carbamate (180 mg, 0.32 mmol) and sodium hydrogen carbonate (133 mg, 1.59 mmol) in CH₂Cl₂ (2 mL) and water (2 mL) at 0° C. was added 3-chloroperoxybenzoic acid (178 mg, 0.79 mmol) in three portions over 5 min. The resulting suspension was stirred at 0° C. for 2 hours before being diluted with sat. aq. NaHCO₃ (15 ml) and extracting with CH₂Cl₂ (10 mL). The aqueous phase was further extracted with CH₂Cl₂ (10 mL×2) and the organic phases combined, dried (Na₂SO₄) and concentrated in vacuo. The crude material was purified by flash column, eluting with 40% EtOAc/hexane then 2% MeOH in 50% EtOAc/hexane to afford (Z)-tert-butyl (4-((2-((4-(N,N-diisopropylsulfamoyl)benzyl)oxy)phenyl)sulfonyl)-3-fluorobut-2-en-1-yl)carbamate (160 mg, 84%) as a white solid. $^1$H-NMR (300 MHz; CDCl₃) δ ppm: 1.29 (12H, d, J=6.8 Hz), 1.43 (9H, s), 3.67-3.80 (3H, m), 4.15 (2H, d, J=18.9 Hz), 4.52 (1H, br. s), 4.93 (1H, dt, J=34.4, 6.9 Hz), 5.33 (2H, s), 7.09 (1H, d, J=8.0 Hz), 7.18 (1H, ddd, J=8.3, 7.8, 0.8 Hz), 7.63 (1H, ddd, J=8.4, 7.6, 1.7 Hz), 7.66 (2H, d, J=8.4), 7.93 (2H, d, J=8.5 Hz), 7.99 (1H, dd, J=7.9, 1.7 Hz). As a modification of this procedure for the preparation of further compounds, the oxidation was effected by slowly adding an aqueous solution of OXONE® (4 eq. in 1.2 mL H₂O per mmol OXONE®) to a solution of the sulfanyl ether starting material in MeOH:THF (1:1, ca. 3 mL each per mmol sulfanyl ether) at rt and allowed to react until LC-MS control indicated a high degree of conversion to the desired sulfone product. The mixture was then partitioned between excess saturated aqueous sodium meta- Procedure I: Preparation of (Z)-4-((2-((4-amino-2-fluorobut-2-en-1-yl)sulfonyl)phenoxy)methyl)-N,N-diisopropylbenzenesulfonamide hydrochloride (Compound 11)

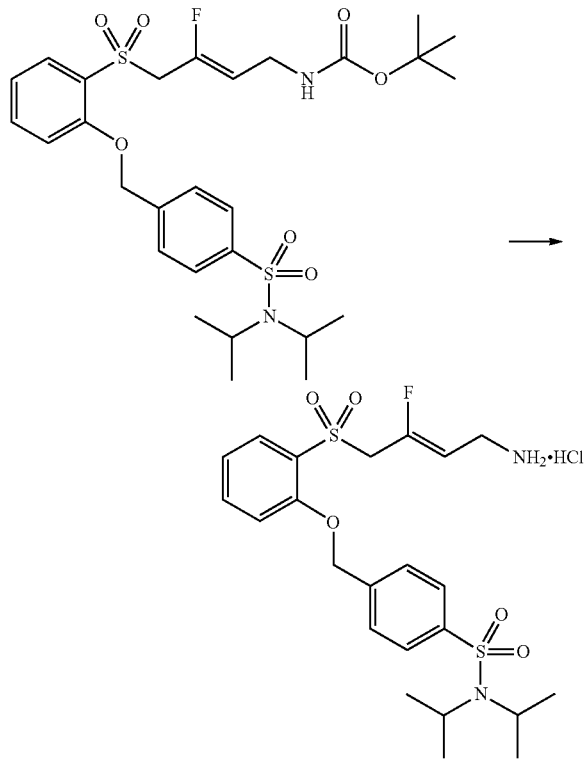

To a stirring solution of (Z)-tert-butyl (4-((2-((4-(N,N-diisopropylsulfamoyl)benzyl)oxy)phenyl)sulfonyl)-3-fluorobut-2-en-1-yl)carbamate (160 mg, 0.27 mmol) in MeOH (1 mL) at rt was added ethereal HCl (2 M; 4.00 mL, 8.00 mmol) and the resulting mixture was left to stir for 1 h. After this time a white solid precipitated which was collected by filtration and dried under high vacuum to give (Z)-4-((2-((4-amino-2-fluorobut-2-en-1-yl)sulfonyl)phenoxy)methyl)-N,N-diisopropylbenzene-sulfonamide hydrochloride (79 mg, 55%). White solid; m.p. 222-224° C.; $^1$H-NMR (300 MHz; CD$_3$OD) δ ppm: 1.27 (12H, d, J=6.8 Hz), 3.59 (2H, dd, J=7.4, 1.8 Hz), 3.79 (2H, hept, J=6.8 Hz), 4.45 (2H, d, J=19.2 Hz), 5.16 (1H, dt, J=32.8, 7.4 Hz), 5.46 (2H, s), 7.23 (1H, ddd, J=7.4, 7.4, 0.9 Hz), 7.38 (1H, d J=7.9 Hz), 7.74 (1H, ddd, J=8.5, 7.5, 1.7 Hz), 7.79 (2H, d, J=8.6 Hz), 7.91-7.95 (3H, m).

Example 3

The following compounds were prepared according to procedures E-I using the appropriately functionalised thiol starting material.

(Z)-4-((2-((4-amino-2-fluorobut-2-en-1-yl)sulfonyl)phenoxy)methyl)-N,N-dimethylbenzenesulfonamide hydrochloride (Compound 5)

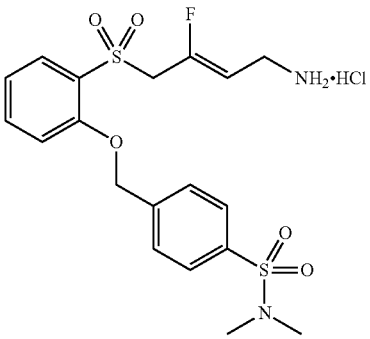

White solid; m.p. 235-236° C.; $^1$H-NMR (300 MHz; CD$_3$OD) δ ppm: 2.72 (6H, s), 3.60 (2H, dd, J=7.4, 1.7 Hz), 4.47 (2H, d, J=19.2 Hz), 5.18 (1H, dt, J=32.9, 7.4 Hz), 5.49 (2H, s), 7.24 (1H, ddd, J=7.9, 7.9, 0.9 Hz), 7.39 (1H, dd, J=8.5, 0.7 Hz), 7.76 (1H, ddd, J=8.4, 7.4, 1.7 Hz), 7.86 (4H, br. s), 7.95 (1H, dd, J=7.9, 1.8 Hz).

(Z)-4-((2-((4-amino-2-fluorobut-2-en-1-yl)sulfonyl)phenoxy)methyl)benzenesulfonamide hydrochloride (Compound 8)

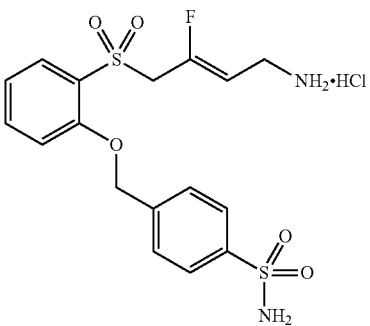

Off-white solid; m.p. 233-235° C.; $^1$H-NMR (300 MHz; CD$_3$OD) δ ppm: 3.59 (2H, dd, J=7.4, 1.6 Hz), 4.44 (2H, d, J=19.2 Hz), 5.14 (1H, dt, J=32.8, 7.4 Hz), 5.45 (2H, s), 7.23 (1H, dd, J=7.3, 7.3 Hz), 7.38 (1H, d, J=8.3 Hz), 7.74 (1H, ddd, J=8.6, 8.6, 1.7 Hz), 7.78 (2H, d, J=8.2 Hz), 7.94 (1H, dd, J=8.1, 1.6 Hz), 7.97 (2H, d, J=8.5 Hz).

77

(Z)-4-((3-((4-amino-2-fluorobut-2-en-1-yl)sulfonyl)phenoxy)methyl)-N,N-dimethylbenzenesulfonamide hydrochloride (Compound 9)

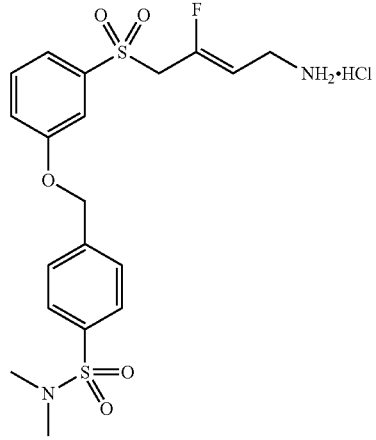

White solid; m.p. 211-213° C.; $^1$H-NMR (300 MHz; d$_6$-DMSO) δ ppm: 2.63 (6H, s), 3.48 (2H, br. s), 4.65 (2H, d, J=19.6 Hz), 5.17 (1H, dt, J=34.6, 7.2 Hz), 5.36 (2H, s), 7.45 (1H, ddd, J=8.1, 2.5, 1.0 Hz), 7.52-7.57 (2H, m), 7.63 (1H, dd, J=8.1, 8.1 Hz), 7.75 (2H, d, J=8.5 Hz), 7.81 (2H, d, J=8.6 Hz), 8.11 (3H, br. s).

(Z)-4-((4-((4-amino-2-fluorobut-2-en-1-yl)sulfonyl)phenoxy)methyl)-N,N-dimethylbenzenesulfonamide hydrochloride (Compound 10)

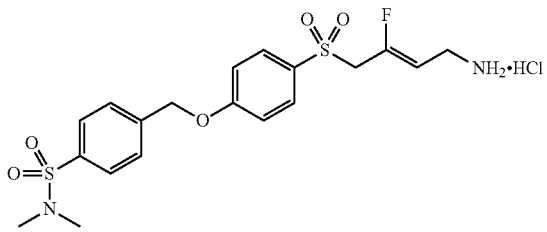

White solid; m.p. 216-218° C.; $^1$H-NMR (300 MHz; d$_6$-DMSO) δ ppm: 2.63 (6H, s), 3.48 (2H, br. s), 4.55 (2H, d, J=19.7 Hz), 5.12 (1H, dt, J=34.8, 7.1 Hz), 5.38 (2H, s), 7.29 (2H, dd, J=9.0, 1.9 Hz), 7.74 (2H, dd, J=8.5, 1.8 Hz), 7.81 (2H, dd, J=8.5, 1.9 Hz), 7.88 (2H, dd, J=8.9, 2.0 Hz), 8.03 (3H, br. s).

78

(Z)-4-((2-((4-amino-2-fluorobut-2-en-1-yl)sulfonyl)phenoxy)methyl)-N-isopropylbenzenesulfonamide hydrochloride (Compound 14)

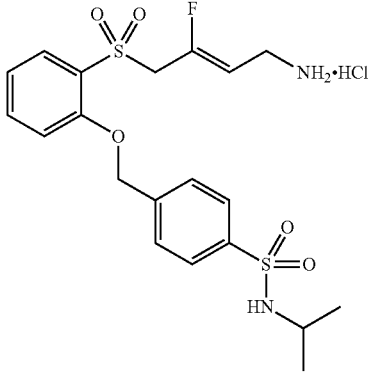

White solid; m.p. 248-250° C.; $^1$H-NMR (300 MHz; CD$_3$OD) δ ppm: 1.05 (6H, d, J=6.6 Hz), 3.40 (1H, hept, J=6.6 Hz), 3.59 (2H, app. d, J=7.3 Hz), 4.45 (2H, d, J=19.1 Hz), 5.16 (1H, dt, J=33.0, 7.4 Hz), 5.46 (2H, s), 7.23 (1H, ddd, J=8.0, 8.0, 1.0 Hz), 7.38 (1H, d, J=8.1 Hz), 7.74 (1H, ddd, J=8.4, 7.4, 1.8 Hz), 7.80 (2H, d, J=8.7 Hz), 7.91-7.95 (3H, m).

Example 4

The following compound was prepared according to procedures F—I using the appropriate thiol starting material.

(Z)-4-((2-(benzyloxy)phenyl)sulfonyl)-3-fluorobut-2-en-1-amine hydrochloride (Compound 7)

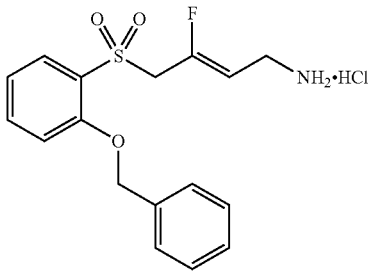

White solid; m.p. 205-207° C.; $^1$H-NMR (300 MHz; CD$_3$OD) δ ppm: 3.57 (2H, app. d, J=7.0 Hz), 4.44 (2H, d, J=19.1 Hz), 5.14 (1H, dt, J=32.8, 7.3 Hz), 5.36 (2H, s), 7.20 (1H, dd, J=7.4, 0.9 Hz), 7.35-7.46 (4H, m), 7.55-7.60 (2H, m), 7.73 (1H, ddd, J=8.5, 7.4, 1.7 Hz), 7.92 (1H, dd, J=7.9, 1.7 Hz).

Example 5

The following compounds were prepared according to procedures F, H and I using the appropriately functionalised thiol starting material.

(Z)-4-((3,5-bis(trifluoromethyl)phenyl)sulfonyl)-3-fluorobut-2-en-1-amine hydrochloride (Compound 2)

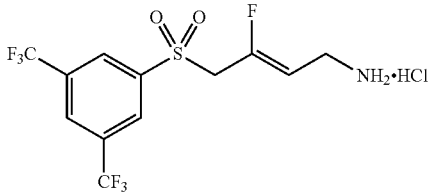

White solid; m.p. 217-220° C.; ¹H-NMR (300 MHz; d₆-DMSO) δ ppm: 3.48 (2H. app. d, J=7.1 Hz), 4.96 (2H, d, J=19.6 Hz), 5.19 (1H, dt, J=34.8, 7.2 Hz), 8.10 (3H, br. s), 8.55 (2H, s), 8.67 (1H, s).

(Z)-4-(biphenyl-2-ylsulfonyl)-3-fluorobut-2-en-1-amine hydrochloride (Compound 20)

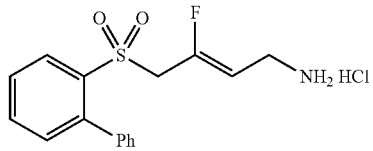

White solid; m.p. 170° C.; ¹H NMR (300 MHz, CD₃OD) δ ppm: 8.18 (dd, J=8.0, 1.4 Hz, 1H), 7.81 (td, J=7.5, 1.4 Hz, 1H), 7.68 (td, J=7.6, 1.6 Hz, 1H), 7.52-7.44 (m, 6H), 5.03 (dt, J=32.9, 7.4 Hz, 1H), 3.83 (d, J=18.9 Hz, 2H), 3.56 (dd, J=7.4, 1.3 Hz, 2H).

(Z)-3-fluoro-4-(2-isopropylphenylsulfonyl)but-2-en-1-amine hydrochloride (Compound 21)

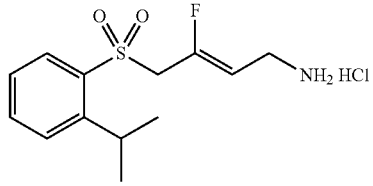

White solid; m.p. 205-215° C.; ¹H NMR (300 MHz, CD₃OD) δ ppm: 8.00-7.95 (m, 1H), 7.77-7.67 (m, 2H), 7.48-7.41 (m, 1H), 5.25 (dt, J=32.8, 7.4 Hz, 1H), 4.34 (d, J=19.2 Hz, 2H), 3.88 (hept, J=6.9 Hz, 1H), 3.63 (dd, J=7.5, 1.9 Hz, 2H), 1.36 (d, J=6.8 Hz, 6H).

(Z)-3-fluoro-4-(2-methoxyphenylsulfonyl)but-2-en-1-amine hydrochloride (Compound 22)

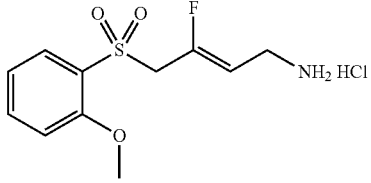

White solid; m.p. 228-221° C.; ¹H NMR (300 MHz, CD₃OD) δ ppm: 7.89 (dd, J=7.9, 1.7 Hz, 1H), 7.75 (ddd, J=8.4, 7.4, 1.8 Hz, 1H), 7.32 (dd, J=8.5, 0.9 Hz, 1H), 7.19 (td, J=7.6, 1.0 Hz, 1H), 5.23 (dt, J=32.8, 7.4 Hz, 1H), 5.17 (t, J=7.4 Hz, 0H), 4.48 (d, J=19.3 Hz, 2H), 4.05 (s, 3H), 3.61 (dd, J=7.4, 1.9 Hz, 2H).

(Z)-3-fluoro-4-(naphthalen-1-ylsulfonyl)but-2-en-1-amine hydrochloride (Compound 23)

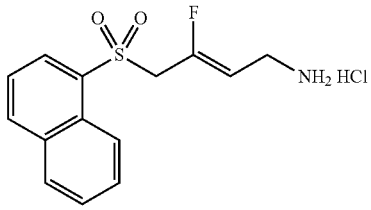

White solid; m.p. 230-240° C.; ¹H NMR (300 MHz, CD₃OD) δ ppm: 8.76 (ddd, J=8.7, 1.2, 0.6 Hz, 1H), 8.33 (d, J=7.8 Hz, 2H), 8.13 (ddd, J=8.2, 1.5, 0.8 Hz, 1H), 7.81 (ddd, J=8.6, 6.9, 1.5 Hz, 1H), 7.72 (td, J=8.0, 1.9 Hz, 2H), 5.13 (dt, J=32.7, 7.4 Hz, 1H), 4.49 (d, J=19.2 Hz, 2H), 3.57 (dd, J=7.4, 1.9 Hz, 2H).

(Z)-3-fluoro-4-(naphthalen-2-ylsulfonyl)but-2-en-1-amine hydrochloride (Compound 24)

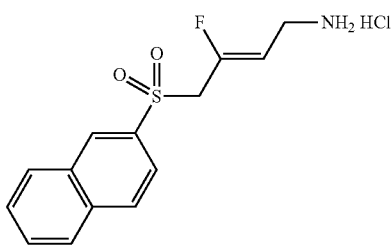

White solid; m.p. 215-220° C.; ¹H NMR (300 MHz, CD₃OD) δ ppm: 8.60 (d, J=1.9 Hz, 1H), 8.18-8.11 (m, 2H), 8.06 (dd, J=8.2, 1.4 Hz, 1H), 7.95 (dd, J=8.7, 1.9 Hz, 1H), 7.81-7.68 (m, 2H), 5.19 (dt, J=32.8, 7.4 Hz, 1H), 4.46 (d, J=19.2 Hz, 2H), 3.63 (dt, J=7.4, 1.3 Hz, 2H).

81

(Z)-4-(2,4-dichlorophenylsulfonyl)-3-fluorobut-2-en-1-amine hydrochloride (Compound 25)

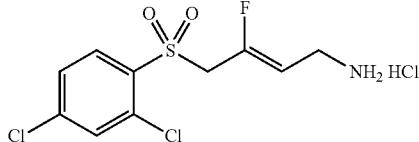

White solid; m.p. 220° C.; ¹H NMR (300 MHz, CD₃OD) δ ppm: 8.10 (d, J=8.6 Hz, 1H), 7.85 (d, J=2.0 Hz, 1H), 7.66 (dd, J=8.6, 2.0 Hz, 1H), 5.28 (dt, J=32.9, 7.4 Hz, 1H), 4.60 (d, J=19.1 Hz, 2H), 3.63 (ddd, J=7.4, 2.0, 0.6 Hz, 2H).

(Z)-4-(3-chlorophenylsulfonyl)-3-fluorobut-2-en-1-amine hydrochloride (Compound 26)

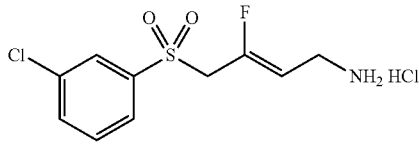

White solid; m.p. 225-235° C.; ¹H NMR (300 MHz, CD₃OD) δ ppm: 8.00 (t, J=1.9 Hz, 1H), 7.92 (ddd, J=7.8, 1.8, 1.1 Hz, 1H), 7.82 (ddd, J=8.1, 2.1, 1.1 Hz, 1H), 7.68 (d, J=8.3 Hz, 1H), 5.22 (dt, J=32.9, 7.4 Hz, 1H), 4.44 (d, J=19.1 Hz, 2H), 3.65 (dd, J=7.4, 1.9 Hz, 2H)

(Z)-4-(4-chlorophenylsulfonyl)-3-fluorobut-2-en-1-amine hydrochloride (Compound 27)

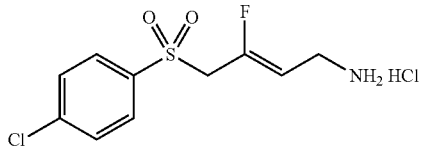

White solid; m.p. 240° C.; ¹H NMR (300 MHz, CD₃OD) δ ppm: 7.96 (dt, J=8.8, 2.3 Hz, 2H), 7.71 (dt, J=8.3, 1.9 Hz, 2H), 5.20 (dt, J=32.9, 7.4 Hz, 1H), 4.40 (d, J=19.1 Hz, 2H), 3.65 (dd, J=7.4, 1.9 Hz, 2H).

(Z)-4-(3,5-dichlorophenylsulfonyl)-3-fluorobut-2-en-1-amine hydrochloride (Compound 28)

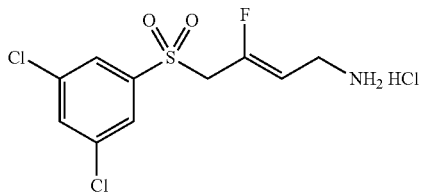

82

White solid; m.p. 250° C.; ¹H NMR (300 MHz, CD₃OD) δ ppm: 7.97 (d, J=1.8 Hz, 2H), 7.93 (t, J=1.9 Hz, 1H), 5.27 (dt, J=33.0, 7.4 Hz, 1H), 4.50 (d, J=19.0 Hz, 2H), 3.67 (dd, J=7.4, 2.0 Hz, 2H).

(Z)-3-fluoro-4-(pyridin-4-ylsulfonyl)but-2-en-1-amine dihydrochloride (Compound 29)

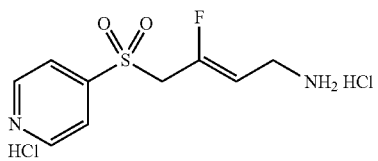

White solid; m.p. 162-164° C.; ¹H NMR (300 MHz, CD₃OD) δ ppm: 9.07 (dd, J=4.9, 1.7 Hz, 2H), 8.22 (dd, J=4.6, 1.6 Hz, 2H), 5.31 (dt, J=33.1, 7.4 Hz, 1H), 4.63 (d, J=19.0 Hz, 2H), 3.67 (d, J=7.4 Hz, 2H)

(Z)-3-fluoro-4-(quinolin-2-ylsulfonyl)but-2-en-1-amine dihydrochloride (Compound 32)

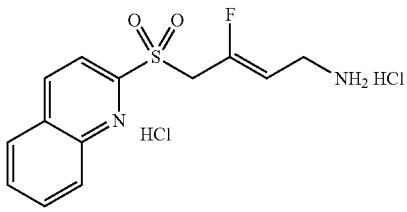

White solid; m.p. 203-205° C.; ¹H NMR (300 MHz, d6 DMSO) δ ppm: 8.82 (d, J=8.6 Hz, 1H), 8.29-8.20 (m, 2H), 8.16 (d, J=8.5 Hz, 1H), 8.12-7.93 (m, 3H), 7.92-7.83 (m, 1H), 5.26 (dt, J=34.8, 7.2 Hz, 1H), 4.92 (d, J=19.6 Hz, 2H), 3.48 (s, 2H).

(Z)-3-fluoro-4-(quinolin-8-ylsulfonyl)but-2-en-1-amine dihydrochloride (Compound 33)

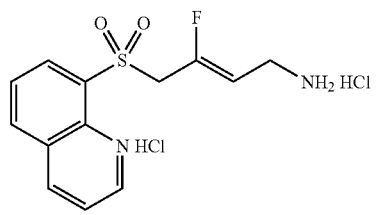

White solid; m.p. 150-153° C.; ¹H NMR (300 MHz, CD₃OD) δ ppm: 9.18 (d, J=4.7 Hz, 1H), 8.70 (dd, J=8.4, 2.6 Hz, 1H), 8.57 (d, J=7.4 Hz, 1H), 8.45 (d, J=8.5 Hz, 1H), 7.99-7.68 (m, 2H), 5.22 (dt, J=32.9, 7.4 Hz, 1H), 5.00 (d, J=19.4 Hz, 2H), 3.60 (d, J=7.7 Hz, 2H); LCMS: for $C_{13}H_{13}FN_2O_2S$ calculated 280.1, found 281.1 [M+1]⁺.

(Z)-3-fluoro-4-(2-fluorophenylsulfonyl)but-2-en-1-amine hydrochloride (Compound 37)

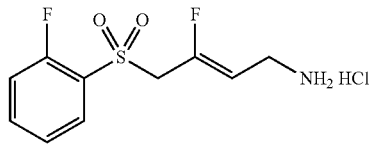

Off-white solid; $^1$H NMR (300 MHz, CD$_3$OD) δ ppm: 8.01-7.90 (m, 1H), 7.89-7.77 (m, 1H), 7.53-7.39 (m, 2H), 5.29 (dt, J=32.8, 7.4 Hz, 1H), 4.49 (d, J=19.1 Hz, 2H), 3.63 (dd, J=7.4, 1.9 Hz, 2H).

(Z)-3-fluoro-4-(3-fluorophenylsulfonyl)but-2-en-1-amine hydrochloride (Compound 38)

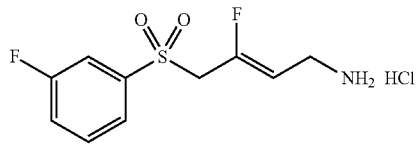 [SMILES: NC/C=C(\F)CS(=O)(=O)c1cccc(F)c1 ; Cl]

Off-white solid; $^1$H NMR (300 MHz, CD$_3$OD) δ ppm: 7.83 (ddd, J=7.8, 1.7, 1.1 Hz, 1H), 7.81-7.66 (m, 2H), 7.56 (tdd, J=8.4, 2.6, 1.1 Hz, 1H), 5.23 (dt, J=32.9, 7.4 Hz, 1H), 4.44 (d, J=19.1 Hz, 2H), 3.65 (dd, J=7.4, 1.9 Hz, 2H).

(Z)-3-fluoro-4-(4-fluorophenylsulfonyl)but-2-en-1-amine hydrochloride (Compound 39)

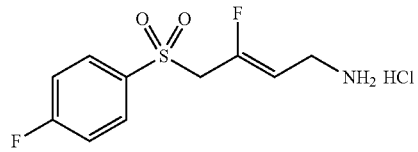 [SMILES: NC/C=C(\F)CS(=O)(=O)c1ccc(F)cc1 ; Cl]

Off-white solid; $^1$H NMR (300 MHz, CD$_3$OD) δ ppm: 8.13-7.99 (m, 2H), 7.51-7.34 (m, 2H), 5.19 (dt, J=32.8, 7.5 Hz, 1H), 4.39 (d, J=19.1 Hz, 2H), 3.62 (ddt, J=7.4, 1.9, 0.6 Hz, 2H).

(Z)-3-fluoro-4-(o-tolylsulfonyl)but-2-en-1-amine hydrochloride (Compound 40)

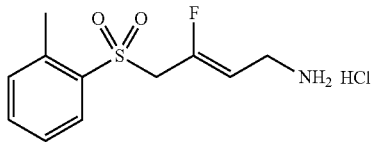 [SMILES: Cc1ccccc1S(=O)(=O)C/C(F)=C/CN ; Cl]

Off-white solid; $^1$H NMR (300 MHz, CD$_3$OD) δ ppm: 7.99 (dd, J=7.6, 1.1 Hz, 1H), 7.71-7.59 (m, 1H), 7.53-7.39 (m, 2H), 5.22 (dt, J=32.8, 7.4 Hz, 1H), 4.35 (dd, J=19.3, 0.5 Hz, 2H), 3.63 (ddt, J=7.4, 2.0, 0.6 Hz, 2H), 2.73 (s, 3H).

(Z)-3-fluoro-4-(m-tolylsulfonyl)but-2-en-1-amine hydrochloride (Compound 41)

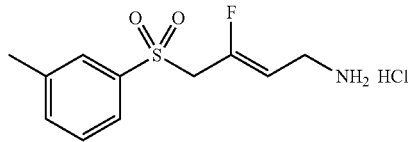 [SMILES: Cc1cccc(S(=O)(=O)C/C(F)=C/CN)c1 ; Cl]

Off-white solid; $^1$H NMR (300 MHz, CD$_3$OD) δ ppm: 7.84-7.72 (m, 2H), 7.67-7.49 (m, 2H), 5.44-5.08 (m, 1H), 4.35 (dq, J=19.1, 0.5 Hz, 2H), 3.64 (ddt, J=7.4, 2.0, 0.6 Hz, 2H), 2.56-2.38 (m, 3H).

(Z)-3-fluoro-4-(p-tolylsulfonyl)but-2-en-1-amine hydrochloride (Compound 42)

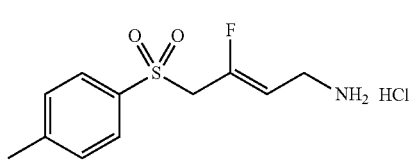 [SMILES: Cc1ccc(S(=O)(=O)C/C(F)=C/CN)cc1 ; Cl]

Off-white solid; $^1$H NMR (300 MHz, CD$_3$OD) δ ppm: 7.88-7.82 (m, 2H), 7.54-7.45 (m, 2H), 5.17 (dt, J=32.8, 7.4 Hz, 1H), 4.32 (dd, J=19.2, 0.5 Hz, 2H), 3.64 (ddt, J=7.4, 2.0, 0.6 Hz, 2H), 2.49 (s, 3H)

(Z)-3-fluoro-4-((3-fluoroquinolin-8-yl)sulfonyl)but-2-en-1-amine dihydrochloride (Compound 51)

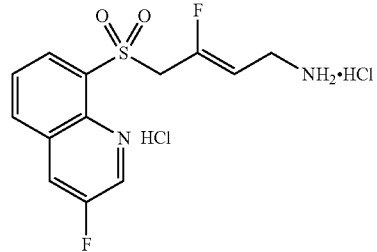

$^1$H NMR (300 MHz, CD$_3$OD) δ ppm: 9.09 (dd, J=2.9, 0.6 Hz, 1H), 8.49 (ddd, J=7.4, 1.4, 0.4 Hz, 1H), 8.38 (ddd, J=8.3, 1.4, 0.4 Hz, 1H), 8.31 (dd, J=8.8, 2.9 Hz, 1H), 7.87 (ddd, J=8.3, 7.3, 0.8 Hz, 1H), 5.20 (dt, J=32.9, 7.4 Hz, 1H), 4.99 (d, J=19.3 Hz, 2H), 3.59 (d, J=7.4 Hz, 2H).

Example 6

The following compounds were prepared according to procedures F, J, H and I using the appropriately functionalised thiol starting material.

Procedure J: Preparation of (Z)-tert-butyl (3-fluoro-4-((4-(methylsulfonyl)phenyl)sulfonyl)but-2-en-1-yl)carbamate

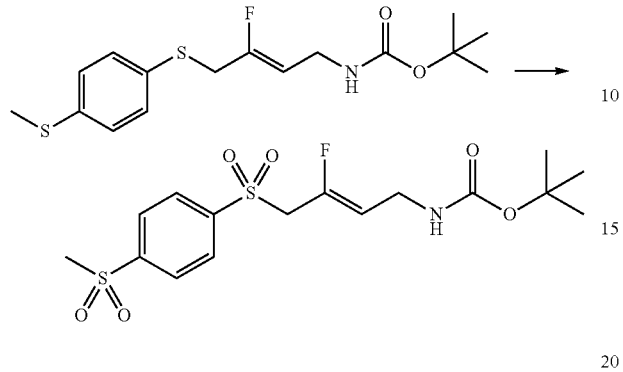

To a stirring suspension of (Z)-tert-butyl (3-fluoro-4-((4-(methylthio)phenyl)thio)but-2-en-1-yl)carbamate (120 mg, 0.35 mmol) and sodium hydrogen carbonate (150 mg, 1.79 mmol) in CH$_2$Cl$_2$ (4 mL) and water (2 mL) at 0° C. was added 3-chloroperoxybenzoic acid (378 mg, 2.19 mmol) in three portions over 5 min. The resulting suspension was stirred at 0° C. for 1.5 hours before being diluted with aq. NaOH (2 M; 1 ml), water (10 mL) and CH$_2$Cl$_2$. The phases were then separated and the aqueous phase extracted with CH$_2$Cl$_2$ (10 mL×2). The organic phases were combined, dried (Na$_2$SO$_4$) and concentrated in vacuo. The crude material was purified by flash column, eluting with 30% EtOAc/hexane to afford (Z)-tert-butyl (3-fluoro-4-((4-(methylsulfonyl)phenyl)sulfonyl)but-2-en-1-yl)carbamate (17 mg, 12%) as a white solid. $^1$H-NMR (300 MHz; d$_6$-DMSO) δ ppm: 1.37 (9H, s), 3.33 (3H, s), 3.54 (2H, app. t, J=5.6 Hz), 4.62 (2H, d, J=19.4 Hz), 4.93 (1H, dt, J=36.4, 6.8 Hz), 7.05 (1H, t, J=5.8 Hz), 8.15 (2H, dd, J=8.7, 2.1 Hz), 8.21 (2H, dd, J=8.7, 2.1 Hz).

(Z)-4-((3,5-bis(trifluoromethyl)phenyl)sulfonyl)-3-fluorobut-2-en-1-amine trifluoroacetate (Compound 3)

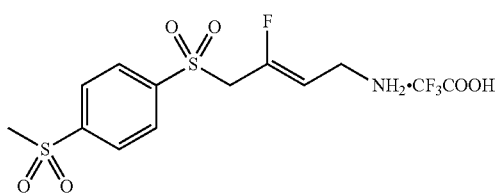

White solid; m.p. 155-157° C.; $^1$H-NMR (300 MHz; d$_6$-DMSO) δ ppm: 3.35 (3H, s), 3.50 (2H, app. d, J=6.7 Hz), 4.80 (2H, d, J=19.7 Hz), 5.12 (1H, dt, J=34.7, 7.3 Hz), 7.88 (3H, br. s), 8.19 (2H, dd, J=8.8, 2.5 Hz), 8.24 (2H, dd, J=8.9, 2.4 Hz).

Example 7

The following compound was prepared according to procedures K, L and M then F, N, H and I.

Preparation of (Z)-4-(2-((4-amino-2-fluorobut-2-en-1-yl)sulfonyl)phenoxy)-N,N-dimethylbenzene-sulfonamide hydrochloride (Compound 6)

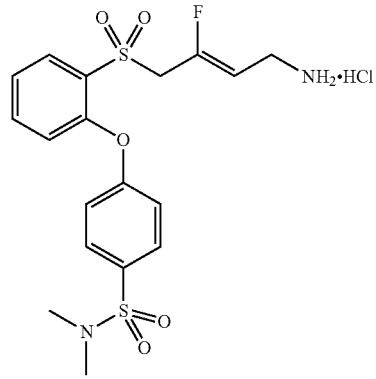

Procedure K: Preparation of 4-bromo-N,N-dimethylbenzenesulfonamide

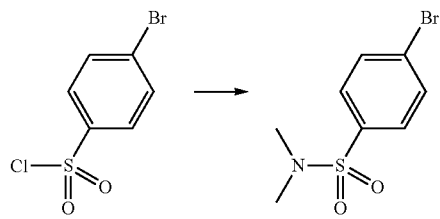

To a stirring solution of dimethylamine (12 mL, 40% w/w aqueous solution) in THF (20 mL) at 5° C. was added a solution of 4-bromobenzenesulfonyl chloride (5.00 g, 19.6 mmol) in THF (10 mL) over 5 min. Following addition, the mixture was left to stir at rt for 1 hour. The reaction mixture was then concentrated in vacuo and the resulting residue partitioned between water (25 mL) and CH$_2$Cl$_2$ (20 mL) and the aqueous layer extracted with further CH$_2$Cl$_2$ (20 mL×2). The combined organics were dried over Na$_2$SO$_4$ and concentrated in vacuo to afford 4-bromo-N,N-dimethylbenzenesulfonamide (4.83 g, 93%) as a white solid. $^1$H-NMR (300 MHz; CDCl$_3$) δ ppm: 2.74 (6H, s), 7.64-7.73 (4H, m).

Procedure L: Preparation of N,N-dimethyl-4-(4,4,5,5-tetramethyl-1,3,2-dioxaborolan-2-yl)benzenesulfonamide

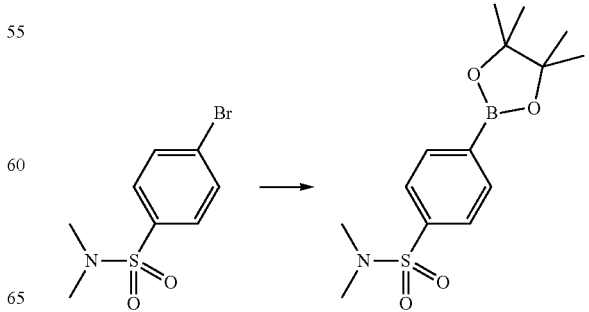

A stirring suspension of 4-bromo-N,N-dimethyl-benzene-sulfonamide (1.00 g, 3.79 mmol) 4,4,5,5-tetramethyl-2-(4,4,5,5-tetramethyl-1,3,2-dioxaborolan-2-yl)-1,3,2-dioxaborolane (1.15 g, 4.54 mmol) and potassium acetate (1.11 g, 11.4 mmol) in 1,4-dioxane (25 mL) was flushed with nitrogen for 15 min before the addition of 1,1'-bis(diphenylphosphino)ferrocene-palladium(II)dichloride dichloromethane complex (155 mg, 0.19 mmol). The resulting suspension was heated at 80° C. under nitrogen for 16 hours. The mixture was cooled to rt, partitioned between EtOAc (40 mL) and water (30 mL) and filtered through Celite. The organic layer was separated and the aqueous layer was extracted with further EtOAc (20 mL×2). The combined organics were then washed with brine, dried ($Na_2SO_4$) and concentrated in vacuo to afford N,N-dimethyl-4-(4,4,5,5-tetramethyl-1,3,2-dioxaborolan-2-yl)benzenesulfonamide (1.60 g, 68%) as a grey solid. $^1$H-NMR (300 MHz; $CDCl_3$) δ ppm: 1.38 (12H, s), 2.71 (6H, s), 7.77 (2H, dd, J=8.4, 1.0 Hz), 7.98 (2H, dd, J=8.4, 0.9 Hz).

Procedure M: Preparation of (4-(N,N-dimethylsulfamoyl)phenyl)boronic acid

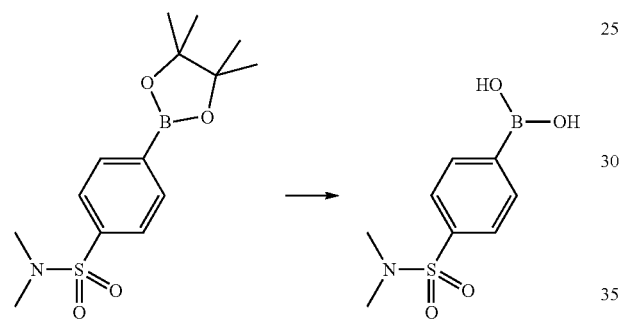

To a stirring solution of N,N-dimethyl-4-(4,4,5,5-tetramethyl-1,3,2-dioxaborolan-2-yl)benzenesulfonamide (1.00 g, 2.25 mmol) in THF (20 mL) and water (5 mL) at 0° C. was added sodium periodate (2.06 g, 9.64 mmol). The mixture was stirred for 5 min at this temperature and then allowed to warm to rt and stirred for a further 30 min. Aqueous HCl (1 M; 1.57 mL, 1.57 mmol) was added and the resulting mixture stirred at rt for a further 1 h. The reaction mixture was diluted with water (30 mL) and extracted with EtOAc (20 mL×3). The organic layers were then combined and washed (brine), dried ($Na_2SO_4$) and concentrated in vacuo. The crude material was purified by flash column, eluting with 50% EtOAc/hexane followed by 10% MeOH in 50% EtOAc/hexane to afford (4-(N,N-dimethylsulfamoyl)phenyl)boronic acid (470 mg, 91%) as a brown solid. $^1$H-NMR (300 MHz; $CD_3OD$) δ ppm: 2.69 (6H, s), 7.75 (2H, d, J=8.2 Hz), 7.88-7.98 (2H, m).

Procedure N: Preparation of (Z)-tert-butyl (4-((2-(4-(N,N-dimethylsulfamoyl)phenoxy)phenyl)thio)-3-fluorobut-2-en-1-yl)carbamate

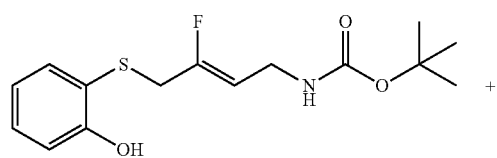

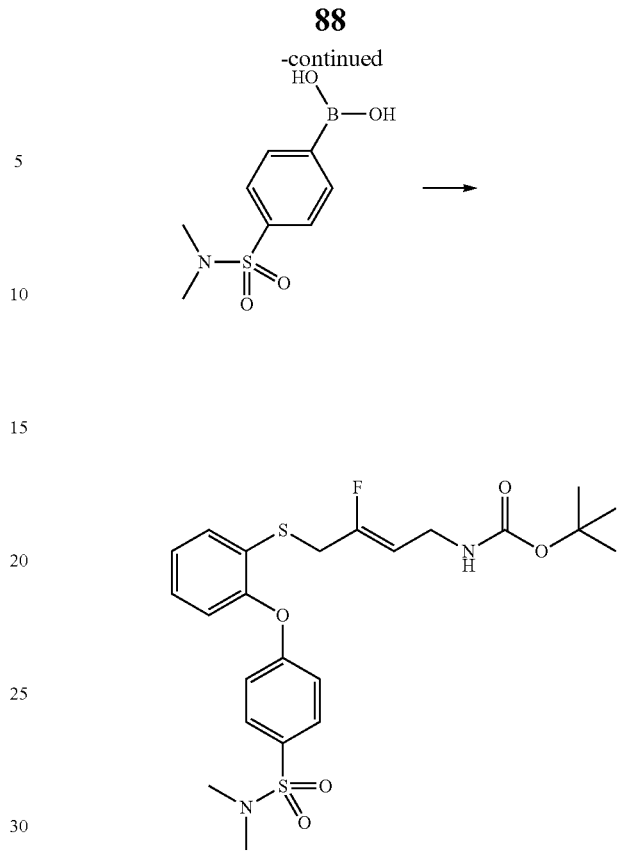

To a stirring solution of (Z)-tert-butyl (3-fluoro-4-((2-hydroxyphenyl)thio)but-2-en-1-yl)carbamate (150 mg, 0.48 mmol), (4-(N,N-dimethylsulfamoyl)phenyl)boronic acid (219 mg, 0.96 mmol) and pyridine (0.19 mL, 2.39 mmol) in $CH_2Cl_2$ (6 mL) at rt was added copper (II) acetate (87 mg, 0.48 mmol) in one lot. The resulting mixture was stirred at this temperature for 16 h. After this time the reaction was diluted by the addition of $CH_2Cl_2$ (30 mL), filtered through Celite and washed with aq. HCl (1 M; 20 mL) followed by sat. aq. $NaHCO_3$ (20 mL) and brine (20 mL). The organic phase was then dried ($Na_2SO_4$) and concentrated in vacuo. The crude material was purified by flash column, eluting with 25% EtOAc/hexane to afford (Z)-tert-butyl (4-((2-(4-(N,N-dimethylsulfamoyl)phenoxy)phenyl)thio)-3-fluorobut-2-en-1-yl)carbamate (80 mg, 34%) as a yellow oil. $^1$H-NMR (300 MHz; $CDCl_3$) δ ppm: 1.45 (9H, s), 2.73 (6H, s), 3.55 (2H, d, J=17.1 Hz), 3.73 (2H, app. t, J=5.6 Hz), 4.46 (1H, br. s), 4.80 (1H, dt, J=34.8, 6.8 Hz), 7.02 (2H, d, J=8.7 Hz), 7.06 (1H, dd, J=8.2, 1.0 Hz), 7.24 (1H, ddd, J=7.5, 7.5, 1.1 Hz), 7.35 (1H, ddd, J=7.6, 7.6, 1.6 Hz), 7.52 (1H, dd, J=7.7, 1.5 Hz), 7.75 (2H, d, J=8.6 Hz).

(Z)-4-(2-((4-amino-2-fluorobut-2-en-1-yl)sulfonyl)phenoxy)-N,N-dimethylbenzenesulfonamide hydrochloride (Compound 6)

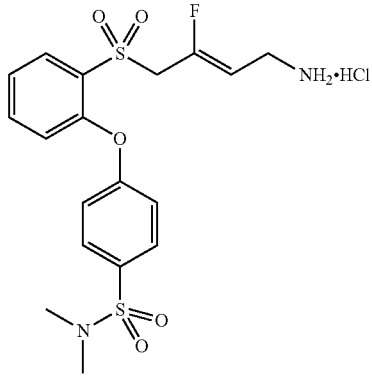

White solid; m.p. 153-156° C.; $^1$H-NMR (300 MHz; CD$_3$OD) δ ppm: 2.73 (6H, s), 3.64 (2H, app. d, J=6.9 Hz), 4.57 (2H, d, J=19.1 Hz), 5.30 (1H, dt, J=32.8, 7.3 Hz), 7.25 (1H, dd, J=8.3, 0.7 Hz), 7.30 (2H, dd, J=8.9, 2.0 Hz), 7.49 (1H, ddd, J=7.9, 7.9, 1.0 Hz), 7.81 (1H, ddd, J=7.8, 8.3, 1.7 Hz), 7.86 (2H, dd, J=8.6, 2.0 Hz), 8.07 (1H, dd, J=7.9, 1.6 Hz).

Example 8

The following compound was prepared according to procedures K, L, M, N, H and I.

(Z)-4-(3-(4-amino-2-fluorobut-2-enylsulfonyl)phenoxy)-N,N-dimethylbenzenesulfonamide hydrochloride (Compound 16)

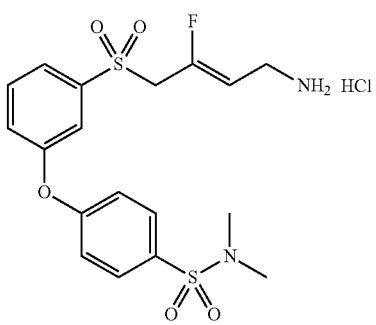 [SMILES: CN(C)S(=O)(=O)c1ccc(Oc2cccc(S(=O)(=O)C/C(F)=C/CN)c2)cc1 ; Cl]

White solid; 1H NMR (300 MHz, CD$_3$OD) δ ppm: 7.89-7.82 (m, 3H), 7.76 (td, J=8.0, 0.5 Hz, 1H), 7.68 (t, J=2.4, 1.7 Hz, 1H), 7.53 (ddd, J=8.1, 2.5, 1.1 Hz, 1H), 7.29-7.22 (m, 2H), 5.28 (dt, J=33.2, 7.4 Hz, 1H), 4.90 (s, 6H), 4.43 (d, J=19.1 Hz, 2H), 3.65 (dd, J=7.4, 1.9 Hz, 2H).

(Z)-3-(3-(4-amino-2-fluorobut-2-enylsulfonyl)phenoxy)-N,N-dimethylbenzenesulfonamide hydrochloride (Compound 17)

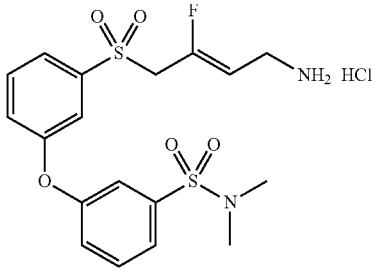 [SMILES: CN(C)S(=O)(=O)c1cccc(Oc2cccc(S(=O)(=O)C/C(F)=C/CN)c2)c1 ; Cl]

White solid; m.p. 220° C.; $^1$H NMR (300 MHz, CD$_3$OD) δ ppm: 7.81 (ddd, J=7.8, 1.7, 1.2 Hz, 1H), 7.77-7.69 (m, 2H), 7.66-7.59 (m, 2H), 7.50 (ddd, J=8.0, 2.5, 1.2 Hz, 1H), 7.46-7.38 (m, 2H), 5.24 (dt, J=32.9, 7.4 Hz, 1H), 4.90 (s, 6H), 4.41 (d, J=19.1 Hz, 2H), 3.65 (dd, J=7.4, 1.9 Hz, 2H).

(Z)-3-(2-(4-amino-2-fluorobut-2-enylsulfonyl)phenoxy)-N,N-dimethylbenzenesulfonamide hydrochloride (Compound 18)

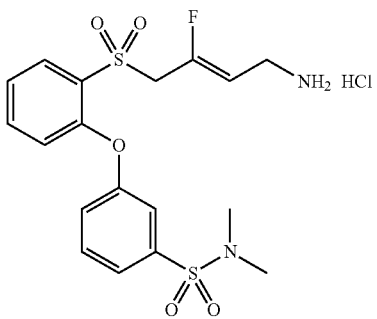 [SMILES: CN(C)S(=O)(=O)c1cccc(Oc2ccccc2S(=O)(=O)C/C(F)=C/CN)c1 ; Cl]

White solid; m.p. 205° C.; $^1$H NMR (300 MHz, CD$_3$OD) δ ppm: 8.06 (ddd, J=7.9, 1.7, 0.3 Hz, 1H), 7.83-7.73 (m, 1H), 7.70 (dd, J=7.7, 0.7 Hz, 1H), 7.65 (dt, J=7.8, 1.4 Hz, 1H), 7.51-7.42 (m, 3H), 7.20 (dd, J=8.3, 1.0 Hz, 1H), 5.31 (dt, J=33.0, 7.4 Hz, 1H), 4.90 (s, 6H), 4.60 (d, J=19.2 Hz, 2H), 3.64 (dd, J=7.4, 1.9 Hz, 2H).

Example 9

The following compound was prepared according to procedures O and P then F, Q, H and I.

Preparation of (Z)-2-((4-amino-2-fluorobut-2-en-1-yl)sulfonyl)-N-(4-(N,N-diisopropylsulfamoyl)-phenyl)benzamide hydrochloride (Compound 15)

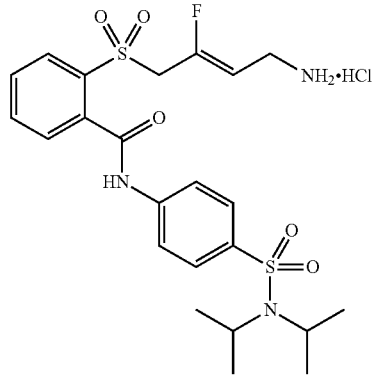

Procedure O: Preparation of N,N-diisopropyl-4-nitrobenzenesulfonamide

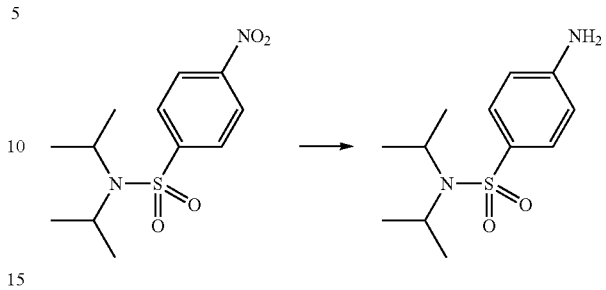

To a stirring solution of diisopropylamine (3.16 mL, 22.6 mmol) in THF (10 mL) at 0-5° C. was added a solution of 4-nitrobenzenesulfonyl chloride (2.00 g, 9.02 mmol) in THF (5 mL) over 5 min. Following addition, the mixture was left to stir at rt for 16 hours. The reaction mixture was then concentrated in vacuo and the resulting residue was partitioned between water (25 mL) and $CH_2Cl_2$ (20 mL). The phases were separated and the aqueous layer was extracted with further $CH_2Cl_2$ (20 mL×2). The combined organics were then dried over $Na_2SO_4$ and concentrated in vacuo. The crude material was purified by flash column, eluting with 20% EtOAc/hexane to afford N,N-diisopropyl-4-nitrobenzenesulfonamide (285 mg, 11% yield) as a yellow solid. $^1$H-NMR (300 MHz; CDCl$_3$) δ ppm: 1.30 (12H, d, J=6.7 Hz), 3.79 (1H, hept, J=6.9 Hz), 8.07 (2H, dd, J=9.2, 2.2 Hz), 8.35 (2H, dd, J=8.9, 1.9 Hz).

Procedure P: Preparation of 4-amino-N,N-diisopropylbenzenesulfonamide

To a stirring solution of N,N-diisopropyl-4-nitrobenzenesulfonamide (260 mg, 0.91 mmol) in methanol (10 mL) at rt was added a slurry of palladium on carbon (10% w/w; 50 mg) in water (50 μL) under a nitrogen blanket. The resulting mixture was stirred under an atmosphere of hydrogen for 3 h. The mixture was filtered through Celite and concentrated in vacuo to afford 4-amino-N,N-diisopropylbenzenesulfonamide (200 mg, 86%) as a brown solid. $^1$H-NMR (300 MHz; CDCl$_3$) δ ppm: 1.27 (12H, d, J=6.8 Hz), 3.66 (2H, hept, J=6.8 Hz), 4.04 (2H, br. s), 6.67 (2H, dd, J=8.7, 2.1 Hz), 7.65 (2H, dd, J=8.6, 1.9 Hz).

Procedure Q: Preparation of (Z)-tert-butyl (4-((2-((4-(N,N-diisopropylsulfamoyl)phenyl)-carbamoyl)phenyl)thio)-3-fluorobut-2-en-1-yl)carbamate

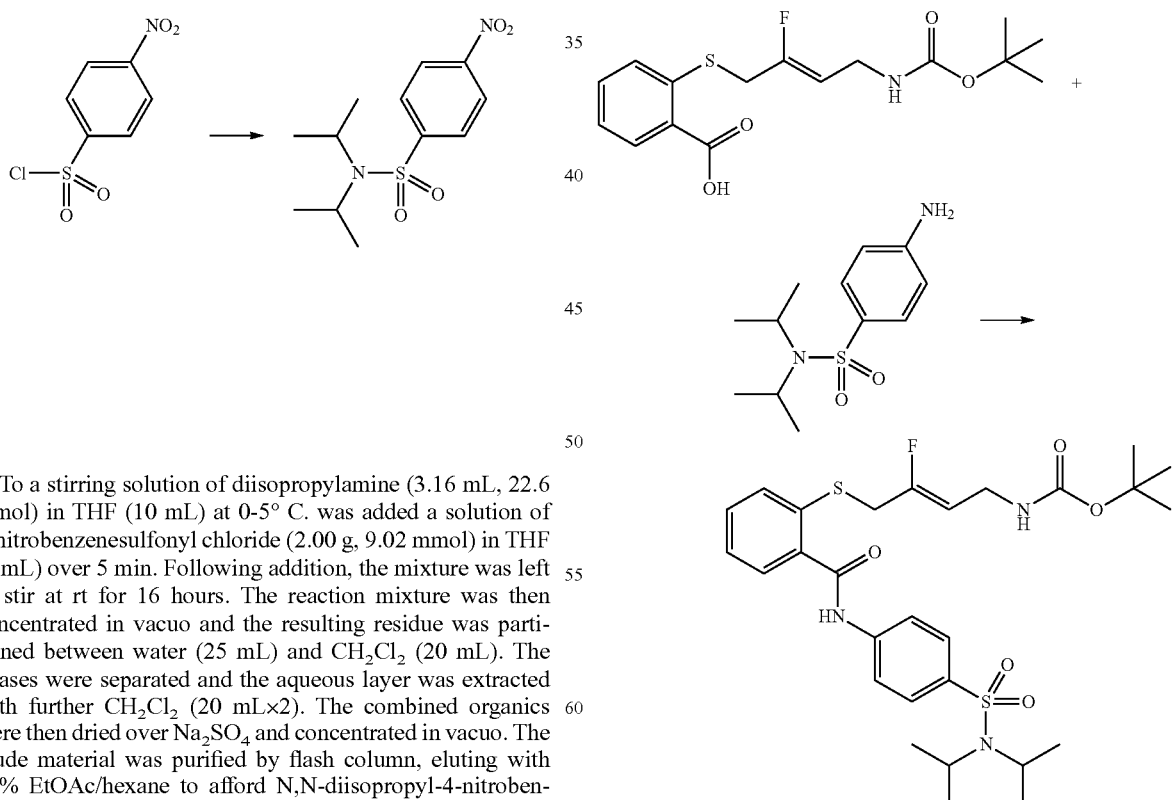

To a stirring solution of (Z)-2-((4-((tert-butoxycarbonyl)amino)-2-fluorobut-2-en-1-yl)thio)benzoic acid (180 mg, 0.53 mmol), 4-amino-N,N-diisopropylbenzenesulfonamide (203 mg, 0.79 mmol) and triethylamine (0.26 mL, 1.85 mmol) in DMF (0.8 mL) at rt was added HATU (301 mg, 0.79 mmol) and the resulting solution was stirred at this temperature for 16 h. The reaction mixture was then partitioned between water (10 mL) and EtOAc (10 mL) and the phases were separated. The aqueous phase was extracted again with EtOAc and the organic phases were combined and washed with HCl (1 M; 20 mL) followed by water (20 mL×3) and brine (20 mL). The organic phase was dried (Na$_2$SO$_4$) and concentrated in vacuo. The crude material was purified by flash column, eluting with 50-100% EtOAc/hexane to afford (Z)-tert-butyl (4-((2-((4-(N,N-diisopropylsulfamoyl)phenyl)carbamoyl)phenyl)thio)-3-fluorobut-2-en-1-yl)carbamate (93 mg, 30%) as a pale lilac oil. $^1$H-NMR (300 MHz; CDCl$_3$) δ ppm: 1.31 (12H, d, J=6.7 Hz), 1.44 (9H, s), 3.57 (2H, d, J=18.5 Hz), 3.63 (2H, app. t, J=5.6 Hz), 3.74 (2H, hept, J=6.7 Hz), 4.40 (1H, dt, J=34.8, 6.9 Hz), 4.75 (1H, br. s), 7.41 (1H, dd, J=7.1, 7.1 Hz), 7.47 (1H, ddd, J=7.8, 7.8, 1.8 Hz), 7.62 (1H, dd, J=7.8, 1.2 Hz), 7.75 (1H, dd, J=7.3 Hz), 7.88 (4H, br. s).

(Z)-2-((4-amino-2-fluorobut-2-en-1-yl)sulfonyl)-N-(4-(N,N-diisopropylsulfamoyl)phenyl)benzamide hydrochloride (Compound 15)

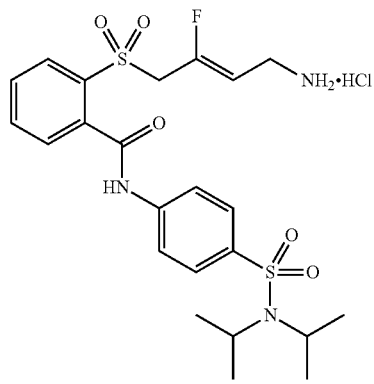

White solid; m.p. 248-250° C.; $^1$H-NMR (300 MHz; CD$_3$OD) δ ppm: 1.29 (12H, d, J=6.9 Hz), 3.64 (2H, dd, J=7.4, 1.5 Hz), 3.78 (2H, hept, J=6.7 Hz), 4.69 (2H, d, J=19.2 Hz), 5.23 (1H, dt, J=32.4, 7.4 Hz), 7.76-7.82 (2H, m), 7.85-7.93 (5H, m), 8.10-8.13 (1H, m).

Example 10

The following compounds were prepared according to procedures Q, H and I using the appropriate thiol and amine starting materials.

N-(adamantan-1-yl)-4-(((Z)-4-amino-2-fluorobut-2-en-1-yl)sulfonyl)benzamide hydrochloride (Compound 4)

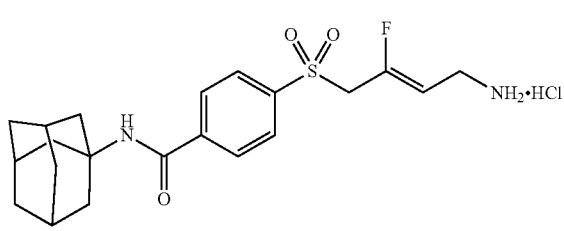

Off-white solid; m.p. 231-233° C.; $^1$H-NMR (300 MHz; d$_6$-DMSO) δ ppm: 1.67 (6H, br. s), 2.08 (9H, br. s), 3.46 (2H, br. s), 4.67 (2H, d, J=19.7 Hz), 5.10 (1H, dt, J=34.6, 7.1 Hz), 7.97 (2H, dd, J=8.6, 1.5 Hz), 8.00 (2H, dd, J=8.8, 1.4 Hz), 8.06 (3H, br. s).

N-(adamantan-1-yl)-2-(((Z)-4-amino-2-fluorobut-2-en-1-yl)sulfonyl)benzamide hydrochloride (Compound 12)

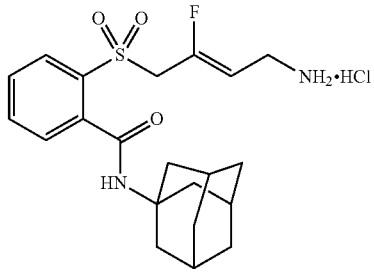 [SMILES: NC/C=C(\F)CS(=O)(=O)c1ccccc1C(=O)NC12CC3CC(CC(C3)C1)C2 ; Cl]

White solid; $^1$H-NMR (300 MHz; CD$_3$OD) δ ppm: 1.77-1.80 (6H, m), 2.09-2.15 (3H, m), 2.16-2.21 (6H, m), 3.61 (2H, app. d, J=7.2 Hz), 4.62 (2H, d, J=19.5 Hz), 5.16 (1H, dt, J=32.6, 7.4 Hz), 7.56 (1H, dd, J=7.5, 1.0 Hz), 7.67 (1H, ddd, J=7.7, 7.7, 1.2 Hz), 7.78 (1H, ddd, J=7.5, 7.5, 1.1 Hz), 8.01 (1H, dd, J=7.8, 1.0 Hz).

N-(adamantan-1-yl)-3-(((Z)-4-amino-2-fluorobut-2-en-1-yl)sulfonyl)benzamide hydrochloride (Compound 13)

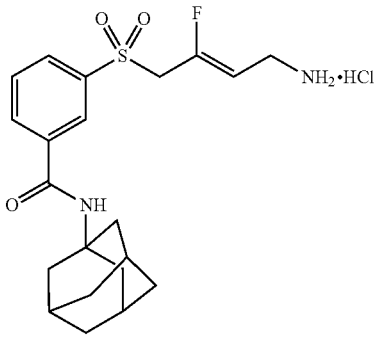 [SMILES: NC/C=C(\F)CS(=O)(=O)c1cccc(C(=O)NC23CC4CC(CC(C4)C2)C3)c1 ; Cl]

White solid; m.p. 230-232° C.; $^1$H-NMR (300 MHz; d$_6$-DMSO) δ ppm: 1.68 (6H, br. s), 2.05-2.12 (9H, m), 3.49 (2H, br. s), 4.68 (2H, d, J 19.8 Hz), 5.12 (1H, dt, J 34.7, 7.0 Hz), 7.73 (1H, dd, J 7.7, 7.7 Hz), 7.98 (3H, br. s), 8.03 (1H, ddd, J 7.8, 1.7, 0.9 Hz), 8.16 (1H, ddd, J 7.8, 1.4, 1.0 Hz), 8.28 (1H, dd, J 1.6, 1.1 Hz).

Example 11

The following compounds were prepared according to procedures R and I.

(Z)-3-fluoro-4-(phenylsulfonyl)but-2-en-1-amine hydrochloride (Compound 1)

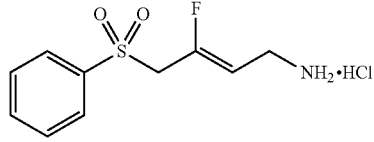

Procedure R: Preparation of tert-butyl (Z)-(3-fluoro-4-(phenylsulfonyl)but-2-en-1-yl)carbamate

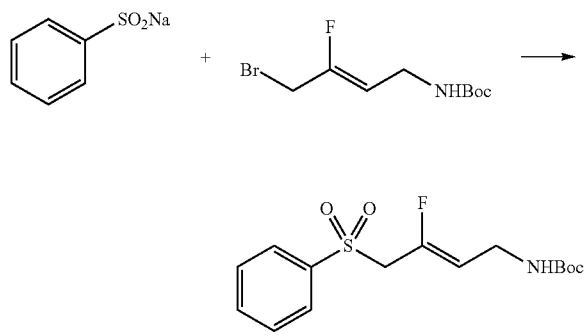

To a stirring solution of tert-butyl (Z)-(4-bromo-3-fluorobut-2-en-1-yl)carbamate (60.0 g, 224 mmol) in DMF (300 mL) was added sodium benzenesulfinate (44.1 g, 269 mmol) portion wise at rt over 15 mins. The resulting reaction mixture was stirred at rt for 2 h. The reaction mixture was diluted with water (2.7 L) and stirring was continued at rt for a further 15 mins. The resulting, precipitated solid was filtered, washed with water (50 mL×2) and then dried in oven at 60° C. to afford tert-butyl (Z)-(3-fluoro-4-(phenylsulfonyl)but-2-en-1-yl)carbamate (74.0 g, 100%) as a white solid which was used as such in the next step. $^1$H NMR (300 MHz, CDCl$_3$) δ ppm: 7.98-7.91 (m, 2H), 7.76-7.67 (m, 1H), 7.61 (ddt, J=8.3, 6.6, 1.3 Hz, 2H), 4.94 (dt, J=34.3, 7.0 Hz, 1H), 4.59 (s, 1H), 3.94 (d, J=18.4 Hz, 2H), 3.79 (t, J=6.5 Hz, 2H), 1.46 (s, 9H).

(Z)-3-fluoro-4-(phenylsulfonyl)but-2-en-1-amine hydrochloride (Compound 1)

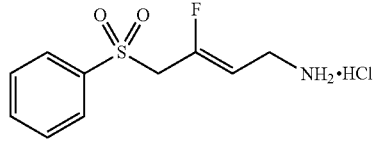 [SMILES: NC/C=C(\F)CS(=O)(=O)c1ccccc1 ; Cl]

Off-white solid; m.p. 209-211° C.; $^1$H-NMR (300 MHz; CD$_3$OD) δ ppm: 3.64 (2H, dd, J=7.3, 1.2 Hz), 4.36 (2H, d, J=19.1 Hz), 5.18 (1H, dt, J=32.7, 7.4 Hz), 7.65-7.71 (2H, m), 7.79 (1H, tt, J=7.4, 1.2 Hz), 7.96-8.00 (2H, m); LCMS: for C$_{10}$H$_{12}$FNO$_2$S calculated 229.1, found 230.1 [M+1]$^+$.

Example 12

The following compounds were prepared according to procedures R and I.

(Z)-4-(2-chlorophenylsulfonyl)-3-fluorobut-2-en-1-amine hydrochloride (Compound 19)

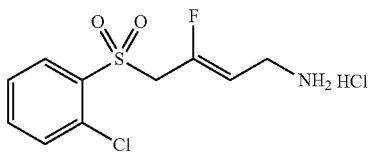 [SMILES: NC/C=C(\F)CS(=O)(=O)c1ccccc1Cl ; Cl]

White solid; m.p. 205-207° C.; $^1$H NMR (300 MHz, CD$_3$OD) δ ppm: 8.13 (ddd, J=7.9, 1.5, 0.6 Hz, 1H), 7.81-7.69 (m, 2H), 7.62 (ddd, J=7.9, 6.4, 2.2 Hz, 1H), 5.27 (dt, J=32.8, 7.4 Hz, 1H), 4.59 (d, J=19.1 Hz, 2H), 3.62 (dd, J=7.4, 1.9 Hz, 2H); LCMS: for C$_{10}$H$_{11}$ClFNO$_2$S calculated 263.0, found 264.0 [M+1]$^+$.

(Z)-3-fluoro-4-(pyridin-2-ylsulfonyl)but-2-en-1-amine dihydrochloride (Compound 30)

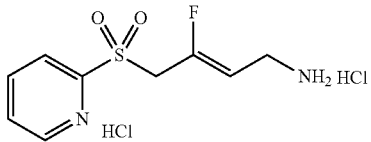 [SMILES: NC/C=C(\F)CS(=O)(=O)c1ccccn1 ; Cl ; Cl]

White solid; m.p. 153-155° C.; $^1$H NMR (300 MHz, CD$_3$OD) δ ppm: 8.88-8.73 (m, 1H), 8.25-8.10 (m, 2H), 7.77 (ddd, J=6.8, 4.7, 1.9 Hz, 1H), 5.26 (dt, J=32.9, 7.4 Hz, 1H), 4.59 (d, J=19.1 Hz, 2H), 3.63 (dd, J=7.3, 1.8 Hz, 2H).

(Z)-3-fluoro-4-(pyridin-3-ylsulfonyl)but-2-en-1-amine dihydrochloride (Compound 31)

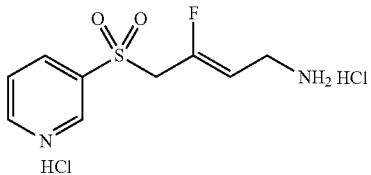 [SMILES: NC/C=C(\F)CS(=O)(=O)c1cccnc1 ; Cl ; Cl]

White solid; m.p. 168-170° C.; $^1$H NMR (300 MHz, CD$_3$OD) δ ppm: 9.23 (dd, J=2.3, 0.8 Hz, 1H), 9.04 (dd, J=5.2, 1.5 Hz, 1H), 8.64 (dt, J=8.2, 1.9 Hz, 1H), 7.94 (ddd, J=8.2, 5.2, 0.8 Hz, 1H), 5.30 (dt, J=33.1, 7.4 Hz, 1H), 4.59 (d, J=19.1 Hz, 2H), 3.68 (d, J=7.4 Hz, 2H).

Example 13

The following compound was prepared according to the procedures S, F, H and I.

(Z)-3-fluoro-4-(3-methylpyridin-2-ylsulfonyl)but-2-en-1-amine dihydrochloride (Compound 43)

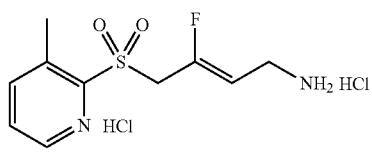 [SMILES: Cc1cccnc1S(=O)(=O)C/C(F)=C/CN ; Cl ; Cl]

Procedure S: Preparation of 3-methylpyridine-2-thiol

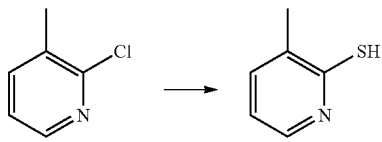

2-Chloro-3-methylpyridine (500 mg, 3.93 mmol) and sodium hydrosulfide hydrate (2.21 g, 39.36 mmol) were taken in DMF (2.0 mL). The resulting mixture was heated at 120° C. for 12 h. Upon completion of reaction (TLC), the reaction mixture was cooled to room temperature, diluted with water (20 mL), acidified (pH=5) with adding acetic acid and extracted with EtOAc (20 mL×3). The combined organic extract was dried over $Na_2SO_4$ and concentrated under reduced pressure to afford 3-methylpyridine-2-thiol (1.50 g, 50.5%). $^1$H NMR (600 MHz, $d_6$ DMSO) δ ppm: 13.5-13.3 (m, 1H), 7.6-7.58 (m, 1H), 7.51 (d, J=6 Hz, 1H). 2.21 (s, 3H)

(Z)-3-fluoro-4-(3-methylpyridin-2-ylsulfonyl)but-2-en-1-amine dihydrochloride (Compound 43)

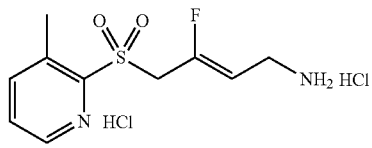 [SMILES: Cc1cccnc1S(=O)(=O)C/C(F)=C/CN ; Cl ; Cl]

Off-white solid; $^1$H NMR (300 MHz, $CD_3OD$) δ ppm: 8.53 (dd, J=4.7, 1.3 Hz, 1H), 7.92 (d, J=7.6 Hz, 1H), 7.60 (dd, J=7.8, 4.5 Hz, 1H), 5.37 (dt, J=32.9, 7.2 Hz, 1H), 4.75 (d, J=19.0 Hz, 2H), 3.67 (d, J=7.1 Hz, 2H), 2.68 (s, 3H).

Example 14

The following compounds were prepared according to the procedures S, F, H and I.

(Z)-3-fluoro-4-(2-methylpyridin-4-ylsulfonyl)but-2-en-1-amine dihydrochloride (Compound 44)

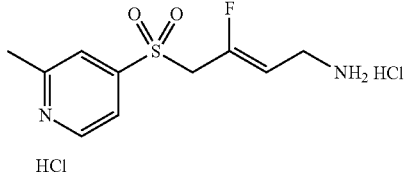 [SMILES: Cc1cc(S(=O)(=O)C/C(F)=C/CN)ccn1 ; Cl ; Cl]

Pale yellow solid; $^1$H NMR (300 MHz, $CD_3OD$) δ 9.00 (d, J=5.6 Hz, 1H), 8.35 (s, 1H), 8.23 (d, J=5.4 Hz, 1H), 5.36 (dt, J=33.0, 7.1 Hz, 1H), 4.68 (d, J=18.9 Hz, 2H), 3.69 (d, J=6.7 Hz, 2H), 2.90 (s, 3H).

(Z)-3-fluoro-4-(5-isopropylpyridin-2-ylsulfonyl)but-2-en-1-amine dihydrochloride (Compound 34)

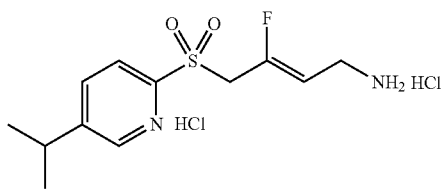 [SMILES: CC(C)c1ccc(S(=O)(=O)C/C(F)=C/CN)nc1 ; Cl ; Cl]

White glassy solid; $^1$H NMR (300 MHz, $CD_3OD$) δ 8.70 (t, J=1.3 Hz, 1H), 8.12-7.94 (m, 2H), 5.28 (dt, J=32.9, 7.4 Hz, 1H), 4.55 (d, J=19.1 Hz, 2H), 3.64 (dd, J=7.6, 1.7 Hz, 2H), 3.15 (hept, J=6.9 Hz, 1H), 1.36 (d, J=6.9 Hz, 6H).

(Z)-3-fluoro-4-(5-methylpyridin-2-ylsulfonyl)but-2-en-1-amine dihydrochloride (Compound 35)

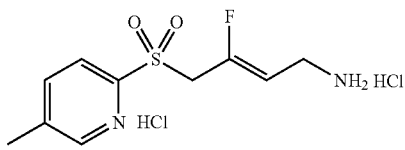 [SMILES: Cc1ccc(S(=O)(=O)C/C(F)=C/CN)nc1 ; Cl ; Cl]

White solid; m.p. 155-157° C.; $^1$H NMR (300 MHz, $d_6$ DMSO) δ 8.67 (d, J=0.9 Hz, 1H), 8.09 (s, 3H), 7.98 (t, J=1.4 Hz, 2H), 5.20 (dt, J=34.8, 7.2 Hz, 1H), 4.70 (d, J=19.6 Hz, 2H), 3.46 (t, J=5.9 Hz, 2H), 2.45 (s, 3H).

(Z)-3-fluoro-4-(6-methylpyridin-2-ylsulfonyl)but-2-en-1-amine dihydrochloride (Compound 36)

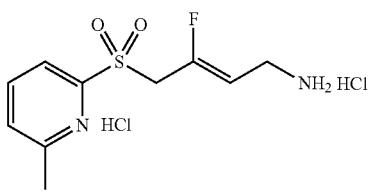 [SMILES: Cc1cccc(S(=O)(=O)C/C(F)=C/CN)n1 ; Cl ; Cl]

Pale yellow solid; m.p. 174-176° C.; $^1$H NMR (300 MHz, $d_6$ DMSO) δ 8.18 (s, 3H), 8.06 (t, J=7.8 Hz, 1H), 7.88 (d, J=7.7 Hz, 1H), 7.66 (d, J=7.5 Hz, 1H), 5.23 (dt, J=34.8, 7.1 Hz, 1H), 4.70 (d, J=19.6 Hz, 2H), 3.46 (t, J=5.9 Hz, 2H), 2.61 (s, 3H).

Example 15

The following compound was prepared according to procedures T, U and V then F, H and I (Z)-3-fluoro-4-(6-isopropylpyridin-3-ylsulfonyl)but-2-en-1-amine dihydrochloride (Compound 49)

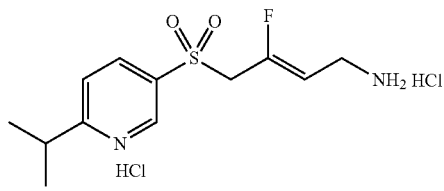 [SMILES: CC(C)c1ccc(S(=O)(=O)C/C(F)=C/CN)cn1 ; Cl ; Cl]

Procedure T: Preparation of methyl 3-((6-chloropyridin-3-yl)thio)propanoate

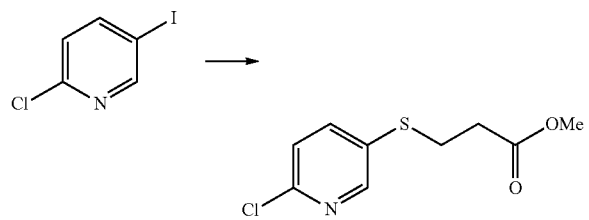

In a 50 mL re-sealable reaction tube, 2-chloro-5-iodopyridine (2.50 g, 10.5 mmol) was dissolved in degassed 1,4-dioxane (25 mL) at rt, under nitrogen atmosphere. $Pd_2(dba)_3$ (100 mg, 0.11 mmol), Xantphos (125 mg, 0.22 mmol), methyl 3-mercaptopropanoate (1.25 g, 10.5 mmol) and DIPEA (2.50 mL, 14.4 mmol) were sequentially added under nitrogen atmosphere. The solution was degassed by purging nitrogen gas for 15 min, and then gradually heated to 70° C. The resulting reaction mixture was stirred at this temperature for 6 h. Upon completion of reaction (TLC), the reaction mixture was cooled to rt, diluted with cold water, and extracted with ethyl acetate (3×30 mL). The combined organics were washed with brine solution and concentrated under reduced pressure. The residue obtained was purified by silica gel (100-200 mesh) column chromatography, eluting with 10% EtOAc-hexanes to give methyl 3-((6-chloropyridin-3-yl)thio)propanoate (2.40 g, 99%) as an off-white solid. $^1$H NMR (400 MHz, $CDCl_3$) δ ppm: 8.36 (d, J=2.4 Hz, 1H), 7.67 (dd, J=8.4, 2.4 Hz, 1H), 7.28 (d, J=9.2 Hz, 1H), 3.69 (s, 3H), 3.17 (t, J=7.2 Hz, 2H), 2.64 (t, J=7.2 Hz, 2H).

Procedure U: Preparation of methyl 3-((6-isopropylpyridin-3-yl)thio)propanoate

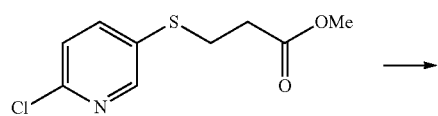

-continued

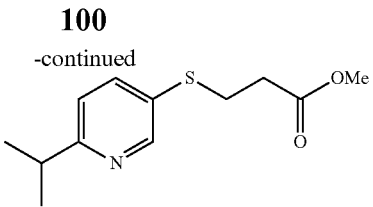

In a 1000 mL round bottom flask, methyl 3-((6-chloropyridin-3-yl)thio)propanoate (5.00 g, 21.6 mmol) was dissolved in anhydrous THF (200 mL) and 1-methyl-2-pyrrolidinone (25 mL) under nitrogen atmosphere. The solution was cooled to −55° C., and a solution of iron (III) acetylacetonate (1.70 g, 4.80 mmol) in THF (50 mL) was added whilst maintaining a nitrogen atmosphere. The resulting mixture was stirred at −55° C. for 15 min at which time a solution of isopropylmagnesium chloride in THF (2 M, 50 mL) was added dropwise at −55° C. under nitrogen atmosphere. The resulting reaction mixture was stirred at −40° C. for further 1 h. Upon completion of reaction (TLC), the reaction mixture was cooled to 0° C., quenched with saturated $NH_4Cl$ solution (50 mL), and the product extracted with ethyl acetate (100 mL×3). The combined organics were dried over $Na_2SO_4$ and concentrated under reduced pressure. The residue obtained was purified over silica gel (100-200 mesh) column chromatography eluting with 10% EtOAc-hexanes to afford methyl 3-((6-isopropylpyridin-3-yl)thio)propanoate (2.60 g, 50%) as a pale yellow liquid.

Procedure V: Preparation of 6-isopropylpyridine-3-thiol

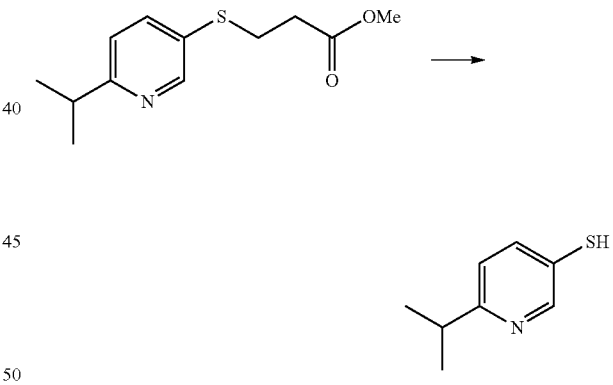

In a 100 mL round bottom flask, methyl 3-((6-isopropylpyridin-3-yl)thio)propanoate (860 mg, 3.59 mmol) was dissolved in anhydrous THF (20 mL) and solution was cooled to −78° C. under nitrogen atmosphere. A solution of potassium tertbutoxide in THF (1.0 M, 3.5 mL, 3.59 mmol) was added to the above mixture under nitrogen atmosphere. The resulting mixture was stirred at −78° C. for 1 h. Upon completion of reaction (TLC), the reaction mixture was warmed to rt and concentrated under reduced pressure. The residue obtained was washed with n-hexane to afford 6-isopropylpyridine-3-thiol (655 mg) as a light brown solid. The compound was used in next step without further purification.

(Z)-3-fluoro-4-(6-isopropylpyridin-3-ylsulfonyl)but-2-en-1-amine dihydrochloride (Compound 49)

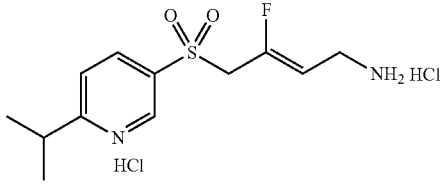 [SMILES: CC(C)c1ccc(S(=O)(=O)C/C(F)=C/CN)cn1 ; Cl ; Cl]

¹H NMR (300 MHz, CD₃OD) δ ppm: 9.29 (dd, J=2.1, 0.7 Hz, 1H), 9.02 (ddd, J=8.6, 3.5, 2.1 Hz, 1H), 8.32 (dd, J=8.6, 3.2 Hz, 1H), 5.48 (t, J=7.3 Hz, 1H), 4.74 (d, J=19.0 Hz, 2H), 3.81-3.65 (m, 2H), 3.55 (dq, J=7.0, 2.2 Hz, 1H), 1.53 (dd, J=7.0, 0.8 Hz, 6H).

Example 16

The following compound was prepared according to procedures T, U and V then F, H and I.

(Z)-3-fluoro-4-(2-isopropylpyridin-3-ylsulfonyl)but-2-en-1-amine dihydrochloride (Compound 45)

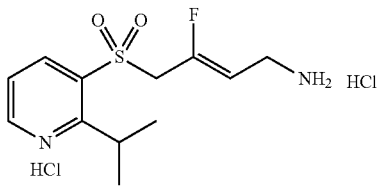 [SMILES: CC(C)c1ncccc1S(=O)(=O)C/C(F)=C/CN ; Cl ; Cl]

¹H NMR (300 MHz, CD₃OD) δ ppm: 8.95 (dd, J=5.2, 1.7 Hz, 1H), 8.66 (dd, J=8.2, 1.8 Hz, 1H), 7.78 (dd, J=8.0, 5.0 Hz, 1H), 5.39 (dt, J=33.2, 7.3 Hz, 1H), 4.58 (d, J=19.0 Hz, 2H), 4.08 (p, J=6.8 Hz, 1H), 3.72-3.62 (m, 2H), 1.45 (d, J=6.7 Hz, 6H).

Example 17

The following compound was prepared according to procedures T and V then F, H and I.

(Z)-3-fluoro-4-(6-methylpyridin-3-ylsulfonyl)but-2-en-1-amine dihydrochloride (Compound 46)

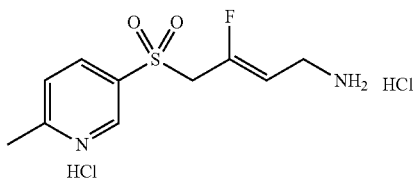 [SMILES: Cc1ccc(S(=O)(=O)C/C(F)=C/CN)cn1 ; Cl ; Cl]

¹H NMR (300 MHz, CD₃OD) δ ppm: 9.17 (d, J=2.2 Hz, 1H), 8.67 (d, J=8.5 Hz, 1H), 7.96 (d, J=8.4 Hz, 1H), 5.33 (dt, J=33.0, 7.3 Hz, 1H), 4.62 (d, J=19.1 Hz, 2H), 3.75-3.63 (m, 2H), 2.85 (s, 3H).

(Z)-3-fluoro-4-(2-methylpyridin-3-ylsulfonyl)but-2-en-1-amine dihydrochloride (Compound 47)

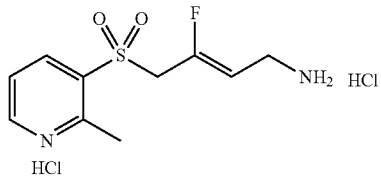 [SMILES: Cc1ncccc1S(=O)(=O)C/C(F)=C/CN ; Cl ; Cl]

¹H NMR (300 MHz, CD₃OD) δ ppm: 9.00 (dd, J=5.6, 1.5 Hz, 1H), 8.91 (dd, J=8.1, 1.5 Hz, 1H), 8.05 (dd, J=8.1, 5.6 Hz, 1H), 5.42 (dt, J=33.2, 7.3 Hz, 1H), 4.67 (d, J=19.0 Hz, 2H), 3.79-3.64 (m, 2H), 3.12 (s, 3H).

(Z)-3-fluoro-4-(4-methylpyridin-3-ylsulfonyl)but-2-en-1-amine dihydrochloride (Compound 48)

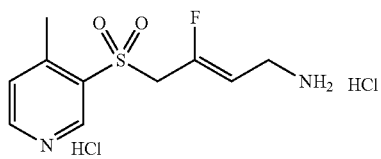 [SMILES: Cc1ccncc1S(=O)(=O)C/C(F)=C/CN ; Cl ; Cl]

Off-white solid; ¹H NMR (300 MHz, CD₃OD) δ ppm: 9.25 (s, 1H), 8.97 (d, J=5.8 Hz, 1H), 8.07 (d, J=5.9 Hz, 1H), 5.42 (dt, J=33.2, 7.3 Hz, 1H), 4.68 (d, J=19.1 Hz, 2H), 3.70 (dd, J=7.4, 1.9 Hz, 2H), 2.99 (d, J=0.6 Hz, 3H).

(Z)-3-fluoro-4-((2-methylbenzo[d]thiazol-4-yl)sulfonyl)but-2-en-1-amine hydrochloride (Compound 50)

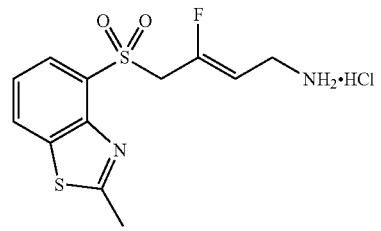

Pale yellow solid; m.p. 243-245° C.; ¹H NMR (300 MHz, CD₃OD) δ ppm: 8.37 (dd, J=8.1, 1.2 Hz, 1H), 8.10 (dd, J=7.7, 1.2 Hz, 1H), 7.63 (t, J=7.9 Hz, 1H), 5.20 (dt, J=32.8, 7.4 Hz, 1H), 4.82 (d, J=19.0 Hz, 2H), 3.60 (d, J=7.4 Hz, 2H), 2.97 (s, 3H).

Example 18

The following compound was prepared according to procedures W, X, Y, Z then H and I (Z)-4-((2,3-dimethyl-1H-indol-7-yl)sulfonyl)-3-fluorobut-2-en-1-amine hydrochloride (Compound 52)

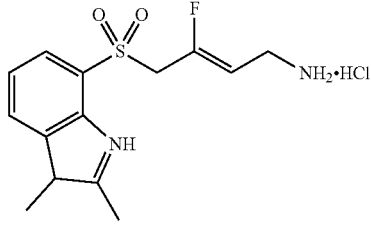

Procedure W: Preparation of (2-iodophenyl)hydrazine

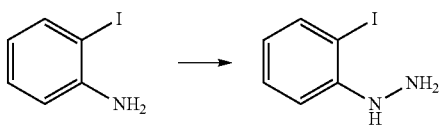 [SMILES: Nc1ccccc1I ; NNc1ccccc1I]

In a 1 L round bottom flask, solution of 2-iodoaniline (40.0 g, 0.182 mmol) in conc. HCl (250 mL) was treated with a solution of NaNO$_2$ (15.1 g, 0.22 mmol) in water (40 mL) at 0° C. The reaction mixture was stirred at 0° C. for 2 h and treated with SnCl$_2$ (86.6 g, 0.46 mmol) slowly at 0° C. The reaction temperature was gradually raised to rt and stirred for further 6 h. Upon completion of reaction (TLC), the reaction mixture was filtered and washed with n-pentane (50 mL) and diethyl ether (50 mL) to yield the title compound (42 g, 98.26%). $^1$H NMR (300 MHz, d$_6$-DMSO) δ ppm: 10.2 (br. s, 2H), 7.79-7.76 (m, 1H), 7.7-7.45 (br, 1H), 7.36 (t, J=8.1 Hz, 1H), 7.02 (d, J=7.8 Hz, 1H), 6.75 (t, J=7.8 Hz, 1H).

Procedure X: Preparation of 7-iodo-2,3-dimethyl-1H-indole

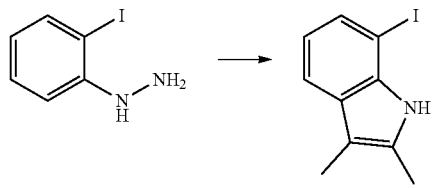

In a 250 mL round bottom flask, a solution of (2-iodophenyl)hydrazine (10 g, 42.73 mmol) in acetic acid (80 mL) was gradually heated to 60° C. and stirred for 1 h. 2-Butanone (6.18 g, 85.36 mmol) was slowly added at 60° C. The resulting reaction mixture was then heated at 80° C. for 5 h. Upon completion of reaction (TLC), the reaction mixture was cooled to rt and then concentrated under reduced pressure. The residue obtained was diluted with cold water, and extracted with ethyl acetate (100 mL×2). The combined organic extract was washed with brine and concentrated under reduced pressure. The residue obtained was purified over silica gel eluting with 10% EtOAc-hexanes to afford the title compound as an off-white solid (2.00 g, 18%). $^1$H NMR (400 MHz, d$_6$-DMSO) δ ppm: 10.54 (s, 1H), 7.37-7.24 (m, 2H), 6.73 (t, J=8 Hz, 1H), 2.32 (s, 3H), 2.12 (s, 3H).

Procedure Y: Preparation of methyl 3-((2,3-dimethyl-1H-indol-7-yl)thio)propanoate

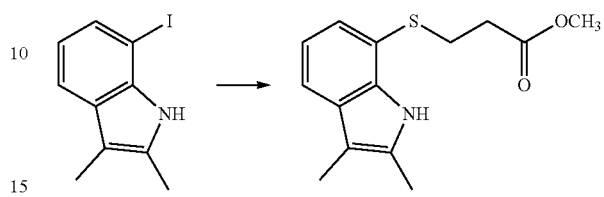

In a 50 mL re-sealable reaction tube, a solution of 7-iodo-2,3-dimethyl-1H-indole (1.60 g, 10.5 mmol) in 1,4-dioxane (10 mL) was degassed under nitrogen atmosphere. Pd$_2$(dba)$_3$ (50.0 mg, 0.06 mmol), xantphos (100 mg, 0.18 mmol), methyl 3-mercaptopropanoate (0.70 g, 5.90 mmol) and DIPEA (2.00 mL, 11.80 mmol) were added sequentially under nitrogen atmosphere. The solution was degassed by purging argon gas for 15 min, gradually heated to 110° C. and stirred at this temperature for 12 h. Upon completion of reaction (TLC), the reaction mixture was cooled to rt, diluted with cold water, and extracted with EtOAc (2×20 mL). The combined organic extract was washed with brine, dried over anhydrous Na$_2$SO$_4$ and concentrated under reduced pressure. The residue obtained was purified over silica gel eluting with 10% EtOAc-hexanes to afford the title compound as an off-white solid (1.50 g, 96%). $^1$H NMR (400 MHz, CDCl$_3$) δ ppm: 8.6 (br, 1H), 7.44 (d, J=8 Hz, 1H), 7.22 (d, J=7.6 Hz, 1H), 7.03 (t, J=7.6 Hz, 1H), 3.7 (s, 3H), 3.08 (t, J=6.8 Hz, 2H), 2.57 (t, J=7.2 Hz, 2H), 2.41 (s, 3H), 2.22 (s, 3H).

Procedure Z: Preparation of tert-butyl (Z)-(4-((2,3-dimethyl-1H-indol-7-yl)thio)-3-fluorobut-2-en-1-yl) carbamate

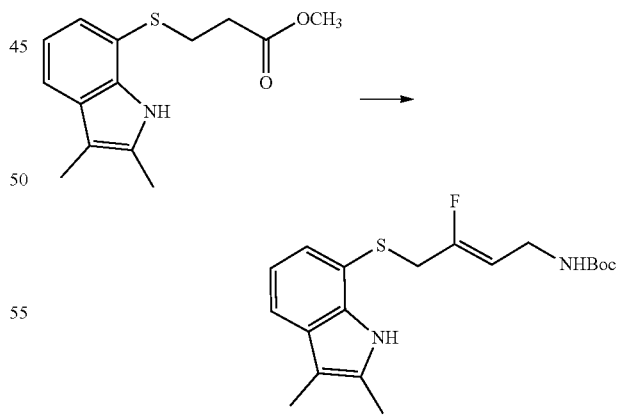

In a 100 mL round bottom flask, cesium carbonate (1.49 g, 4.56 mmol) was added to a stirred solution of methyl 3-((2,3-dimethyl-1H-indol-7-yl)thio)propanoate (0.40 g 1.52 mmol) and tert-butyl (Z)-(4-bromo-3-fluorobut-2-en-1-yl)carbamate (0.41 g, 1.53 mmol) in DMF (15 mL) at rt. The reaction mixture was stirred at rt for 5 h. Upon completion of reaction (TLC), the reaction mixture was quenched by addition of ice cold water (10 mL) and extracted with ethyl acetate (10 mL×3). The combined organic extract was dried over anhydrous Na$_2$SO$_4$ and concentrated under reduced pressure. The crude material was purified over silica gel, eluting with 20% ethyl acetate in hexanes to afford the title compound as a pale-yellow liquid (350 mg, 63%). $^1$H NMR (300 MHz, d$_6$-DMSO) δ ppm: 10.65 (s, 1H), 7.31 (d, J=7.5 Hz, 1H), 7.07 (d, J=7.8 Hz, 1H), 6.93-6.83 (m, 2H), 4.66 (dt, J=36.3, 7.2 Hz, 1H), 3.67 (d, J=19.5 Hz, 2H), 3.47 (t, J=6 Hz, 2H), 2.32 (s, 3H), 2.13 (s, 3H), 1.34 (s, 9H).

(Z)-4-((2,3-dimethyl-1H-indol-7-yl)sulfonyl)-3-fluorobut-2-en-1-amine hydrochloride (Compound 52)

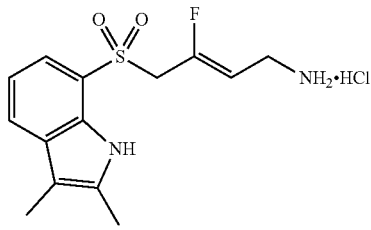

$^1$H NMR (300 MHz, CD$_3$OD) δ ppm: 10.25 (s, 1H), 7.80 (dd, J=7.8, 1.0 Hz, 1H), 7.55 (dd, J=7.7, 1.1 Hz, 1H), 7.20 (t, J=7.7 Hz, 1H), 5.05 (dt, J=32.7, 7.4 Hz, 1H), 4.34 (d, J=19.2 Hz, 2H), 3.55 (dd, J=7.4, 1.9 Hz, 2H), 2.49-2.39 (m, 3H), 2.26 (d, J=0.8 Hz, 3H).

Example 19

Preparation of (Z)-tert-butyl (4-bromo-3-fluorobut-2-en-1-yl)carbamate

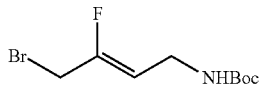

Procedure AA: Preparation of tert-butyl 2-oxoethylcarbamate

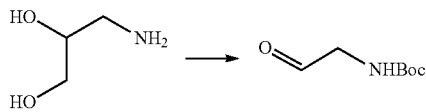 [SMILES: NCC(O)CO ; CC(C)(C)OC(=O)NCC=O]

A vessel charged with 3-amino-1,2-propanediol (50.0 kg, 549 mol) and ethyl acetate (150 L) was cooled to 0-5° C. To this was added di-tert-butyl dicarbonate (120 kg, 550 mol) in portions. The resulting mixture was stirred at 20-25° C. for 12 h. After cooling the reaction mixture to 0-5° C., sodium periodate (120 kg, 561 mol) was added in portions. The suspension was stirred at this temperature for 1 h. The reaction mixture was then filtered, and the filter "cake" was washed with ethyl acetate (180 L). The combined filtrate was washed with aqueous NaCl (10% w/w, 300 L), dried over Na$_2$SO$_4$ and then concentrated in vacuo to afford crude tert-butyl 2-oxoethylcarbamate (70.0 kg, 80%). The crude material was used in the subsequent step without purification.

Procedure AB: Preparation of (E)-ethyl 4-(tert-butoxycarbonylamino)-2-fluorobut-2-enoate

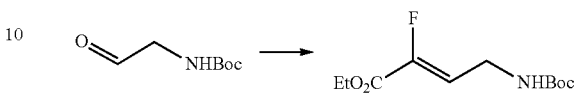

A vessel charged with ethyl 2-fluorophosphonoacetate (46.0 kg, 190 mol), acetonitrile (250 L) and 1,8-diazabicyclo[5.4.0]undec-7-ene (DBU) (38.0 kg, 250 mol) was cooled to 0-10° C. To this was added tert-butyl 2-oxoethylcarbamate (68.0 kg, 427 mol) drop-wise and the resulting mixture was stirred at 0-10° C. for 4 h. The reaction mixture was diluted with tert-butyl methyl ether (500 L) and water (500 L), and stirring was continued for 30 min. After standing for a further 30 min, the aqueous layer was removed. The Organic layer was washed with water (250 L) and then concentrated in vacuo. The residue was dissolved in ethyl acetate (56 L) and petroleum ether (240 L) and purified over silica gel (40 kg, mesh size: 100-200), eluting with ethyl acetate in petroleum ether (1:10) to afford crude (E)-ethyl 4-(tert-butoxycarbonylamino)-2-fluorobut-2-enoate (90 kg). The crude material was used in the subsequent step without further purification.

Procedure AC: Preparation of (Z)-tert-butyl 3-fluoro-4-hydroxybut-2-enylcarbamate

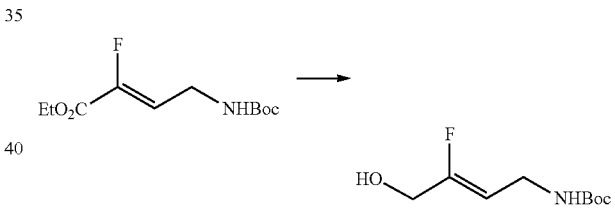

To a reaction vessel charged with crude (E)-ethyl 4-(tert-butoxycarbonylamino)-2-fluorobut-2-enoate (90.0 kg, 364 mol), THF (314 L) and methanol (36 L) at 0-10° C. was added sodium borohydride (16.6 kg, 439 mol) portion-wise over 4 h. After complete addition the resulting mixture was stirred at 0-10° C. for 3 h. The reaction was quenched by the addition of aqueous HCl (0.5 N, 900 L). The product was then extracted with ethyl acetate (720 L×2). The combined organics were washed with water (450 L), and concentrated in vacuo. Residual water was removed by co-evaporation with THF (200 L×3) to afford crude (Z)-tert-butyl 3-fluoro-4-hydroxybut-2-enylcarbamate (85 kg). This material was progressed to the next step without further purification.

Procedure AD: Preparation of (Z)-4-((tert-butoxycarbonyl)amino)-2-fluorobut-2-en-1-yl 3,5-dinitrobenzoate

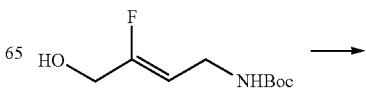

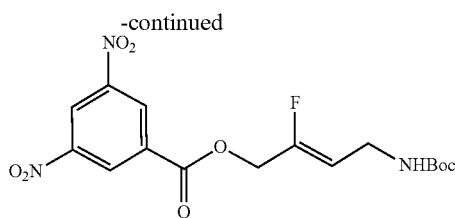

To a reaction vessel charged with crude (Z)-tert-butyl 3-fluoro-4-hydroxybut-2-enylcarbamate (170 kg, 828 mol), THF (765 L) and triethylamine (174 L, 1245 mol) at 0-20° C. was added 3,5-dinitrobenzoyl chloride (190 kg, 824 mol) in portions. The resulting mixture was stirred at 0-20° C. for 2 h and then diluted with water (850 L) and ethyl acetate (1700 L). The aqueous layer was removed and the organics were washed with aqueous $Na_2CO_3$ (10% w/w, 850 L×2) and then water (850 L). After concentrating in vacuo (to approximately 190 L), ethyl acetate (245 L) was added. The mixture was stirred at 55° C. until a clear solution was obtained. The mixture was cooled to 10-20° C., n-heptane (730 L) was added and the mixture was stirred for 6 h. The solid thus formed was isolated by filtration and washed with n-heptane/ethyl acetate (4:1, 170 L). HPLC analysis indicated an E-isomer content of 30%. The E-isomer content was reduced to 4.3% by a process of precipitation as follows. The solid was dissolved in ethyl acetate (570 L). To this was added n-heptane and the resulting slurry was stirred at 20-30° C. for 4-6 h. The solid was isolated by filtration and the filter "cake" was washed with n-heptane/ethyl acetate (4:1). This process was repeated once more to afford (Z)-4-((tert-butoxycarbonyl)amino)-2-fluorobut-2-en-1-yl 3,5-dinitrobenzoate (84 kg as a wet "cake"). This material was progressed to the next step.

Procedure AE: Preparation of (Z)-tert-butyl 3-fluoro-4-hydroxybut-2-enylcarbamate

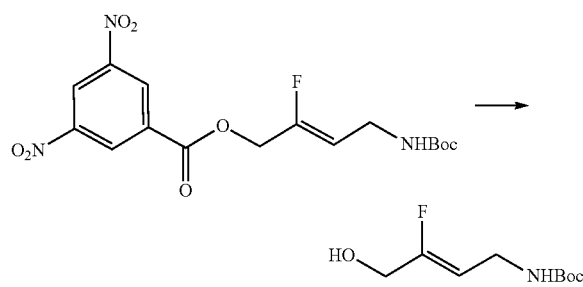

A reaction vessel charged with (Z)-4-((tert-butoxycarbonyl)amino)-2-fluorobut-2-en-1-yl 3,5-dinitrobenzoate (84 kg, 210 mol), THF (187 L) and aqueous NaOH (1.00 M, 420 L) was stirred at 15-25° C. for 2-5 h. The reaction progress was monitored by tlc. The reaction mixture was diluted with isopropyl acetate (966 L) and stirring was continued for 10-30 min. After standing for 10-30 min and subsequent separation of the layers, the aqueous layer was extracted with further isopropyl acetate (483 L). The combined organics were washed with aqueous $Na_2CO_3$ (10% w/w, 420 L×2), aqueous NaCl (10% w/w, 420 L) and then concentrated to approximately 84 L. Residual water was removed by co-evaporation with THF (468 L) to afford (Z)-tert-butyl 3-fluoro-4-hydroxybut-2-enylcarbamate (29.0 kg, 67%). HPLC analysis indicated the E-isomer content to be 3.8%.

Procedure AF: Preparation of (Z)-tert-butyl 4-bromo-3-fluorobut-2-enylcarbamate

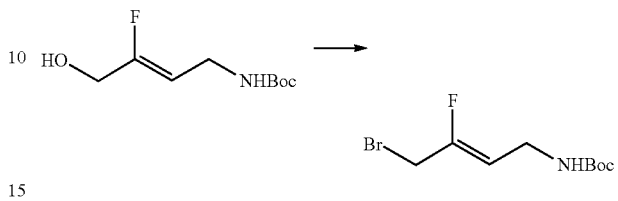

A reaction vessel charged with (Z)-tert-butyl 3-fluoro-4-hydroxybut-2-enylcarbamate (29.0 kg, 141 mol) THF (290 L) and diisopropylethylamine (DIPEA) (74.0 L, 425 mol) was cooled to 0-10° C. To this was added a solution of methanesulfonic anhydride (50.0 kg, 287 mol) in THF (145 L) dropwise. After complete addition, lithium bromide (74.0 kg, 852 mol) was added in portions while maintaining the temperature between 0-10° C. The resulting mixture was stirred at 0–10° C. for 4 h. Tlc after this time indicated complete consumption of starting material. The reaction mixture was diluted with water (290 L) and the product was extracted with ethyl acetate (290 L+145 L). The combined organics were washed with water (150 L) and then concentrated to dryness. The crude residue was taken up in ethyl acetate (67 L) and n-heptane (440 L) and purification was performed over silica gel (40 kg; mesh size 100-200), eluting with ethyl acetate/n-heptane (1:5). All fractions containing the desired product were concentrated to dryness. Ethyl acetate (56 L) was added and stirring at 40-50° C. was continued until a clear solution was obtained. To this was added n-heptane (280 L) drop-wise. The mixture was cooled to 10-15° C. and stirred for 8 h. The resulting solid was collected by filtration. HPLC analysis indicated the E-isomer content to be 0.9%. To further reduce the E-isomer content the process of precipitation was repeated as follows. Ethyl acetate (33 L) was added and stirring at 40-50° C. was continued until a clear solution was obtained. To this was added n-heptane (164 L) drop-wise. The mixture was cooled to 10-15° C. and stirred for 8 h. The resulting solid was collected by filtration and dried to afford (Z)-tert-butyl 4-bromo-3-fluorobut-2-enylcarbamate (29.5 kg, 68%). HPLC analysis indicated the E-isomer content to be 0.1%. $^1$H-NMR (300 MHz; $CDCl_3$) δ ppm: 1.46 (9H, s), 3.85 (2H, dd, J 6.2, 6.2 Hz), 3.93 (2H, d, J 19.5 Hz), 4.66 (1H, br. s), 5.16 (1H, dt, J=34.0, 6.5 Hz).

Example 20

The following compound was prepared according to procedures AG and AH.

Preparation of (Z)-3-fluoro-4-(phenylsulfonyl)but-2-en-1-amine hydrochloride (Compound 1)

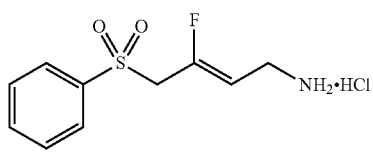

Procedure AG: Preparation of tert-butyl (Z)-(3-fluoro-4-(phenylsulfonyl)but-2-en-1-yl)carbamate

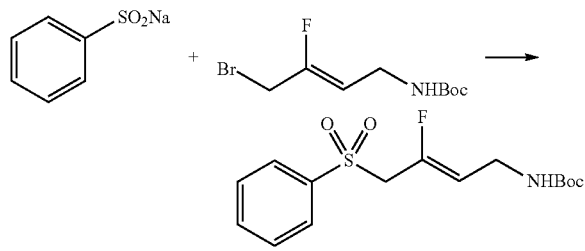

A vessel charged with tert-butyl (Z)-(4-bromo-3-fluorobut-2-en-1-yl)carbamate (2.40 kg, 8.95 mol) and DMF (12.0 L) was cooled to between 15-20° C. To this was added sodium benzenesulfinate (2.20 kg, 13.4 mol) and the resulting mixture was stirred at 15-20° C. for 4 h. The reaction mixture was diluted with water (12.0 L) and stirring was continued at rt for a further 1 h. The solid thus formed was isolated by filtration, and the filter "cake" was washed with further water (6.0 L). The solid was then dried under vacuum at 50-55° C. for 20 h to give tert-butyl (Z)-(3-fluoro-4-(phenylsulfonyl)but-2-en-1-yl)carbamate (2.70 kg, 92%). Retention time (RT)=13.75 min; Method—Agilent LC/MSD 1200 Series; column: ZORBAX SB—C18, ODS 2000 (50×4.6 mm, 5 μm) operating in ES (+) or (−) ionization mode; flow rate 1.5 mL/min; Temperature (T)=30° C.; detection wavelength: 214 nm; mobile phase: from 5% acetonitrile (containing 0.05% trifluoroacetic acid (TFA)) and 95% water (containing 0.05% TFA) to 90% acetonitrile and 10% water, over 24 min.

Procedure AH: Preparation of (Z)-3-fluoro-4-(phenylsulfonyl)but-2-en-1-amine hydrochloride (Compound 1)

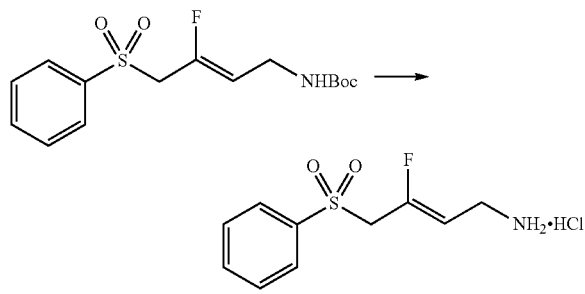

To a vessel charged with HCl (4.00 M in ethyl acetate; 13.5 L, 54.0 mol) and cooled to between 10-20° C. was added a filtered solution (hyflo) of tert-butyl (Z)-(3-fluoro-4-(phenylsulfonyl)but-2-en-1-yl)carbamate (2.70 kg, 8.20 mol) in ethyl acetate (27.0 L). The reaction mixture was stirred at 10-20° C. for 6 h. The resulting solid was isolated by filtration, and the filter "cake" was washed with ethyl acetate (8.0 L). The solid was then dried under vacuum at 50-55° C. for 40 h to afford (Z)-3-fluoro-4-(phenylsulfonyl)but-2-en-1-amine hydrochloride (Compound 1) (2.10 kg; 96%). $^1$H-NMR (300 MHz; CD$_3$OD) δ ppm: 3.64 (2H, dd, J=7.3, 1.2 Hz), 4.36 (2H, d, J=19.1 Hz), 5.18 (1H, dt, J=32.7, 7.4 Hz), 7.65-7.71 (2H, m), 7.79 (1H, tt, J=7.4, 1.2 Hz), 7.96-8.00 (2H, m); LCMS: for C$_{10}$H$_{12}$FNO$_2$S calculated 229.1, found 230.1 [M+1]$^+$.

Example 21

The following compound was prepared according to procedures AI, AJ and AK.

Preparation of (Z)-3-fluoro-4-(quinolin-8-ylsulfonyl)but-2-en-1-amine dihydrochloride monohydrate (Compound 33)

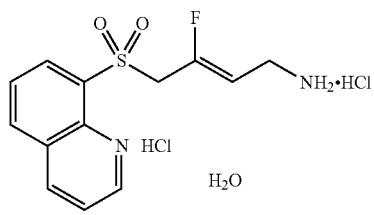

Procedure AI: Preparation of sodium quinoline-8-sulfinate

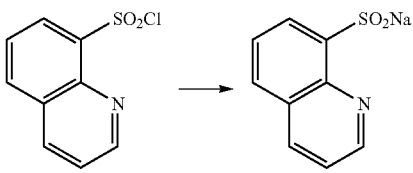

A vessel charged with Na$_2$SO$_3$ (6.70 kg, 53.2 mol) and water (21.0 L) was stirred at rt for 20 min. To the vessel was added Na$_2$CO$_3$ (5.50 kg, 51.9 mol) and stirring was continued at rt for 20 min. Quinoline-8-sulfonyl chloride (6.00 kg, 26.4 mol) was then added portion-wise while maintaining the temperature below 40° C. The resulting mixture was stirred at rt for 3 h. The reaction mixture was filtered and the filter "cake" was washed with methanol (7.0 L). The filtrate was concentrated to dryness in vacuo, and to the resulting residue was added methanol (7.0 L). After stirring at rt for 1 h, the mixture was filtered and the filtrate concentrated to dryness. In a second, and final, washing cycle the residue was taken up in methanol (10.0 L) and stirring was continued at rt for 1 h. The mixture was filtered and the filtrate was concentrated in vacuo to afford sodium quinoline-8-sulfinate (4.10 kg, 72%).

Procedure AJ: Preparation of tert-butyl (Z)-(3-fluoro-4-(quinolin-8-ylsulfonyl)but-2-en-1-yl)carbamate

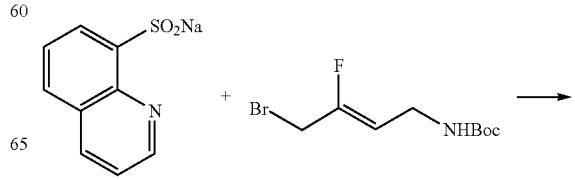

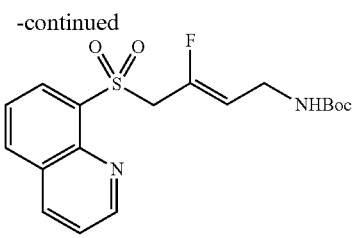

A vessel charged with tert-butyl (Z)-(4-bromo-3-fluorobut-2-en-1-yl)carbamate (3.50 kg, 13.1 mol), sodium quinoline-8-sulfinate (4.20 kg, 19.5 mol) and DMF (17.5 L) was cooled to 15-20° C. The resulting mixture was stirred at this temperature for 20 h. The mixture was then diluted with ethyl acetate (35.0 L) and water (35.0 L), and stirring was continued for a further 10 min. The organic layer was then separated and washed with water (20.0 L×2). After concentrating the organic layer to approximately 20 L, n-heptane (42.0 L) was added drop-wise. The resulting suspension was stirred at 20-30° C. for 20 h. The solid was isolated by filtration, washed with n-heptane and then dried under vacuum at 50–55° C. for 20 h to afford tert-butyl (Z)-(3-fluoro-4-(quinolin-8-ylsulfonyl)but-2-en-1-yl)carbamate (3.80 kg, 77%). RT=12.97 min; Method—Agilent LC/MSD 1200 Series; column: ZORBAX SB—C18, ODS 2000 (50× 4.6 mm, 5 μm) operating in ES (+) or (−) ionization mode; flow rate 1.5 mL/min; Temperature (T)=30° C.; detection wavelength: 214 nm; mobile phase: from 5% acetonitrile (containing 0.05% trifluoroacetic acid (TFA)) and 95% water (containing 0.05% TFA) to 90% acetonitrile and 10% water, over 24 min.

Procedure AK: Preparation of (Z)-3-fluoro-4-(quinolin-8-ylsulfonyl)but-2-en-1-amine dihydrochloride monohydrate (Compound 33)

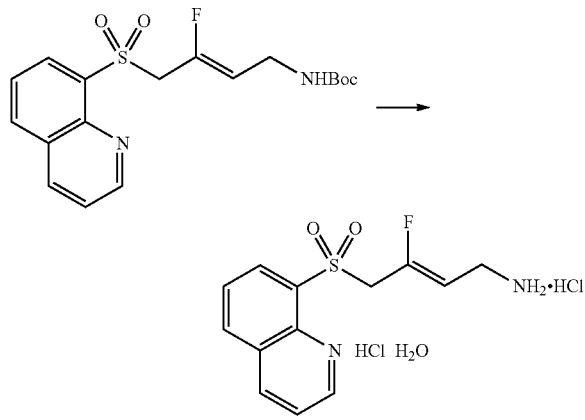

To a vessel charged with HCl (1.5 M in ethyl acetate; 53 L) at 10-20° C. was added tert-butyl (Z)-(3-fluoro-4-(quinolin-8-ylsulfonyl)but-2-en-1-yl)carbamate (5.3 kg, 14 mol). The mixture was stirred at 15° C. for 4 h. The resulting solid was isolated by filtration and washed with ethyl acetate (20 L). To a flask containing the solid was added ethyl acetate (53 L). The suspension was then stirred at 10-20° C. for 2 h. The solid was isolated by filtration and washed with ethyl acetate (20 L). The solid was dissolved in methanol (53 L) and the solution was filtered. To this was then added water (500 mL) and tert-butyl methyl ether (53 L) drop-wise and stirring was continued at 15° C. for a further 20 h. The solid was collected by filtration and dried under vacuum at 55-60° C. to afford (Z)-3-fluoro-4-(quinolin-8-ylsulfonyl)but-2-en-1-amine dihydrochloride monohydrate (Compound 33) (4.4 kg, 90%). $^1$H NMR (300 MHz, CD$_3$OD) δ ppm: 9.18 (d, J=4.7 Hz, 1H), 8.70 (dd, J=8.4, 2.6 Hz, 1H), 8.57 (d, J=7.4 Hz, 1H), 8.45 (d, J=8.5 Hz, 1H), 7.99-7.68 (m, 2H), 5.22 (dt, J=32.9, 7.4 Hz, 1H), 5.00 (d, J=19.4 Hz, 2H), 3.60 (d, J=7.7 Hz, 2H); LCMS: for C$_{13}$H$_{13}$FN$_2$O$_2$S calculated 280.1, found 281.1 [M+1]$^+$.

Example 22

The following compound was prepared according to procedures AL and AM.

Preparation of (Z)-3-fluoro-4-((quinolin-8-yl-d$_6$)sulfonyl)but-2-en-1-amine dihydrochloride (Compound 53)

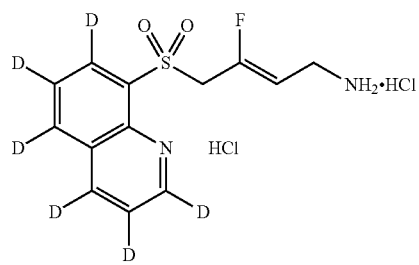

Procedure AL: Preparation of tert-butyl (Z)-(3-fluoro-4-((quinolin-8-yl-d$_6$)sulfonyl)but-2-en-1-yl)carbamate

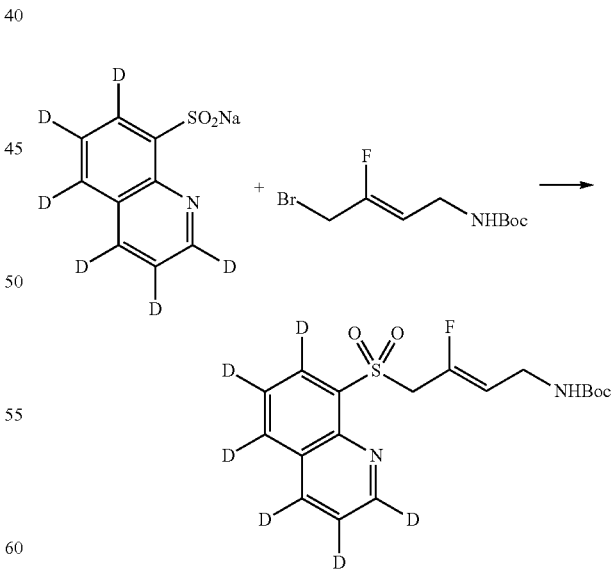

To a stirred solution of tert-butyl (Z)-(4-bromo-3-fluorobut-2-en-1-yl)carbamate (606 mg, 2.26 mmol) in DMF (4.0 mL) was added sodium 2,3,4,5,6,7-hexadeuterioquinoline-8-sulfinate (500 mg, 2.26 mmol) in one lot. The reaction mixture was stirred at rt for 2 h. The reaction mixture was then diluted with water (40 mL), and the product was extracted with ethyl acetate (20 mL×3). The combined organic layer was washed with sat. aq. NH₄Cl (20 mL×3) and brine (20 mL), dried over Na₂SO₄ and then concentrated in vacuo. The crude product was purified by normal-phase chromatography (Reveleris), eluting with 20-50% ethyl acetate in hexanes to afford tert-butyl (Z)-(3-fluoro-4-((quinolin-8-yl-d₆)sulfonyl)but-2-en-1-yl)carbamate (470 mg, 53%) as an off-white solid.

Procedure AM: Preparation of (Z)-3-fluoro-4-((quinolin-8-yl-d₆)sulfonyl)but-2-en-1-amine dihydrochloride (Compound 53)

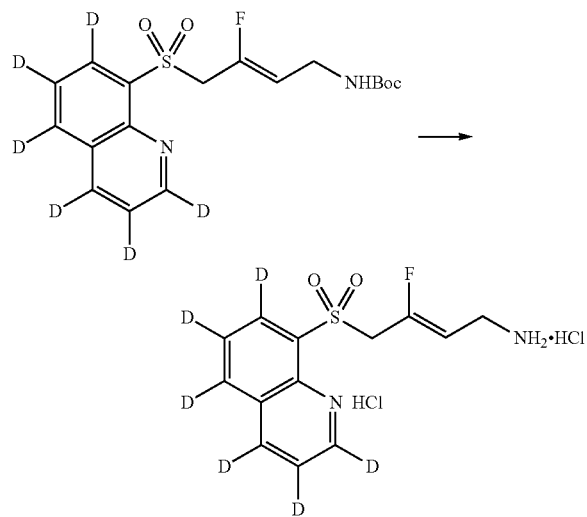

To a stirred solution of tert-butyl (Z)-(3-fluoro-4-((quinolin-8-yl-d₆)sulfonyl)but-2-en-1-yl)carbamate (450 mg, 1.22 mmol) in methanol (1.0 mL) at rt was added HCl (2.0 M in diethyl ether; 4.0 mL, 8.0 mmol). The reaction mixture was stirred at rt for 1 h during which time a solid precipitated. The reaction mixture was transferred to a vial and spundown in a centrifuge (4000 rpm, 4 min). The supernatant was carefully decanted, and the remaining solid "cake" was dried under high vacuum to afford (Z)-3-fluoro-4-((quinolin-8-yl-d₆)sulfonyl)but-2-en-1-amine dihydrochloride (355 mg, 81%) as a white solid. ¹H NMR (300 MHz, CD₃OD) δ ppm: 5.20 (dt, J=32.8, 7.4 Hz, 1H), 5.08-4.96 (m, 2H), 3.59 (d, J=7.4 Hz, 2H).

Example 23

Method to Determine the Ability of Compounds of the Invention to Inhibit LOX and LOXL1-4 from Different Sources Lysyl oxidase (LOX) is an extracellular copper dependent enzyme which oxidizes peptidyl lysine and hydroxylysine residues in collagen and lysine residues in elastin to produce peptidyl alpha-aminoadipic-delta-semialdehydes. This catalytic reaction can be irreversibly inhibited by β-aminopropionitrile (BAPN) that binds to the active site of LOX (Tang S. S., Trackman P C and Kagan H. M., Reaction of aortic lysyl oxidase with beta-aminoproprionitrile. J Biol Chem 1983; 258: 4331-4338). There are five LOX family members; these are LOX, LOXL1, LOXL2, LOXL3 and LOXL4. LOX and LOXL family members can be acquired as recombinant active proteins from commercial sources, or extracted from animal tissues like bovine aorta, tendons, pig skin; or prepared from cell cultures. The inhibitory effects of the compounds of the present invention were tested against the given LOX-LOXL preparation using a method based on the detection of hydrogen peroxide with an Amplex Red oxidation assay (Zhou et al. A stable nonfluorescent derivative of resorufin for the fluorometric determination of trace hydrogen peroxide: applications in detecting the activity of phagocyte NADPH oxidase and other oxidases. Anal. Biochem. 1997; 253, 162-168). The assay was developed using either 384 or 96 well format. Briefly, in a standard black, clear bottom 384 well plate assay 25 μL of a dilution of any of the isoenzymes and orthologues in 1.2 M urea, 50 mM sodium borate buffer (pH 8.2) were added into each well in the presence of 1 μM mofegiline and 0.5 mM pargyline (to inhibit SSAO and MAO-B and MAO-A, respectively; not necessary if the enzyme is from a recombinant or purified form). Test compounds were dissolved in DMSO and tested in a Concentration Response Curve (CRC) with 11 data points, typically in the micromolar or nanomolar range after incubation with the enzyme for 30 min at 37° C. Twenty five μL of a reaction mixture containing twice the KM concentration of putrescine (Sigma Aldrich, e.g. 20 mM for LOX, or 10 mM for LOXL2 and LOXL3), 120 μM Amplex Red (Sigma Aldrich) and 1.5 U/mL horseradish peroxidase (Sigma Aldrich) prepared in 1.2 M urea, 50 mM sodium borate buffer (pH 8.2) were then added to the corresponding wells. The above volumes were doubled in the case of 96 wells plate. The fluorescence (RFU) was read every 2.5 min for 30 min at a range of temperatures from 37° C., excitation 565 nm and emission 590 (Optima; BMG labtech). The slope of the kinetics for each well was calculated using MARS data analysis software (BMG labtech) and this value was used to deduce the IC₅₀ value (Dotmatics). The ability of the inventive compounds to inhibit the amine oxidase activity LOX and other family members is shown in Table 3.

TABLE 3

LOX and LOXL2 inhibitory activities of examples of compounds of the invention

| Compound | Bovine LOX Activity IC₅₀ (micromolar) | Human LOXL2 Activity IC₅₀ (micromolar) |
| --- | --- | --- |
| BAPN | <10 | <1 |
| 1 | <10 | <10 |
| 2 | <10 | <10 |
| 3 | <10 | <10 |
| 4 | <10 | <10 |
| 5 | <1 | <1 |
| 6 | <10 | <1 |
| 7 | <10 | <1 |
| 8 | <1 | <1 |
| 9 | <1 | <1 |
| 10 | <10 | <10 |
| 11 | <1 | <1 |
| 12 | <10 | <1 |
| 13 | <10 | <10 |
| 14 | <1 | <1 |
| 15 | <10 | <1 |
| 16 | <1 | <1 |
| 17 | <10 | <1 |
| 18 | <1 | <1 |
| 19 | <10 | <1 |
| 20 | <10 | <1 |
| 21 | <10 | <1 |
| 22 | <10 | <1 |
| 23 | <10 | <1 |

TABLE 3-continued

LOX and LOXL2 inhibitory activities of
examples of compounds of the invention

| Compound | Bovine LOX Activity $IC_{50}$ (micromolar) | Human LOXL2 Activity $IC_{50}$ (micromolar) |
|---|---|---|
| 24 | <10 | <1 |
| 25 | <10 | <1 |
| 26 | <10 | <1 |
| 27 | <10 | <1 |
| 28 | <10 | <1 |
| 29 | <10 | <1 |
| 30 | <10 | <1 |
| 31 | <10 | <1 |
| 32 | <10 | <1 |
| 33 | <10 | <1 |
| 34 | <10 | <1 |
| 35 | <10 | <1 |
| 36 | <10 | <1 |
| 37 | <10 | <1 |
| 38 | <10 | <1 |
| 39 | <10 | <1 |
| 40 | <10 | <1 |
| 41 | <10 | <1 |
| 42 | <10 | <1 |
| 43 | <10 | <1 |
| 44 | <10 | <1 |
| 45 | <10 | <1 |
| 46 | <10 | <1 |
| 47 | <10 | <1 |
| 48 | <10 | <1 |
| 49 | <10 | <1 |
| 50 | <10 | <1 |
| 51 | <10 | <1 |
| 52 | <10 | <1 |

TABLE 4

Measure of the sustained inhibition of LOXL1
and LOXL2 by compounds of the invention

| Compound | LOXL1 - Recovery of activity. (%) | LOXL2 - Recovery of activity. (%) |
|---|---|---|
| Reversible standard (control) | 80.9 | 96.8 |
| 1 | 2.4 | 9.5 |
| 4 | 16.7 | 21.2 |
| 5 | 3.6 | 10.0 |
| 6 | 2.5 | 10.4 |
| 7 | 3.0 | |
| 8 | 35.1 | |
| 9 | 4.4 | 15.1 |
| 10 | | 15.2 |
| 11 | 10.2 | |
| 12 | 2.6 | 9.3 |
| 13 | 3.5 | 8.9 |
| 14 | 1.9 | |
| 15 | 26.1 | |
| 16 | | 14.4 |
| 17 | | 5.3 |
| 18 | | 6.9 |
| 19 | 7.8 | 7.9 |
| 29 | 8.6 | |
| 30 | 1.9 | |
| 31 | 8.2 | |
| 33 | 4.5 | 6.9 |
| 38 | 1.6 | |
| 45 | 6.6 | |
| 46 | 1.0 | |

Example 24

Compounds of the Current Invention Exhibit Sustained Inhibition of LOXL1 and LOXL2

For meaningful pharmacological effect in the presence of high substrate concentration, compounds that exert sustained, long lasting inhibition of LOX and LOXL1-4 present a strong advantage over competitive inhibitors as the pharmacological effect outlasts the presence of the unbound inhibitor. In a preferred embodiment compounds in the current invention exhibit sustained inhibition of LOX and LOXL1-4.

Method of Determining Sustained Inhibition of LOX and LOXL1-4 by Compounds of the Invention Jump Dilution experiment: The assay was developed using a 96 well format and the starting enzyme concentration was set 100 times higher than for the inhibition studies. The enzyme was incubated for 40 minutes at 37° C. in presence of 10× or (where needed to ascertain inhibitor concentration exceeding enzyme concentration) 30× $IC_{50}$ concentrations of the test inhibitor. After the incubation, the mixture was diluted 50× in assay buffer, followed by a further 2× dilution in Amplex Red-horseradish peroxidase-putrescine reaction mix (same as per the inhibition studies) prior to the fluorescent measurement. Results were expressed in % recovery of the signal after a specified time by comparison with non-inhibited controls. The results are shown in Table 4.

Example 25

In Vivo Pharmacokinetics

Test compounds (10 mg/kg and 30 mg/kg in PBS, p.o. n=3) were administered to 7-9 weeks old male Wistar rats. Test compound blood samples were collected at time points from 0.25 h-8.00 h (Compound 1); 0.5 h-8.00 h (Compound 33) post administration, from tail vein.

Sample preparation: 20 µL of calibration samples (in single), QC samples (in duplicate) and rat plasma samples were mixed with 60 µL acetonitrile containing internal standard (IS; 200 ng/mL of tolbutamide and 50 ng/mL propanolol) in Eppendorf tubes. The mixture was vortexed for 1 min, then centrifuged for 10 min, 50 µL of supernatant was transferred to a 96 well-plate with 100 µL water. After shaking for 10 min, 10 µL was injected into the liquid chromatography mass spectrometry (LC-MS/MS) system for analysis.

LC Method (Compound 1)
HPLC: Agilent 1100; Mass Spectrometer: API 4000
Column: Phenomenex Gemini C18 5 µm 50×4.6 mm
Mobile phase: 0.1% formic acid in water, 0.1% formic acid in acetonitrile LC Method (Compound 33)
HPLC: Shimadzu LC30AD; Mass Spectrometer: API 4000
Column: Agilent SB C18 1.8 µm 50×2.1 mm
Mobile phase: 0.1% formic acid in water, 0.1% formic acid in acetonitrile For dilution samples: 10 µL sample was added to 90 µL blank rat plasma. The mixture was precipitated with 300 µL acetonitrile containing IS in Eppendorf tubes. The mixture was vortexed for 1 min, then centrifuged for 10 min, 50 µL supernatant was transferred to a 96 well-plate with 100 µL water. After shaking for 10 min, 10 µL was injected into the LC-MS/MS system for analysis. Determined, mean plasma concentrations for Compounds 1 and 33 are shown in Table 5 and Table 6 respectively.

TABLE 5

Mean plasma concentration of Compound 1 following
p.o. dosing of 10 and 30 mg/kg
Compound 1

| | Dose p.o. (mg/kg) | | | |
|---|---|---|---|---|
| | 10 | | 30 | |
| Time (hours) | Mean plasma concentration (ng/mL) | Std. Dev. | Mean plasma concentration (ng/mL) | Std. Dev |
| 0.25 | 379.0 | 201.0 | 1057.3 | 9.4 |
| 0.50 | 736.2 | 127.5 | 2088.0 | 180.9 |
| 1.00 | 449.6 | 0.7 | 1202.9 | 186.7 |
| 2.00 | 133.6 | 38.5 | 657.4 | 60.8 |
| 3.00 | 66.4 | 18.0 | 238.5 | 14.2 |
| 5.00 | 27.2 | 11.8 | 41.3 | 20.6 |
| 8.00 | 6.4 | 2.7 | 13.5 | NA |

TABLE 6

Mean plasma concentration of Compound 33 following
p.o. dosing of 10 and 30 mg/kg
Compound 33

| | Dose p.o. (mg/kg) | | | |
|---|---|---|---|---|
| | 10 | | 30 | |
| Time (hours) | Mean plasma concentration (ng/mL) | Std. Dev. | Mean plasma concentration (ng/mL) | Std. Dev |
| 0.50 | 771.3 | 465.4 | 3714.2 | 352.1 |
| 1.00 | 548.3 | 243.4 | 3013.6 | 309.2 |
| 2.00 | 246.0 | 100.2 | 1474.8 | 187.1 |
| 4.00 | 56.4 | 49.4 | 184.7 | 23.0 |
| 8.00 | 8.4 | 5.2 | 13.7 | 0.7 |

Example 26

Target Engagement

A single dose of a mechanism-based inhibitor may be sufficient to block enzymatic activity in vivo for a prolonged period.

Measurement of Lysyl Oxidase Activity—Ear Slice Assay

The ears, collected right after sacrifice of the rats (treated or untreated with a LOX inhibitor), were snap frozen in dry ice for −80° C. storage. For the assay, 5×5 mm samples were cut (still half-thawed), embedded in agarose gel and cut in cross sections 200 μM thick (vibratome). The thin sections were collected in ice cold PBS containing protease inhibitors, and allowed to rest in the bath for 2-3 hours, to allow soluble contaminants to diffuse away prior to the assay. For a 96 well plate format: three thin slices were collected, gently blotted dry on Kimwipe, and transferred to each well containing 100 μl of assay buffer (1.2 M urea, 50 mM sodium borate buffer, pH 8.2), for a 30 minute pre-incubation at 37° C. in presence of 1 μM mofegiline and 500 μM pargyline. BAPN (500 μM) had been added to all the "low control" wells. A minimum of three replicas were performed for each condition.

After pre-incubation, 100 μl of Amplex Red-horseradish peroxidase (HRP) mix (120 μM Amplex Red, 1.5 U/mL HRP, 20 mM putrescine) were added to all wells, and the plate was read at 37° C. every 2.5 minutes for 13 times, (544 nm excitation and 590 nm emission, on a BMG Clariostar, in orbital, top reading mode). The slope of the kinetic curves, subtracted by the values obtained in the low controls (in presence of BAPN), was considered a measure of the specific lysyl oxidase activity in the sample.

Example 27

Measurement of Lysyl Oxidase Activity in the Aorta

Sample preparation: All preparation activities were performed on ice, with buffers in presence of proteases inhibitors (PMSF: Sigma P7626, 0.25 mM, Aprotinin: Sigma A6279, 1 μL per mL) (*Methods in Cell Biology,* 2018; 143: 147-156). The surrounding adventitia and muscle/fat from the frozen aorta sample was removed in ice-cold Wash Buffer (0.15 M NaCl, 50 mM sodium borate, pH=8.0, with protease inhibitors) using fine forceps, under a dissecting microscope. The aorta was blotted on a Kimwipe and weighed in a 1.5 mL Eppendorf tube and left on ice. After snap-freezing the aorta in liquid nitrogen, a mortar and the pestle (stored at −80° C.) was used to pulverize the tissue. The pulverized tissue was transferred to a designated tube containing metal beads, 10× v/w Wash Buffer+protease inhibitors. The tissues was homogenized for 5 seconds using a bead-mill. The homogenate was centrifuged at 10,000×g for 10 minutes at 4° C. and the supernatant was discarded. Homogenization and washing steps were repeated twice more. The resulting pellet was re-suspended in 3× v/w of 6 M Urea Buffer (50 mM sodium borate, 6 M urea, pH=8.2)+ protease inhibitors, and then vortexed. The sample was then left at 4° C. on a roller for 3 hours extraction. After extraction, the sample was centrifuged (10,000×g at 4° C. for 20 min.) and the supernatant was retained. An equal volume from all samples was transferred into a fresh tube for diluting (minimum required is 33 μL). The samples were diluted to 2.4 M urea (sample at this stage is ~4.5 M urea) with Na Borate buffer (50 mM sodium borate, pH 8.2)+ protease inhibitors, and used in the subsequent assay.

Assay: Pargyline (final concentration 0.5 mM) and mofegiline (final concentration 1 μM) were added to the samples. Duplicate wells were set up in black 384 plate, 25 μL per well. To one duplicate was added 0.5 μL of 30 mM BAPN (pan-lox inhibitor); providing the background value (low control). Samples were then incubate for 30 minutes at 37° C. Reaction Mix (25 μL) was added to each well (concentrations were shown as 2× the final in the assay: 120 μM Amplex red, 1.5 U/mL HRP, 20 mM putrescine). Plate fluorescence was then measured every 2.5 min (Ex: 544 nm/Em: 590 nm/gain: 1260; 37° C.) on Fluostar™.

Figure 2A:
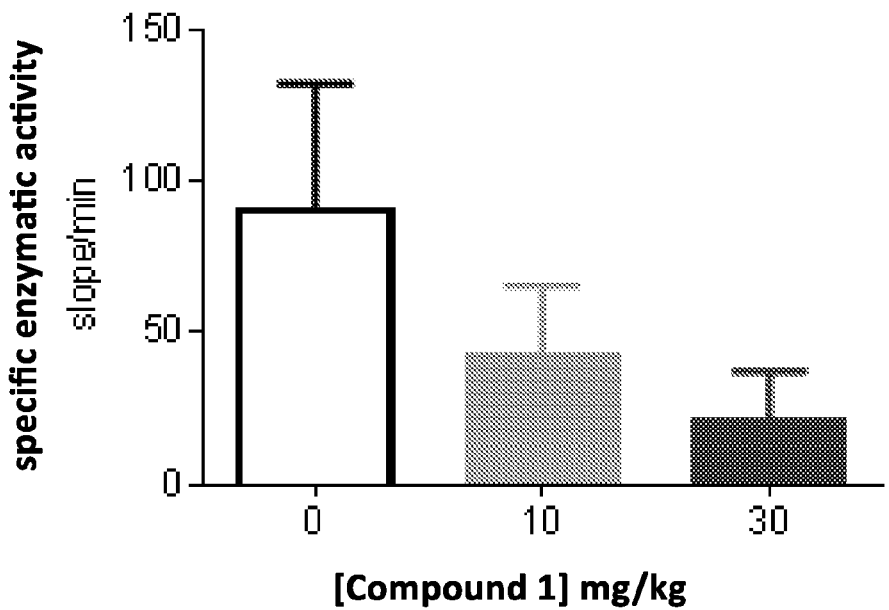
FIGS. 2(a-c) depicts dose-dependent block of lysyl oxidase enzymatic activity by Compound 1 and 33. Measurement of lysyl oxidase activity compared to untreated control in rat tissues (a) ear (24 hours after single oral dose at 10 and 30 mg/kg, Compound 1); (b) ear (4, 24, 48 and 120 hours after single oral dose of 30 mg/kg, Compound 33) and; (c) aorta (single oral dose at 5, 10 or 30 mg/kg, Compound 33)

Young male Wistar rats were given a single oral dose (10 or 30 mg/kg) of Compounds 1 or 33 (Table 5 and 6 respectively) and the enzymatic activity was measured in tissues with a high basal activity at this age, in the ear (FIGS. 2a and b; Compound 1 and 33 respectively) and aorta (FIG. 3c; Compound 33 only). The responses were normalised to the activity measured in animals treated with saline (control).

Compound 1 described herein exerts long lasting inhibition of LOX. While plasma concentrations of Compound 1 are far below the $IC_{50}$ after 8 hours (Table 5) in the plasma of rats, dose dependent, sustained reduction in LOX activity is measureable 24 hours after a single oral dose (FIG. 2a); >20 hours after plasma concentrations of Compound 1 fell below the $IC_{50}$.

Figure 2B:
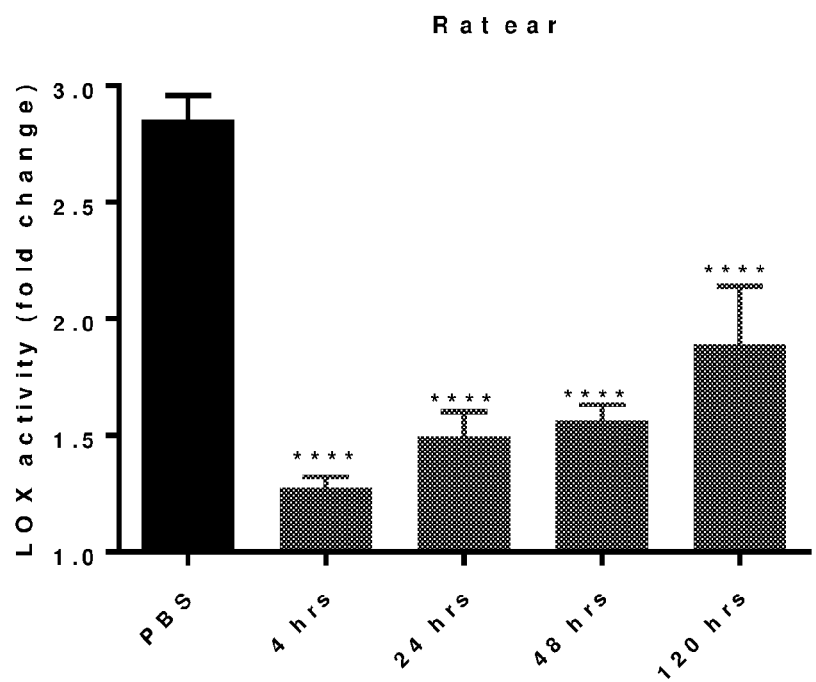
Figure 2C:
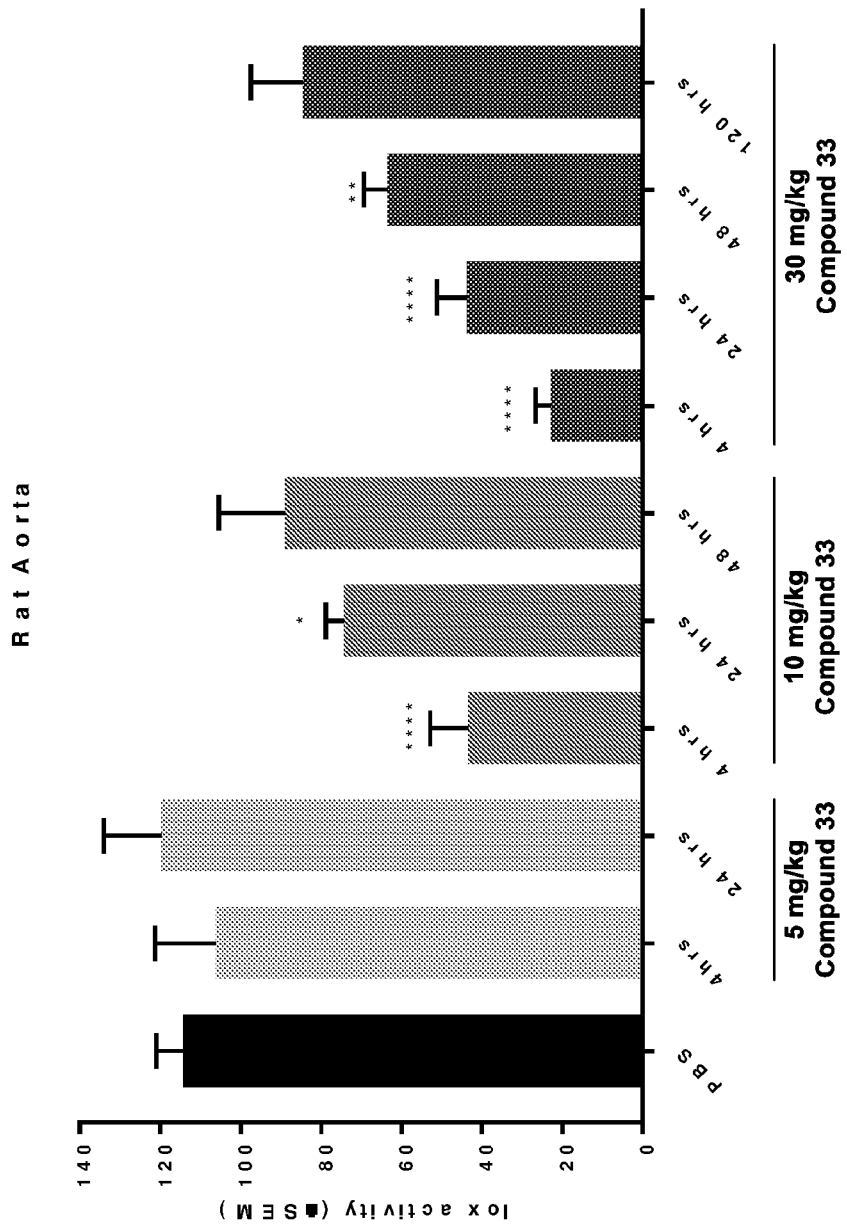

A single high (30 mg/kg) dose of Compound 33 was found to completely abolish lysyl oxidase activity. While plasma concentrations of Compound 33 are far below the $IC_{50}$ after 8 hours (Table 6), the half-life of recovery is between 2-3 days (ear) and 24 hours (aorta) (FIGS. 2b and 2c). Thus, Compound 33 elicits long-lasting inhibition that outlasts the presence of the active compound in plasma.

Example 28

Method to Determine the Ability of Compounds of Formula I to Inhibit Human Recombinant SSAO/VAP-1

Human recombinant SSAO/VAP-1 amine oxidase activity was determined using the coupled colorimetric method as described for monoamine oxidase, copper-containing amine oxidases and related enzymes (Holt A. and Palcic M., A peroxidase-coupled continuous absorbance plate-reader assay for flavin monoamine oxidases, copper-containing amine oxidases and related enzymes. Nat Protoc 2006; 1: 2498-2505). Briefly, a cloned cDNA template corresponding to residues 34-763 of human SSAO/VAP-1, and incorporating a mouse Ig kappa (κ) signal sequence, N-terminal flag epitope tag and tobacco etch virus (TEV) cleavage site, was assembled in a mammalian expression vector (pLO-CMV) by Geneart AG. This vector containing human SSAO/VAP-1 residues was transfected into CHO-K1 glycosylation mutant cell line, Lec 8. A clone stably expressing human SSAO/VAP-1 was isolated and cultured in large scale. Active human SSAO/VAP-1 was purified and recovered using immunoaffinity chromatography. This was used as the source for SSAO/VAP-1 activity. A high-throughput colorimetric assay was developed using either 96 or 384 well format. Briefly, in a standard 96 well plate assay 50 μL of purified human SSAO/VAP-1 (0.25 μg/mL) in 0.1 M sodium phosphate buffer (pH 7.4) was added into each well. Test compounds were dissolved in DMSO and tested in a Concentration Response Curve (CRC) with 4-11 data points, typically in the micromolar or nanomolar range after incubation with human SSAO/VAP-1 for 30 min at 37° C. After 30 min incubation, 50 μL of the reaction mixture containing 600 μM benzylamine (Sigma Aldrich), 120 μM Amplex Red (Sigma Aldrich) and 1.5 U/mL horseradish peroxidase (Sigma Aldrich) prepared in 0.1 M sodium phosphate buffer (pH 7.4) were added to the corresponding well. The fluorescence unit (RFU) was read every 2.5 min for 30 min at 37° C. excitation 565 nm and emission 590 (Optima; BMG labtech). The slope of the kinetics for each well was calculated using MARS data analysis software (BMG labtech) and this value was used to deduce the $IC_{50}$ value (Dotmatics). The ability of the compounds of Formula I to inhibit SSAO/VAP-1 is shown in Table 7

Example 29

Method to Determine the Ability of Compounds of Formula I to Inhibit Human Recombinant MAO-B The specificity of the compounds of this invention was tested by determining their ability to inhibit MAO-B activities in vitro. Recombinant human MAO-B (0.06 mg/mL; Sigma Aldrich) was used as source of MAO-B enzyme activities. The assay was performed in a similar way as for human SSAO/VAP-1 (Example 28) except, the substrate benzylamine was used at 100 μM. The ability of compounds of Formula I to inhibit MAO-B is shown in Table 7.

TABLE 7

Selectivity of Compounds of Formula I for LOX and LOXL2 compared to SSAO/VAP-1 and MAO-B

| Compound | SSAO/VAP-1 Activity $IC_{50}$ (micromolar) | MAO-B Activity $IC_{50}$ (micromolar) |
|---|---|---|
| BAPN | >30 | >30 |
| 1 | >30 | >30 |
| 2 | >30 | >30 |
| 3 | >30 | >30 |
| 4 | >30 | <10 |
| 5 | >30 | >30 |
| 6 | >30 | >30 |
| 7 | >30 | >30 |
| 8 | >30 | >30 |
| 9 | >30 | <10 |
| 10 | >30 | >30 |
| 11 | >30 | >30 |
| 12 | >30 | >30 |
| 13 | >30 | <10 |
| 14 | >30 | >30 |
| 15 | >30 | >30 |
| 19 | >30 | >30 |
| 23 | >30 | — |
| 28 | >30 | — |
| 31 | >30 | — |
| 32 |  | >30 |
| 33 | >10 | >30 |
| 45 | >30 |  |
| 50 | >30 |  |
| 51 | >10 | >30 |
| 53 | >30 |  |

LOX and LOXL1-4 enzymes are members of a large family of flavin-dependent and copper-dependent amine oxidases, which includes SSAO/VAP-1 and monoamine oxidase-B (MAO-B). Compounds of the present invention selectively inhibit members of the LOX family of enzymes with respect to SSAO/VAP-1, MAO-B and other family member amine oxidases. Examples of the magnitude of selectivity can be seen in Table 7.

Example 30

Rodent Injury Model

Mice received injury by excision of dermal tissue. In the treatment group, 1% Compound 1 solution was applied topically from 24 hours post injury to 1 week post injury. Wounds were then left to heal for an additional week. Mice were euthanized at 14 days post injury and the tissue was analyzed for collagen I content, and changes in gross morphology and histology.

Collagen I quantity (measured using LCMS and normalized for protein content) was reduced in treated tissue compared to control (FIG. 3a). Histology showed thick parallel collagen bundles in control scar tissue. Tissue treated with Compound 1 showed decreased density of bundles, and more 'normal' structure of collagen (FIGS. 3b and 3c).

Example 31

Porcine Burn Injury Model

Pigs received 4×25 cm² deep dermal burn injuries, 2 on each flank. From the time of re-epithelialisation, on each pig, 2 wounds were treated with 3% Compound 1 cream daily for 4 weeks and 2 received control cream. Pigs were euthanized and tissue was processed for analysis.

LOX activity was significantly reduced in treated tissue (FIG. 4a), as was total collagen I protein (FIG. 4b). Gross morphology (FIGS. 4c-f) and histology (FIGS. 4g-h) support reduced density of thick collagen fibers in treated wounds.

Example 32

Mouse Model of Pancreatic Cancer

Figure 5C:
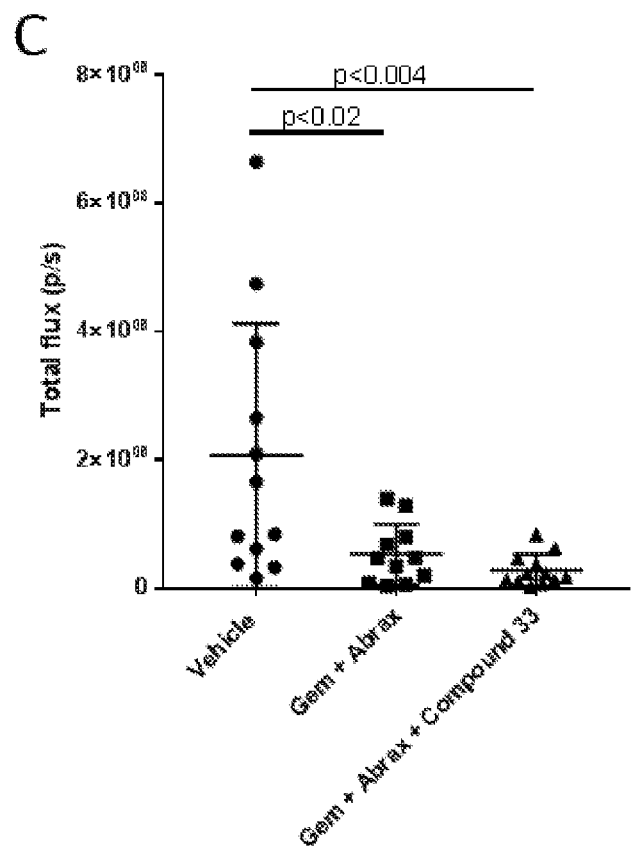
FIG. 5(a-e) Tumour growth data from orthotopic human pancreatic cancer xenograft model: Efficacy data. A. Diagram of the growth and treatment strategy. B. In vivo monitoring of tumour growth by bioluminescent imaging. C. Ex vivo bioluminescent signal of the total tumour burden. D. Ex vivo bioluminescent signal of the primary tumour. E. Ex vivo bioluminescent signal of the metastatic burden.
Figure 5D:
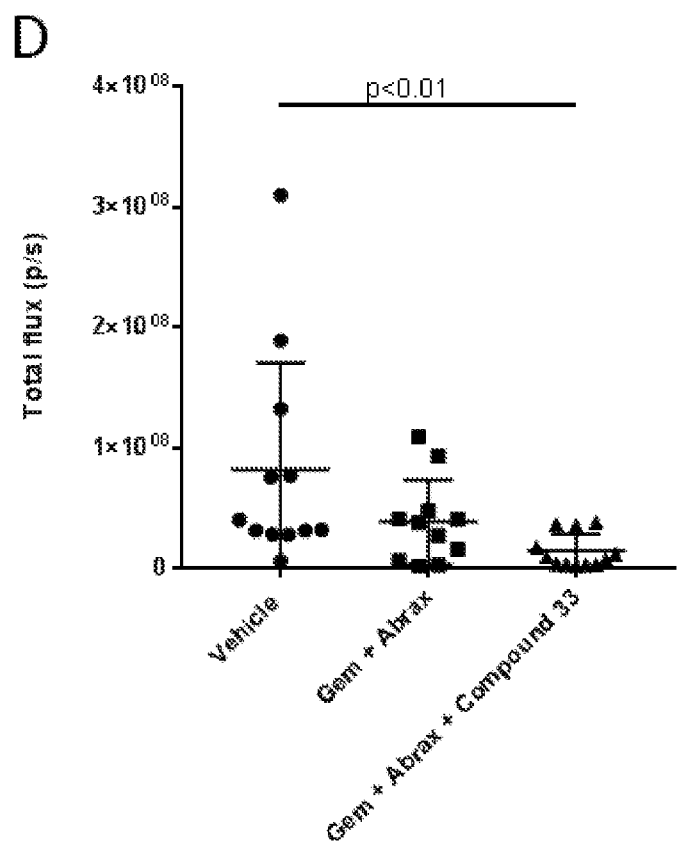
Figure 5E:
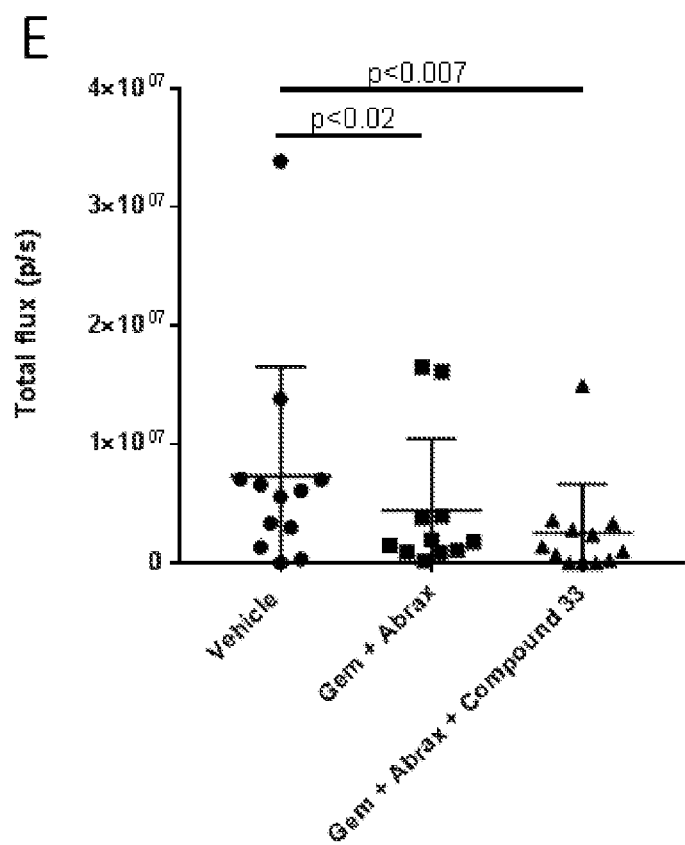

Female athymic nude mice (4-5 weeks old) received inoculation of MiaPaca-2luc (Human Pancreatic cell line) directly into the pancreas. Measured bioluminescent signal intensity and body weight were utilised to stratify tumours into treatment groups on day 14 after initial inoculation. Treatment groups included 1. Vehicle, i.p. 3 times a week. 2. Abraxane (10 mg/kg, i.p. 2 times a week) and gemcitabine (initial dose 100 mg/kg i.p., for the second dose this was reduced to 60 mg/kg i.p. due to acute toxicity and given twice a week). 3. Abraxane (dosed as described above) and gemcitabine (dosed as described above) and Compound 33 (10 mg/kg i.p. 3 times a week) (See FIG. 5a). Mice were euthanized at day 43 after tumour inoculation. Mice were monitored for condition and weight changes twice a week. The tumour growth was monitored in vivo by bioluminescent imaging throughout the studies (FIG. 5b) and organs monitored ex vivo at time of tissue harvest (FIG. 5c-e).

Example 33

Mouse Model of Sclerosis

Subcutaneous bleomycin was administered every second day (for 20 days total) to female C57BL/6 to induced skin fibrosis as a model of sclerosis. The lesions were treated with either Vehicle, 0.5%, 1% or 3% Compound 1. Histology was completed after 21 days. The histological analysis is shown in FIGS. 6(a-c).

Example 34

Mouse Model of Primary Myelofibrosis

Fifteen to sixteen week old GATA1low male and female mice were intra-peritoneal injected with either vehicle (olive oil), or Compound 19 at a dose of 15 mg/kg, four times a week for 10 weeks. The mice were then sacrificed and the spleens and femurs were harvested for histology and analysis (FIGS. 7(a-e) and FIGS. 8(a-d)).

Mice treated with Compound 19 had significantly lower spleen weights adjusted to body weight compared to vehicle group (242.25±18 mg vs 305.11±22.4 mg, $p<0.05$). There was no difference in pre-treatment hematologic parameters, however, mice in the treatment group had significantly lower platelet count compared to vehicle mice post-treatment (77.5±4.4 K/uL vs 106±12, $p<0.05$). Bone marrow (BM) and splenic fibrosis was significantly decreased in mice in the treatment group compared to vehicle. Morphologic BM megakaryocytes (MKs) on H&E stain were counted and were decreased in mice in the treatment group compared to vehicle (24.65±0.6 per 20× field vs 32.91±0.71, $p<0.001$).

Example 35

Unilateral Ureteral Obstruction (UUO) Model

Figure 9:
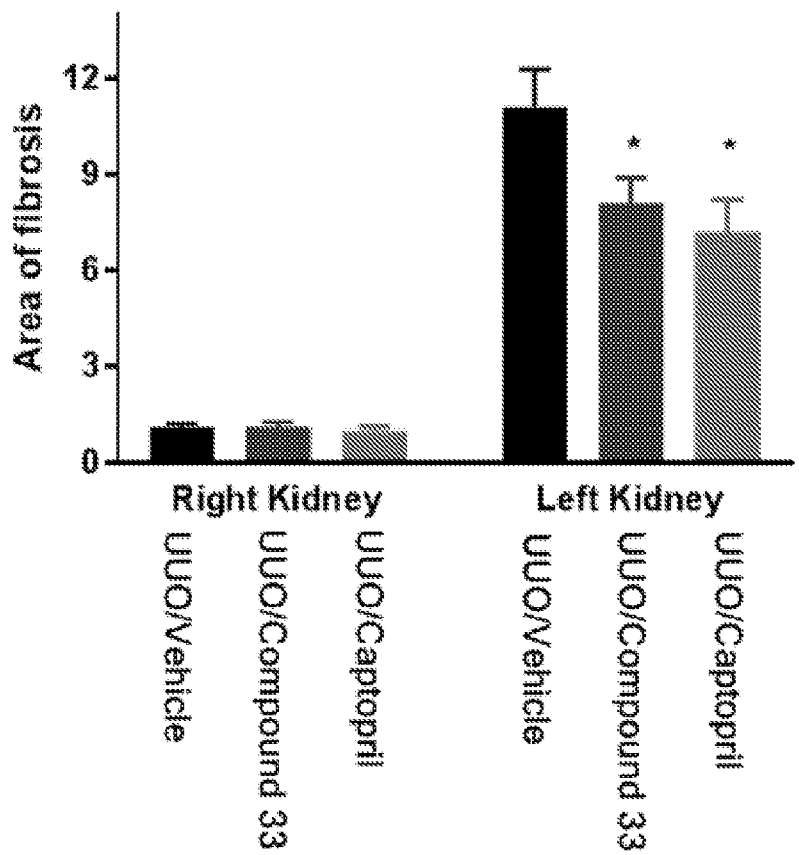
FIG. 9 depicts changes in the area of fibrosis in a mouse UUO model.

A 14-day unilateral ureteric obstruction (UUO) model of acute kidney fibrosis in mice was conducted to mimic the different stages of obstructive nephropathy leading to tubulointerstitial fibrosis in an accelerated manner UUO surgery was performed by ligation of the left ureter and induced decrease of left kidney thickness and atrophy (indicated by a significant decrease in kidney weight and ratio of kidney/body weight when compared to the contralateral side) as well as a significant increase in kidney fibrosis. Treatment groups received Compound 33 (10 mg/kg daily) orally for the duration of the study. Compound 33 increased kidney weight and thickness and reduced the area of fibrosis as measured by Picrosirius Red (FIG. 9). Captopril (~32 mg/kg/day in drinking water) was used as a positive control.

Example 36

Bleomycin-Induced Lung Fibrosis Model

C57Bl/6 mice were given 1.5 U/kg amounts of generic clinical Bleomycin (Blenoxane) via oropharyngeal administration. Compound 33 was dosed daily via oral gavage for 21 days, after which time, tissues were harvested and analyzed. As shown in FIG. 10, Compound 33 significantly reduced the Ashcroft score and the lung weight. As expected for a lysyl oxidase inhibitor, the number of immature (DHLNL) and mature (PYD) cross-links per lung were also reduced by 37- and 45-percent, respectively.

Example 37

Compound 33 Reduces Fibrosis Associated Metastasis

Growing evidence suggests that for cancer metastasis to occur, a pre-metastatic niche needs to be established to aid extravasation and metastatic colonisation. A fibrotic microenvironment is thought to potentiate tumor invasion and the metastasis.

Hepatic fibrosis was induced by treated of BALB/c mice twice weekly with 1 mg/kg carbon tetrachloride ($CCl_4$) for a period of 8 wks. In parallel, treatment with Compound 33 (20 mg/kg daily ip) was provided, which significantly reduced liver fibrosis (FIGS. 11a and b). At the end of week 4 a mouse breast cancer cell line (4t1) was injected orthotopically (as indicated in FIG. 11a). Treatment with Compound 33 significantly reduced liver fibrosis (FIG. 11b), collagen cross-links and the metastatic load in the liver (FIGS. 11c and 11d). No differences in the primary tumor growth or collagen cross-links were observed.

Example 38

Compounds of the Current Invention have Reduced Substrate Activity at SSAO Compared to the E-Alkene, Isomeric Counterparts Minimizing off-target activity is a key consideration in the design and development of compounds destined for therapeutic application. Compounds including E-1 have been exemplified as inhibitors of semicarbazide sensitive amine oxidase (SSAO) [WO2009/066152]. It has been reported that molecules of this type can also be turned over as substrates for SSAO, generating potentially toxic metabolites (Foot et. al., 2012). In a preferred embodiment compounds of the current invention are neither inhibitors nor substrates of SSAO.

Measurement of Substrate Turnover by SSAO

In brief, the assay employed determines the substrate propensity of a compound relative to background (dimethyl sulfoxide only). Compound oxidation by rhSSAO was measured by fluorometric assay (Holt and Palcic, 2006). Briefly, rhSSAO was incubated for 2 hours at 37° C. in HEPES buffer before the addition of an equal volume of Amplex Red (20 mM), horseradish peroxidase (4 U/ml), and Compound (2.5 mM) in the same buffer. The kinetics of the formation of resorufin was measured immediately using Optima reader (BMG Labtech GmbH, Ortenburg, Germany), at 37° C. Representative results are shown in Table 6.

TABLE 6

| Structure | Compound | Recombinant human SSAO (rhSSAO) inhibition (IC$_{50}$) | Substrate activity for rhSSAO |
|---|---|---|---|
| 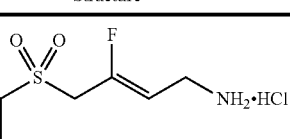 | 1 | >100 µM | no significant turnover |
| 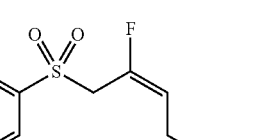 | E-1 | — | turned over as a substrate |
| 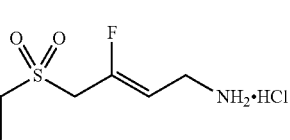 | 31 | 27 µM | no significant turnover |
| 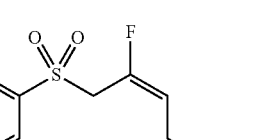 | E-31 | — | turned over as a substrate |

The invention claimed is:

1. A Z-isomer compound of Formula I:

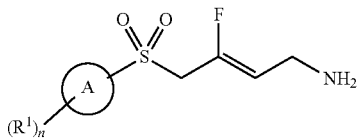

Formula I or a pharmaceutically acceptable salt, polymorphic form, solvate, hydrate or tautomeric form thereof; wherein:

A is selected from the group consisting of:

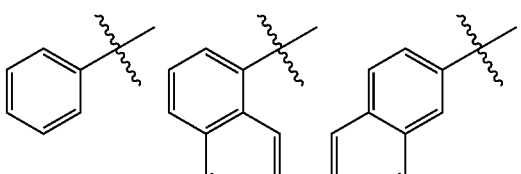

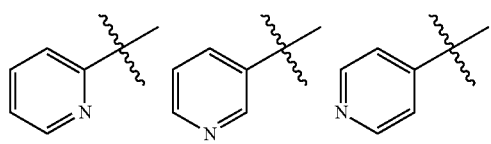

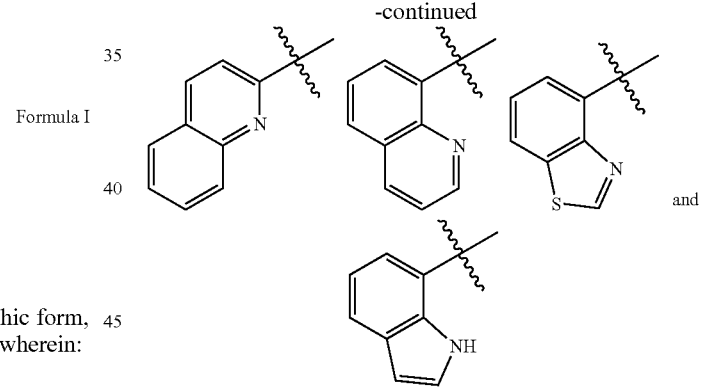

each $R^1$ is independently selected from the group consisting of X—$R^2$, halogen, deuterium, $C_{1-6}$alkyl, O—$C_{1-6}$alkyl, aryl, heteroaryl, cycloalkyl, heterocycloalkyl, —CN, —C(O) $OR^3$, —C(O) $NR^4R^5$, —S(O)$_2$NR$^4$R$^5$, —S(O)$_2$R$^6$, —NR$^8$C(O)R$^9$, and —NR$^8$S(O)$_2$R$^9$; wherein each $C_{1-6}$alkyl, aryl, heteroaryl, cycloalkyl and heterocycloalkyl is optionally substituted by one or more substituents selected from the group consisting of halogen, —OH, —SO$_2$CH$_3$, —C$_{1-4}$alkyl, —O—C$_{1-4}$alkyl, —CF$_3$, —CH$_2$CF$_3$ and —O—CF$_3$;

X is selected from the group consisting of O, CH$_2$, OCH$_2$, CH$_2$O, CH$_2$S(O)$_2$, CONH and NHCO;

$R^2$ is selected from the group consisting of cycloalkyl, heterocycloalkyl, aryl and heteroaryl; wherein each $R^2$ is optionally substituted by one or more $R^7$;

$R^3$ is selected from the group consisting of hydrogen, $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —SO$_2$CH$_3$, —C$_{1-4}$alkyl, —O—C$_{1-4}$alkyl, —CF$_3$, —CH$_2$CF$_3$ and —O—CF$_3$;

R$^4$ and R$^5$ are independently selected from the group consisting of hydrogen, C$_{1-6}$alkyl and C$_{3-7}$cycloalkyl; wherein each C$_{1-6}$alkyl and C$_{3-7}$cycloalkyl is optionally substituted by one or more substituents selected from the group consisting of halogen, —OH, —SO$_2$CH$_3$, —C$_{1-4}$alkyl, —O—C$_{1-4}$alkyl, —CF$_3$, —CH$_2$CF$_3$ and —O—CF$_3$; or R$^4$ and R$^5$ when attached to the same nitrogen atom are combined to form a 4- to 7-membered ring having from 0 to 1 additional heteroatoms as ring members;

R$^6$ is selected from the group consisting of C$_{1-6}$alkyl and C$_{3-7}$cycloalkyl; wherein each C$_{1-6}$alkyl and C$_{3-7}$cycloalkyl is optionally substituted by one or more substituents selected from the group consisting of halogen, —OH, —C$_{1-4}$alkyl, —O—C$_{1-4}$alkyl, —CF$_3$, —CH$_2$CF$_3$, and —O—CF$_3$;

R$^7$ is selected from the group consisting of halogen, —OH, C$_{1-6}$alkyl, O—C$_{1-6}$alkyl C$_{3-7}$cycloalkyl, —C(O) OR$^3$, —C(O) NR$^4$R$^5$, —NR$^4$C(O)R$^6$, —S(O)$_2$NR$^4$R$^5$, —NR$^4$S(O)$_2$R$^6$ and —S(O)$_2$R$^6$; wherein each C$_{1-6}$alkyl is optionally substituted by one or more substituents selected from the group consisting of halogen and —OH;

R$^8$ is hydrogen or C$_{1-6}$alkyl;

R$^9$ is selected from the group consisting of C$_{1-6}$alkyl and C$_{3-7}$cycloalkyl; wherein each C$_{1-6}$alkyl and C$_{3-7}$cycloalkyl is optionally substituted by one or more substituents selected from the group consisting of halogen, —OH, —C$_{1-4}$alkyl, —O—C$_{1-4}$alkyl, —CF$_3$, —CH$_2$CF$_3$, and —O—CF$_3$; or R$^8$ and R$^9$ are combined to form a 5- to 7-membered ring having from 0 to 1 additional heteroatoms as ring members;

and n is 0, 1, 2, 3, 4, 5 or 6.

2. The Z-isomer compound according to claim 1, wherein A is selected from the group consisting of

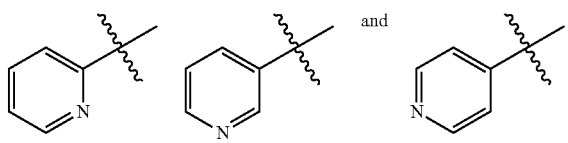

R1 is methyl or isopropyl; and
n is 0 or 1.

3. The Z-isomer compound according to claim 1, wherein A is

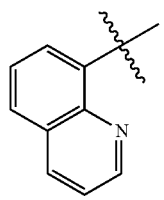 [SMILES: *c1cccc2cccnc12]

and n is 0.

4. The Z-isomer compound according to claim 1, of Formula Ia:

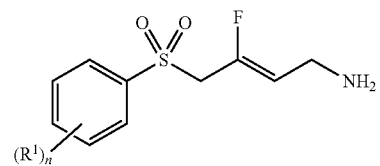

Formula Ia or a pharmaceutically acceptable salt, polymorphic form, solvate, hydrate or tautomeric form thereof; wherein:

each R$^1$ is independently selected from the group consisting of X—R$^2$, halogen, C$_{1-6}$alkyl, O—C$_{1-6}$alkyl, aryl, heteroaryl, cycloalkyl, heterocycloalkyl, —CN, —C(O) OR$^3$, —C(O) NR$^4$R$^5$, —S(O)$_2$NR$^4$R$^5$, —S(O)$_2$R$^6$, —NR$^8$C(O)R$^9$, and —NR$^8$S(O)$_2$R$^9$; wherein each C$_{1-6}$alkyl, aryl, heteroaryl, cycloalkyl and heterocycloalkyl is optionally substituted by one or more substituents selected from the group consisting of halogen, —OH, —SO$_2$CH$_3$, —C$_{1-4}$alkyl, —O—C$_{1-4}$alkyl, —CF$_3$, —CH$_2$CF$_3$ and —O—CF$_3$;

X is selected from the group consisting of O, CH$_2$, OCH$_2$, CH$_2$O, CH$_2$S(O)$_2$, CONH and NHCO;

R$^2$ is selected from the group consisting of cycloalkyl, heterocycloalkyl, aryl and heteroaryl; wherein each R$^2$ is optionally substituted by one or more R$^7$;

R$^3$ is selected from the group consisting of hydrogen, C$_{1-6}$alkyl and C$_{3-7}$cycloalkyl;

R$^4$ and R$^5$ are independently selected from the group consisting of hydrogen, C$_{1-6}$alkyl and C$_{3-7}$cycloalkyl; or R$^4$ and R$^5$ when attached to the same nitrogen atom are combined to form a 4- to 7-membered ring having from 0 to 1 additional heteroatoms as ring members;

R$^6$ is selected from the group consisting of C$_{1-6}$alkyl and C$_{3-7}$cycloalkyl;

R$^7$ is selected from the group consisting of halogen, —OH, C$_{1-6}$alkyl, O—C$_{1-6}$alkyl, C$_{3-7}$cycloalkyl, —C(O) OR$^3$, —C(O) NR$^4$R$^5$, —NR$^4$C(O)R$^6$, —S(O)$_2$NR$^4$R$^5$, —NR$^4$S(O)$_2$R$^6$ and —S(O)$_2$R$^6$; wherein each C$_{1-6}$alkyl is optionally substituted by one or more substituents selected from the group consisting of halogen and —OH;

R$^8$ is hydrogen or C$_{1-6}$alkyl;

R$^9$ is selected from the group consisting of C$_{1-6}$alkyl and C$_{3-7}$cycloalkyl; wherein each C$_{1-6}$alkyl and C$_{3-7}$cycloalkyl is optionally substituted by one or more substituents selected from the group consisting of halogen, —OH, —C$_{1-4}$alkyl, —O—C$_{1-4}$alkyl, —CF$_3$, —CH$_2$CF$_3$, and —O—CF$_3$; or R$^8$ and R$^9$ are combined to form a 5- to 7-membered ring having from 0 to 1 additional heteroatoms as ring members;

and n is 0, 1, 2 or 3.

5. The Z-isomer compound according to claim 4, wherein n is 0.

6. The Z-isomer compound according to claim 4, wherein each R$^1$ is independently selected from the group consisting of halogen, C$_{1-6}$alkyl, O—C$_{1-6}$alkyl, aryl, and —S(O)$_2$R$^6$; wherein each C$_{1-6}$alkyl is optionally substituted by one or more halogen;

R$^6$ is C$_{1-6}$alkyl;

and n is 1 or 2.

7. The Z-isomer compound according to claim 1 selected from the group consisting of

| | | |
|---|---|---|
| 1 | 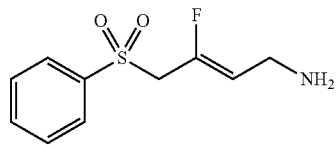 [SMILES: NC/C=C(\F)CS(=O)(=O)c1ccccc1] | (Z)-3-fluoro-4-(phenylsulfonyl)but-2-en-1-amine |
| 2 | 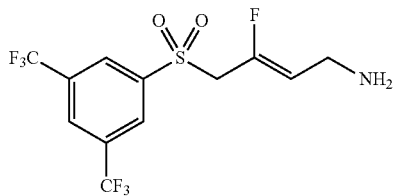 [SMILES: NC/C=C(\F)CS(=O)(=O)c1cc(C(F)(F)F)cc(C(F)(F)F)c1] | (Z)-4-((3,5-bis(trifluoromethyl)phenyl)sulfonyl)-3-fluorobut-2-en-1-amine |
| 3 | 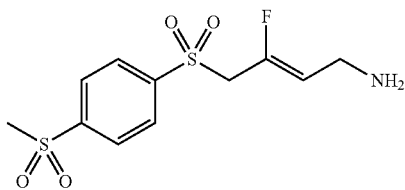 [SMILES: CS(=O)(=O)c1ccc(S(=O)(=O)C/C(F)=C/CN)cc1] | (Z)-3-fluoro-4-((4-(methylsulfonyl)phenyl)sulfonyl)but-2-en-1-amine |
| 4 | 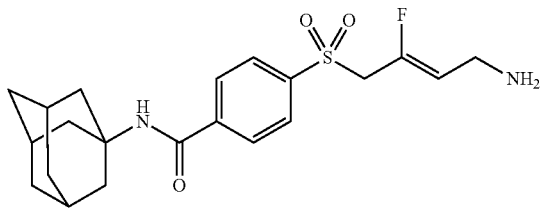 [SMILES: NC/C=C(\F)CS(=O)(=O)c1ccc(C(=O)NC23CC4CC(CC(C4)C2)C3)cc1] | N-((1R,3R,5S)-adamantan-1-yl)-4-(((Z)-4-amino-2-fluorobut-2-en-1-yl)sulfonyl)benzamide |
| 5 | 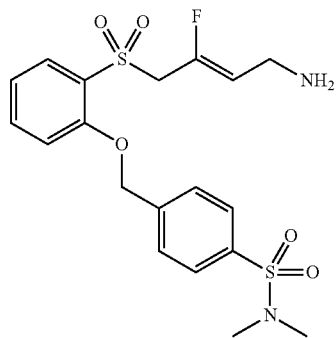 [SMILES: CN(C)S(=O)(=O)c1ccc(COc2ccccc2S(=O)(=O)C/C(F)=C/CN)cc1] | (Z)-4-((2-((4-amino-2-fluorobut-2-en-1-yl)sulfonyl)phenoxy)methyl)-N,N-dimethylbenzene-sulfonamide |
| 6 | 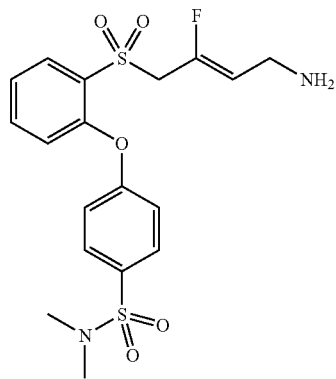 [SMILES: CN(C)S(=O)(=O)c1ccc(Oc2ccccc2S(=O)(=O)C/C(F)=C/CN)cc1] | (Z)-4-(2-((4-amino-2-fluorobut-2-en-1-yl)sulfonyl)phenoxy)-N,N-dimethylbenzene-sulfonamide |

| | | |
|---|---|---|
| 7 | 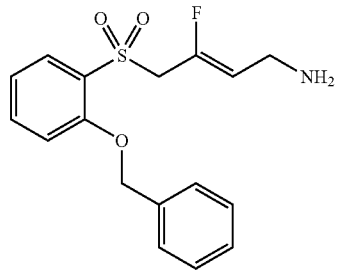 [SMILES: NC/C=C(\F)CS(=O)(=O)c1ccccc1OCc1ccccc1] | (Z)-4-((2-(benzyloxy)phenyl)sulfonyl)-3-fluorobut-2-en-1-amine |
| 8 | 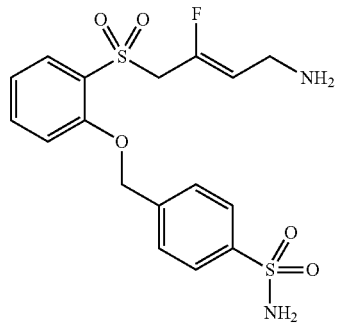 [SMILES: NC/C=C(\F)CS(=O)(=O)c1ccccc1OCc1ccc(S(N)(=O)=O)cc1] | (Z)-4-((2-((4-amino-2-fluorobut-2-en-1-yl)sulfonyl)phenoxy)methyl)benzenesulfonamide |
| 9 | 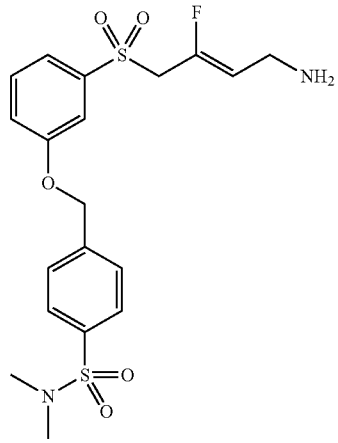 [SMILES: CN(C)S(=O)(=O)c1ccc(COc2cccc(S(=O)(=O)C/C(F)=C/CN)c2)cc1] | (Z)-4-((3-((4-amino-2-fluorobut-2-en-1-yl)sulfonyl)phenoxy)methyl)-N,N-dimethylbenzenesulfonamide |
| 10 | 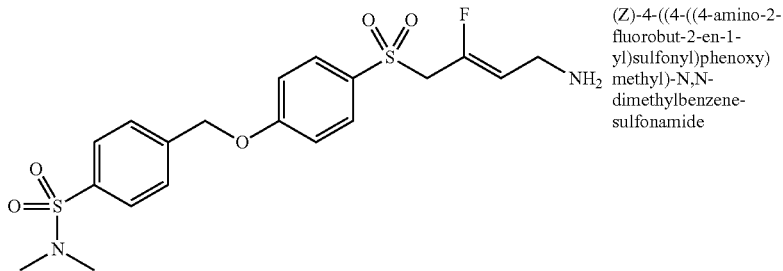 | (Z)-4-((4-((4-amino-2-fluorobut-2-en-1-yl)sulfonyl)phenoxy)methyl)-N,N-dimethylbenzenesulfonamide |

| | | |
|---|---|---|
| 11 | 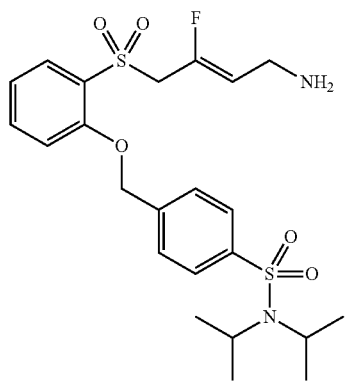 [SMILES: CC(C)N(C(C)C)S(=O)(=O)c1ccc(COc2ccccc2S(=O)(=O)C/C(F)=C/CN)cc1] | (Z)-4-((2-((4-amino-2-fluorobut-2-en-1-yl)sulfonyl)phenoxy)methyl)-N,N-diisopropylbenzenesulfonamide |
| 12 | 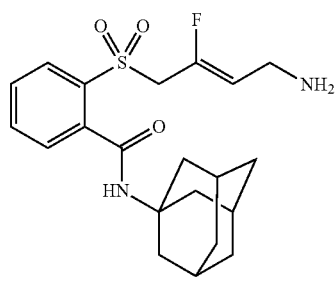 [SMILES: NC/C=C(\F)CS(=O)(=O)c1ccccc1C(=O)NC12CC3CC(CC(C3)C1)C2] | N-((1S,3R,5S)-adamantan-1-yl)-2-(((Z)-4-amino-2-fluorobut-2-en-1-yl)sulfonyl)benzamide |
| 13 | 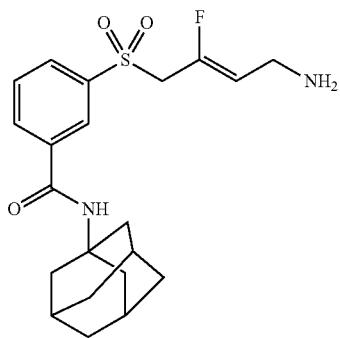 [SMILES: NC/C=C(\F)CS(=O)(=O)c1cccc(C(=O)NC23CC4CC(CC(C4)C2)C3)c1] | N-((1S,3R,5S)-adamantan-1-yl)-3-(((Z)-4-amino-2-fluorobut-2-en-1-yl)sulfonyl)benzamide |
| 14 | 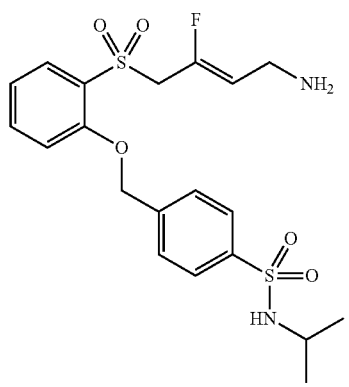 [SMILES: CC(C)NS(=O)(=O)c1ccc(COc2ccccc2S(=O)(=O)C/C(F)=C/CN)cc1] | (Z)-4-((2-((4-amino-2-fluorobut-2-en-1-yl)sulfonyl)phenoxy)methyl)-N-isopropylbenzenesulfonamide |

| | | |
|---|---|---|
| 15 | 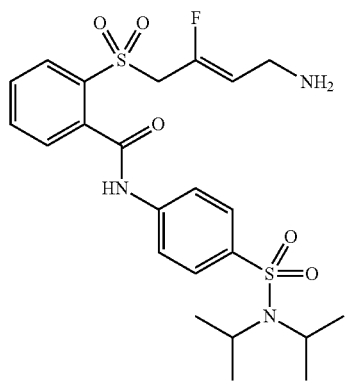 [SMILES: CC(C)N(C(C)C)S(=O)(=O)c1ccc(NC(=O)c2ccccc2S(=O)(=O)C/C(F)=C/CN)cc1] | (Z)-2-((4-amino-2-fluorobut-2-en-1-yl)sulfonyl)-N-(4-(N,N-diisopropylsulfamoyl)phenyl)benzamide |
| 16 | 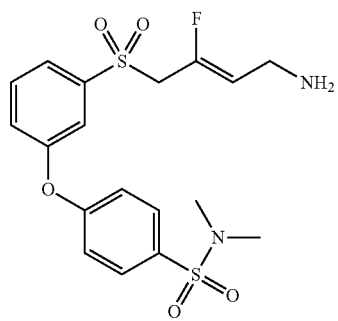 [SMILES: CN(C)S(=O)(=O)c1ccc(Oc2cccc(S(=O)(=O)C/C(F)=C/CN)c2)cc1] | (Z)-4-(3-(4-amino-2-fluorobut-2-enylsulfonyl)phenoxy)-N,N-dimethylbenzenesulfonamide |
| 17 | 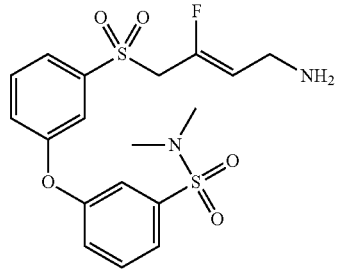 [SMILES: CN(C)S(=O)(=O)c1cccc(Oc2cccc(S(=O)(=O)C/C(F)=C/CN)c2)c1] | (Z)-3-(3-(4-amino-2-fluorobut-2-enylsulfonyl)phenoxy)-N,N-dimethylbenzenesulfonamide |
| 18 | 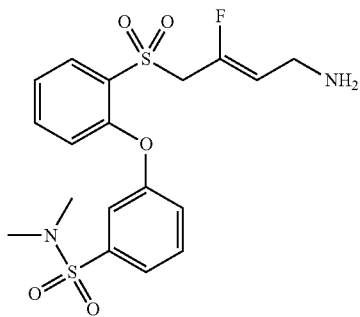 [SMILES: CN(C)S(=O)(=O)c1cccc(Oc2ccccc2S(=O)(=O)C/C(F)=C/CN)c1] | (Z)-3-(2-(4-amino-2-fluorobut-2-enylsulfonyl)phenoxy)-N,N-dimethylbenzenesulfonamide |
| 19 | 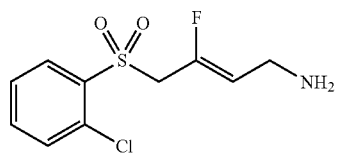 | (Z)-4-(2-chlorophenylsulfonyl)-3-fluorobut-2-en-1-amine |

| # | | Name |
|---|---|---|
| 20 | 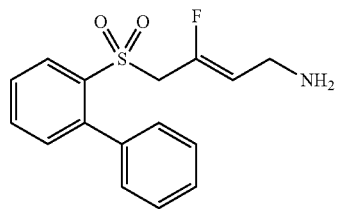 [SMILES: NC/C=C(\F)CS(=O)(=O)c1ccccc1-c1ccccc1] | (Z)-4-(biphenyl-2-ylsulfonyl)-3-fluorobut-2-en-1-amine |
| 21 | 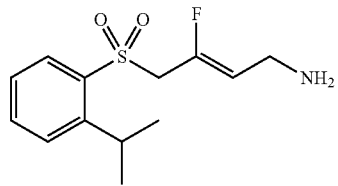 [SMILES: CC(C)c1ccccc1S(=O)(=O)C/C(F)=C/CN] | (Z)-3-fluoro-4-(2-isopropylphenylsulfonyl)but-2-en-1-amine |
| 22 | 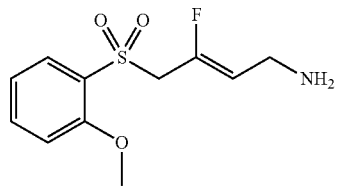 [SMILES: COc1ccccc1S(=O)(=O)C/C(F)=C/CN] | (Z)-3-fluoro-4-(2-methoxyphenylsulfonyl)but-2-en-1-amine |
| 23 | 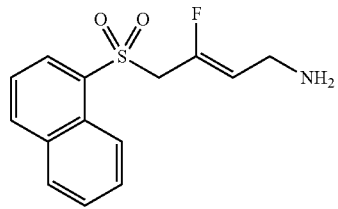 | (Z)-3-fluoro-4-(naphthalen-1-ylsulfonyl)but-2-en-1-amine |
| 24 | 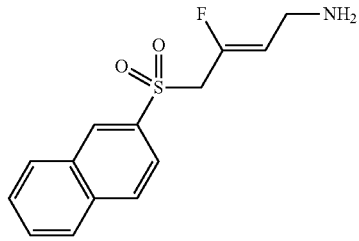 [SMILES: NC/C=C(\F)CS(=O)(=O)c1ccc2ccccc2c1] | (Z)-3-fluoro-4-(naphthalen-2-ylsulfonyl)but-2-en-1-amine |
| 25 | 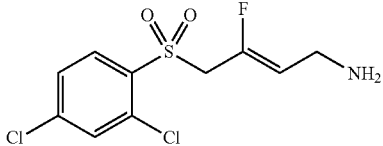 [SMILES: NC/C=C(\F)CS(=O)(=O)c1ccc(Cl)cc1Cl] | (Z)-4-(2,4-dichlorophenylsulfonyl)-3-fluorobut-2-en-1-amine |
| 26 | 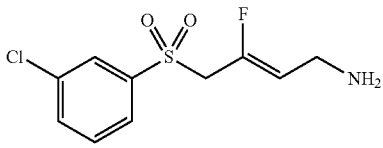 [SMILES: NC/C=C(\F)CS(=O)(=O)c1cccc(Cl)c1] | (Z)-4-(3-chlorophenylsulfonyl)-3-fluorobut-2-en-1-amine |
| 27 | 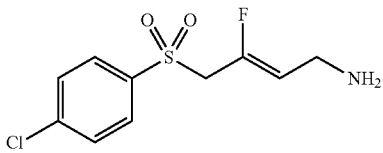 [SMILES: NC/C=C(\F)CS(=O)(=O)c1ccc(Cl)cc1] | (Z)-4-(4-chlorophenylsulfonyl)-3-fluorobut-2-en-1-amine |

| | | |
|---|---|---|
| 28 | 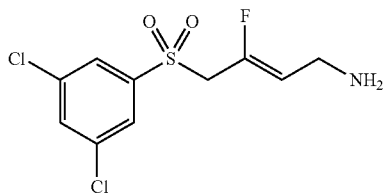 [SMILES: NC/C=C(\F)CS(=O)(=O)c1cc(Cl)cc(Cl)c1] | (Z)-4-(3,5-dichlorophenylsulfonyl)-3-fluorobut-2-en-1-amine |
| 29 | 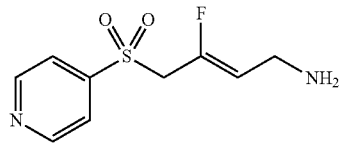 [SMILES: NC/C=C(\F)CS(=O)(=O)c1ccncc1] | (Z)-3-fluoro-4-(pyridin-4-ylsulfonyl)but-2-en-1-amine |
| 30 | 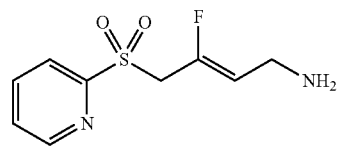 [SMILES: NC/C=C(\F)CS(=O)(=O)c1ccccn1] | (Z)-3-fluoro-4-(pyridin-2-ylsulfonyl)but-2-en-1-amine |
| 31 | 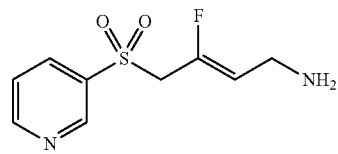 [SMILES: NC/C=C(\F)CS(=O)(=O)c1cccnc1] | (Z)-3-fluoro-4-(pyridin-3-ylsulfonyl)but-2-en-1-amine |
| 32 | 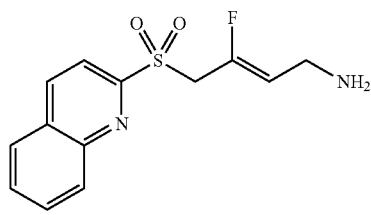 [SMILES: NC/C=C(\F)CS(=O)(=O)c1ccc2ccccc2n1] | (Z)-3-fluoro-4-(quinolin-2-ylsulfonyl)but-2-en-1-amine |
| 33 | 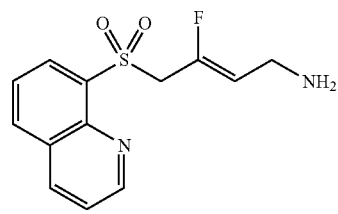 [SMILES: NC/C=C(\F)CS(=O)(=O)c1cccc2cccnc12] | (Z)-3-fluoro-4-(quinolin-8-ylsulfonyl)but-2-en-1-amine |
| 34 | 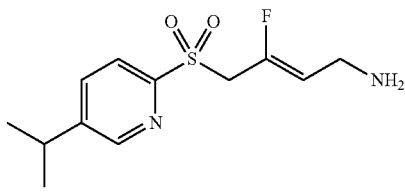 [SMILES: CC(C)c1ccc(S(=O)(=O)C/C(F)=C/CN)nc1] | (Z)-3-fluoro-4-(5-isopropylpyridin-2-ylsulfonyl)but-2-en-1-amine |
| 35 | 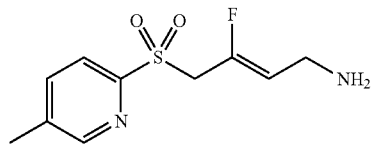 [SMILES: Cc1ccc(S(=O)(=O)C/C(F)=C/CN)nc1] | (Z)-3-fluoro-4-(5-methylpyridin-2-ylsulfonyl)but-2-en-1-amine |

| | | |
|---|---|---|
| 36 | 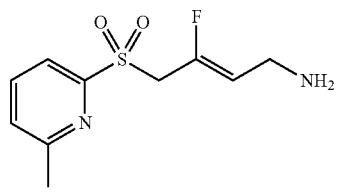 [SMILES: Cc1cccc(S(=O)(=O)C/C(F)=C/CN)n1] | (Z)-3-fluoro-4-(6-methylpyridin-2-ylsulfonyl)but-2-en-1-amine |
| 37 | 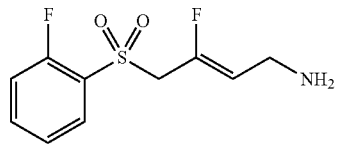 [SMILES: NC/C=C(\F)CS(=O)(=O)c1ccccc1F] | (Z)-3-fluoro-4-(2-fluorophenylsulfonyl)but-2-en-1-amine |
| 38 | 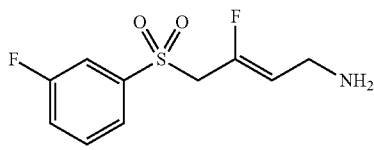 [SMILES: NC/C=C(\F)CS(=O)(=O)c1cccc(F)c1] | (Z)-3-fluoro-4-(3-fluorophenylsulfonyl)but-2-en-1-amine |
| 39 | 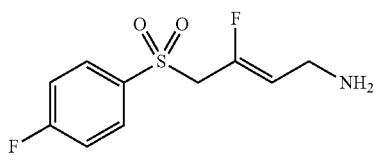 [SMILES: NC/C=C(\F)CS(=O)(=O)c1ccc(F)cc1] | (Z)-3-fluoro-4-(4-fluorophenylsulfonyl)but-2-en-1-amine |
| 40 | 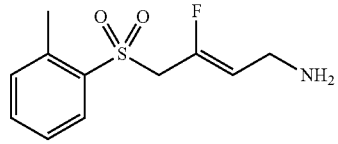 [SMILES: Cc1ccccc1S(=O)(=O)C/C(F)=C/CN] | (Z)-3-fluoro-4-(o-tolylsulfonyl)but-2-en-1-amine |
| 41 | 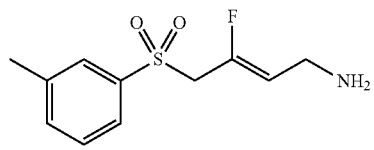 | (Z)-3-fluoro-4-(m-tolylsulfonyl)but-2-en-1-amine |
| 42 | 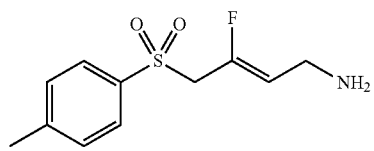 [SMILES: Cc1ccc(S(=O)(=O)C/C(F)=C/CN)cc1] | (Z)-3-fluoro-4-tosylbut-2-en-1-amine |
| 43 | 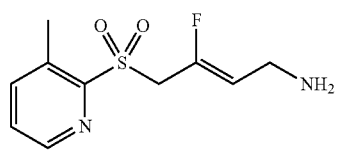 [SMILES: Cc1cccnc1S(=O)(=O)C/C(F)=C/CN] | (Z)-3-fluoro-4-(3-methylpyridin-2-ylsulfonyl)but-2-en-1-amine |
| 44 | 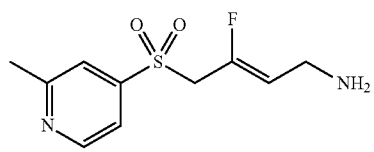 | (Z)-3-fluoro-4-(2-methylpyridin-4-ylsulfonyl)but-2-en-1-amine |

-continued

| | | |
|---|---|---|
| 45 | | (Z)-3-fluoro-4-(2-isopropylpyridin-3-ylsulfonyl)but-2-en-1-amine |
| 46 | | (Z)-3-fluoro-4-(6-methylpyridin-3-ylsulfonyl)but-2-en-1-amine |
| 47 | | (Z)-3-fluoro-4-(2-methylpyridin-3-ylsulfonyl)but-2-en-1-amine |
| 48 | | (Z)-3-fluoro-4-(4-methylpyridin-3-ylsulfonyl)but-2-en-1-amine |
| 49 | | (Z)-3-fluoro-4-(6-isopropylpyridin-3-ylsulfonyl)but-2-en-1-amine |
| 50 | | (Z)-3-fluoro-4-((2-methylbenzo[d]thiazol-4-yl)sulfonyl)but-2-en-1-amine |
| 51 | | (Z)-3-fluoro-4-((3-fluoroquinolin-8-yl)sulfonyl)but-2-en-1-amine |
| 52 | | (Z)-4-((2,3-dimethyl-1H-indol-7-yl)sulfonyl)-3-fluorobut-2-en-1-amine; and |

| | | |
|---|---|---|
| 53 | 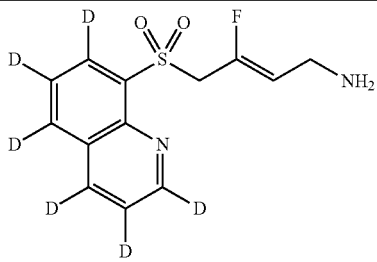 | (Z)-3-fluoro-4-((quinolin-8-yl-d₆)sulfonyl)but-2-en-1-amine | or a pharmaceutically acceptable salt or solvate thereof.

8. The Z-isomer compound according to claim 1 selected from the group consisting of

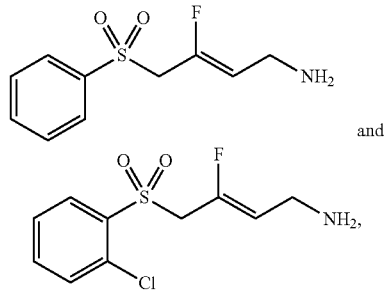

or a pharmaceutically acceptable salt or solvate thereof.

9. The Z-isomer compound according to claim 1 selected from the group consisting of

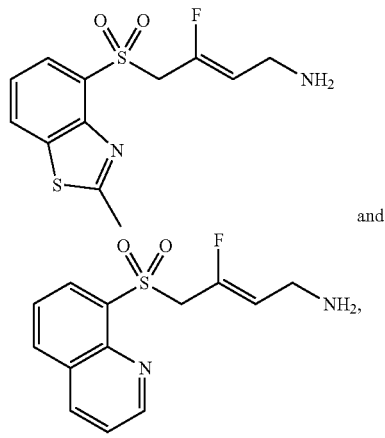

or a pharmaceutically acceptable salt or solvate thereof.

10. A pharmaceutical composition comprising a Z-isomer compound according to claim 1, or a pharmaceutically acceptable salt or solvate thereof, and at least one pharmaceutically acceptable excipient, carrier or diluent.

11. A method of inhibiting the amine oxidase activity of any one of LOX, LOXL1, LOXL2, LOXL3 or LOXL4 in a subject in need thereof, comprising administering to the subject an effective amount of a Z-isomer compound according to claim 1.

12. A method of remedying a condition associated with any one of LOX, LOXL1, LOXL2, LOXL3 or LOXL4 protein, comprising administering to a subject in need thereof a therapeutically effective amount of Z-isomer compound according to claim 1, or a pharmaceutically acceptable salt or solvate thereof, wherein the condition is selected from the group consisting of fibrosis, cancer and angiogenesis.

13. The method of claim 12, wherein in a case that the condition is fibrosis, the fibrosis is selected from the group consisting of mediastinal fibrosis, myelofibrosis, retroperitoneal fibrosis, progressive massive fibrosis, nephrogenic systemic fibrosis, Crohn's Disease, keloid, systemic sclerosis, arthrofibrosis, Dupuytren's contracture, adhesive capsulitis, fibrosis of the pancreas, fibrosis of the intestine, liver fibrosis, lung fibrosis, kidney fibrosis, cardiac fibrosis, fibrostenosis, cystic fibrosis, idiopathic pulmonary fibrosis, radiation-induced fibrosis, Peyronie's disease and scleroderma or is associated with respiratory disease, abnormal wound healing and repair, scarring, hypertrophic scarring/keloids, scarring post surgery, cardiac arrest and all conditions where excess or aberrant deposition of fibrous material is associated with disease, injury, implants or surgery; and wherein in a case that the condition is cancer, the cancer is selected from the group consisting of lung cancer; breast cancer; colorectal cancer; anal cancer; pancreatic cancer; prostate cancer; ovarian carcinoma; liver and bile duct carcinoma; esophageal carcinoma; mesothelioma; non-Hodgkin's lymphoma; bladder carcinoma; carcinoma the of uterus; glioma, glioblastoma, medullablastoma, and other tumours of the brain; myelofibrosis, kidney cancer; cancer of the head and neck; cancer of the stomach; multiple myeloma; testicular cancer; germ cell tumour; neuroendocrine tumour; cervical cancer; oral cancer, carcinoids of the gastrointestinal tract, breast, and other organs; signet ring cell carcinoma; mesenchymal tumours including sarcomas, fibrosarcomas, haemangioma, angiomatosis, haemangiopericytoma, pseudoangiomatous stromal hyperplasia, myofibroblastoma, fibromatosis, inflammatory myofibroblastic tumour, lipoma, angiolipoma, granular cell tumour, neurofibroma, schwannoma, angiosarcoma, liposarcoma, rhabdomyosarcoma, osteosarcoma, leiomyoma or a leiomysarcoma.

14. The method according to claim 12, further comprising administering a second therapeutic agent.

15. The method according to claim 14, wherein the second therapeutic agent is selected from the group consisting of an anti-cancer agent, an anti-inflammatory agent, an anti-hypertensive agent, an anti-fibrotic agent, an anti-angiogenic agent, an immunosuppressive agent and a metabolic agent.

16. A pharmaceutical composition comprising a Z-isomer compound according to claim 8, or a pharmaceutically acceptable salt thereof, and at least one pharmaceutically acceptable excipient, carrier or diluent.

17. A pharmaceutical composition comprising a Z-isomer compound according to claim 9, or a pharmaceutically acceptable salt thereof, and at least one pharmaceutically acceptable excipient, carrier or diluent.

18. The method of claim 12, wherein in a case that the condition is fibrosis, the fibrosis is selected from the group consisting of myelofibrosis, systemic sclerosis, liver fibrosis, lung fibrosis, kidney fibrosis, cardiac fibrosis and radiation induced fibrosis.

\* \* \* \* \*